(12) United States Patent
Kearney et al.

(10) Patent No.: US 9,091,651 B2
(45) Date of Patent: Jul. 28, 2015

(54) SELECTED REACTION MONITORING ASSAYS

(71) Applicant: Integrated Diagnostics, Inc., Seattle, WA (US)

(72) Inventors: Paul Edward Kearney, Montreal (CA); Xiao-Jun Li, Bellevue, WA (US); Clive Hayward, Seattle, WA (US); Miguel Dominguez Geeraerts, Pierrefonds (CA)

(73) Assignee: Integrated Diagnostics, Inc., Seattle, WA (US)

( * ) Notice: Subject to any disclaimer, the term of this patent is extended or adjusted under 35 U.S.C. 154(b) by 0 days.

(21) Appl. No.: 13/725,098

(22) Filed: Dec. 21, 2012

(65) Prior Publication Data

US 2013/0203096 A1    Aug. 8, 2013

Related U.S. Application Data

(60) Provisional application No. 61/578,718, filed on Dec. 21, 2011, provisional application No. 61/614,818, filed on Mar. 23, 2012.

(51) Int. Cl.
| | | |
|---|---|---|
| *C12Q 1/37* | (2006.01) | |
| *G01N 27/62* | (2006.01) | |
| *G01N 33/68* | (2006.01) | |

(52) U.S. Cl.
CPC ............ *G01N 27/62* (2013.01); *G01N 33/6848* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 2002/0045164 A1* | 4/2002 | Billing-Medel et al. | 435/6 |
| 2013/0217057 A1* | 8/2013 | Kearney et al. | 435/23 |
| 2013/0230877 A1* | 9/2013 | Kearney et al. | 435/23 |
| 2015/0031065 A1* | 1/2015 | Kearney et al. | 435/23 |

FOREIGN PATENT DOCUMENTS

WO    WO-11103330 A2    8/2011

OTHER PUBLICATIONS

Ostroff et al. Unlocking Biomarker Discovery: Large Scale Application of Aptamer Proteomic Technology for Early Detection of Lung Cancer, PLOS One, Dec. 2010, vol. 5, No. 12, 10 pages.*
Li et al. A Blood-Based Proteomic Classifier for the Molecular Characterization of Pulmonary Nodules. Sci Transl Med 2013 vol. 5, No. 207, pp. 1-10.*
Zeng et al. Abstract 4564: Lung cancer serum biomarker discovery using label free LC-MS/MS. Cancer Research: Apr. 15, 2010. vol. 70, Isssue 8, Supplement 1, Proceedings from the AACR 101st Annual Meeting, 2010, Apr. 17-21, 2010. Washington DC. 1 page.*
Lin et al. Malignant pleural effusion cells show aberrant glucose metabolism gene expression. Eur Respir J 2011, vol. 37, pp. 1453-1465.*
Hüttenhaim et al. "Reproducible Quantification of Cancer-Associated Proteins in Body Fluids using Targeted Proteomics." *Sci. Transl. Med.* 4.142(2012):149ra194.
Kearney et al. "Protein Identification and Peptide Expression Resolver: Harmonizing Protein Identification with Protein Expression Data." *J. Proteome Res.* 7.1(2008):234-244.
Lange et al. "Selected Reaction Monitoring for Quantitative Proteomics: A Tutorial." *Mol. Sys. Biol.* 4(2008):222.
Perkins et al. "Probability-Based Protein Identification by Searching Sequence Databases Using Mass Spectrometry Data." *Electrophoresis.* 20.18(1999):3551-3567.
Picotti et al. "High-Throughput Generation of Selected Reaction-Monitoring Assays for Proteins and Proteomes." *Nat. Meth.* 7.1(2010):43-46.
Cho et al. "Verification of a Biomarker Discovery Approach for Detection of Down Syndrome in Amniotic Fluid via Multiplex Selected Reaction Monitoring (SRM) Assay." *J. Prot.* 74.10(2011):2052-2059.
Gallien et al. "Selected Reaction Monitoring Applied to Proteomics." *J. Mass Spectrom.* 46.3(2011):298-312.
Kiyonami et al. "Increased Selectivity, Analytical Precision, and Throughput in Targeted Proteomics." *Mol. Cell. Proteomics.* 10.2(2011):M110.

* cited by examiner

*Primary Examiner* — Marcela M Cordero Garcia
(74) *Attorney, Agent, or Firm* — Cooley LLP; Ivor Elrifi; Matthew Pavao

(57) ABSTRACT

Provided herein are methods for developing selected reaction monitoring mass spectrometry (LC-SRM-MS) assays.

12 Claims, 2 Drawing Sheets

Venn diagram of the 388 candidate proteins, including 217 from MS/MS analysis of tissues and 319 from literature search. The overlap was 148.

```
                              SEQUENCE LISTING

<160> NUMBER OF SEQ ID NOS: 1731

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1

Ala Val Thr Glu Gln Gly His Glu Leu Ser Asn Glu Glu Arg
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 2

Asp Asn Leu Thr Leu Trp Thr Ser Glu Asn Gln Gly Asp Glu Gly Asp
1               5                   10                  15

Ala Gly Glu Gly Glu Asn
            20

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 3

Ser Glu Leu Val Gln Lys
1               5

<210> SEQ ID NO 4
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 4

Thr Ala Phe Asp Glu Ala Ile Ala Glu Leu Asp Thr Leu Asn Glu Glu
1               5                   10                  15

Ser Tyr Lys

<210> SEQ ID NO 5
<211> LENGTH: 12
<212> TYPE: PRT
<213> ORGANISM: Artificial Sequence
<220> FEATURE:
```

```
<223> OTHER INFORMATION: Synthetic Polypeptide

<400> SEQUENCE: 5

Tyr Leu Ile Pro Asn Ala Thr Gln Pro Glu Ser Lys
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 6

Ala Ala Phe Asp Asp Ala Ile Ala Glu Leu Asp Thr Leu Ser Glu Glu
1               5                   10                  15

Ser Tyr Lys

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Glu Asp Leu Val Tyr Gln Ala Lys
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

His Leu Ile Pro Ala Ala Asn Thr Gly Glu Ser Lys
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Ile Ile Ser Ser Ile Glu Gln Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Val Phe Tyr Tyr Lys
1               5

<210> SEQ ID NO 11
<211> LENGTH: 24
<212> TYPE: PRT
<213> ORGANISM: Artificial Sequence
```

```
<220> FEATURE:
<223> OTHER INFORMATION: Synthetic Polypeptide

<400> SEQUENCE: 11

Asp Asn Leu Thr Leu Trp Thr Ala Asp Asn Ala Gly Glu Glu Gly
1               5                   10                  15

Glu Ala Pro Gln Glu Pro Gln Ser
            20

<210> SEQ ID NO 12
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 12

Glu Ala Gly Asp Ala Glu Ser Arg
1               5

<210> SEQ ID NO 13
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 13

Leu Gly Leu Ala Leu Asn Phe Ser Val Phe His Tyr Glu Ile Ala Asn
1               5                   10                  15

Ser Pro Glu Glu Ala Ile Ser Leu Ala Lys
            20                  25

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Ser Asn Glu Glu Gly Ser Glu Glu Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Val Leu Ser Ser Ile Glu Gln Lys
1               5

<210> SEQ ID NO 16
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 16

Ala Val Thr Glu Gln Gly Ala Glu Leu Ser Asn Glu Glu Arg
1               5                   10
```

```
<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Glu Met Gln Pro Thr His Pro Ile Arg
1               5

<210> SEQ ID NO 18
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 18

Gln Thr Ile Asp Asn Ser Gln Gly Ala Tyr Gln Glu Ala Phe Asp Ile
1               5                   10                  15

Ser Lys

<210> SEQ ID NO 19
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 19

Thr Ala Phe Asp Glu Ala Ile Ala Glu Leu Asp Thr Leu Asn Glu Asp
1               5                   10                  15

Ser Tyr Lys

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

Tyr Leu Ile Ala Asn Ala Thr Asn Pro Glu Ser Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 21

Phe Leu Ile Pro Asn Ala Ser Gln Ala Glu Ser Lys
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 22
```

```
Gly Ile Val Asp Gln Ser Gln Gln Ala Tyr Gln Glu Ala Phe Glu Ile
1               5                   10                  15

Ser Lys

<210> SEQ ID NO 23
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 23

Ser Val Thr Glu Gln Gly Ala Glu Leu Ser Asn Glu Glu Arg
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 24

Thr Ala Phe Asp Glu Ala Ile Ala Glu Leu Asp Thr Leu Ser Glu Glu
1               5                   10                  15

Ser Tyr Lys

<210> SEQ ID NO 25
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 25

Ala Gly Gln Ala Val Asp Asp Phe Ile Glu Lys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 26

His Glu Met Leu Pro Ala Ser Leu Ile Gln Ala Gln Arg
1               5                   10

<210> SEQ ID NO 27
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 27

Leu Val Pro Leu Leu Asp Thr Gly Asp Ile Ile Ile Asp Gly Gly Asn
1               5                   10                  15

Ser Glu Tyr Arg
            20

<210> SEQ ID NO 28
<211> LENGTH: 11
<212> TYPE: PRT
```

<213> ORGANISM: Artificial Sequence
<220> FEATURE:
<223> OTHER INFORMATION: Synthetic Polypeptide

<400> SEQUENCE: 28

Tyr Gly Pro Ser Leu Met Pro Gly Gly Asn Lys
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 29

Asn Trp Gly Leu Ser Val Tyr Ala Asp Lys Pro Glu Thr Thr Lys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 30

Ser Val Gln Glu Ile Gln Ala Thr Phe Phe Tyr Phe Thr Pro Asn Lys
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 31

Thr Glu Asp Thr Ile Phe Leu Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Trp Phe Tyr Ile Ala Ser Ala Phe Arg
1               5

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 33

Tyr Val Gly Gly Gln Glu His Phe Ala His Leu Leu Ile Leu Arg
1               5                   10                  15

<210> SEQ ID NO 34
<211> LENGTH: 17
<212> TYPE: PRT
<213> ORGANISM: Artificial Sequence

```
<220> FEATURE:
<223> OTHER INFORMATION: Synthetic Polypeptide

<400> SEQUENCE: 34

Asp Ala Gly Ile Ala Leu Leu Ser Ile Thr His Arg Pro Ser Leu Trp
1               5                   10                  15

Lys

<210> SEQ ID NO 35
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 35

Glu Leu Glu Asp Ala Gln Ala Gly Ser Gly Thr Ile Gly Arg
1               5                   10

<210> SEQ ID NO 36
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 36

Gly Leu Gln Ala Pro Ala Gly Glu Pro Thr Gln Glu Ala Ser Gly Val
1               5                   10                  15

Ala Ala Ala Lys
            20

<210> SEQ ID NO 37
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 37

Asn Leu Leu Thr Ala Ala Ala Asp Ala Ile Glu Arg
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 38

Tyr His Thr His Leu Leu Gln Phe Asp Gly Glu Gly Gly Trp Lys
1               5                   10                  15

<210> SEQ ID NO 39
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 39

Ala Asp Glu Val Val Ser Ala Ser Val Gly Ser Gly Asp Leu Trp Ile
1               5                   10                  15

Pro Val Lys
```

```
<210> SEQ ID NO 40
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 40

Phe Gly Phe Gly Gly Ser Thr Asp Ser Gly Pro Ile Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 41

Leu Ile Glu Ile Ala Asn His Val Asp Lys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Asn His Pro Glu Val Leu Asn Ile Arg
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 43

Tyr Val Glu Leu Val Ile Val Ala Asp Asn Arg
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 44

Leu Ala His Gln Ile Tyr Gln Phe Thr Asp Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 45

Ser Pro Glu Asp Ser Ser Pro Asp Ala Ala Arg
1               5                   10
```

<210> SEQ ID NO 46
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 46

Thr Leu Val Ser Ser Lys Pro Gln Ala His Gly Ala Pro Ala Pro Pro
1               5                   10                  15

Ser Gly Ser Ala Pro His Phe Leu
            20

<210> SEQ ID NO 47
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 47

Gly Trp Gly Asp Gln Leu Ile Trp Thr Gln Thr Tyr Glu Glu Ala Leu
1               5                   10                  15

Tyr Lys

<210> SEQ ID NO 48
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 48

His Leu Ser Pro Asp Gly Gln Tyr Val Pro Arg
1               5                   10

<210> SEQ ID NO 49
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 49

Ile Pro Val Ser Ala Phe Leu Leu Leu Val Ala Leu Ser Tyr Thr Leu
1               5                   10                  15

Ala Arg

<210> SEQ ID NO 50
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 50

Leu Ala Glu Gln Phe Val Leu Leu Asn Leu Val Tyr Glu Thr Thr Asp
1               5                   10                  15

Lys

<210> SEQ ID NO 51
<211> LENGTH: 7
<212> TYPE: PRT
<213> ORGANISM: Artificial Sequence

```
<220> FEATURE:
<223> OTHER INFORMATION: Synthetic Polypeptide

<400> SEQUENCE: 51

Leu Pro Gln Thr Leu Ser Arg
1               5

<210> SEQ ID NO 52
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 52

Ala Leu Gly Thr Glu Val Ile Gln Leu Phe Pro Glu Lys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 53

Glu Leu Trp Phe Ser Asp Asp Pro Asn Val Thr Lys
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 54

Gly Val Ile Phe Tyr Leu Arg
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 55

Leu Asn Asp Gly Ser Gln Ile Thr Tyr Glu Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 56

Thr Gly Gly Leu Glu Ile Asp Ser Asp Phe Gly Gly Phe Arg
1               5                   10

<210> SEQ ID NO 57
<211> LENGTH: 12
<212> TYPE: PRT
<213> ORGANISM: Artificial Sequence
<220> FEATURE:
```

<223> OTHER INFORMATION: Synthetic Polypeptide

<400> SEQUENCE: 57

Ala Asp Asp Gly Arg Pro Phe Pro Gln Val Ile Lys
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 58

Ala Leu Gln Ala Ser Ala Leu Lys
1               5

<210> SEQ ID NO 59
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 59

Gly Val Val Pro Leu Ala Gly Thr Asn Gly Glu Thr Thr Thr Gln Gly
1               5                   10                  15

Leu Asp Gly Leu Ser Glu Arg
            20

<210> SEQ ID NO 60
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 60

Gln Leu Leu Leu Thr Ala Asp Asp Arg
1               5

<210> SEQ ID NO 61
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 61

Tyr Thr Pro Ser Gly Gln Ala Gly Ala Ala Ser Glu Ser Leu Phe
1               5                   10                  15

Val Ser Asn His Ala Tyr
            20

<210> SEQ ID NO 62
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 62

Ala Leu Glu Gln Ala Leu Glu Lys
1               5

```
<210> SEQ ID NO 63
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 63

Asp His Ser Ala Ile Pro Val Ile Asn Arg
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 64

Glu Asn Ser Leu Leu Phe Asp Pro Leu Ser Ser Ser Ser Ser Asn Lys
1               5                   10                  15

<210> SEQ ID NO 65
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 65

Glu Val Val Leu Gln Trp Phe Thr Glu Asn Ser Lys
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 66

Ser Ile Gln Leu Pro Thr Thr Val Arg
1               5

<210> SEQ ID NO 67
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 67

Asp Ala Pro His Val Glu Pro Asp Phe Ser Ser Gln Lys
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 68

Leu Glu Ile Gln Leu Leu Glu Asn Ser Leu Ser Thr Tyr Lys
1               5                   10

<210> SEQ ID NO 69
```

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 69

Gln Leu Leu Gln Gln Thr Asn Glu Ile Leu Lys
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 70

Gln Ser Ser Leu Ile Leu His Gly Ala Asp Phe Ser Thr Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 71

Gln Thr Tyr Ile Ile Gln Glu Leu Glu Lys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 72

Asp Ala Pro Leu Glu Tyr Asp Asp Ser Val Gln Arg
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 73

Asp Gln Leu Gln Val Leu Val Ser Lys
1               5

<210> SEQ ID NO 74
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 74

Ile Ser Ser Ile Ser Gln Pro Gly Asn Asp Phe Ser Thr Lys
1               5                   10

<210> SEQ ID NO 75
<211> LENGTH: 11
```

```
<212> TYPE: PRT
<213> ORGANISM: Artificial Sequence
<220> FEATURE:
<223> OTHER INFORMATION: Synthetic Polypeptide

<400> SEQUENCE: 75

Gln Ile Leu Asp Gln Thr Ser Glu Ile Asn Lys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 76

Ser Ser Ser Ser Pro Tyr Val Ser Asn Ala Val Gln Arg
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 77

Ala Glu Leu Gln Glu Gly Ala Arg
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 78

Ala Lys Pro Ala Leu Glu Asp Leu Arg
1               5

<210> SEQ ID NO 79
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 79

Ala Thr Glu His Leu Ser Thr Leu Ser Glu Lys
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 80

Leu Ala Glu Tyr His Ala Lys
1               5

<210> SEQ ID NO 81
<211> LENGTH: 7
<212> TYPE: PRT
```

```
<213> ORGANISM: Artificial Sequence
<220> FEATURE:
<223> OTHER INFORMATION: Synthetic Polypeptide

<400> SEQUENCE: 81

Leu His Glu Leu Gln Glu Lys
1               5

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

Ala Ala Thr Val Gly Ser Leu Ala Gly Gln Pro Leu Gln Glu Arg
1               5                   10                  15

<210> SEQ ID NO 83
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 83

Ala Leu Met Asp Glu Thr Met Lys
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 84

Phe Trp Asp Tyr Leu Arg
1               5

<210> SEQ ID NO 85
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

Gly Glu Val Gln Ala Met Leu Gly Gln Ser Thr Glu Glu Leu Arg
1               5                   10                  15

<210> SEQ ID NO 86
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 86

Leu Ala Val Tyr Gln Ala Gly Ala Arg
1               5

<210> SEQ ID NO 87
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 87

Leu Gly Pro Leu Val Glu Gln Gly Arg
1               5

<210> SEQ ID NO 88
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 88

Ser Glu Leu Glu Glu Gln Leu Thr Pro Val Ala Glu Glu Thr Arg
1               5                   10                  15

<210> SEQ ID NO 89
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 89

Ser Trp Phe Glu Pro Leu Val Glu Asp Met Gln Arg
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 90

Trp Glu Leu Ala Leu Gly Arg
1               5

<210> SEQ ID NO 91
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 91

Trp Val Gln Thr Leu Ser Glu Gln Val Gln Glu Glu Leu Leu Ser Ser
1               5                   10                  15

Gln Val Thr Gln Glu Leu Arg
            20

<210> SEQ ID NO 92
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 92

Glu Ile Glu Pro Glu Pro Asp Phe Ile Leu Trp Thr Gly Asp Asp Thr
1               5                   10                  15

Pro His Val Pro Asp Glu Lys
            20
```

```
<210> SEQ ID NO 93
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 93

Phe Trp His Ile Ala Asp Leu His Leu Asp Pro Asp Tyr Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 94

Ile Ala Gly Asp Gln Ser Thr Leu Gln Arg
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 95

Leu Gly Glu Ala Ala Val Leu Glu Ile Val Glu Arg
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 96

Val Ile Ala Gly Gln Phe Phe Gly His His Thr Asp Ser Phe Arg
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 97

Ala Glu Ile Gly Ile Ala Met Gly Ser Gly Thr Ala Val Ala Lys
1               5                   10                  15

<210> SEQ ID NO 98
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 98

Ile Gly Ile Phe Gly Gln Asp Glu Asp Val Thr Ser Lys
1               5                   10
```

```
<210> SEQ ID NO 99
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 99

Asn Met Leu Phe Ser Gly Thr Asn Ile Ala Ala Gly Lys
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 100

Ala Ser Phe Gly Ser Gly Pro Ala Val Glu Trp Ile Pro Lys
1               5                   10

<210> SEQ ID NO 101
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 101

Gly Ala Phe Tyr Leu Leu Gly Glu Ala Tyr Phe Ile Gln Pro Leu Pro
1               5                   10                  15

Ala Ala Ser Glu Arg
            20

<210> SEQ ID NO 102
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 102

Gly Ile Gly Tyr Phe Phe Val Leu Gln Pro Lys
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 103

Gly Pro Glu Val Thr Ser Asn Ala Ala Leu Thr Leu Arg
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 104

His Tyr Leu Leu Thr Leu Phe Ser Val Ala Ala Arg
1               5                   10
```

```
<210> SEQ ID NO 105
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 105

Glu Gly Ser Gly Tyr Val Asp Ile Gly Leu Ile Pro Lys
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 106

Leu Ile Leu Leu Glu Glu Glu Glu Gln Gly Leu Lys
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 107

Gln Leu Gln Tyr Asp Pro Thr Pro Leu Thr Trp Ser Lys
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 108

Gln Trp Gln Asp Ser Ser Thr Gln Pro Glu Leu Ser Ser Arg
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 109

Trp Val Glu Thr Leu Val Val Ala Asp Thr Lys
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 110

Glu Gln Pro Ile Leu Leu Ser Glu Lys
1               5
```

```
<210> SEQ ID NO 111
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 111

Gly Gln Asn Leu Gly Asp Val Ser Trp Ser Arg
1               5                   10

<210> SEQ ID NO 112
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 112

Leu Arg Pro Pro Pro Ser Glu Gly Glu Glu Asp Glu Glu Leu Glu
1               5                   10                  15

Ser Gln Glu Leu Pro Arg
            20

<210> SEQ ID NO 113
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 113

Asn Ile Ser Ile Val Asp Asn Glu Lys
1               5

<210> SEQ ID NO 114
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 114

Ser Val Ala Pro Val Pro Leu Glu Glu Pro Val Glu Gly Arg
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 115

Ala Val Phe Leu Ala Leu Ser Ala Gln Leu Leu Gln Ala Arg
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 116

Glu Glu Ser Pro Val Val Ser Trp Arg
```

```
1               5

<210> SEQ ID NO 117
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 117

Glu Glu Ser Pro Val Val Ser Trp Trp Leu Glu Pro Glu Asp Gly Thr
1               5                   10                  15

Ala Leu

<210> SEQ ID NO 118
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 118

Ala Ala Glu Ala Ala Ala Ala Pro Ala Glu Ser Ala Ala Pro Ala Ala
1               5                   10                  15

Gly Glu Glu Pro Ser Lys
            20

<210> SEQ ID NO 119
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 119

Ala Glu Gly Ala Ala Thr Glu Glu Gly Thr Pro Lys
1               5                   10

<210> SEQ ID NO 120
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 120

Ala Pro Glu Gln Glu Gln Ala Ala Pro Gly Pro Ala Ala Gly Gly Glu
1               5                   10                  15

Ala Pro Lys

<210> SEQ ID NO 121
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 121

Ala Gln Gly Pro Ala Ala Ser Ala Glu Glu Pro Lys Pro Val Glu Ala
1               5                   10                  15

Pro Ala Ala Asn Ser Asp Gln Thr Val Thr Val Lys
            20                  25

<210> SEQ ID NO 122
```

```
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 122

Glu Lys Pro Asp Gln Asp Ala Glu Gly Lys
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 123

Glu Ser Glu Pro Gln Ala Ala Glu Pro Ala Glu Ala Lys
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 124

Glu Thr Pro Ala Ala Thr Glu Ala Pro Ser Ser Thr Pro Lys
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 125

Gly Tyr Asn Val Asn Asp Glu Lys
1               5

<210> SEQ ID NO 126
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 126

Ser Asp Gly Ala Pro Ala Ser Asp Ser Lys Pro Gly Ser Ser Glu Ala
1               5                   10                  15

Ala Pro Ser Ser Lys
            20

<210> SEQ ID NO 127
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 127

Thr Glu Ala Pro Ala Ala Pro Ala Ala Gln Glu Thr Lys
1               5                   10
```

<210> SEQ ID NO 128
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 128

Thr Gly Ala Leu Leu Leu Gln Gly Phe Ile Gln Asp Arg
1               5                   10

<210> SEQ ID NO 129
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 129

Val Pro Glu Leu Ile Arg
1               5

<210> SEQ ID NO 130
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 130

Val Val Ala Leu Phe Tyr Phe Ala Ser Lys
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 131

Asp Ala Asp Leu Tyr Thr Ser Arg
1               5

<210> SEQ ID NO 132
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 132

Gly Leu Thr Ser Leu Ala Asp Thr Phe Glu His Val Ile Glu Glu Leu
1               5                   10                  15

Leu Asp Glu Asp Gln Lys
            20

<210> SEQ ID NO 133
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 133

Gly Gln Gly Gly Leu Ala Tyr Pro Gly Val Arg

-continued

```
<210> SEQ ID NO 134
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 134

Gln Tyr Phe Tyr Glu Thr Lys
1               5

<210> SEQ ID NO 135
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 135

Thr His Gly Thr Leu Glu Ser Val Asn Gly Pro Lys
1               5                   10

<210> SEQ ID NO 136
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 136

Ala Asp His His Ala Thr Asn Gly Val Val His Leu Ile Asp Lys
1               5                   10                  15

<210> SEQ ID NO 137
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 137

Asp Ile Leu Ala Thr Asn Gly Val Ile His Tyr Ile Asp Glu Leu Leu
1               5                   10                  15

Ile Pro Asp Ser Ala Lys
            20

<210> SEQ ID NO 138
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 138

Glu Gly Val Tyr Thr Val Phe Ala Pro Thr Asn Glu Ala Phe Arg
1               5                   10                  15

<210> SEQ ID NO 139
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 139
```

```
Leu Thr Leu Leu Ala Pro Leu Asn Ser Val Phe Lys
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 140

Ser Pro Tyr Gln Leu Val Leu Gln His Ser Arg
1               5                   10

<210> SEQ ID NO 141
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 141

Ile Asn Ile Tyr Glu Ile Ile Lys Pro Ala Thr Ala Asn Ser Lys
1               5                   10                  15

<210> SEQ ID NO 142
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 142

Leu Val Asn Gln Asn Ala Ser Arg
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 143

Ser Phe His His Glu Glu Ser Leu Glu Glu Leu Pro Glu Thr Ser Gly
1               5                   10                  15

Lys

<210> SEQ ID NO 144
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 144

Ser Leu His Gln Asp Glu His Ser Trp Ser Gln Ile Arg Pro Leu Leu
1               5                   10                  15

Val Thr Phe Gly His Asp Gly Lys
            20

<210> SEQ ID NO 145
<211> LENGTH: 21
<212> TYPE: PRT
<213> ORGANISM: Artificial Sequence
```

```
<220> FEATURE:
<223> OTHER INFORMATION: Synthetic Polypeptide

<400> SEQUENCE: 145

Trp Thr Ala Gln Gly His Ala Asn His Gly Phe Val Val Glu Val Ala
1               5                   10                  15

His Leu Glu Glu Lys
            20

<210> SEQ ID NO 146
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 146

Ala Gly Leu Ile Ile Pro Leu Phe Leu Val Leu Ala Ser Arg
1               5                   10

<210> SEQ ID NO 147
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 147

Ala Leu Leu Ser Pro Glu Gln Arg
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 148

Asp Ile Phe Leu Gly Arg
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 149

Gly Glu Gly Thr Ser Ala His Leu Arg
1               5

<210> SEQ ID NO 150
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 150

Gly Phe Phe Ala Asp Tyr Glu Ile Pro Asn Leu Gln Lys
1               5                   10

<210> SEQ ID NO 151
<211> LENGTH: 17
```

```
<212> TYPE: PRT
<213> ORGANISM: Artificial Sequence
<220> FEATURE:
<223> OTHER INFORMATION: Synthetic Polypeptide

<400> SEQUENCE: 151

Glu Ala Glu Phe Gly Gln Gly Thr Gly Pro Ile Trp Leu Asn Glu Val
1               5                   10                  15

Lys

<210> SEQ ID NO 152
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 152

Gly Glu Asn Leu Val His Gln Ile Gln Tyr Arg
1               5                   10

<210> SEQ ID NO 153
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 153

Ile Asn Pro Ala Ser Leu Asp Lys
1               5

<210> SEQ ID NO 154
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 154

Leu Glu Val Phe Tyr Asn Gly Ala Trp Gly Thr Val Gly Lys
1               5                   10

<210> SEQ ID NO 155
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 155

Thr Ser Tyr Gln Val Tyr Ser Lys
1               5

<210> SEQ ID NO 156
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 156

Glu Asp Val Tyr Val Val Gly Thr Val Leu Arg
1               5                   10

<210> SEQ ID NO 157
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 157

Gly Tyr Ile Leu Val Gly Gln Ala Lys
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 158

Ile Ala His Gly His Tyr Lys
1               5

<210> SEQ ID NO 159
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 159

Leu Ser Leu Glu Ile Glu Gln Leu Glu Leu Gln Arg
1               5                   10

<210> SEQ ID NO 160
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 160

Thr Trp Tyr Pro Glu Val Pro Lys
1               5

<210> SEQ ID NO 161
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 161

Phe Pro Ala Glu Ile His Val Val His Leu Ser Thr Ala Phe Ala Arg
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 162

Gly Gly Val Ser Tyr Arg Pro Ala Glu Val Ala Glu Thr Gly Ala
1               5                   10                  15

<210> SEQ ID NO 163
<211> LENGTH: 28
```

```
<212> TYPE: PRT
<213> ORGANISM: Artificial Sequence
<220> FEATURE:
<223> OTHER INFORMATION: Synthetic Polypeptide

<400> SEQUENCE: 163

Leu Glu Glu Ile Ala Glu Glu Gly Ser Glu Thr Gln Val Pro Gly Leu
1               5                   10                  15

Asp Ile Ser Ala Leu Leu Pro Ser Asp Phe Ser Arg
            20                  25

<210> SEQ ID NO 164
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 164

Val Ile Glu Ala Ser Phe Pro Ala Gly Val Asp Ser Ser Pro Arg
1               5                   10                  15

<210> SEQ ID NO 165
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 165

Tyr Gly Gly Asp Pro Pro Trp Pro Arg
1               5

<210> SEQ ID NO 166
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 166

Asp Asp Glu Phe Thr His Leu Tyr Thr Leu Ile Val Arg Pro Asp Asn
1               5                   10                  15

Thr Tyr Glu Val Lys
            20

<210> SEQ ID NO 167
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 167

Asp Pro Asp Ala Ser Lys Pro Glu Asp Trp Asp Glu Arg
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 168

Phe Tyr Gly Asp Glu Glu Lys
```

```
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 169

Gly Leu Gln Thr Ser Gln Asp Ala Arg
1               5

<210> SEQ ID NO 170
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 170

Gly Gln Thr Leu Val Val Gln Phe Thr Val Lys
1               5                   10

<210> SEQ ID NO 171
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 171

Asp Trp Ile Leu Pro Ser Asp Tyr Asp His Ala Glu Ala Glu Ala Arg
1               5                   10                  15

<210> SEQ ID NO 172
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 172

Glu Gln Phe Val Glu Phe Arg
1               5

<210> SEQ ID NO 173
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 173

Gly His Asp Leu Asn Glu Asp Gly Leu Val Ser Trp Glu Glu Tyr Lys
1               5                   10                  15

<210> SEQ ID NO 174
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 174

Thr Phe Asp Gln Leu Thr Pro Glu Glu Ser Lys
1               5                   10
```

<210> SEQ ID NO 175
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 175

Val His Asn Asp Ala Gln Ser Phe Asp Tyr Asp His Asp Ala Phe Leu
1               5                   10                  15

Gly Ala Glu Glu Ala Lys
            20

<210> SEQ ID NO 176
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 176

Ala Glu Glu Asp Glu Ile Leu Asn Arg
1               5

<210> SEQ ID NO 177
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 177

Ala Pro Val Pro Thr Gly Glu Val Tyr Phe Ala Asp Ser Phe Asp Arg
1               5                   10                  15

<210> SEQ ID NO 178
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 178

Gly Thr Leu Ser Gly Trp Ile Leu Ser Lys
1               5                   10

<210> SEQ ID NO 179
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 179

Ile Pro Asp Pro Glu Ala Val Lys Pro Asp Trp Asp Glu Asp Ala
1               5                   10                  15

Pro Ala Lys

<210> SEQ ID NO 180
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 180

Thr Gly Ile Tyr Glu Glu Lys
1               5

<210> SEQ ID NO 181
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 181

Asp Trp Ile Asp Gly Val Leu Asn Asn Pro Gly Pro Gly Pro Ala
1               5                   10                  15

<210> SEQ ID NO 182
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 182

Glu Ala Asn Leu Thr Ser Ser Val Thr Ile Leu Pro Leu Pro Leu Gln
1               5                   10                  15

Asn Ala Thr Val Glu Ala Gly Thr Arg
            20                  25

<210> SEQ ID NO 183
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 183

Gly Pro Asp Phe Phe Thr Arg
1               5

<210> SEQ ID NO 184
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 184

Leu Thr Val Leu Ala Leu Leu Ala Gly Leu Leu Ala Ser Ser Arg
1               5                   10                  15

<210> SEQ ID NO 185
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 185

Gln Phe Pro Phe Leu Ala Ser Ile Gln Asn Gln Gly Arg
1               5                   10

<210> SEQ ID NO 186
<211> LENGTH: 14
<212> TYPE: PRT
<213> ORGANISM: Artificial Sequence
<220> FEATURE:

<223> OTHER INFORMATION: Synthetic Polypeptide

<400> SEQUENCE: 186

His Tyr Gly Tyr Asn Ser Tyr Ser Val Ser Asn Ser Glu Lys
1               5                   10

<210> SEQ ID NO 187
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 187

Ile Leu Gly Trp Gly Val Glu Asn Gly Thr Pro Tyr Trp Leu Val Ala
1               5                   10                  15

Asn Ser Trp Asn Thr Asp Trp Gly Asp Asn Gly Phe Phe Lys
            20                  25                  30

<210> SEQ ID NO 188
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 188

Leu Pro Ala Ser Phe Asp Ala Arg
1               5

<210> SEQ ID NO 189
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 189

Asn Gly Pro Val Glu Gly Ala Phe Ser Val Tyr Ser Asp Phe Leu Leu
1               5                   10                  15

Tyr Lys

<210> SEQ ID NO 190
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 190

Thr Asp Gln Tyr Trp Glu Lys
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 191

His Pro Gln Tyr Asn Gln Arg
1               5

<210> SEQ ID NO 192

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 192

Asn Val Asn Pro Val Ala Leu Pro Arg
1               5

<210> SEQ ID NO 193
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 193

Ser Ser Gly Val Pro Pro Glu Val Phe Thr Arg
1               5                   10

<210> SEQ ID NO 194
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 194

Val Ser Ser Phe Leu Pro Trp Ile Arg
1               5

<210> SEQ ID NO 195
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 195

Ala Ser Ala Ser Tyr Tyr Glu Gln Tyr His Ser Leu Asn Glu Ile Tyr
1               5                   10                  15

Ser Trp Ile Glu Phe Ile Thr Glu Arg
            20                  25

<210> SEQ ID NO 196
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 196

Ala Tyr Ile Ser Met His Ser Tyr Ser Gln His Ile Val Phe Pro Tyr
1               5                   10                  15

Ser Tyr Thr Arg
            20

<210> SEQ ID NO 197
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 197
```

Asp His Glu Glu Leu Ser Leu Val Ala Ser Glu Ala Val Arg
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 198

Asp Thr Gly Thr Tyr Gly Phe Leu Leu Pro Glu Arg
1               5                   10

<210> SEQ ID NO 199
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 199

Glu Ala Phe Ala Ala Val Ser Lys
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 200

Ile His Ile Gly Ser Ser Phe Glu Lys
1               5

<210> SEQ ID NO 201
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 201

Leu Val Asp Phe Tyr Val Met Pro Val Val Asn Val Asp Gly Tyr Asp
1               5                   10                  15

Tyr Ser Trp Lys
            20

<210> SEQ ID NO 202
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 202

Gln Val His Phe Phe Val Asn Ala Ser Asp Val Asp Asn Val Lys
1               5                   10                  15

<210> SEQ ID NO 203
<211> LENGTH: 7
<212> TYPE: PRT
<213> ORGANISM: Artificial Sequence
<220> FEATURE:
<223> OTHER INFORMATION: Synthetic Polypeptide

```
<400> SEQUENCE: 203

Tyr Pro Leu Tyr Val Leu Lys
1               5

<210> SEQ ID NO 204
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 204

Tyr Thr His Gly His Gly Ser Glu Thr Leu Tyr Leu Ala Pro Gly Gly
1               5                   10                  15

Gly Asp Asp Trp Ile Tyr Asp Leu Gly Ile Lys
            20                  25

<210> SEQ ID NO 205
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: No sequence here
<220> FEATURE:
<221> NAME/KEY: misc_feature
<222> LOCATION: (1)..(6)
<223> OTHER INFORMATION: Xaa can be any naturally occurring amino acid

<400> SEQUENCE: 205

Xaa Xaa Xaa Xaa Xaa Xaa
1               5

<210> SEQ ID NO 206
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 206

Ala Phe Pro Ala Leu Thr Ser Leu Asp Leu Ser Asp Asn Pro Gly Leu
1               5                   10                  15

Gly Glu Arg

<210> SEQ ID NO 207
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 207

Ala Thr Val Asn Pro Ser Ala Pro Arg
1               5

<210> SEQ ID NO 208
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 208
```

```
Glu Leu Thr Leu Glu Asp Leu Lys
1               5

<210> SEQ ID NO 209
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 209

Phe Pro Ala Ile Gln Asn Leu Ala Leu Arg
1               5                   10

<210> SEQ ID NO 210
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 210

Ile Thr Gly Thr Met Pro Pro Leu Pro Leu Glu Ala Thr Gly Leu Ala
1               5                   10                  15

Leu Ser Ser Leu Arg
            20

<210> SEQ ID NO 211
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 211

Leu Thr Val Gly Ala Ala Gln Val Pro Ala Gln Leu Leu Val Gly Ala
1               5                   10                  15

Leu Arg

<210> SEQ ID NO 212
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 212

Asn Val Ser Trp Ala Thr Gly Arg
1               5

<210> SEQ ID NO 213
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 213

Ser Thr Leu Ser Val Gly Val Ser Gly Thr Leu Val Leu Leu Gln Gly
1               5                   10                  15

Ala Arg

<210> SEQ ID NO 214
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 214

Ser Trp Leu Ala Glu Leu Gln Gln Trp Leu Lys Pro Gly Leu Lys
1               5                   10                  15

<210> SEQ ID NO 215
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 215

Val Asp Ala Asp Ala Asp Pro Arg
1               5

<210> SEQ ID NO 216
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 216

Ala Ala Gly Gly Ala Leu Gln Ser Thr Ala Ser Leu Phe Val Val Ser
1               5                   10                  15

Leu Ser Leu Leu His Leu Tyr Ser
            20

<210> SEQ ID NO 217
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 217

His Ser His Pro Thr Arg
1               5

<210> SEQ ID NO 218
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 218

Val Phe Val Val His Ile Pro Arg
1               5

<210> SEQ ID NO 219
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 219

Asp Leu Ala His Gln Phe Thr Gln Val Gln Arg
1               5                   10

<210> SEQ ID NO 220
```

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 220

Ile Leu Leu Trp Ser Arg
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 221

Asn Ile Tyr Arg Pro Asp Lys
1               5

<210> SEQ ID NO 222
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 222

Asn Ser Thr Phe Gly Ser Val Glu Val His Asn Leu Gln Pro Glu Lys
1               5                   10                  15

<210> SEQ ID NO 223
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 223

Val Gln Thr Leu Glu Ala Trp Val Ile His Gly Gly Arg
1               5                   10

<210> SEQ ID NO 224
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 224

Gly Asp Gln Asn Pro Gln Ile Ala Ala His Val Ile Ser Glu Ala Ser
1               5                   10                  15

Ser Lys

<210> SEQ ID NO 225
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 225

Ser Gln Phe Glu Gly Phe Val Lys
1               5
```

<210> SEQ ID NO 226
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 226

Thr Thr Ser Val Leu Gln Trp Ala Glu Lys
1               5                   10

<210> SEQ ID NO 227
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 227

Phe Ala Gly Val Phe His Val Glu Lys
1               5

<210> SEQ ID NO 228
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 228

His Leu Ser Phe Ser Gly Ser Gly Ile Asp Asp Glu Asp Phe Ile
1               5                   10                  15

Ser Ser Thr Ile Ser Thr Thr Pro Arg
            20                  25

<210> SEQ ID NO 229
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 229

Lys Pro Ser Gly Leu Asn Gly Glu Ala Ser Lys
1               5                   10

<210> SEQ ID NO 230
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 230

Thr Asn Pro Glu Asp Ile Tyr Pro Ser Asn Pro Thr Asp Asp Val
1               5                   10                  15

Ser Ser Gly Ser Ser Ser Glu Arg
            20

<210> SEQ ID NO 231
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 231

Tyr Gly Phe Ile Glu Gly His Val Val Ile Pro Arg
1               5                   10

<210> SEQ ID NO 232
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 232

Ala Gly Leu Gln Val Tyr Asn Lys
1               5

<210> SEQ ID NO 233
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 233

Thr Val Leu Leu Leu Val Thr Pro Phe Leu Ala Ala Ala Trp Ser Leu
1               5                   10                  15

His Pro

<210> SEQ ID NO 234
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 234

Glu Leu Asn Ser Pro Ile Leu Phe Ala Phe Ser His Leu Glu Ser Ser
1               5                   10                  15

Asp Gly Glu Ala Gly Arg
            20

<210> SEQ ID NO 235
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 235

Phe Ile Pro Glu Asp Pro Lys
1               5

<210> SEQ ID NO 236
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 236

Thr Ser Ser Ala Glu Val Thr Ile Gln Asn Val Ile Lys
1               5                   10

<210> SEQ ID NO 237
<211> LENGTH: 10
<212> TYPE: PRT
<213> ORGANISM: Artificial Sequence

```
<220> FEATURE:
<223> OTHER INFORMATION: Synthetic Polypeptide

<400> SEQUENCE: 237

Val Phe Gln Gly Gln Gly Leu Ser Thr Arg
1               5                   10

<210> SEQ ID NO 238
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 238

Tyr Ser Glu Phe Thr Ser Thr Thr Ser Gly Thr Gly His Asn Gln Thr
1               5                   10                  15

Arg

<210> SEQ ID NO 239
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 239

Glu Glu Gly Val Phe Thr Val Thr Pro Asp Thr Lys
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 240

Ile Tyr Val Val Asp Leu Ser Asn Glu Arg
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 241

Leu Ser Leu Val Leu Val Pro Ala Gln Lys
1               5                   10

<210> SEQ ID NO 242
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 242

Ser Pro Pro Glu Ser Glu Ser Glu Pro Tyr Thr Phe Ser His Pro Asn
1               5                   10                  15

Asn Gly Asp Val Ser Ser Lys
            20
```

```
<210> SEQ ID NO 243
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 243

Val Glu Tyr Tyr Ile Pro Gly Ser Thr Thr Asn Pro Glu Val Phe Lys
1               5                   10                  15

<210> SEQ ID NO 244
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 244

Ala Pro Pro Pro Gly Leu Pro Ala Glu Thr Ile Lys
1               5                   10

<210> SEQ ID NO 245
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 245

Asp Leu Lys Pro Glu Asn Ile Leu Val Thr Ser Gly Gly Thr Val Lys
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 246

Ile Phe Asp Leu Ile Gly Leu Pro Pro Glu Asp Asp Trp Pro Arg
1               5                   10                  15

<210> SEQ ID NO 247
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 247

Val Pro Asn Gly Gly Gly Gly Gly Gly Leu Pro Ile Ser Thr Val
1               5                   10                  15

Arg

<210> SEQ ID NO 248
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 248

Val Thr Leu Val Phe Glu His Val Asp Gln Asp Leu Arg
1               5                   10
```

-continued

<210> SEQ ID NO 249
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 249

Glu Val Leu Leu Leu Val His Asn Leu Pro Gln His Leu Phe Gly Tyr
1               5                   10                  15

Ser Trp Tyr Lys
            20

<210> SEQ ID NO 250
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 250

Ile Asn Gly Ile Pro Gln Gln His Thr Gln Val Leu Phe Ile Ala Lys
1               5                   10                  15

<210> SEQ ID NO 251
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 251

Leu Thr Ile Glu Ser Thr Pro Phe Asn Val Ala Glu Gly Lys
1               5                   10

<210> SEQ ID NO 252
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 252

Gln Ile Ile Gly Tyr Val Ile Gly Thr Gln Gln Ala Thr Pro Gly Pro
1               5                   10                  15

Ala Tyr Ser Gly Arg
            20

<210> SEQ ID NO 253
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 253

Ser Asp Leu Val Asn Glu Glu Ala Thr Gly Gln Phe Arg
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Synthetic Polypeptide

```
<400> SEQUENCE: 254

Glu Val Leu Leu Leu Val His Asn Leu Pro Gln Asp Pro Arg
1               5                   10

<210> SEQ ID NO 255
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 255

Gly Tyr Asn Trp Tyr Lys
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 256

Leu Phe Ile Pro Asn Ile Thr Thr Lys
1               5

<210> SEQ ID NO 257
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 257

Thr Leu Thr Leu Leu Ser Val Thr Arg
1               5

<210> SEQ ID NO 258
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 258

Gly Ala Tyr Pro Leu Ser Ile Glu Pro Ile Gly Val Arg
1               5                   10

<210> SEQ ID NO 259
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 259

Gly Pro Glu Glu Glu His Leu Gly Ile Leu Gly Pro Val Ile Trp Ala
1               5                   10                  15

Glu Val Gly Asp Thr Ile Arg
            20

<210> SEQ ID NO 260
<211> LENGTH: 10
<212> TYPE: PRT
<213> ORGANISM: Artificial Sequence
<220> FEATURE:
```

<223> OTHER INFORMATION: Synthetic Polypeptide

<400> SEQUENCE: 260

Ile Tyr His Ser His Ile Asp Ala Pro Lys
1               5                   10

<210> SEQ ID NO 261
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 261

Asn Asn Glu Gly Thr Tyr Tyr Ser Pro Asn Tyr Asn Pro Gln Ser Arg
1               5                   10                  15

<210> SEQ ID NO 262
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 262

Ser Val Pro Pro Ser Ala Ser His Val Ala Pro Thr Glu Thr Phe Thr
1               5                   10                  15

Tyr Glu Trp Thr Val Pro Lys
            20

<210> SEQ ID NO 263
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 263

Asp Gly Asp Ile Leu Gly Lys
1               5

<210> SEQ ID NO 264
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 264

Asp Tyr Phe Leu Phe Arg
1               5

<210> SEQ ID NO 265
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 265

Gly Gly Glu Ile Gln Pro Val Ser Val Lys
1               5                   10

<210> SEQ ID NO 266
<211> LENGTH: 10
<212> TYPE: PRT

<210> SEQ ID NO 267
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 266

Val Leu Leu Pro Glu Tyr Gly Gly Thr Lys
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 267

Val Leu Gln Ala Thr Val Val Ala Val Gly Ser Gly Ser Lys
1               5                   10

<210> SEQ ID NO 268
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 268

Gly Ile Ile Asp Pro Thr Lys
1               5

<210> SEQ ID NO 269
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 269

Gly Tyr Ile Ser Pro Tyr Phe Ile Asn Thr Ser Lys
1               5                   10

<210> SEQ ID NO 270
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 270

Leu Val Gln Asp Val Ala Asn Asn Thr Asn Glu Glu Ala Gly Asp Gly
1               5                   10                  15
Thr Thr Thr Ala Thr Val Leu Ala Arg
            20                  25

<210> SEQ ID NO 271
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 271

Thr Ala Leu Leu Asp Ala Ala Gly Val Ala Ser Leu Leu Thr Thr Ala
1               5                   10                  15
Glu Val Val Val Thr Glu Ile Pro Lys
            20                  25

<210> SEQ ID NO 272
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 272

Thr Val Ile Ile Glu Gln Ser Trp Gly Ser Pro Lys
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 273

Asp Phe Thr Ser Leu Glu Asn Thr Val Glu Glu Arg
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 274

Ile Glu Thr Asn Glu Asn Asn Leu Glu Ser Ala Lys
1               5                   10

<210> SEQ ID NO 275
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 275

Leu Glu Gly Leu Gly Ser Ser Glu Ala Asp Gln Asp Gly Leu Ala Ser
1               5                   10                  15

Thr Val Arg

<210> SEQ ID NO 276
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 276

Leu Pro Pro Gln Asp Phe Leu Asp Arg
1               5

<210> SEQ ID NO 277
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 277

Val Gln Ser Leu Gln Ala Thr Phe Gly Thr Phe Glu Ser Ile Leu Arg

```
1               5                   10                  15
```

<210> SEQ ID NO 278
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 278

```
Ala Ser Ala Pro Leu Ser Gln Ser Gly Leu Ala Thr Ala Asn Gly Lys
1               5                   10                  15

Pro Glu Pro Thr Ser Ile Ser
            20
```

<210> SEQ ID NO 279
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 279

```
Gly Asp Pro Asp Ser Glu Ala Asp Ser Ile Asp Ser Asp Gln Glu Asp
1               5                   10                  15

Pro Leu Lys
```

<210> SEQ ID NO 280
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 280

```
Ile Leu Asp Glu Asp Ser Trp Ser Asp Gly Glu Gln Glu Pro Ile Thr
1               5                   10                  15

Val Asp Gln Thr Trp Arg
            20
```

<210> SEQ ID NO 281
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 281

```
Thr Glu Leu Gly Ser Gln Thr Pro Glu Ser Ser Arg
1               5                   10
```

<210> SEQ ID NO 282
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 282

```
Tyr Gly Val Glu Ala Leu Leu His Arg
1               5
```

<210> SEQ ID NO 283
<211> LENGTH: 13
<212> TYPE: PRT

```
<213> ORGANISM: Artificial Sequence
<220> FEATURE:
<223> OTHER INFORMATION: Synthetic Polypeptide

<400> SEQUENCE: 283

Ala Ser Val Thr Ala Leu Ile Glu Ser Val Asn Gly Lys
1               5                   10

<210> SEQ ID NO 284
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 284

Ser Glu Ile Ser Asn Ile Ala Arg
1               5

<210> SEQ ID NO 285
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 285

Thr Ser Ser Gly Gly Ser Phe Val Ala Ser Asp Val Pro Asn Ala Pro
1               5                   10                  15

Ile Pro Asp Leu Phe Pro Pro Gly Gln Ile Thr Asp Leu Lys
            20                  25                  30

<210> SEQ ID NO 286
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 286

Thr Val Thr Leu Glu Leu Leu Asp Asn Gly Ala Gly Ala Asp Ala Thr
1               5                   10                  15

Lys

<210> SEQ ID NO 287
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 287

Trp Gly Val Phe Asp Glu Tyr Asn Asn Asp Glu Lys
1               5                   10

<210> SEQ ID NO 288
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 288

Phe Ser Ala Tyr Ile Lys
1               5
```

```
<210> SEQ ID NO 289
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 289

Gly Phe Thr Ile Pro Glu Ala Phe Arg
1               5

<210> SEQ ID NO 290
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 290

Leu Ala Ala Leu Asn Pro Glu Ser Asn Thr Ala Gly Leu Asp Ile Phe
1               5                   10                  15

Ala Lys

<210> SEQ ID NO 291
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 291

Asn Ser Asn Pro Ala Leu Asn Asp Asn Leu Glu Lys
1               5                   10

<210> SEQ ID NO 292
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 292

Tyr Leu Ser Asn Ala Tyr Ala Arg
1               5

<210> SEQ ID NO 293
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 293

Ala Ser Ser Ile Ile Asp Glu Leu Phe Gln Asp Arg
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 294

Glu Ile Gln Asn Ala Val Asn Gly Val Lys
1               5                   10
```

<210> SEQ ID NO 295
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 295

Ile Asp Ser Leu Leu Glu Asn Asp Arg
1               5

<210> SEQ ID NO 296
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 296

Leu Ala Asn Leu Thr Gln Gly Glu Asp Gln Tyr Tyr Leu Arg
1               5                   10

<210> SEQ ID NO 297
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 297

Val Thr Thr Val Ala Ser His Thr Ser Asp Ser Asp Val Pro Ser Gly
1               5                   10                  15

Val Thr Glu Val Val Val Lys
            20

<210> SEQ ID NO 298
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 298

Ala Glu Gly Asn Asn Gln Ala Pro Gly Glu Glu Glu Glu Glu Glu Glu
1               5                   10                  15

Glu Ala Thr Asn Thr His Pro Pro Ala Ser Leu Pro Ser Gln Lys
            20                  25                  30

<210> SEQ ID NO 299
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 299

Glu Ala Val Glu Glu Pro Ser Ser Lys
1               5

<210> SEQ ID NO 300
<211> LENGTH: 23
<212> TYPE: PRT
<213> ORGANISM: Artificial Sequence
<220> FEATURE:
<223> OTHER INFORMATION: Synthetic Polypeptide -continued

```
<400> SEQUENCE: 300

Ser Glu Ala Leu Ala Val Asp Gly Ala Gly Lys Pro Gly Ala Glu Glu
1               5                   10                  15

Ala Gln Asp Pro Glu Gly Lys
            20

<210> SEQ ID NO 301
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 301

Ser Gly Glu Leu Glu Gln Glu Glu Glu Arg
1               5                   10

<210> SEQ ID NO 302
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 302

Tyr Pro Gly Pro Gln Ala Glu Gly Asp Ser Glu Gly Leu Ser Gln Gly
1               5                   10                  15

Leu Val Asp Arg
            20

<210> SEQ ID NO 303
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 303

Ala His Ser Asp Gly Gly Asp Gly Val Val Ser Gln Val Lys
1               5                   10

<210> SEQ ID NO 304
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 304

Asp Gly Glu Tyr Val Val Glu Val Arg
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 305

His Ser Ile Glu Val Pro Ile Pro Arg
1               5

<210> SEQ ID NO 306
```

```
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 306

Ser Thr Glu Ala Thr Leu Ser Phe Gly Tyr Leu Asp Pro Phe Pro Pro
1               5                   10                  15

Glu Glu Arg Pro Glu Val Arg
            20

<210> SEQ ID NO 307
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 307

Thr Thr Lys Pro Tyr Pro Ala Asp Ile Val Val Gln Phe Lys
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 308

Gly Asp Pro Gly Thr Pro Gly Val Pro Gly Lys
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 309

Gly Glu Pro Gly Val Gly Leu Pro Gly Leu Lys
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 310

Gly Pro Pro Gly Gly Val Gly Phe Pro Gly Ser Arg
1               5                   10

<210> SEQ ID NO 311
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 311

Gly Pro Pro Gly Pro Gln Gly Pro Pro Gly Glu Ile Gly Phe Pro Gly
1               5                   10                  15
```

Gln Pro Gly Ala Lys
        20

<210> SEQ ID NO 312
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 312

Ile Leu Tyr His Gly Tyr Ser Leu Leu Tyr Val Gln Gly Asn Glu Arg
1               5                   10                  15

<210> SEQ ID NO 313
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 313

Asp Gly Glu Val Gly Pro Ser Gly Pro Val Gly Pro Pro Gly Leu Ala
1               5                   10                  15

Gly Glu Arg

<210> SEQ ID NO 314
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 314

Gly Pro Glu Gly Pro Pro Gly Lys Pro Gly Glu Asp Gly Glu Pro Gly
1               5                   10                  15

Arg

<210> SEQ ID NO 315
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 315

Gly Thr Gln Gly Pro Pro Gly Ala Thr Gly Phe Pro Gly Ser Ala Gly
1               5                   10                  15

Arg

<210> SEQ ID NO 316
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 316

Leu Gly Pro Leu Gly Ala Pro Gly Glu Asp Gly Arg Pro Gly Pro Pro
1               5                   10                  15

Gly Ser Ile Gly Ile Arg
        20

<210> SEQ ID NO 317

```
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 317

Val Gly Pro Pro Gly Pro Ala Gly Ala Pro Gly Pro Ala Gly Pro Leu
1               5                   10                  15

Gly Glu Pro Gly Lys
            20

<210> SEQ ID NO 318
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 318

Ala Leu Gly Ser Ala Ile Glu Tyr Thr Ile Glu Asn Val Phe Glu Ser
1               5                   10                  15

Ala Pro Asn Pro Arg
            20

<210> SEQ ID NO 319
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 319

Ile Gly Asp Leu His Pro Gln Ile Val Asn Leu Leu Lys
1               5                   10

<210> SEQ ID NO 320
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 320

Asn Ala Asp Pro Ala Glu Leu Glu Gln Ile Val Leu Ser Pro Ala Phe
1               5                   10                  15

Ile Leu Ala Ala Glu Ser Leu Pro Lys
            20                  25

<210> SEQ ID NO 321
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 321

Val Ala Val Val Gln Tyr Ser Asp Arg
1               5

<210> SEQ ID NO 322
<211> LENGTH: 8
<212> TYPE: PRT
<213> ORGANISM: Artificial Sequence
<220> FEATURE:
<223> OTHER INFORMATION: Synthetic Polypeptide
```

```
<400> SEQUENCE: 322

Trp Tyr Tyr Asp Pro Asn Thr Lys
1               5

<210> SEQ ID NO 323
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 323

Gly Pro Gly Asp Leu Glu Ala Pro Ser Asn Leu Val Ile Ser Glu Arg
1               5                   10                  15

<210> SEQ ID NO 324
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 324

Ile Thr Val Asp Pro Thr Thr Asp Gly Pro Thr Lys
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 325

Ser Leu Tyr Asp Asp Val Asp Thr Gly Glu Lys
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 326

Ser Gln Asp Glu Val Glu Ile Pro Ala Arg
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 327

Val Thr Asp Glu Thr Thr Asp Ser Phe Lys
1               5                   10

<210> SEQ ID NO 328
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 328

Glu Ile Leu Val Gly Asp Val Gly Gln Thr Val Asp Asp Pro Tyr Ala
1               5                   10                  15

Thr Phe Val Lys
            20

<210> SEQ ID NO 329
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 329

Leu Gly Gly Ser Ala Val Ile Ser Leu Glu Gly Lys Pro Leu
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 330

Tyr Ala Leu Tyr Asp Ala Thr Tyr Glu Thr Lys
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 331

Ala Asp Asp Ile Leu Ala Ser Pro Pro Arg
1               5                   10

<210> SEQ ID NO 332
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 332

Ala Val Gly Leu Ala Gly Thr Phe Arg
1               5

<210> SEQ ID NO 333
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 333

Asp Glu Leu Leu Phe Pro Ser Trp Glu Ala Leu Phe Ser Gly Ser Glu
1               5                   10                  15

Gly Pro Leu Lys Pro Gly Ala Arg
            20

<210> SEQ ID NO 334
<211> LENGTH: 30
```

```
<212> TYPE: PRT
<213> ORGANISM: Artificial Sequence
<220> FEATURE:
<223> OTHER INFORMATION: Synthetic Polypeptide

<400> SEQUENCE: 334

Leu Ser Gly Val Gln Asp Gly His Gln Asp Ile Ser Leu Leu Tyr Thr
1               5                   10                  15

Glu Pro Gly Ala Gly Gln Thr His Thr Ala Ala Ser Phe Arg
            20                  25                  30

<210> SEQ ID NO 335
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 335

Thr Glu Ala Pro Ser Ala Thr Gly Gln Ala Ser Ser Leu Leu Gly Gly
1               5                   10                  15

Arg

<210> SEQ ID NO 336
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 336

Glu Ile Tyr Pro Tyr Val Ile Gln Glu Leu Arg Pro Thr Leu Asn Glu
1               5                   10                  15

Leu Gly Ile Ser Thr Pro Glu Glu Leu Gly Leu Asp Lys
            20                  25

<210> SEQ ID NO 337
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 337

Gly Leu Leu His Ser Ala Arg
1               5

<210> SEQ ID NO 338
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 338

Ile Ile Asp Ala Ala Leu Arg
1               5

<210> SEQ ID NO 339
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 339
```

```
Ile Leu Glu Val Val Lys
1               5

<210> SEQ ID NO 340
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 340

Thr Pro Gly Pro Ala Val Ala Ile Gln Ser Val Arg
1               5                   10

<210> SEQ ID NO 341
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 341

Ala Pro Leu Thr Lys Pro Leu Lys
1               5

<210> SEQ ID NO 342
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 342

Glu Ser Asp Thr Ser Tyr Val Ser Leu Lys
1               5                   10

<210> SEQ ID NO 343
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 343

Tyr Glu Val Gln Gly Glu Val Phe Thr Lys Pro Gln Leu Trp Pro
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 344

Ala Gln Ala Asp Leu Leu Ala His Leu Val Pro Glu Pro Asp Arg
1               5                   10                  15

<210> SEQ ID NO 345
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 345
```

```
Asp Thr Gly Val Ala Phe Glu Leu Arg
1               5
```

<210> SEQ ID NO 346
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 346

```
Gly Tyr Trp Gly Asp Ile Ala Thr Gly Pro Phe Val Ala Phe Gly Ile
1               5                   10                  15

Glu Ala Asp Asp Glu Ser Leu Leu Arg
            20                  25
```

<210> SEQ ID NO 347
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 347

```
Leu Glu Glu Gln Leu Pro Trp Leu Ser Leu Arg
1               5                   10
```

<210> SEQ ID NO 348
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 348

```
Thr Ala Gly Glu Ile Thr Gln His Asn Val Thr Glu Leu Leu Arg
1               5                   10                  15
```

<210> SEQ ID NO 349
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 349

```
Asp Asn Thr Pro Asn Ala Ile Ala Ile Val Gln Leu Gln Glu Leu Ser
1               5                   10                  15

Leu Arg
```

<210> SEQ ID NO 350
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 350

```
Asp Pro Pro Glu Pro Gly Ser Pro Arg
1               5
```

<210> SEQ ID NO 351
<211> LENGTH: 13
<212> TYPE: PRT
<213> ORGANISM: Artificial Sequence
<220> FEATURE:

```
<223> OTHER INFORMATION: Synthetic Polypeptide

<400> SEQUENCE: 351

Phe Asn Ser Val Pro Leu Thr Asp Thr Gly His Glu Arg
1               5                   10

<210> SEQ ID NO 352
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 352

Ile Ser Ser Leu Arg Pro Gln Gly Leu Ser Asn Pro Ser Thr Leu Ser
1               5                   10                  15

Ala Gln Pro Gln Leu Ser Arg
            20

<210> SEQ ID NO 353
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 353

Thr Phe Tyr Glu Thr Pro Leu Gln Leu Leu Glu Lys
1               5                   10

<210> SEQ ID NO 354
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 354

Ile Glu Leu Pro Glu Arg
1               5

<210> SEQ ID NO 355
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 355

Ile Arg Pro Val Thr Pro Val Glu Lys
1               5

<210> SEQ ID NO 356
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 356

Gln Asn Trp Pro Gln Asn Trp Gly Phe Leu Thr Thr Pro Phe Glu Glu
1               5                   10                  15

Leu Ile Lys

<210> SEQ ID NO 357
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 357

Ser Ala Val Pro Gly Leu Asn Lys
1               5

<210> SEQ ID NO 358
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 358

Val Phe Pro Ser Pro Pro Val Pro Gln Thr Thr Gln Gly Phe Ile Gly
1               5                   10                  15

Trp Arg

<210> SEQ ID NO 359
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 359

Asp Gln Thr Val Val Gly Pro Ala Leu Ala Ala Tyr Arg
1               5                   10

<210> SEQ ID NO 360
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 360

Thr Thr Thr Leu Pro Val Glu Phe Lys
1               5

<210> SEQ ID NO 361
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 361

Ala Leu Ala Leu Val Val Thr Leu Leu His Leu Thr Arg
1               5                   10

<210> SEQ ID NO 362
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 362

Glu Leu Gly Phe Asp Ala Ser Glu Val Glu Leu Thr Arg
1               5                   10
```

```
<210> SEQ ID NO 363
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 363

Ile Leu Tyr Asn Pro Leu Gln Gly Gln Lys
1               5                   10

<210> SEQ ID NO 364
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 364

Leu Phe Asn Asp Ile His Lys
1               5

<210> SEQ ID NO 365
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 365

Asn Asn Glu Leu Ile Ala Val Gly Lys
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 366

Leu Glu Ala Val Gln Tyr Lys
1               5

<210> SEQ ID NO 367
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 367

Ser Leu Pro Gly Gln Asn Glu Asp Leu Val Leu Thr Gly Tyr Gln Val
1               5                   10                  15

Asp Lys

<210> SEQ ID NO 368
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 368

Thr Asn Glu Thr Tyr Gly Lys
1               5
```

```
<210> SEQ ID NO 369
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 369

Thr Gln Val Val Ala Gly Thr Asn Tyr Tyr Ile Lys
1               5                   10

<210> SEQ ID NO 370
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 370

Val Lys Pro Gln Leu Glu Glu Lys
1               5

<210> SEQ ID NO 371
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 371

His Asp Glu Leu Thr Tyr Phe
1               5

<210> SEQ ID NO 372
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 372

Ser Gln Leu Glu Glu Lys
1               5

<210> SEQ ID NO 373
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 373

Ser Gln Val Val Ala Gly Thr Asn Tyr Phe Ile Lys
1               5                   10

<210> SEQ ID NO 374
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 374

Val Phe Gln Ser Leu Pro His Glu Asn Lys Pro Leu Thr Leu Ser Asn
1               5                   10                  15

Tyr Gln Thr Asn Lys
```

<210> SEQ ID NO 375
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 375

Val His Val Gly Asp Glu Asp Phe Val His Leu Arg
1               5                   10

<210> SEQ ID NO 376
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 376

Asp Trp Val Leu Asn Glu Phe Arg
1               5

<210> SEQ ID NO 377
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 377

Phe Val Ile Asn Tyr Asp Tyr Pro Asn Ser Ser Glu Asp Tyr Val His
1               5                   10                  15

Arg

<210> SEQ ID NO 378
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 378

Leu Ile Asp Phe Leu Glu Ser Gly Lys
1               5

<210> SEQ ID NO 379
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 379

Ser Ser Gln Ser Ser Ser Gln Gln Phe Ser Gly Ile Gly Arg
1               5                   10

<210> SEQ ID NO 380
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 380

Val Leu Glu Glu Ala Asn Gln Ala Ile Asn Pro Lys
1               5                   10

<210> SEQ ID NO 381
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 381

Ile Gln Ser Gln Phe Thr Asp Ala Gln Lys
1               5                   10

<210> SEQ ID NO 382
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 382

Ile Thr Asn Leu Thr Gln Gln Leu Glu Gln Ala Ser Ile Val Lys
1               5                   10                  15

<210> SEQ ID NO 383
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 383

Asn Met Pro Leu Gln His Leu Leu Glu Gln Ile Lys
1               5                   10

<210> SEQ ID NO 384
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 384

Tyr Gly Asp Gly Ile Gln Leu Thr Arg
1               5

<210> SEQ ID NO 385
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 385

Ala Leu Pro Ser Leu Thr Asp Ser Lys
1               5

<210> SEQ ID NO 386
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 386

Gly Ser Leu Val Val Val Ser Ser Leu Leu Gly Arg

<210> SEQ ID NO 387
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 387

Leu Gly Gly Leu Asp Tyr Leu Val Leu Asn His Ile Gly Gly Ala Pro
1               5                   10                  15

Ala Gly Thr Arg
            20

<210> SEQ ID NO 388
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 388

Asn Asp Gly His Leu Glu Pro Val Thr Ala Trp Glu Val Gln Val Pro
1               5                   10                  15

Arg

<210> SEQ ID NO 389
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 389

Val Pro Thr Ser Phe Ser Thr Pro Tyr Ser Ala Ala Lys
1               5                   10

<210> SEQ ID NO 390
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 390

Phe Gly Gln Gly Ser Gly Pro Ile Val Leu Asp Asp Val Arg
1               5                   10

<210> SEQ ID NO 391
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 391

Ile Asn Leu Gly Phe Ser Asn Leu Lys
1               5

<210> SEQ ID NO 392
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 392

Val Asp Val Val Leu Gly Pro Ile Gln Leu Gln Thr Pro Pro Arg
1               5                   10                  15

<210> SEQ ID NO 393
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 393

Gly Gly Val Ser Pro Ser Ser Ser Ala Ser Arg
1               5                   10

<210> SEQ ID NO 394
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 394

Leu Gly Phe Ile Asn Trp Asp Ala Ile Asn Lys
1               5                   10

<210> SEQ ID NO 395
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 395

Gln Val Pro Gly Phe Gly Val Ala Asp Ala Leu Gly Asn Arg
1               5                   10

<210> SEQ ID NO 396
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 396

Val Gly Glu Ala Ala His Ala Leu Gly Asn Thr Gly His Glu Ile Gly
1               5                   10                  15

Arg

<210> SEQ ID NO 397
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 397

Val Ser Glu Ala Leu Gly Gln Gly Thr Arg
1               5                   10

<210> SEQ ID NO 398
<211> LENGTH: 14
<212> TYPE: PRT
<213> ORGANISM: Artificial Sequence
<220> FEATURE:

<223> OTHER INFORMATION: Synthetic Polypeptide

<400> SEQUENCE: 398

Leu Gly Thr Phe Glu Val Glu Asp Gln Ile Glu Ala Ala Arg
1               5                   10

<210> SEQ ID NO 399
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 399

Met Leu Gln Asn Val Gln Met Pro Ser Lys
1               5                   10

<210> SEQ ID NO 400
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 400

Trp Glu Tyr Tyr Asp Ser Val Tyr Thr Glu Arg
1               5                   10

<210> SEQ ID NO 401
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 401

Trp Ile Ser Asp His Glu Tyr Leu Tyr Lys
1               5                   10

<210> SEQ ID NO 402
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 402

Tyr Met Gly Leu Pro Thr Pro Glu Asp Asn Leu Asp His Tyr Arg
1               5                   10                  15

<210> SEQ ID NO 403
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 403

Gly Asn Asn Val Glu Lys Pro Leu Glu Leu Arg
1               5                   10

<210> SEQ ID NO 404
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 404

Gly Gln Ile Ile Gly Asn Phe Gln Ala Phe Asp Glu Asp Thr Gly Leu
1               5                   10                  15

Pro Ala His Ala Arg
            20

<210> SEQ ID NO 405
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 405

Ile Leu Asp Val Asn Asp Asn Ile Pro Val Val Glu Asn Lys
1               5                   10

<210> SEQ ID NO 406
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 406

Asn Leu Asp Phe Ser Val Ile Val Ala Asn Lys
1               5                   10

<210> SEQ ID NO 407
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 407

Val Tyr Ala Pro Ala Ser Thr Leu Val Asp Gln Pro Tyr Ala Asn Glu
1               5                   10                  15

Gly Thr Val Val Val Thr Glu Arg
            20

<210> SEQ ID NO 408
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 408

Asp Phe Leu Leu Lys Pro Glu Leu Leu Arg
1               5                   10

<210> SEQ ID NO 409
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 409

Phe Glu Val Asn Val Ala Glu Leu Pro Glu Glu Ile Asp Ile Ser Thr
1               5                   10                  15

Tyr Ile Glu Gln Ser Arg
            20

<210> SEQ ID NO 410
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 410

Gly Leu Ala Ile Thr Phe Val Ser Asp Glu Asn Asp Ala Lys
1               5                   10

<210> SEQ ID NO 411
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 411

Ile Leu Asn Asp Val Gln Asp Arg
1               5

<210> SEQ ID NO 412
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 412

Leu Thr Pro His Glu Lys
1               5

<210> SEQ ID NO 413
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 413

Glu Leu Ala Phe Gln Ile Ser Lys
1               5

<210> SEQ ID NO 414
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 414

Phe Glu Val Asn Ile Ser Glu Leu Pro Asp Glu Ile Asp Ile Ser Ser
1               5                   10                  15

Tyr Ile Glu Gln Thr Arg
            20

<210> SEQ ID NO 415
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 415

```
Ala Pro Glu Val Ile Leu Gly Ala Arg
1               5
```

<210> SEQ ID NO 416
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 416

```
Ala Ser Asn Ala Ala Ala Ala Ala His Thr Ile Gly Gly Ser Lys
1               5                   10                  15
```

<210> SEQ ID NO 417
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 417

```
Gln Leu Gln Ala Ser Pro Gly Leu Gly Ala Gly Ala Thr Arg
1               5                   10
```

<210> SEQ ID NO 418
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 418

```
Ser Gly Val Gly Thr Gly Pro Pro Ser Pro Ile Ala Leu Pro Pro Leu
1               5                   10                  15

Arg
```

<210> SEQ ID NO 419
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 419

```
Thr Gly Leu Pro Val Val Pro Glu Arg
1               5
```

<210> SEQ ID NO 420
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 420

```
Gly Gln Ala Ala Ala Thr Leu Glu Gln Pro Ala Ser Ser Ser His Ala
1               5                   10                  15

Gln Gly Thr His Leu Arg
            20
```

<210> SEQ ID NO 421
<211> LENGTH: 11
<212> TYPE: PRT
<213> ORGANISM: Artificial Sequence
<220> FEATURE:

```
<223> OTHER INFORMATION: Synthetic Polypeptide

<400> SEQUENCE: 421

Thr Gly Ala Thr Thr Gly Glu Leu Leu Gln Arg
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 422

Glu His Ala Leu Leu Ala Tyr Thr Leu Gly Val Lys
1               5                   10

<210> SEQ ID NO 423
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 423

Ile Gly Gly Ile Gly Thr Val Pro Val Gly Arg
1               5                   10

<210> SEQ ID NO 424
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 424

Leu Pro Leu Gln Asp Val Tyr Lys
1               5

<210> SEQ ID NO 425
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 425

Met Asp Ser Thr Glu Pro Pro Tyr Ser Gln Lys
1               5                   10

<210> SEQ ID NO 426
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 426

Gln Thr Val Ala Val Gly Val Ile Lys
1               5

<210> SEQ ID NO 427
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 427

Ser Thr Thr Thr Gly His Leu Ile Tyr Lys
1               5                   10

<210> SEQ ID NO 428
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 428

Thr His Ile Asn Ile Val Val Ile Gly His Val Asp Ser Gly Lys
1               5                   10                  15

<210> SEQ ID NO 429
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 429

Val Glu Thr Gly Val Leu Lys Pro Gly Met Val Val Thr Phe Ala Pro
1               5                   10                  15

Val Asn Val Thr Thr Glu Val Lys
            20

<210> SEQ ID NO 430
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 430

Tyr Ala Trp Val Leu Asp Lys
1               5

<210> SEQ ID NO 431
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 431

Tyr Tyr Val Thr Ile Ile Asp Ala Pro Gly His Arg
1               5                   10

<210> SEQ ID NO 432
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 432

Phe Glu Glu His Val Gln Ser Val Asp Ile Ala Ala Phe Asn Lys
1               5                   10                  15

<210> SEQ ID NO 433
<211> LENGTH: 12
<212> TYPE: PRT
<213> ORGANISM: Artificial Sequence
```

<220> FEATURE:
<223> OTHER INFORMATION: Synthetic Polypeptide

<400> SEQUENCE: 433

Gly Val Val Gln Glu Leu Gln Gln Ala Ile Ser Lys
1               5                   10

<210> SEQ ID NO 434
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 434

Leu Asn Val Leu Glu Lys
1               5

<210> SEQ ID NO 435
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 435

Ser Ile Gln Leu Asp Gly Leu Val Trp Gly Ala Ser Lys
1               5                   10

<210> SEQ ID NO 436
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 436

Val Gly Thr Asp Leu Leu Glu Glu Glu Ile Thr Lys
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 437

Asp Ser Val Val Ala Gly Phe Gln Trp Ala Thr Lys
1               5                   10

<210> SEQ ID NO 438
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 438

Glu Gly Ile Pro Ala Leu Asp Asn Phe Leu Asp Lys
1               5                   10

<210> SEQ ID NO 439
<211> LENGTH: 8
<212> TYPE: PRT
<213> ORGANISM: Artificial Sequence
<220> FEATURE:

```
<223> OTHER INFORMATION: Synthetic Polypeptide

<400> SEQUENCE: 439

Phe Ser Val Ser Pro Val Val Arg
1               5

<210> SEQ ID NO 440
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 440

Gly Glu Gly Gln Leu Gly Pro Ala Glu Arg
1               5                   10

<210> SEQ ID NO 441
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 441

Gly Val Gln Tyr Leu Asn Glu Ile Lys
1               5

<210> SEQ ID NO 442
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 442

Phe Ile Phe Trp Ser Ser Glu Val Ala Gly Ser Leu Tyr Arg
1               5                   10

<210> SEQ ID NO 443
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 443

Ile Asn Leu His Ser Ser Phe Val Pro Leu Gly Glu Leu Lys
1               5                   10

<210> SEQ ID NO 444
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 444

Leu Val Ile Ala Ser Ser Asp Leu Ile Trp Pro Ser Gly Ile Thr Ile
1               5                   10                  15

Asp Phe Leu Thr Asp Lys
            20

<210> SEQ ID NO 445
<211> LENGTH: 11
<212> TYPE: PRT
```

```
<213> ORGANISM: Artificial Sequence
<220> FEATURE:
<223> OTHER INFORMATION: Synthetic Polypeptide

<400> SEQUENCE: 445

Asn Gln Val Thr Pro Leu Asp Ile Leu Ser Lys
1               5                   10

<210> SEQ ID NO 446
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 446

Tyr Pro Ala Asn Val Ala Val Asp Pro Val Glu Arg
1               5                   10

<210> SEQ ID NO 447
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 447

Glu Asp Asp Phe Asp Trp Asn Pro Ala Asp Arg
1               5                   10

<210> SEQ ID NO 448
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 448

Gly Asp Val Phe Phe Pro Lys
1               5

<210> SEQ ID NO 449
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 449

Ile Gln Leu Tyr Gln Gly Thr Asp Ala Thr Lys
1               5                   10

<210> SEQ ID NO 450
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 450

Asn Ser Asn Asn Ala Leu Ala Trp Glu Lys
1               5                   10

<210> SEQ ID NO 451
<211> LENGTH: 14
<212> TYPE: PRT
<213> ORGANISM: Artificial Sequence
```

```
<220> FEATURE:
<223> OTHER INFORMATION: Synthetic Polypeptide

<400> SEQUENCE: 451

Val Asn Leu Gln Pro Phe Asn Tyr Glu Glu Ile Val Ser Arg
1               5                   10

<210> SEQ ID NO 452
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 452

Ala Val Glu His Ile Asn Lys
1               5

<210> SEQ ID NO 453
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 453

Gly Asn Pro Thr Val Glu Val Asp Leu Phe Thr Ser Lys
1               5                   10

<210> SEQ ID NO 454
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 454

Ile Gly Ala Glu Val Tyr His Asn Leu Lys
1               5                   10

<210> SEQ ID NO 455
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 455

Tyr Ile Ser Pro Asp Gln Leu Ala Asp Leu Tyr Lys
1               5                   10

<210> SEQ ID NO 456
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 456

Tyr Asn Gln Leu Leu Arg
1               5

<210> SEQ ID NO 457
<211> LENGTH: 26
<212> TYPE: PRT
<213> ORGANISM: Artificial Sequence
<220> FEATURE:
```

<223> OTHER INFORMATION: Synthetic Polypeptide

<400> SEQUENCE: 457

Asp Ala Thr Asn Val Gly Asp Glu Gly Gly Phe Ala Pro Asn Ile Leu
1               5                   10                  15
Glu Asn Ser Glu Ala Leu Glu Leu Val Lys
            20                  25

<210> SEQ ID NO 458
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 458

Gly Asn Pro Thr Val Glu Val Asp Leu Tyr Thr Ala Lys
1               5                   10

<210> SEQ ID NO 459
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 459

Ile Glu Glu Glu Leu Gly Asp Glu Ala Arg
1               5                   10

<210> SEQ ID NO 460
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 460

Leu Gly Ala Glu Val Tyr His Thr Leu Lys
1               5                   10

<210> SEQ ID NO 461
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 461

Tyr Ile Thr Gly Asp Gln Leu Gly Ala Leu Tyr Gln Asp Phe Val Arg
1               5                   10                  15

<210> SEQ ID NO 462
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 462

Ala Leu Tyr Leu Ser Gly Tyr Arg
1               5

<210> SEQ ID NO 463
<211> LENGTH: 15
<212> TYPE: PRT

```
<213> ORGANISM: Artificial Sequence
<220> FEATURE:
<223> OTHER INFORMATION: Synthetic Polypeptide

<400> SEQUENCE: 463

Glu Thr Glu Glu Ser Ala Leu Val Ser Gln Ala Glu Ala Leu Lys
1               5                   10                  15

<210> SEQ ID NO 464
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 464

Phe Ser Glu Ala Val Gln Thr Leu Leu Thr Trp Ile Glu Arg
1               5                   10

<210> SEQ ID NO 465
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 465

Gln Ala Leu Ser Gly Ile Leu Ile Gln Phe Glu Gln Ile Val Ala Val
1               5                   10                  15

Tyr His Ser Ala Ser Lys
            20

<210> SEQ ID NO 466
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 466

Trp Leu Trp Val Tyr Glu Ile Gly Tyr Ala Ala Asp Asn Ser Arg
1               5                   10                  15

<210> SEQ ID NO 467
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 467

Glu Val Glu Glu Asp Glu Tyr Lys
1               5

<210> SEQ ID NO 468
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 468

Leu Ile Ser Leu Thr Asp Glu Asn Ala Leu Ser Gly Asn Glu Glu Leu
1               5                   10                  15

Thr Val Lys
```

<210> SEQ ID NO 469
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 469

Ser Gly Thr Ser Glu Phe Leu Asn Lys
1               5

<210> SEQ ID NO 470
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 470

Ser Gly Tyr Leu Leu Pro Asp Thr Lys
1               5

<210> SEQ ID NO 471
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 471

Thr Asp Asp Glu Val Val Gln Arg
1               5

<210> SEQ ID NO 472
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 472

Arg Pro His Phe Asp Gln Leu Val Ala Ala Phe Asp Lys
1               5                   10

<210> SEQ ID NO 473
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 473

Ser Phe Gly Pro Leu Thr Gln Arg
1               5

<210> SEQ ID NO 474
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 474

Val Asp Thr Ile Ala Ala Asp Glu Ser Phe Pro Ser Ser Ser Ser
1               5                   10                  15

Ser Ser Ser Ser Ser Ser Ala Ala Trp Ala Val Gly Pro His Gly Ala

```
                    20                  25                  30

Gly Gln Arg
 35

<210> SEQ ID NO 475
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 475

Val Tyr Phe Gln Thr Leu Pro Gln Gly Glu Leu Ser Ser Gln Leu Pro
 1               5                  10                  15

Glu Arg

<210> SEQ ID NO 476
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 476

Trp Ala Ala Pro Glu Val Ile Ala His Gly Lys
 1               5                  10

<210> SEQ ID NO 477
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 477

Ile Trp Pro Gly Ile Pro Ser Pro Glu Ser Glu Phe Glu Gly Leu Phe
 1               5                  10                  15

Thr Thr His Lys
            20

<210> SEQ ID NO 478
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 478

Leu Ala Asp Glu Ser Gly His Val Val Leu Arg
 1               5                  10

<210> SEQ ID NO 479
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 479

Val Ile His Ile Asn Glu Val Val Leu Leu Asp Ala Pro Val Gly Leu
 1               5                  10                  15

Val Ala Arg

<210> SEQ ID NO 480
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 480

Val Thr Ala Ala Ser Gly Ala Pro Arg
1               5

<210> SEQ ID NO 481
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 481

Tyr Glu Val Asp Val Ser Ala Gly Asn Gly Ala Gly Ser Val Gln Arg
1               5                   10                  15

<210> SEQ ID NO 482
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 482

Gly Ala Leu Gly Pro Gln Leu Leu Leu Asn Trp Gly Val Gln Ile Ala
1               5                   10                  15

Lys

<210> SEQ ID NO 483
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 483

Gly Glu Ser Ile Glu Pro Leu Asp Pro Ser Glu Lys
1               5                   10

<210> SEQ ID NO 484
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 484

Leu Ala Glu Val Pro Asp Leu Leu Glu Lys
1               5                   10

<210> SEQ ID NO 485
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 485

Ser Leu Glu Ala Thr Asp Ser Ala Phe Asp Asn Pro Asp Tyr Trp His
1               5                   10                  15

Ser Arg
```

<210> SEQ ID NO 486
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 486

Ser Pro Ser Gln Val Gln Val Ala Asp Phe Gly Val Ala Asp Leu Leu
1               5                   10                  15

Pro Pro Asp Asp Lys
            20

<210> SEQ ID NO 487
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 487

Val Ala Gln Val Ser Ile Thr Lys
1               5

<210> SEQ ID NO 488
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 488

Val Thr Ser Gly Asp Pro Glu Leu Pro Gln Val
1               5                   10

<210> SEQ ID NO 489
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 489

Ala Val Leu Gln Trp Thr Lys
1               5

<210> SEQ ID NO 490
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 490

Leu Gly Ala Val Asp Glu Ser Leu Ser Glu Glu Thr Gln Lys
1               5                   10

<210> SEQ ID NO 491
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 491

```
Leu Leu Glu Ser Asp Tyr Phe Arg
1               5
```

<210> SEQ ID NO 492
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 492

```
Asn Leu Leu Gln Asn Ile His
1               5
```

<210> SEQ ID NO 493
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 493

```
Val Leu Pro Phe Phe Glu Arg Pro Asp Phe Gln Leu Phe Thr Gly Asn
1               5                   10                  15

Lys
```

<210> SEQ ID NO 494
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 494

```
Phe Pro Phe Phe Gln Tyr Ser Val Thr Lys
1               5                   10
```

<210> SEQ ID NO 495
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 495

```
Glu Ala Gln Asp Asp Leu Val Lys
1               5
```

<210> SEQ ID NO 496
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 496

```
Glu Leu Ser Glu Gln Ile Gln Arg
1               5
```

<210> SEQ ID NO 497
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 497

```
Ile Gln Val Trp His Ala Glu His Arg
1               5

<210> SEQ ID NO 498
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 498

Leu Gln Asp Tyr Glu Glu Lys
1               5

<210> SEQ ID NO 499
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 499

Ser Gly Tyr Leu Ser Ser Glu Arg
1               5

<210> SEQ ID NO 500
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 500

Ala Asp Glu Pro Ser Ser Glu Glu Ser Asp Leu Glu Ile Asp Lys
1               5                   10                  15

<210> SEQ ID NO 501
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 501

Ala Ile Asp Leu Phe Thr Asp Ala Ile Lys
1               5                   10

<210> SEQ ID NO 502
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 502

Ala Ile Glu Ile Asn Pro Asp Ser Ala Gln Pro Tyr Lys
1               5                   10

<210> SEQ ID NO 503
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 503
```

```
Leu Gln Lys Pro Asn Ala Ala Ile Arg
1               5

<210> SEQ ID NO 504
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 504

Tyr Gln Ser Asn Pro Lys
1               5

<210> SEQ ID NO 505
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 505

Gly Ile Asn Val Ala Leu Ala Asn Gly Lys
1               5                   10

<210> SEQ ID NO 506
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 506

Leu Val Val Ala Val Ala Val Phe Leu Leu Thr Phe Tyr Val Ile Ser
1               5                   10                  15

Gln Val Phe Glu Ile Lys
            20

<210> SEQ ID NO 507
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 507

Ser Ala Leu Asp Thr Ala Ala Arg
1               5

<210> SEQ ID NO 508
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 508

Ser Pro Phe Glu Gln His Ile Lys
1               5

<210> SEQ ID NO 509
<211> LENGTH: 8
<212> TYPE: PRT
<213> ORGANISM: Artificial Sequence
<220> FEATURE:
<223> OTHER INFORMATION: Synthetic Polypeptide
```

<400> SEQUENCE: 509

Thr Gly Glu Val Leu Asp Thr Lys
1               5

<210> SEQ ID NO 510
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 510

Gly Asn Ala Gly Gln Ser Asn Tyr Gly Phe Ala Asn Ser Ala Met Glu
1               5                   10                  15

Arg

<210> SEQ ID NO 511
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 511

Leu Pro Glu Asp Pro Leu Leu Ser Gly Leu Leu Asp Ser Pro Ala Leu
1               5                   10                  15

Lys

<210> SEQ ID NO 512
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 512

Leu Gln Val Val Asp Gln Pro Leu Pro Val Arg
1               5                   10

<210> SEQ ID NO 513
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 513

Met Val Val Pro Gly Leu Asp Gly Ala Gln Ile Pro Arg
1               5                   10

<210> SEQ ID NO 514
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 514

Ser Glu Gly Val Val Ala Val Leu Leu Thr Lys
1               5                   10

<210> SEQ ID NO 515
<211> LENGTH: 9
<212> TYPE: PRT
<213> ORGANISM: Artificial Sequence

```
<220> FEATURE:
<223> OTHER INFORMATION: Synthetic Polypeptide

<400> SEQUENCE: 515

Val Leu Glu Ala Leu Leu Pro Leu Lys
1               5

<210> SEQ ID NO 516
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 516

Gly Trp Leu Leu Leu Gln Val Ser Ser Arg
1               5                   10

<210> SEQ ID NO 517
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 517

His Leu Glu Glu Glu Leu Lys
1               5

<210> SEQ ID NO 518
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 518

Leu Val Tyr Asn Val Leu Tyr Tyr Arg
1               5

<210> SEQ ID NO 519
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 519

Val Phe Thr Glu Gly Glu Pro Leu Ala Leu Arg
1               5                   10

<210> SEQ ID NO 520
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 520

Tyr Thr Ser Ala Gly Ile Ser Val Thr Val Lys
1               5                   10

<210> SEQ ID NO 521
<211> LENGTH: 19
<212> TYPE: PRT
<213> ORGANISM: Artificial Sequence
<220> FEATURE:
```

```
<223> OTHER INFORMATION: Synthetic Polypeptide

<400> SEQUENCE: 521

Ile Glu Glu Asn Gly Tyr Asn Thr Tyr Ala Ser Phe Asn Trp Gln His
1               5                   10                  15
Asn Gly Arg

<210> SEQ ID NO 522
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 522

Ser Tyr Asn His Leu Gln Gly Asp Val Arg
1               5                   10

<210> SEQ ID NO 523
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 523

Leu Glu Ser Asn Asn Tyr Asn Thr Tyr Arg
1               5                   10

<210> SEQ ID NO 524
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 524

Leu Gln Leu Gln Ala Glu Glu Arg
1               5

<210> SEQ ID NO 525
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 525

Asn Gly Gly Phe Phe Leu Arg
1               5

<210> SEQ ID NO 526
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 526

Glu Leu Ile Leu Glu Asn His Tyr Asn Thr Tyr Ala Ser Ala Lys
1               5                   10                  15

<210> SEQ ID NO 527
<211> LENGTH: 6
<212> TYPE: PRT
<213> ORGANISM: Artificial Sequence
```

<220> FEATURE:
<223> OTHER INFORMATION: Synthetic Polypeptide

<400> SEQUENCE: 527

Thr Gln Trp Tyr Leu Arg
1               5

<210> SEQ ID NO 528
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 528

Thr Val Ala Val Gly Ile Val Ala Ile Lys
1               5                   10

<210> SEQ ID NO 529
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 529

Trp Ile Leu Thr Trp Ile Leu Pro Thr Leu Leu Tyr Arg
1               5                   10

<210> SEQ ID NO 530
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 530

Glu Gln Phe Glu Glu Asn Trp Tyr Asn Thr Tyr Ser Ser Asn Leu Tyr
1               5                   10                  15

Lys

<210> SEQ ID NO 531
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 531

Phe Gly Ile Leu Glu Phe Ile Ser Ile Ala Val Gly Leu Val Ser Ile
1               5                   10                  15

Arg

<210> SEQ ID NO 532
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 532

Phe Thr His Phe Leu Pro Arg Pro Val Asp Pro Asp Lys
1               5                   10

<210> SEQ ID NO 533

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 533

Gly Glu Leu Tyr Gly Ser Glu Lys
1               5

<210> SEQ ID NO 534
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 534

Gly Pro Ala Val Thr Asp Leu Asp His Leu Lys
1               5                   10

<210> SEQ ID NO 535
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 535

Glu Ile Glu Val Leu Tyr Ile Arg
1               5

<210> SEQ ID NO 536
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 536

Gln Leu Val Glu Asp Leu Asp Arg
1               5

<210> SEQ ID NO 537
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 537

Thr Val Leu Ile Gly Glu Tyr Leu Gln Ile Lys
1               5                   10

<210> SEQ ID NO 538
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 538

Tyr Gly Pro Asp Gly Leu Pro Tyr Leu Lys
1               5                   10

<210> SEQ ID NO 539
<211> LENGTH: 20
```

```
<212> TYPE: PRT
<213> ORGANISM: Artificial Sequence
<220> FEATURE:
<223> OTHER INFORMATION: Synthetic Polypeptide

<400> SEQUENCE: 539

Tyr Gln Ile Ser Gln Pro Glu Val Tyr Val Ala Ala Pro Gly Glu Ser
1               5                   10                  15

Leu Glu Val Arg
            20

<210> SEQ ID NO 540
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 540

Asp Gly Thr Gly Leu Val Pro Ser Glu Arg
1               5                   10

<210> SEQ ID NO 541
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 541

Leu Ser Ser Gly Glu Gly Pro Thr Leu Ala Asn Val Ser Glu Leu Glu
1               5                   10                  15

Leu Pro Ala Asp Pro Lys
            20

<210> SEQ ID NO 542
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 542

Thr Ala Gly Ala Asn Thr Thr Asp Lys
1               5

<210> SEQ ID NO 543
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 543

Val Gly Pro Asp Gly Thr Pro Tyr Val Thr Val Leu Lys
1               5                   10

<210> SEQ ID NO 544
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 544

Glu Leu Glu Ser Glu Val Asn Lys
```

```
<210> SEQ ID NO 545
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 545

Leu His Val Gly Asn Tyr Asn Gly Thr Ala Gly Asp Ala Leu Arg
1               5                   10                  15

<210> SEQ ID NO 546
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 546

Leu Gln Ala Asp Asp Asn Gly Asp Pro Gly Arg
1               5                   10

<210> SEQ ID NO 547
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 547

Asn Gly Leu Leu Leu Pro Ser Thr Gly Ala Pro Gly Glu Val Gly Asp
1               5                   10                  15

Asn Arg

<210> SEQ ID NO 548
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 548

Val Ala Asn Leu Thr Phe Val Val Asn Ser Leu Asp Gly Lys
1               5                   10

<210> SEQ ID NO 549
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 549

Glu Asp Phe Pro Ala Ser Trp Arg
1               5

<210> SEQ ID NO 550
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 550
```

```
Phe Gly Gln His Leu Ile Lys Pro Ser Val Val Phe Leu Lys
1               5                   10
```

<210> SEQ ID NO 551
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 551

```
Phe His Asp Leu Arg Pro Asp Glu Val Ala Asp Leu Phe Gln Thr Thr
1               5                   10                  15

Gln Arg
```

<210> SEQ ID NO 552
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 552

```
Asn Asp Ser Ile Tyr Glu Glu Leu Gln Lys
1               5                   10
```

<210> SEQ ID NO 553
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 553

```
Val Gly Thr Val Val Glu Lys
1               5
```

<210> SEQ ID NO 554
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 554

```
Gly Gly Ser Thr Ser Tyr Gly Thr Gly Ser Glu Thr Glu Ser Pro Arg
1               5                   10                  15
```

<210> SEQ ID NO 555
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 555

```
Gly Leu Ile Asp Glu Val Asn Gln Asp Phe Thr Asn Arg
1               5                   10
```

<210> SEQ ID NO 556
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 556

Asn Ser Leu Phe Glu Tyr Gln Lys
1               5

<210> SEQ ID NO 557
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 557

Thr Val Ile Gly Pro Asp Gly His Lys
1               5

<210> SEQ ID NO 558
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 558

Val Gln His Ile Gln Leu Leu Gln Lys
1               5

<210> SEQ ID NO 559
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 559

His Thr Ser Val Gln Thr Thr Ser Ser Gly Ser Gly Pro Phe Thr Asp
1               5                   10                  15

Val Arg

<210> SEQ ID NO 560
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 560

Ser Ser Pro Val Val Ile Asp Ala Ser Thr Ala Ile Asp Ala Pro Ser
1               5                   10                  15

Asn Leu Arg

<210> SEQ ID NO 561
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 561

Ser Tyr Thr Ile Thr Gly Leu Gln Pro Gly Thr Asp Tyr Lys
1               5                   10

<210> SEQ ID NO 562
<211> LENGTH: 15
<212> TYPE: PRT
<213> ORGANISM: Artificial Sequence
<220> FEATURE:

<223> OTHER INFORMATION: Synthetic Polypeptide

<400> SEQUENCE: 562

Val Pro Gly Thr Ser Thr Ser Ala Thr Leu Thr Gly Leu Thr Arg
1               5                   10                  15

<210> SEQ ID NO 563
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 563

Val Val Thr Pro Leu Ser Pro Pro Thr Asn Leu His Leu Glu Ala Asn
1               5                   10                  15

Pro Asp Thr Gly Val Leu Thr Val Ser Trp Glu Arg
            20                  25

<210> SEQ ID NO 564
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 564

Ala Glu Ala Gly Leu Glu Thr Glu Ser Pro Val Arg
1               5                   10

<210> SEQ ID NO 565
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 565

Ala Asn Tyr Trp Leu Lys
1               5

<210> SEQ ID NO 566
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 566

Asp Pro Leu Val Ile Glu Leu Gly Gln Lys
1               5                   10

<210> SEQ ID NO 567
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 567

Ile Ile Asp Thr Ser Leu Thr Arg
1               5

<210> SEQ ID NO 568
<211> LENGTH: 22
<212> TYPE: PRT

```
<213> ORGANISM: Artificial Sequence
<220> FEATURE:
<223> OTHER INFORMATION: Synthetic Polypeptide

<400> SEQUENCE: 568

Asp Ser Trp Val Phe Gly Gly Ile Asp Pro Gln Ser Gly Ala Ala Val
1               5                   10                  15

Val His Glu Ile Val Arg
            20

<210> SEQ ID NO 569
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 569

Gly Val Ile Leu Tyr Ser Asp Pro Ala Asp Tyr Phe Ala Pro Gly Val
1               5                   10                  15

Lys

<210> SEQ ID NO 570
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 570

Leu Gly Ser Gly Asn Asp Phe Glu Val Phe Phe Gln Arg
1               5                   10

<210> SEQ ID NO 571
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 571

Ser Tyr Pro Asp Gly Trp Asn Leu Pro Gly Gly Val Gln Arg
1               5                   10                  15

<210> SEQ ID NO 572
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 572

Thr Tyr Ser Val Ser Phe Asp Ser Leu Phe Ser Ala Val Lys
1               5                   10

<210> SEQ ID NO 573
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 573

Asp Val Ser Tyr Leu Tyr Arg
1               5
```

<210> SEQ ID NO 574
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 574

Glu Lys Pro Gly Pro Glu Asp Lys
1               5

<210> SEQ ID NO 575
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 575

Gly Trp Asn Trp Thr Ser Gly Phe Asn Lys
1               5                   10

<210> SEQ ID NO 576
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 576

Val Ser Asn Tyr Ser Arg
1               5

<210> SEQ ID NO 577
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 577

Ala Tyr Glu Gln Val Met His Tyr Pro Gly Tyr Gly Ser Pro Met Pro
1               5                   10                  15

Gly Ser Leu Ala Met Gly Pro Val Thr Asn Lys
            20                  25

<210> SEQ ID NO 578
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 578

Glu Ala Ala Gly Ala Ala Gly Ser Gly Lys
1               5                   10

<210> SEQ ID NO 579
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 579

Met His Ser Ala Ser Ser Met Leu Gly Ala Val Lys

```
1               5                   10
```

<210> SEQ ID NO 580
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 580

```
Met Leu Thr Leu Ser Glu Ile Tyr Gln Trp Ile Met Asp Leu Phe Pro
1               5                   10                  15

Phe Tyr Arg
```

<210> SEQ ID NO 581
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 581

```
Ser Tyr Thr His Ala Lys Pro Pro Tyr Ser Tyr Ile Ser Leu Ile Thr
1               5                   10                  15

Met Ala Ile Gln Gln Ser Pro Asn Lys
            20                  25
```

<210> SEQ ID NO 582
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 582

```
Thr Gly Leu Asp Ala Ser Pro Leu Ala Ala Asp Thr Ser Tyr Tyr Gln
1               5                   10                  15

Gly Val Tyr Ser Arg Pro Ile Met Asn Ser Ser
            20                  25
```

<210> SEQ ID NO 583
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 583

```
Trp Gln Asn Ser Ile Arg
1               5
```

<210> SEQ ID NO 584
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 584

```
Ala Glu Tyr Leu Pro Pro Ser Val Ala Ser Ile Lys
1               5                   10
```

<210> SEQ ID NO 585
<211> LENGTH: 9
<212> TYPE: PRT

```
<213> ORGANISM: Artificial Sequence
<220> FEATURE:
<223> OTHER INFORMATION: Synthetic Polypeptide

<400> SEQUENCE: 585

Ala Pro Ser Pro Leu Gly Pro Thr Arg
1               5

<210> SEQ ID NO 586
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 586

Glu Leu Leu Ser Gly Ile Gly Asn Ile Ser Glu Arg
1               5                   10

<210> SEQ ID NO 587
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 587

Glu Pro Gly Ser Gln Pro Ala Gly Pro Ala Ser Leu Arg
1               5                   10

<210> SEQ ID NO 588
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 588

Ser Ala Pro Gly Asp Pro Asn Ala Leu Val Lys
1               5                   10

<210> SEQ ID NO 589
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 589

His Thr Leu Gly Asp Ser Asp Asn Glu Ser
1               5                   10

<210> SEQ ID NO 590
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 590

Asn Val Asn Gln Ser Leu Leu Glu Leu His Lys
1               5                   10

<210> SEQ ID NO 591
<211> LENGTH: 13
<212> TYPE: PRT
<213> ORGANISM: Artificial Sequence
```

<220> FEATURE:
<223> OTHER INFORMATION: Synthetic Polypeptide

<400> SEQUENCE: 591

Gln Asn Tyr His Gln Asp Ser Glu Ala Ala Ile Asn Arg
1               5                   10

<210> SEQ ID NO 592
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 592

Tyr Phe Leu His Gln Ser His Glu Glu Arg
1               5                   10

<210> SEQ ID NO 593
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 593

Ala Leu Phe Gln Asp Ile Lys
1               5

<210> SEQ ID NO 594
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 594

Asp Asp Val Ala Leu Glu Gly Val Ser His Phe Phe Arg
1               5                   10

<210> SEQ ID NO 595
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 595

Lys Pro Ala Glu Asp Glu Trp Gly Lys
1               5

<210> SEQ ID NO 596
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 596

Leu Gly Gly Pro Glu Ala Gly Leu Gly Glu Tyr Leu Phe Glu Arg
1               5                   10                  15

<210> SEQ ID NO 597
<211> LENGTH: 15
<212> TYPE: PRT
<213> ORGANISM: Artificial Sequence
<220> FEATURE:

<223> OTHER INFORMATION: Synthetic Polypeptide

<400> SEQUENCE: 597

Leu Asn Gln Ala Leu Leu Asp Leu His Ala Leu Gly Ser Ala Arg
1               5                   10                  15

<210> SEQ ID NO 598
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 598

Met Gly Asp His Leu Thr Asn Leu His Arg
1               5                   10

<210> SEQ ID NO 599
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 599

Gly Ala Leu Gln Asn Ile Ile Pro Ala Ser Thr Gly Ala Ala Lys
1               5                   10                  15

<210> SEQ ID NO 600
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 600

Leu Ile Ser Trp Tyr Asp Asn Glu Phe Gly Tyr Ser Asn Arg
1               5                   10

<210> SEQ ID NO 601
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 601

Leu Val Ile Asn Gly Asn Pro Ile Thr Ile Phe Gln Glu Arg
1               5                   10

<210> SEQ ID NO 602
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 602

Val Val Asp Leu Met Ala His Met Ala Ser Lys
1               5                   10

<210> SEQ ID NO 603
<211> LENGTH: 15
<212> TYPE: PRT
<213> ORGANISM: Artificial Sequence
<220> FEATURE:
<223> OTHER INFORMATION: Synthetic Polypeptide -continued

<400> SEQUENCE: 603

Asp Gly Leu Leu Pro Glu Asn Thr Phe Ile Val Gly Tyr Ala Arg
1               5                   10                  15

<210> SEQ ID NO 604
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 604

Gly Gly Tyr Phe Asp Glu Phe Gly Ile Ile Arg
1               5                   10

<210> SEQ ID NO 605
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 605

Ile Phe Thr Pro Leu Leu His Gln Ile Glu Leu Glu Lys Pro Lys Pro
1               5                   10                  15

Ile Pro Tyr Ile Tyr Gly Ser Arg
            20

<210> SEQ ID NO 606
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 606

Leu Pro Asp Ala Tyr Glu Arg
1               5

<210> SEQ ID NO 607
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 607

Asn Ser Tyr Val Ala Gly Gln Tyr Asp Asp Ala Ala Ser Tyr Gln Arg
1               5                   10                  15

<210> SEQ ID NO 608
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 608

Ala Val Leu His Val Ala Leu Arg
1               5

<210> SEQ ID NO 609
<211> LENGTH: 21
<212> TYPE: PRT
<213> ORGANISM: Artificial Sequence

```
<220> FEATURE:
<223> OTHER INFORMATION: Synthetic Polypeptide

<400> SEQUENCE: 609

Phe Asn His Phe Ser Leu Thr Leu Asn Thr Asn His Gly His Ile Leu
1               5                   10                  15

Val Asp Tyr Ser Lys
            20

<210> SEQ ID NO 610
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 610

Thr Leu Ala Gln Leu Asn Pro Glu Ser Ser Leu Phe Ile Ile Ala Ser
1               5                   10                  15

Lys

<210> SEQ ID NO 611
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 611

Val Asp His Gln Thr Gly Pro Ile Val Trp Gly Glu Pro Gly Thr Asn
1               5                   10                  15

Gly Gln His Ala Phe Tyr Gln Leu Ile His Gln Gly Thr Lys
            20                  25                  30

<210> SEQ ID NO 612
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 612

Val Phe Glu Gly Asn Arg Pro Thr Asn Ser Ile Val Phe Thr Lys
1               5                   10                  15

<210> SEQ ID NO 613
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 613

Ala Ala Pro Pro Ala Pro Asn Ala Pro Ala Ala Gly Glu Asp Thr Thr
1               5                   10                  15

Glu Thr Ala Pro Ala Pro Gly Thr Pro Ala Arg
            20                  25

<210> SEQ ID NO 614
<211> LENGTH: 19
<212> TYPE: PRT
<213> ORGANISM: Artificial Sequence
<220> FEATURE:
<223> OTHER INFORMATION: Synthetic Polypeptide
```

```
<400> SEQUENCE: 614

Ala Leu Glu Ala Val Ala Ser Val Thr Pro Thr Gly Pro Val Pro Asp
1               5                   10                  15

Pro Ala Arg

<210> SEQ ID NO 615
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 615

Leu Val Gln Phe Glu Gln Glu Ile Glu Arg
1               5                   10

<210> SEQ ID NO 616
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 616

Val Gly Asp Ser Ser Leu Leu Ile Phe Val Arg
1               5                   10

<210> SEQ ID NO 617
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 617

Val Ser Ser Pro Ser Pro Glu Leu Gly Thr Thr Pro Ala Ser Ile Phe
1               5                   10                  15

Arg

<210> SEQ ID NO 618
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 618

Glu Ile Ile Leu Val Asp Asp Tyr Ser Asn Asp Pro Glu Asp Gly Ala
1               5                   10                  15

Leu Leu Gly Lys
            20

<210> SEQ ID NO 619
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 619

Gly Gly Phe Asp Trp Asn Leu Val Phe Lys
1               5                   10

<210> SEQ ID NO 620
```

<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 620

Asn Phe Tyr Tyr Ala Ala Val Pro Ser Ala Arg
1               5                   10

<210> SEQ ID NO 621
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 621

Val Asp Leu Pro Ala Thr Ser Val Val Ile Thr Phe His Asn Glu Ala
1               5                   10                  15

Arg

<210> SEQ ID NO 622
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 622

Trp Tyr Leu Glu Asn Val Tyr Pro Glu Leu Arg
1               5                   10

<210> SEQ ID NO 623
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 623

Asp Gly Glu Ala Thr Leu Glu Val Asp Gly Thr Arg
1               5                   10

<210> SEQ ID NO 624
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 624

Glu Val Phe Glu Asn Asp Pro Glu Thr Asp Tyr Phe Tyr Pro Arg
1               5                   10                  15

<210> SEQ ID NO 625
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 625

Gly Gln Ser Glu Val Ser Ala Ala Gln Leu Gln Glu Arg
1               5                   10

```
<210> SEQ ID NO 626
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 626

Ile Ala Val Ala Gly Asp Leu Phe Gln Pro Glu Arg
1               5                   10

<210> SEQ ID NO 627
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 627

Ser Trp Asn Trp Leu Asn Gly Glu Asp Thr Thr Ile Gln Glu Thr Val
1               5                   10                  15
Lys

<210> SEQ ID NO 628
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 628

Ala Pro Glu Pro His Val Glu Glu Asp Asp Asp Glu Leu Asp Ser
1               5                   10                  15
Lys

<210> SEQ ID NO 629
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 629

Asp Ile Val Ser Gly Leu Lys
1               5

<210> SEQ ID NO 630
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 630

Leu Asn Tyr Lys Pro Pro Pro Gln Lys
1               5

<210> SEQ ID NO 631
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 631

Gln Asp His Leu Ser Trp Glu Trp Asn Leu Ser Ile Lys
```

<210> SEQ ID NO 632
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 632

Ser Phe Phe Thr Asp Asp Asp Lys
1               5

<210> SEQ ID NO 633
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 633

Thr Leu Leu Gly Asp Gly Pro Val Val Thr Asp Pro Lys
1               5                   10

<210> SEQ ID NO 634
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 634

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 635
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 635

Glu Pro Gly Leu Gln Ile Trp Arg
1               5

<210> SEQ ID NO 636
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 636

Phe Asp Leu Val Pro Val Pro Thr Asn Leu Tyr Gly Asp Phe Phe Thr
1               5                   10                  15

Gly Asp Ala Tyr Val Ile Leu Lys
            20

<210> SEQ ID NO 637
<211> LENGTH: 8
<212> TYPE: PRT
<213> ORGANISM: Artificial Sequence
<220> FEATURE:

<223> OTHER INFORMATION: Synthetic Polypeptide

<400> SEQUENCE: 637

Thr Ala Ser Asp Phe Ile Thr Lys
1               5

<210> SEQ ID NO 638
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 638

Thr Pro Ser Ala Ala Tyr Leu Trp Val Gly Thr Gly Ala Ser Glu Ala
1               5                   10                  15

Glu Lys

<210> SEQ ID NO 639
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 639

Asp Tyr Glu Ile Leu Phe Lys
1               5

<210> SEQ ID NO 640
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 640

Asn Leu Asp Gly Ile Ser His Ala Pro Asn Ala Val Lys
1               5                   10

<210> SEQ ID NO 641
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 641

Tyr Leu Glu Ser Ala Gly Ala Arg
1               5

<210> SEQ ID NO 642
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 642

Tyr Pro Val Tyr Gly Val Gln Trp His Pro Glu Lys
1               5                   10

<210> SEQ ID NO 643
<211> LENGTH: 9
<212> TYPE: PRT
<213> ORGANISM: Artificial Sequence

```
<220> FEATURE:
<223> OTHER INFORMATION: Synthetic Polypeptide

<400> SEQUENCE: 643

Tyr Tyr Ile Ala Ala Ser Tyr Val Lys
1               5

<210> SEQ ID NO 644
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 644

Phe Leu Ala Glu Leu Ala Tyr Asp Leu Asp Val Asp Asp Ala Pro Gly
1               5                   10                  15

Asn Ser Gln Gln Ala Thr Pro Lys
            20

<210> SEQ ID NO 645
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 645

Phe Leu Ile Ile Gln Asn Ala Ala Val Phe Gln Glu Ala Phe Glu Ile
1               5                   10                  15

Val Val Arg

<210> SEQ ID NO 646
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 646

Gly Pro Glu Pro Val Val Ser Gln Ile Ile Asp Lys
1               5                   10

<210> SEQ ID NO 647
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 647

Ile Phe Leu Gln Ala Leu Asn Leu Gly Ile Glu Val Ile Asn Thr Thr
1               5                   10                  15

Asp His Leu Lys
            20

<210> SEQ ID NO 648
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 648

Asn Gln Phe Asn Leu His Glu Leu Lys
```

```
<210> SEQ ID NO 649
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 649

Glu Leu Trp Ala Ala Leu Asn Ala Trp Lys
1               5                   10

<210> SEQ ID NO 650
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 650

Ala Ser Gln Gly Pro Pro Ser Ala Ile Ser Arg
1               5                   10

<210> SEQ ID NO 651
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 651

Glu Val Asn Tyr Glu Leu Val Thr Gly Lys
1               5                   10

<210> SEQ ID NO 652
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 652

Ile Leu Ser Glu Ser Leu Leu Thr Pro Ala Glu Tyr Gln Lys
1               5                   10

<210> SEQ ID NO 653
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 653

Thr Ala Leu Glu Gln Glu Leu Gly Leu Ala Ala Tyr Phe Val Ser Asn
1               5                   10                  15

Glu Val Pro Leu Glu Lys
            20

<210> SEQ ID NO 654
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 654
```

```
Thr Gly Ala Tyr Leu Gln Phe Leu Ser Val Leu Ser Arg
1               5                   10

<210> SEQ ID NO 655
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 655

Ala Gln His Asn Asp Ser Glu Gln Thr Gln Ser Pro Gln Gln Pro Gly
1               5                   10                  15

Ser Arg

<210> SEQ ID NO 656
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 656

Ala Leu Gly Asn Gln Gln Pro Ser Trp Asp Ser Glu Asp Ser Ser Asn
1               5                   10                  15

Phe Lys

<210> SEQ ID NO 657
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 657

Ala Val Pro Leu Pro Ala Gly Gly Gly Thr Val Leu Thr Lys
1               5                   10

<210> SEQ ID NO 658
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 658

Leu Ser Ala Pro Gly Ser Gln Arg
1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 659

Asn Leu Leu Gly Leu Ile Glu Ala Lys
1               5

<210> SEQ ID NO 660
<211> LENGTH: 7
<212> TYPE: PRT
<213> ORGANISM: Artificial Sequence
<220> FEATURE:
```

-continued

<223> OTHER INFORMATION: Synthetic Polypeptide

<400> SEQUENCE: 660

Asn Pro Gln Leu Asn Gln Gln
1               5

<210> SEQ ID NO 661
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 661

Gly Val Pro Gln Ile Glu Val Thr Phe Glu Ile Asp Val Asn Gly Ile
1               5                   10                  15

Leu Arg

<210> SEQ ID NO 662
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 662

Leu Thr Pro Glu Glu Ile Glu Arg
1               5

<210> SEQ ID NO 663
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 663

Leu Tyr Gly Ser Ala Gly Pro Pro Pro Thr Gly Glu Glu Asp Thr Ala
1               5                   10                  15

Glu Lys

<210> SEQ ID NO 664
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 664

Thr Trp Asn Asp Pro Ser Val Gln Gln Asp Ile Lys
1               5                   10

<210> SEQ ID NO 665
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 665

Val Tyr Glu Gly Glu Arg Pro Leu Thr Lys
1               5                   10

<210> SEQ ID NO 666
<211> LENGTH: 11

```
<212> TYPE: PRT
<213> ORGANISM: Artificial Sequence
<220> FEATURE:
<223> OTHER INFORMATION: Synthetic Polypeptide

<400> SEQUENCE: 666

Ile Ile Ile Gln Glu Ser Ala Leu Asp Tyr Arg
1               5                   10

<210> SEQ ID NO 667
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 667

Leu Asp Pro Ala Leu Gln Asp Lys
1               5

<210> SEQ ID NO 668
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 668

Leu Ile Ala Gln Asp Tyr Lys
1               5

<210> SEQ ID NO 669
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 669

Asn Asp Ile Asn Ile Leu Lys
1               5

<210> SEQ ID NO 670
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 670

Val Ala Glu Leu Ser Ser Asp Asp Phe His Leu Asp Arg
1               5                   10

<210> SEQ ID NO 671
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 671

Ala Phe Leu Ala Ser Pro Glu Tyr Val Asn Leu Pro Ile Asn Gly Asn
1               5                   10                  15

Gly Lys

<210> SEQ ID NO 672
```

-continued

```
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 672

Ala Leu Pro Gly Gln Leu Lys Pro Phe Glu Thr Leu Leu Ser Gln Asn
1               5                   10                  15

Gln Gly Gly Lys
            20

<210> SEQ ID NO 673
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 673

Glu Glu Val Val Thr Val Glu Thr Trp Gln Glu Gly Ser Leu Lys
1               5                   10                  15

<210> SEQ ID NO 674
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 674

Phe Gln Asp Gly Asp Leu Thr Leu Tyr Gln Ser Asn Thr Ile Leu Arg
1               5                   10                  15

<210> SEQ ID NO 675
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 675

Tyr Ile Ser Leu Ile Tyr Thr Asn Tyr Glu Ala Gly Lys
1               5                   10

<210> SEQ ID NO 676
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 676

Ala Gly Val Gln Gln Pro Val Tyr Ala Thr Ile Gly Ser Gly Ile Val
1               5                   10                  15

Asn Thr Ala Phe Thr Val Val Ser Leu Phe Val Val Glu Arg
            20                  25                  30

<210> SEQ ID NO 677
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 677
```

Gln Pro Ile Leu Ile Ala Val Val Leu Gln Leu Ser Gln Gln Leu Ser
1               5                   10                  15

Gly Ile Asn Ala Val Phe Tyr Tyr Ser Thr Ser Ile Phe Glu Lys
            20                  25                  30

<210> SEQ ID NO 678
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 678

Thr Phe Asp Glu Ile Ala Ser Gly Phe Arg
1               5                   10

<210> SEQ ID NO 679
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 679

Thr Pro Glu Glu Leu Phe His Pro Leu Gly Ala Asp Ser Gln Val
1               5                   10                  15

<210> SEQ ID NO 680
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 680

Val Ile Glu Glu Phe Tyr Asn Gln Thr Trp Val His Arg
1               5                   10

<210> SEQ ID NO 681
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 681

Ala Phe Glu Gly Gln Ala His Gly Ala Asp Arg
1               5                   10

<210> SEQ ID NO 682
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 682

Asp Ala Gly Val Gln Glu Pro Ile Tyr Ala Thr Ile Gly Ala Gly Val
1               5                   10                  15

Val Asn Thr Ile Phe Thr Val Ser Leu Phe Leu Val Glu Arg
            20                  25                  30

<210> SEQ ID NO 683
<211> LENGTH: 13
<212> TYPE: PRT
<213> ORGANISM: Artificial Sequence

```
<220> FEATURE:
<223> OTHER INFORMATION: Synthetic Polypeptide

<400> SEQUENCE: 683

Asp Gly Val Met Glu Met Asn Ser Ile Glu Pro Ala Lys
1               5                   10

<210> SEQ ID NO 684
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 684

Phe Leu Leu Ile Asn Arg
1               5

<210> SEQ ID NO 685
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 685

Leu Trp Gly Thr Gln Asp Val Ser Gln Asp Ile Gln Glu Met Lys
1               5                   10                  15

<210> SEQ ID NO 686
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 686

Gln Pro Ile Ile Ile Ser Ile Val Leu Gln Leu Ser Gln Gln Leu Ser
1               5                   10                  15

Gly Ile Asn Ala Val Phe Tyr Tyr Ser Thr Gly Ile Phe Lys
            20                  25                  30

<210> SEQ ID NO 687
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 687

Gln Val Thr Val Leu Glu Leu Phe Arg
1               5

<210> SEQ ID NO 688
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 688

Ser Val Glu Met Leu Ile Leu Gly Arg
1               5

<210> SEQ ID NO 689
<211> LENGTH: 7
```

```
<212> TYPE: PRT
<213> ORGANISM: Artificial Sequence
<220> FEATURE:
<223> OTHER INFORMATION: Synthetic Polypeptide

<400> SEQUENCE: 689

Thr Phe Glu Asp Ile Thr Arg
1               5

<210> SEQ ID NO 690
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 690

Val Thr Pro Ala Leu Ile Phe Ala Ile Thr Val Ala Thr Ile Gly Ser
1               5                   10                  15

Phe Gln Phe Gly Tyr Asn Thr Gly Val Ile Asn Ala Pro Glu Lys
            20                  25                  30

<210> SEQ ID NO 691
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 691

Ala Gly Leu Gln Phe Pro Val Gly Arg
1               5

<210> SEQ ID NO 692
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 692

His Leu Gln Leu Ala Ile Arg
1               5

<210> SEQ ID NO 693
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 693

Asn Asp Glu Glu Leu Asn Lys
1               5

<210> SEQ ID NO 694
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 694

Val Gly Ala Gly Ala Pro Val Tyr Leu Ala Ala Val Leu Glu Tyr Leu
1               5                   10                  15

Thr Ala Glu Ile Leu Glu Leu Ala Gly Asn Ala Ala Arg
```

20                  25

<210> SEQ ID NO 695
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 695

Gly Ala Leu Tyr Thr Gly Phe Ser Ile Leu Val Thr Leu Leu Ala
1               5                   10                  15

Gly Gln Ala Thr Thr Ala Tyr Phe Leu Tyr Gln Gln Gln Gly Arg
            20                  25                  30

<210> SEQ ID NO 696
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 696

Gly Ser Phe Pro Glu Asn Leu Arg
1               5

<210> SEQ ID NO 697
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 697

His Ser Leu Glu Gln Lys Pro Thr Asp Ala Pro Pro Lys
1               5                   10

<210> SEQ ID NO 698
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 698

Leu Pro Lys Pro Pro Lys Pro Val Ser Lys
1               5                   10

<210> SEQ ID NO 699
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 699

Leu Thr Val Thr Ser Gln Asn Leu Gln Leu Glu Asn Leu Arg
1               5                   10

<210> SEQ ID NO 700
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 700

```
Asp Tyr Glu Ala Trp Leu Gly Ile His Asp Val His Gly Arg
1               5                   10
```

<210> SEQ ID NO 701
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 701

```
Glu Ser Trp Val Leu Thr Ala Arg
1               5
```

<210> SEQ ID NO 702
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 702

```
His Ile Phe Trp Glu Pro Asp Ala Ser Lys
1               5                   10
```

<210> SEQ ID NO 703
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 703

```
Val Val Asn Gly Ile Pro Thr Arg
1               5
```

<210> SEQ ID NO 704
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 704

```
Trp Asp His Gln Thr Pro His Arg
1               5
```

<210> SEQ ID NO 705
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 705

```
Glu Glu Glu Glu Gly Ile Ser Gln Glu Ser Ser Glu Glu Glu Gln
1               5                   10                  15
```

<210> SEQ ID NO 706
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 706

```
Ser Ser Gln Pro Leu Ala Ser Lys
1               5
```

<210> SEQ ID NO 707
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 707

```
Phe Phe Ala Asp Leu Leu Asp Tyr Ile Lys
1               5                   10
```

<210> SEQ ID NO 708
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 708

```
Phe Val Val Gly Tyr Ala Leu Asp Tyr Asn Glu Tyr Phe Arg
1               5                   10
```

<210> SEQ ID NO 709
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 709

```
Asn Val Leu Ile Val Glu Asp Ile Ile Asp Thr Gly Lys
1               5                   10
```

<210> SEQ ID NO 710
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 710

```
Ser Val Gly Tyr Lys Pro Asp Phe Val Gly Phe Glu Ile Pro Asp Lys
1               5                   10                  15
```

<210> SEQ ID NO 711
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 711

```
Val Ile Gly Gly Asp Asp Leu Ser Thr Leu Thr Gly Lys
1               5                   10
```

<210> SEQ ID NO 712
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 712

```
Glu Asp Phe Leu Asn Pro Asp Val Leu Asp Ile Phe Ile Ser Ser Val
```

```
1               5                  10                 15

Gln Lys

<210> SEQ ID NO 713
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 713

Phe Leu Ile Leu Leu Gly Ser Pro Lys
1               5

<210> SEQ ID NO 714
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 714

Leu Pro Tyr Pro Phe Ser Asn Lys
1               5

<210> SEQ ID NO 715
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 715

Ser Val Gln Leu Asn Gly Leu Thr Leu Lys
1               5                  10

<210> SEQ ID NO 716
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 716

Tyr Leu Leu Arg Pro Leu Gly Pro His Gly Leu Leu Ser Lys
1               5                  10

<210> SEQ ID NO 717
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 717

Asp Tyr Ala Glu Val Gly Arg
1               5

<210> SEQ ID NO 718
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 718
```

```
Thr Glu Gly Asp Gly Val Tyr Thr Leu Asn Asn Glu Lys
1               5                   10

<210> SEQ ID NO 719
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 719

Val Gly Tyr Val Ser Gly Trp Gly Arg
1               5

<210> SEQ ID NO 720
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 720

Val Thr Ser Ile Gln Asp Trp Val Gln Lys
1               5                   10

<210> SEQ ID NO 721
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 721

Val Val Leu His Pro Asn Tyr Ser Gln Val Asp Ile Gly Leu Ile Lys
1               5                   10                  15

<210> SEQ ID NO 722
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 722

Asp Asn Ser Thr Met Gly Tyr Met Ala Ala Lys
1               5                   10

<210> SEQ ID NO 723
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 723

His Leu Glu Ile Asn Pro Asp His Ser Ile Ile Glu Thr Leu Arg
1               5                   10                  15

<210> SEQ ID NO 724
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 724

Ser Leu Thr Asn Asp Trp Glu Asp His Leu Ala Val Lys
1               5                   10
```

1               5                   10

<210> SEQ ID NO 725
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 725

Thr Leu Thr Ile Val Asp Thr Gly Ile Gly Met Thr Lys
1               5                   10

<210> SEQ ID NO 726
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 726

Ala Asp His Gly Glu Pro Ile Gly Arg
1               5

<210> SEQ ID NO 727
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 727

Asp Leu Val Val Leu Leu Phe Glu Thr Ala Leu Leu Ser Ser Gly Phe
1               5                   10                  15

Ser Leu Glu Asp Pro Gln Thr His Ser Asn Arg
            20                  25

<210> SEQ ID NO 728
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 728

Ile Asp Ile Ile Pro Asn Pro Gln Glu Arg
1               5                   10

<210> SEQ ID NO 729
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 729

Leu Gly Leu Gly Ile Asp Glu Asp Glu Val Ala Ala Glu Glu Pro Asn
1               5                   10                  15

Ala Ala Val Pro Asp Glu Ile Pro Pro Leu Glu Gly Asp Glu Asp Ala
            20                  25                  30

Ser Arg

<210> SEQ ID NO 730
<211> LENGTH: 15
<212> TYPE: PRT

```
<213> ORGANISM: Artificial Sequence
<220> FEATURE:
<223> OTHER INFORMATION: Synthetic Polypeptide

<400> SEQUENCE: 730

Asn Pro Asp Asp Ile Thr Gln Glu Glu Tyr Gly Glu Phe Tyr Lys
1               5                   10                  15

<210> SEQ ID NO 731
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 731

Ala Gln Leu Gly Gly Pro Glu Ala Ala Lys
1               5                   10

<210> SEQ ID NO 732
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 732

Asp Gly Val Val Glu Ile Thr Gly Lys
1               5

<210> SEQ ID NO 733
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 733

Gly Pro Ser Trp Asp Pro Phe Arg
1               5

<210> SEQ ID NO 734
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 734

Leu Ala Thr Gln Ser Asn Glu Ile Thr Ile Pro Val Thr Phe Glu Ser
1               5                   10                  15

Arg

<210> SEQ ID NO 735
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 735

Leu Phe Asp Gln Ala Phe Gly Leu Pro Arg
1               5                   10

<210> SEQ ID NO 736
<211> LENGTH: 9
```

```
<212> TYPE: PRT
<213> ORGANISM: Artificial Sequence
<220> FEATURE:
<223> OTHER INFORMATION: Synthetic Polypeptide

<400> SEQUENCE: 736

Gln Asp Glu His Gly Tyr Ile Ser Arg
1               5

<210> SEQ ID NO 737
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 737

Gln Leu Ser Ser Gly Val Ser Glu Ile Arg
1               5                   10

<210> SEQ ID NO 738
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 738

Val Pro Phe Ser Leu Leu Arg
1               5

<210> SEQ ID NO 739
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 739

Val Ser Leu Asp Val Asn His Phe Ala Pro Asp Glu Leu Thr Val Lys
1               5                   10                  15

<210> SEQ ID NO 740
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 740

Tyr Thr Leu Pro Pro Gly Val Asp Pro Thr Gln Val Ser Ser Ser Leu
1               5                   10                  15

Ser Pro Glu Gly Thr Leu Thr Val Glu Ala Pro Met Pro Lys
            20                  25                  30

<210> SEQ ID NO 741
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 741

Leu His Arg Pro Pro Val Ile Val Leu Gln Arg
1               5                   10
```

```
<210> SEQ ID NO 742
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 742

Leu Pro Val Leu Leu Leu Gly Arg
1               5

<210> SEQ ID NO 743
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 743

Ser Ser Glu Leu Arg Pro Gly Glu Phe Val Val Ala Ile Gly Ser Pro
1               5                   10                  15

Phe Ser Leu Gln Asn Thr Val Thr Thr Gly Ile Val Ser Thr Thr Gln
            20                  25                  30

Arg

<210> SEQ ID NO 744
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 744

Val Thr Ala Gly Ile Ser Phe Ala Ile Pro Ser Asp Lys
1               5                   10

<210> SEQ ID NO 745
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 745

Tyr Asn Phe Ile Ala Asp Val Val Glu Lys
1               5                   10

<210> SEQ ID NO 746
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 746

Asp Phe Asn Pro Thr Ala Thr Val Lys
1               5

<210> SEQ ID NO 747
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 747
```

```
Phe Leu Leu Ser Glu Ser Gly Ser Gly Lys
1               5                   10
```

<210> SEQ ID NO 748
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 748

```
His Ile Asp Leu Val Glu Gly Asp Glu Gly Arg
1               5                   10
```

<210> SEQ ID NO 749
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 749

```
Leu Val Asp Glu Tyr Ser Leu Asn Ala Gly Lys
1               5                   10
```

<210> SEQ ID NO 750
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 750

```
Ser Ala Asn Leu Val Ala Ala Thr Leu Gly Ala Ile Leu Asn Arg
1               5                   10                  15
```

<210> SEQ ID NO 751
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 751

```
His Pro Asp Trp Pro Pro Asp Arg
1               5
```

<210> SEQ ID NO 752
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 752

```
Asn Asp Gln Leu Ala Trp Leu Trp Ala Glu Ser Thr Ala Leu Phe Pro
1               5                   10                  15

Ser Val Tyr Leu Asp Glu Thr Leu Ala Ser Ser Arg
            20                  25
```

<210> SEQ ID NO 753
<211> LENGTH: 30
<212> TYPE: PRT
<213> ORGANISM: Artificial Sequence
<220> FEATURE:
<223> OTHER INFORMATION: Synthetic Polypeptide

```
<400> SEQUENCE: 753

Gln Ala Ala Gly Gly Ala Ser Glu Ala Trp Ala Gly Ser His Leu Thr
1               5                   10                  15

Ser Leu Leu Ala Leu Ala Ala Leu Ala Phe Thr Trp Thr Leu
            20                  25                  30

<210> SEQ ID NO 754
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 754

Thr Gln Glu Ser Ala Gly Leu Ala Val Ile Asp Trp Glu Asp Trp Arg
1               5                   10                  15

Pro Val Trp Val Arg
            20

<210> SEQ ID NO 755
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 755

Val Pro Leu Asp Leu Asn Ala Phe Asp Val Gln Ala Ser Pro Asn Glu
1               5                   10                  15

Gly Phe Val Asn Gln Asn Ile Thr Ile Phe Tyr Arg
            20                  25

<210> SEQ ID NO 756
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 756

Phe Phe Gly Asp Ser Ala Ala Ser Met Ala Ile Lys
1               5                   10

<210> SEQ ID NO 757
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 757

Phe Pro Glu His Glu Leu Thr Phe Asp Pro Gln Arg
1               5                   10

<210> SEQ ID NO 758
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 758

Leu Ala Gly Leu Phe Asn Glu Gln Arg
1               5
```

```
<210> SEQ ID NO 759
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 759

Leu Gly Asn Thr Ile Ser Ser Leu Phe Gly Gly Gly Thr Thr Pro Asp
1               5                   10                  15

Ala Lys

<210> SEQ ID NO 760
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 760

Leu Pro Ala Thr Glu Lys Pro Val Leu Leu Ser Lys
1               5                   10

<210> SEQ ID NO 761
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 761

Val Ala Ile Val Lys Pro Gly Val Pro Met Glu Ile Val Leu Asn Lys
1               5                   10                  15

<210> SEQ ID NO 762
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 762

Ala Glu Val Leu Phe Arg
1               5

<210> SEQ ID NO 763
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 763

Glu Leu Ala Val Phe Arg
1               5

<210> SEQ ID NO 764
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 764

His Gly Leu Tyr Asn Leu Lys
1               5
```

```
<210> SEQ ID NO 765
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 765

Leu Ile Gln Gly Ala Pro Thr Ile Arg
1               5

<210> SEQ ID NO 766
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 766

Val Thr Glu Gln His Arg
1               5

<210> SEQ ID NO 767
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 767

Ala Tyr Leu Leu Pro Ala Pro Pro Ala Pro Gly Asn Ala Ser Glu Ser
1               5                   10                  15

Glu Glu Asp Arg
            20

<210> SEQ ID NO 768
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 768

Phe His Pro Leu His Ser Lys
1               5

<210> SEQ ID NO 769
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 769

Phe Leu Asn Val Leu Ser Pro Arg
1               5

<210> SEQ ID NO 770
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 770
```

Ser Ala Gly Ser Val Glu Ser Pro Ser Val Ser Thr His Arg
1               5                   10                  15

<210> SEQ ID NO 771
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 771

Tyr Gly Gln Pro Leu Pro Gly Tyr Thr Thr Lys
1               5                   10

<210> SEQ ID NO 772
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 772

Ala Ser Val Ser Val Thr Ala Glu Asp Glu Gly Thr Gln Arg
1               5                   10

<210> SEQ ID NO 773
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 773

Asp Gly Thr Phe Pro Leu Pro Ile Gly Glu Ser Val Thr Val Thr Arg
1               5                   10                  15

<210> SEQ ID NO 774
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 774

Leu Asn Pro Thr Val Thr Tyr Gly Asn Asp Ser Phe Ser Ala Lys
1               5                   10                  15

<210> SEQ ID NO 775
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 775

Thr Phe Leu Thr Val Tyr Trp Thr Pro Glu Arg
1               5                   10

<210> SEQ ID NO 776
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 776

Val Glu Leu Ala Pro Leu Pro Ser Trp Gln Pro Val Gly Lys

```
1               5                   10
```

<210> SEQ ID NO 777
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 777

```
Ala Asp Gln Glu Gly Ala Arg
1               5
```

<210> SEQ ID NO 778
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 778

```
Glu Glu Ser Thr Tyr Leu Pro Leu Thr Ser Met Gln Pro Thr Glu Ala
1               5                   10                  15

Met Gly Glu Glu Pro Ser Arg
            20
```

<210> SEQ ID NO 779
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 779

```
Gly Asn Pro Tyr Pro Glu Leu Arg
1               5
```

<210> SEQ ID NO 780
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 780

```
Ile Ala Leu Glu Thr Ser Leu Ser Lys
1               5
```

<210> SEQ ID NO 781
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 781

```
Gln Pro Ala Val Glu Glu Pro Ala Glu Val Thr Ala Thr Val Leu Ala
1               5                   10                  15

Ser Arg
```

<210> SEQ ID NO 782
<211> LENGTH: 20
<212> TYPE: PRT
<213> ORGANISM: Artificial Sequence
<220> FEATURE:
<223> OTHER INFORMATION: Synthetic Polypeptide

```
<400> SEQUENCE: 782

Thr Glu Leu Asp Met Gln Pro Gln Gly Leu Gly Leu Phe Val Asn Thr
1               5                   10                  15

Ser Ala Pro Arg
            20

<210> SEQ ID NO 783
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 783

Thr Phe Val Leu Pro Val Thr Pro Pro Arg
1               5                   10

<210> SEQ ID NO 784
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 784

Val Glu Leu Ala Pro Leu Pro Pro Trp Gln Pro Val Gly Gln Asn Phe
1               5                   10                  15

Thr Leu Arg

<210> SEQ ID NO 785
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 785

Val Gln Val Thr Leu Asp Gly Val Pro Ala Ala Ala Pro Gly Gln Pro
1               5                   10                  15

Ala Gln Leu Gln Leu Asn Ala Thr Glu Ser Asp Asp Gly Arg
            20                  25                  30

<210> SEQ ID NO 786
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 786

Ala Thr Asp Phe Val Ala Asp Arg
1               5

<210> SEQ ID NO 787
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 787

Asp Ile Phe Gln Glu Ile Phe Asp Lys
1               5
```

<210> SEQ ID NO 788
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 788

Ile Ile Trp Gln Phe Ile Lys
1               5

<210> SEQ ID NO 789
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 789

Leu Ile Leu Pro His Val Asp Ile Gln Leu Lys
1               5                   10

<210> SEQ ID NO 790
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 790

Tyr Phe Asp Leu Gly Leu Pro Asn Arg
1               5

<210> SEQ ID NO 791
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 791

Gly Ile Tyr Ala Tyr Gly Phe Glu Lys Pro Ser Ala Ile Gln Gln Arg
1               5                   10                  15

<210> SEQ ID NO 792
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 792

Gly Tyr Asp Val Ile Ala Gln Ala Gln Ser Gly Thr Gly Lys
1               5                   10

<210> SEQ ID NO 793
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 793

Leu Gln Met Glu Ala Pro His Ile Ile Val Gly Thr Pro Gly Arg
1               5                   10                  15

```
<210> SEQ ID NO 794
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 794

Met Phe Val Leu Asp Glu Ala Asp Glu Met Leu Ser Arg
1               5                   10

<210> SEQ ID NO 795
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 795

Val Phe Asp Met Leu Asn Arg
1               5

<210> SEQ ID NO 796
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 796

Val Leu Ile Thr Thr Asp Leu Leu Ala Arg
1               5                   10

<210> SEQ ID NO 797
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 797

Glu Gly Thr Glu Ala Ser Leu Gln Ile Arg
1               5                   10

<210> SEQ ID NO 798
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 798

Ile Ser Ser Leu Pro Thr Gln Leu Phe Lys
1               5                   10

<210> SEQ ID NO 799
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 799

Thr His Pro Gly Gly Glu Gln Lys
1               5

<210> SEQ ID NO 800
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 800

Tyr Gln Pro Pro Ser Thr Asn Lys
1               5

<210> SEQ ID NO 801
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 801

Leu Glu Pro Leu Val Asn Asp Leu Thr Leu Arg
1               5                   10

<210> SEQ ID NO 802
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 802

Leu Glu Thr Asn Glu Phe Gln Gln Leu Gln Ser Lys
1               5                   10

<210> SEQ ID NO 803
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 803

Asn Ile Gly Asp Leu Leu Ser Ser Ile Asp Arg
1               5                   10

<210> SEQ ID NO 804
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 804

Ser Ser Gly Gly Gly Gly Trp Ala Asp Pro Arg
1               5                   10

<210> SEQ ID NO 805
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 805

Thr Val Thr Phe Ala Asn Asp Leu Lys Pro Lys
1               5                   10

<210> SEQ ID NO 806
<211> LENGTH: 23
```

```
<212> TYPE: PRT
<213> ORGANISM: Artificial Sequence
<220> FEATURE:
<223> OTHER INFORMATION: Synthetic Polypeptide

<400> SEQUENCE: 806

Phe Ile Asp Asn Thr Leu Tyr Phe Ile Ala Glu Asp Glu Asn Leu
1               5                   10                  15
Glu Ser Asp Tyr Phe Gly Lys
            20

<210> SEQ ID NO 807
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 807

Ser Asp Ile Ile Phe Phe Gln Arg
1               5

<210> SEQ ID NO 808
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 808

Ser Val Pro Gly His Asp Asn Lys
1               5

<210> SEQ ID NO 809
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 809

Asp His Gln Glu Pro Asn Pro Lys
1               5

<210> SEQ ID NO 810
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 810

Asn Leu Leu Ala Phe Tyr Val Asp Arg
1               5

<210> SEQ ID NO 811
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 811

Gln Glu Ala Thr Asn Ala Thr Arg
1               5
```

-continued

```
<210> SEQ ID NO 812
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 812

Ser Leu Gly Glu Leu Asp Val Phe Leu Ala Trp Ile Asn Lys
1               5                   10

<210> SEQ ID NO 813
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 813

Val Ile His Asp Asn Tyr Asp Gln Leu Glu Val His Ala Ala Ala Ile
1               5                   10                  15

Lys

<210> SEQ ID NO 814
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 814

Glu Ala Ser Leu Ala Asp Asn Asn Thr Asp Val Arg
1               5                   10

<210> SEQ ID NO 815
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 815

Gln Val Leu Asn Phe Thr Leu Glu Glu Val Leu Phe Pro Gln Ser Asp
1               5                   10                  15

Arg

<210> SEQ ID NO 816
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 816

Ser Asn Phe Gln Gln Pro Tyr Ile Thr Asn Arg
1               5                   10

<210> SEQ ID NO 817
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 817

Glu Glu Leu Thr Pro Gln Lys
```

-continued

```
1               5

<210> SEQ ID NO 818
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 818

Glu Gly Tyr Leu Glu Thr Val Ala Ala Tyr Tyr Glu Glu Gln His Pro
1               5                   10                  15

Glu Leu Thr Pro Leu Leu Glu Lys
            20

<210> SEQ ID NO 819
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 819

Leu Gln Thr Trp Trp His Gly Val Leu Ala Trp Val Lys
1               5                   10

<210> SEQ ID NO 820
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 820

Val Val Ala Leu Val His Ala Val Gln Ala Leu Trp Lys
1               5                   10

<210> SEQ ID NO 821
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 821

Ser Leu Glu Glu Asn Lys
1               5

<210> SEQ ID NO 822
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 822

Glu Asn Trp Val Gln Arg
1               5

<210> SEQ ID NO 823
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 823
```

```
Thr Tyr Ser Lys Pro Phe His Pro Lys
1               5
```

<210> SEQ ID NO 824
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 824

```
Glu Ala Thr Thr Asn Ala Pro Phe Arg
1               5
```

<210> SEQ ID NO 825
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 825

```
Leu Glu Glu Ser Tyr Thr Leu Asn Ser Asp Leu Ala Arg
1               5                   10
```

<210> SEQ ID NO 826
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 826

```
Leu His Glu Trp Thr Lys Pro Glu Asn Leu Asp Phe Ile Glu Val Asn
1               5                   10                  15

Val Ser Leu Pro Arg
            20
```

<210> SEQ ID NO 827
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 827

```
Thr Phe His Phe Asn Thr Val Glu Glu Val His Ser Arg
1               5                   10
```

<210> SEQ ID NO 828
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 828

```
Thr Tyr Asn Phe Leu Pro Glu Phe Leu Val Ser Thr Gln Lys
1               5                   10
```

<210> SEQ ID NO 829
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 829

Gly Asp Asp Thr Pro Leu His Leu Ala Ala Ser His Gly His Arg
1               5                   10                  15

<210> SEQ ID NO 830
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 830

His Ser Gly Ile Asp Phe Lys
1               5

<210> SEQ ID NO 831
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 831

Leu Asn Glu Asn His Ser Gly Glu Leu Trp Lys
1               5                   10

<210> SEQ ID NO 832
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 832

Gln Leu Asn Phe Leu Thr Lys
1               5

<210> SEQ ID NO 833
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 833

Trp Gln Gly Asn Asp Ile Val Val Lys
1               5

<210> SEQ ID NO 834
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 834

Ala Glu Val Trp Leu Phe Leu Lys
1               5

<210> SEQ ID NO 835
<211> LENGTH: 10
<212> TYPE: PRT
<213> ORGANISM: Artificial Sequence
<220> FEATURE:
<223> OTHER INFORMATION: Synthetic Polypeptide

```
<400> SEQUENCE: 835

Glu Gly Ser Asp Leu Ser Val Val Glu Arg
1               5                   10

<210> SEQ ID NO 836
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 836

Gly His Ser Pro Phe Ala Asn Leu Lys
1               5

<210> SEQ ID NO 837
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 837

His Pro Gln Gly Ser Leu Asp Thr Gly Glu Glu Ala Glu Glu Val Gly
1               5                   10                  15

Leu Lys

<210> SEQ ID NO 838
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 838

Ser Glu Leu Leu Leu Ser Glu Lys
1               5

<210> SEQ ID NO 839
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 839

Ala Leu Pro Gly Thr Pro Val Ala Ser Ser Gln Pro Arg
1               5                   10

<210> SEQ ID NO 840
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 840

Glu Val Pro Leu Leu Gln Ser Leu Trp Leu Ala His Asn Glu Ile Arg
1               5                   10                  15

<210> SEQ ID NO 841
<211> LENGTH: 10
<212> TYPE: PRT
<213> ORGANISM: Artificial Sequence
<220> FEATURE:
<223> OTHER INFORMATION: Synthetic Polypeptide
```

<400> SEQUENCE: 841

Leu Pro Gly Leu Pro Glu Gly Ala Phe Arg
1               5                   10

<210> SEQ ID NO 842
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 842

Ser Leu Asp Leu Ser His Asn Leu Ile Ser Asp Phe Ala Trp Ser Asp
1               5                   10                  15

Leu His Asn Leu Ser Ala Leu Gln Leu Leu Lys
            20                  25

<210> SEQ ID NO 843
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 843

Thr Val Ala Ala Gly Ala Leu Ala Ser Leu Ser His Leu Lys
1               5                   10

<210> SEQ ID NO 844
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 844

Asp Leu Asp Gly Asn Gly Tyr Pro Asp Leu Ile Val Gly Ser Phe Gly
1               5                   10                  15

Val Asp Lys

<210> SEQ ID NO 845
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 845

Leu Leu Glu Ser Ser Leu Ser Ser Ser Glu Gly Glu Glu Pro Val Glu
1               5                   10                  15

Tyr Lys

<210> SEQ ID NO 846
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 846

Ser Leu Gln Trp Phe Gly Ala Thr Val Arg
1               5                   10

```
<210> SEQ ID NO 847
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 847

Ser Ser Ala Ser Ser Gly Pro Gln Ile Leu Lys
1               5                   10

<210> SEQ ID NO 848
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 848

Val Thr Ala Pro Pro Glu Ala Glu Tyr Ser Gly Leu Val Arg
1               5                   10

<210> SEQ ID NO 849
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 849

Leu Phe Thr Ala Leu Phe Pro Phe Glu Lys
1               5                   10

<210> SEQ ID NO 850
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 850

Ser Leu Pro Ile Ser Leu Val Phe Leu Val Pro Val Arg
1               5                   10

<210> SEQ ID NO 851
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 851

Ser Leu Val Lys Pro Ile Thr Gln Leu Leu Gly Arg
1               5                   10

<210> SEQ ID NO 852
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 852

Val Gln Ser Leu Val Leu Gly Ala Pro Arg
1               5                   10

<210> SEQ ID NO 853
```

```
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 853

Tyr Val Ile Gly Val Gly Asp Ala Phe Arg
1               5                   10

<210> SEQ ID NO 854
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 854

Ala Leu Val Gln Thr Glu Asp His Leu Leu Phe Leu Gln Gln Leu
1               5                   10                  15

Ala Gly Lys

<210> SEQ ID NO 855
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 855

Phe Asn Val Glu Asp Gly Glu Ile Val Gln Gln Val Arg
1               5                   10

<210> SEQ ID NO 856
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 856

His Leu Leu Ile Gly Leu Pro Ser Gly Ala Ile Leu Ser Leu Pro Lys
1               5                   10                  15

<210> SEQ ID NO 857
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 857

Leu Phe Gly Ile Glu Ser Ser Ser Gly Thr Ile Leu Trp Lys
1               5                   10

<210> SEQ ID NO 858
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 858

Val Leu Leu Leu Ile Asp Asp Glu Tyr Lys
1               5                   10
```

```
<210> SEQ ID NO 859
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 859

Asp Trp Ser His Tyr Phe Lys
1               5

<210> SEQ ID NO 860
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 860

Gly Leu Gln Ala Gln Ile Ala Ser Ser Gly Leu Thr Val Glu Val Asp
1               5                   10                  15

Ala Pro Lys

<210> SEQ ID NO 861
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 861

Leu Ala Ser Tyr Leu Asp Arg
1               5

<210> SEQ ID NO 862
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 862

Leu Gln Leu Glu Thr Glu Ile Glu Ala Leu Lys
1               5                   10

<210> SEQ ID NO 863
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 863

Val Val Ser Glu Thr Asn Asp Thr Lys
1               5

<210> SEQ ID NO 864
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 864

Ala Pro Ser Ile His Gly Gly Ser Gly Gly Arg
1               5                   10
```

<210> SEQ ID NO 865
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 865

Phe Gly Ala Gln Leu Ala His Ile Gln Ala Leu Ile Ser Gly Ile Glu
1               5                   10                  15

Ala Gln Leu Gly Asp Val Arg
            20

<210> SEQ ID NO 866
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 866

Phe Gly Pro Gly Val Ala Phe Arg
1               5

<210> SEQ ID NO 867
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 867

Gly Gln Val Gly Gly Gln Val Ser Val Glu Val Asp Ser Ala Pro Gly
1               5                   10                  15

Thr Asp Leu Ala Lys
            20

<210> SEQ ID NO 868
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 868

Ser Leu Leu Glu Gly Gln Glu Asp His Tyr Asn Asn Leu Ser Ala Ser
1               5                   10                  15

Lys

<210> SEQ ID NO 869
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 869

Ile Ser Ser Ser Ser Phe Ser Arg
1               5

<210> SEQ ID NO 870
<211> LENGTH: 9
<212> TYPE: PRT
<213> ORGANISM: Artificial Sequence
<220> FEATURE:

<223> OTHER INFORMATION: Synthetic Polypeptide

<400> SEQUENCE: 870

Leu Gln Ala Glu Ile Glu Gly Leu Lys
1               5

<210> SEQ ID NO 871
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 871

Ser Tyr Thr Ser Gly Pro Gly Ser Arg
1               5

<210> SEQ ID NO 872
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 872

Trp Ser Leu Leu Gln Gln Gln Lys
1               5

<210> SEQ ID NO 873
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 873

Tyr Glu Glu Leu Gln Ser Leu Ala Gly Lys
1               5                   10

<210> SEQ ID NO 874
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 874

Ile Asn Ser Val Gly Ser Thr Ala Ser Ser Gln Pro Leu Leu Val
1               5                   10                  15

His Asp Asp Val
            20

<210> SEQ ID NO 875
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 875

Leu Val Val Gln Ser Ser Ile Asp Ser Ser Ala Phe Lys
1               5                   10

<210> SEQ ID NO 876
<211> LENGTH: 10
<212> TYPE: PRT

```
<213> ORGANISM: Artificial Sequence
<220> FEATURE:
<223> OTHER INFORMATION: Synthetic Polypeptide

<400> SEQUENCE: 876

Gln Ala Thr Leu Thr Ile Ser Ser Ala Arg
1               5                   10

<210> SEQ ID NO 877
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 877

Thr Ser Ala Tyr Phe Asn Phe Ala Phe Lys
1               5                   10

<210> SEQ ID NO 878
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 878

Tyr Val Ser Glu Leu His Leu Thr Arg
1               5

<210> SEQ ID NO 879
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 879

Glu Val Glu Val Ile Gly Gly Ala Asp Lys
1               5                   10

<210> SEQ ID NO 880
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 880

Lys Pro Phe Gly Ala Ile Leu Asn Leu Val Pro Leu Ala Glu Ser Val
1               5                   10                  15

Val Lys

<210> SEQ ID NO 881
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 881

Ile Leu Gln Leu Ile Leu Leu Ala Leu Ala Thr Gly Leu Val Gly Gly
1               5                   10                  15

Glu Thr Arg
```

```
<210> SEQ ID NO 882
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 882

Leu Pro His Thr Leu Arg
1               5

<210> SEQ ID NO 883
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 883

Thr Ala Thr Glu Ser Phe Pro His Pro Gly Phe Asn Asn Ser Leu Pro
1               5                   10                  15

Asn Lys

<210> SEQ ID NO 884
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 884

Tyr Ile Val His Leu Gly Gln His Asn Leu Gln Lys
1               5                   10

<210> SEQ ID NO 885
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 885

Val Glu Ala Gly Glu Gln Val Arg
1               5

<210> SEQ ID NO 886
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 886

Val Ser Gly Trp Gly Thr Thr Thr Ser Pro Gln Val Asn Tyr Pro Lys
1               5                   10                  15

<210> SEQ ID NO 887
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 887

Tyr Val Leu Trp Ile Arg
1               5
```

```
<210> SEQ ID NO 888
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 888

Gln Val Thr His Pro Asn Tyr Asn Ser Arg
1               5                   10

<210> SEQ ID NO 889
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 889

Val Leu Gly Ser Gly Thr Trp Pro Ser Ala Pro Lys
1               5                   10

<210> SEQ ID NO 890
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 890

Val Ser Gly Trp Gly Thr Ile Ser Ser Pro Ile Ala Arg
1               5                   10

<210> SEQ ID NO 891
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 891

Glu Ser Ser Gln Glu Gln Ser Ser Val Val Arg
1               5                   10

<210> SEQ ID NO 892
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 892

Leu Ser Glu Leu Ile Gln Pro Leu Pro Leu Glu Arg
1               5                   10

<210> SEQ ID NO 893
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 893

Tyr Thr Asn Trp Ile Gln Lys
1               5
```

```
<210> SEQ ID NO 894
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 894

Asp Phe Val Gln Pro Pro Thr Lys
1               5

<210> SEQ ID NO 895
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 895

Asp Ile Pro Thr Asn Ser Pro Glu Leu Glu Glu Thr Leu Thr His Thr
1               5                   10                  15

Ile Thr Lys

<210> SEQ ID NO 896
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 896

Gly His Gly Leu Gly His Gly His Glu Gln Gln His Gly Leu Gly His
1               5                   10                  15

Gly His Lys

<210> SEQ ID NO 897
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 897

Leu Asp Asp Asp Leu Glu His Gln Gly Gly His Val Leu Asp His Gly
1               5                   10                  15

His Lys

<210> SEQ ID NO 898
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 898

Thr Val Gly Ser Asp Thr Phe Tyr Ser Phe Lys
1               5                   10

<210> SEQ ID NO 899
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 899
```

Ala Pro Ile Ile Ala Val Thr Arg
1               5

<210> SEQ ID NO 900
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 900

Asp Pro Val Gln Glu Ala Trp Ala Glu Asp Val Asp Leu Arg
1               5                   10

<210> SEQ ID NO 901
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 901

Gly Asp Tyr Pro Leu Glu Ala Val Arg
1               5

<210> SEQ ID NO 902
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 902

Ile Tyr Val Asp Asp Gly Leu Ile Ser Leu Gln Val Lys
1               5                   10

<210> SEQ ID NO 903
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 903

Leu Asp Ile Asp Ser Pro Pro Ile Thr Ala Arg
1               5                   10

<210> SEQ ID NO 904
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 904

Asp Ala Leu Glu Ser Thr Leu Ala Glu Thr Glu Ala Arg
1               5                   10

<210> SEQ ID NO 905
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 905

```
Leu Asn Val Glu Val Asp Ala Ala Pro Pro Val Asp Leu Asn Arg
1               5                   10                  15
```

<210> SEQ ID NO 906
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 906

```
Leu Pro Ser Leu Ser Pro Val Ala Arg
1               5
```

<210> SEQ ID NO 907
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 907

```
Leu Val Val Glu Ile Asp Asn Ala Lys
1               5
```

<210> SEQ ID NO 908
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 908

```
Tyr Glu Thr Glu Val Ser Leu Arg
1               5
```

<210> SEQ ID NO 909
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 909

```
Asp Thr Glu Gln Thr Leu Tyr Gln Val Gln Glu Arg
1               5                   10
```

<210> SEQ ID NO 910
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 910

```
Ile Gln Gly Thr Leu Gln Pro His Ala Arg
1               5                   10
```

<210> SEQ ID NO 911
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 911

```
Ser Leu Ala Asp Val Asp Ala Ile Leu Ala Arg
```

-continued

```
1               5                   10

<210> SEQ ID NO 912
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 912

Thr Gly Gly Ser Ala Gln Pro Glu Thr Pro Tyr Ser Gly Pro Gly Leu
1               5                   10                  15

Leu Ile Asp Ser Leu Val Leu Leu Pro Arg
            20                  25

<210> SEQ ID NO 913
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 913

Val Leu Glu Leu Ser Ile Pro Ala Ser Ala Glu Gln Ile Gln His Leu
1               5                   10                  15

Ala Gly Ala Ile Ala Glu Arg
            20

<210> SEQ ID NO 914
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 914

Asp Gln Leu Ile Tyr Asn Leu Leu Lys
1               5

<210> SEQ ID NO 915
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 915

Phe Ile Ile Pro Asn Val Val Lys
1               5

<210> SEQ ID NO 916
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 916

Leu Leu Ile Val Ser Asn Pro Val Asp Ile Leu Thr Tyr Val Ala Trp
1               5                   10                  15

Lys

<210> SEQ ID NO 917
<211> LENGTH: 9
<212> TYPE: PRT
```

-continued

```
<213> ORGANISM: Artificial Sequence
<220> FEATURE:
<223> OTHER INFORMATION: Synthetic Polypeptide

<400> SEQUENCE: 917

Leu Val Ile Ile Thr Ala Gly Ala Arg
1               5

<210> SEQ ID NO 918
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 918

Thr Leu His Pro Asp Leu Gly Thr Asp Lys
1               5                   10

<210> SEQ ID NO 919
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 919

Asp Tyr Ser Val Thr Ala Asn Ser Lys
1               5

<210> SEQ ID NO 920
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 920

Phe Ile Ile Pro Gln Ile Val Lys
1               5

<210> SEQ ID NO 921
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 921

Gly Leu Thr Ser Val Ile Asn Gln Lys
1               5

<210> SEQ ID NO 922
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 922

Leu Ile Ala Pro Val Ala Glu Glu Glu Ala Thr Val Pro Asn Asn Lys
1               5                   10                  15

<210> SEQ ID NO 923
<211> LENGTH: 6
<212> TYPE: PRT
<213> ORGANISM: Artificial Sequence
```

```
<220> FEATURE:
<223> OTHER INFORMATION: Synthetic Polypeptide

<400> SEQUENCE: 923

Asn Val Asn Val Phe Lys
1               5

<210> SEQ ID NO 924
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 924

Asp Gly Gly Ala Trp Gly Thr Glu Gln Arg
1               5                   10

<210> SEQ ID NO 925
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 925

Gly Glu Val Ala Pro Asp Ala Lys
1               5

<210> SEQ ID NO 926
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 926

Leu Pro Asp Gly Tyr Glu Phe Lys
1               5

<210> SEQ ID NO 927
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 927

Ser Phe Val Leu Asn Leu Gly Lys
1               5

<210> SEQ ID NO 928
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 928

Gly Asn Asp Val Ala Phe His Phe Asn Pro Arg
1               5                   10

<210> SEQ ID NO 929
<211> LENGTH: 7
<212> TYPE: PRT
<213> ORGANISM: Artificial Sequence
<220> FEATURE:
```

<223> OTHER INFORMATION: Synthetic Polypeptide

<400> SEQUENCE: 929

Ile Ala Leu Asp Phe Gln Arg
1               5

<210> SEQ ID NO 930
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 930

Ile Gln Val Leu Val Glu Pro Asp His Phe Lys
1               5                   10

<210> SEQ ID NO 931
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 931

Leu Asp Asn Asn Trp Gly Arg
1               5

<210> SEQ ID NO 932
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 932

Val Ala Val Asn Asp Ala His Leu Leu Gln Tyr Asn His Arg
1               5                   10

<210> SEQ ID NO 933
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 933

Phe Ala Val Asn Phe Gln Thr Gly Phe Ser Gly Asn Asp Ile Ala Phe
1               5                   10                  15

His Phe Asn Pro Arg
            20

<210> SEQ ID NO 934
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 934

Phe Asp Glu Asn Ala Val Val Arg
1               5

<210> SEQ ID NO 935
<211> LENGTH: 13
<212> TYPE: PRT

<213> ORGANISM: Artificial Sequence
<220> FEATURE:
<223> OTHER INFORMATION: Synthetic Polypeptide

<400> SEQUENCE: 935

Asn Thr Gln Ile Asp Asn Ser Trp Gly Ser Glu Glu Arg
1               5                   10

<210> SEQ ID NO 936
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 936

Ser Ile Leu Leu Ser Gly Thr Val Leu Pro Ser Ala Gln Arg
1               5                   10

<210> SEQ ID NO 937
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 937

Val Ala Val Asp Gly Gln His Leu Phe Glu Tyr Tyr His Arg
1               5                   10

<210> SEQ ID NO 938
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 938

Ala Ser His Glu Glu Val Glu Gly Leu Val Glu Lys
1               5                   10

<210> SEQ ID NO 939
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 939

Ala Val Asp Thr Trp Ser Trp Gly Glu Arg
1               5                   10

<210> SEQ ID NO 940
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 940

Ser Thr His Thr Leu Asp Leu Ser Arg
1               5

<210> SEQ ID NO 941
<211> LENGTH: 6
<212> TYPE: PRT
<213> ORGANISM: Artificial Sequence

```
<220> FEATURE:
<223> OTHER INFORMATION: Synthetic Polypeptide

<400> SEQUENCE: 941

Val Glu Ile Phe Tyr Arg
1               5

<210> SEQ ID NO 942
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 942

Tyr Ser Ser Asp Tyr Phe Gln Ala Pro Ser Asp Tyr Arg
1               5                   10

<210> SEQ ID NO 943
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 943

Ala Gln Leu Ala Pro Ser Ala Thr Lys
1               5

<210> SEQ ID NO 944
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 944

Leu Glu Glu Trp Leu Ser His Val Val Gly Ala Val Tyr Ala Pro Lys
1               5                   10                  15

<210> SEQ ID NO 945
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 945

Leu Asn Val Ala Leu Asp Val Gly Ile Pro Leu Pro Lys
1               5                   10

<210> SEQ ID NO 946
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 946

Ser Val Ala Gly Asp Ile Ile Asp Phe Pro Lys
1               5                   10

<210> SEQ ID NO 947
<211> LENGTH: 24
<212> TYPE: PRT
<213> ORGANISM: Artificial Sequence
<220> FEATURE:
```

```
<223> OTHER INFORMATION: Synthetic Polypeptide

<400> SEQUENCE: 947

Val Leu Asn Ile Asn Phe Ser Asn Ser Val Leu Glu Ile Val Glu Asn
1               5                   10                  15
Ala Val Val Leu Thr Val Ala Ser
            20

<210> SEQ ID NO 948
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 948

Gly Leu Leu Pro Asn Leu Val Asp Asn Leu Val Asn Arg
1               5                   10

<210> SEQ ID NO 949
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 949

Ile Leu Asn Ile Asp Phe Ser Asn Ala Asp Ile Asp Val Leu Glu Asp
1               5                   10                  15
Leu Leu Val Leu Ser Ala
            20

<210> SEQ ID NO 950
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 950

Ile Val Glu Leu Thr Leu Pro Arg
1               5

<210> SEQ ID NO 951
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 951

Leu Leu Pro Gly Val Gly Val Tyr Leu Ser Leu Tyr Thr Arg
1               5                   10

<210> SEQ ID NO 952
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 952

Tyr Gly Glu Ile Leu Glu Ser Glu Gly Ser Ile Arg
1               5                   10
```

```
<210> SEQ ID NO 953
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 953

Asp Ala Gly Ile Glu Pro Gly Pro Asp Thr Tyr Leu Ala Leu Leu Asn
1               5                   10                  15

Ala Tyr Ala Glu Lys
            20

<210> SEQ ID NO 954
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 954

Asn Val Gln Gly Ile Ile Glu Ile Leu Lys
1               5                   10

<210> SEQ ID NO 955
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 955

Ser Gly Gly Leu Gly Gly Ser His Ala Leu Leu Leu Leu Arg
1               5                   10

<210> SEQ ID NO 956
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 956

Thr Val Leu Asp Gln Gln Gln Thr Pro Ser Arg
1               5                   10

<210> SEQ ID NO 957
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 957

Thr Val Gln Leu Thr Ser Ser Glu Leu Glu Ser Thr Leu Glu Thr Leu
1               5                   10                  15

Lys

<210> SEQ ID NO 958
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 958
```

```
Ala Ala Leu Ser Gly Ala Asn Val Leu Thr Leu Ile Glu Lys
1               5                   10
```

<210> SEQ ID NO 959
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 959

```
Thr Val Leu Trp Pro Asn Gly Leu Ser Leu Asp Ile Pro Ala Gly Arg
1               5                   10                  15
```

<210> SEQ ID NO 960
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 960

```
Val Phe Phe Thr Asp Tyr Gly Gln Ile Pro Lys
1               5                   10
```

<210> SEQ ID NO 961
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 961

```
Leu Pro Ser Gly Leu Pro Val Ser Leu Leu Thr Leu Tyr Leu Asp Asn
1               5                   10                  15

Asn Lys
```

<210> SEQ ID NO 962
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 962

```
Asn Ile Pro Thr Val Asn Glu Asn Leu Glu Asn Tyr Tyr Leu Glu Val
1               5                   10                  15

Asn Gln Leu Glu Lys
            20
```

<210> SEQ ID NO 963
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 963

```
Asn Asn Gln Ile Asp His Ile Asp Glu Lys
1               5                   10
```

<210> SEQ ID NO 964
<211> LENGTH: 11
<212> TYPE: PRT
<213> ORGANISM: Artificial Sequence
<220> FEATURE:

<223> OTHER INFORMATION: Synthetic Polypeptide

<400> SEQUENCE: 964

Ser Leu Glu Asp Leu Gln Leu Thr His Asn Lys
1               5                   10

<210> SEQ ID NO 965
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 965

Ser Leu Glu Tyr Leu Asp Leu Ser Phe Asn Gln Ile Ala Arg
1               5                   10

<210> SEQ ID NO 966
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 966

Asp Pro Glu Asp Ser Gln Arg
1               5

<210> SEQ ID NO 967
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 967

Thr Asp Glu Gly Asp Asn Arg
1               5

<210> SEQ ID NO 968
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 968

Val Trp Thr Asp Ala Asn Leu Thr Ala Arg
1               5                   10

<210> SEQ ID NO 969
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 969

Asn Trp Ala Pro Gly Glu Pro Asn Asn Arg
1               5                   10

<210> SEQ ID NO 970
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 970

Gln Pro Gln Asn Gly Ser Val Arg
1               5

<210> SEQ ID NO 971
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 971

Tyr Thr His Leu Val Ala Ile Gln Asn Lys
1               5                  10

<210> SEQ ID NO 972
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 972

Glu Val Ala Ala Trp Thr Tyr His Tyr Ser Thr Lys
1               5                  10

<210> SEQ ID NO 973
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 973

Asn Glu Ile Asp Tyr Leu Asn Lys
1               5

<210> SEQ ID NO 974
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 974

Tyr Thr Asp Leu Val Ala Ile Gln Asn Lys
1               5                  10

<210> SEQ ID NO 975
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 975

His Trp Phe Gln Ala Gly Tyr Ser Thr Ser Arg
1               5                  10

<210> SEQ ID NO 976
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 976

Asn Gln Gly Thr Ser Asp Phe Leu Pro Ser Arg Pro Arg
1               5                   10

<210> SEQ ID NO 977
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 977

Thr Pro Ile Leu Leu Ile Arg
1               5

<210> SEQ ID NO 978
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 978

Val Ser Val Asn Pro Ser Tyr Leu Val Pro Glu Ser Asp Tyr Thr Asn
1               5                   10                  15

Asn Val Val Arg
            20

<210> SEQ ID NO 979
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 979

Tyr Arg Pro Gly Tyr Gly Thr Gly Tyr Phe Gln Tyr Gly Leu Pro Asp
1               5                   10                  15

Leu Val Ala Asp Pro Tyr Tyr Ile Gln Ala Ser Thr Tyr Val Gln Lys
            20                  25                  30

<210> SEQ ID NO 980
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 980

Gly Gly Pro Gln Gln Pro His Asn Lys
1               5

<210> SEQ ID NO 981
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 981

Leu Asn Leu Thr Ser Arg
1               5

<210> SEQ ID NO 982
<211> LENGTH: 11

```
<212> TYPE: PRT
<213> ORGANISM: Artificial Sequence
<220> FEATURE:
<223> OTHER INFORMATION: Synthetic Polypeptide

<400> SEQUENCE: 982

Leu Thr Gly Gly Ala Ala Gly His Gln Asp Arg
1               5                   10

<210> SEQ ID NO 983
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 983

Ser Asn Ser Gly Gln Tyr Pro Ala Lys
1               5

<210> SEQ ID NO 984
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 984

Thr Tyr Phe Ser Pro Arg
1               5

<210> SEQ ID NO 985
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 985

Glu Ala Ala Leu Leu Glu Glu Glu Glu Gly Val
1               5                   10

<210> SEQ ID NO 986
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 986

Ile Ala Tyr Pro Ser Leu Arg
1               5

<210> SEQ ID NO 987
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 987

Gln Pro Asn Glu Gly Ser Ser Ser Gln Glu Glu Glu Gly Pro Ser Thr
1               5                   10                  15

Ser Pro Asp Ala Glu Ser Leu Phe Arg
            20                  25
```

```
<210> SEQ ID NO 988
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 988

Val Leu Glu His Val Val Arg
1               5

<210> SEQ ID NO 989
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 989

Tyr Glu Phe Leu Trp Gly Pro Arg
1               5

<210> SEQ ID NO 990
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 990

Ala Pro Glu Pro Ile Ser Thr Gln Ser His Ser Val Leu Ile Leu Phe
1               5                   10                  15

His Ser Asp Asn Ser Gly Glu Asn Arg
            20                  25

<210> SEQ ID NO 991
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 991

Ala Pro Gly Glu Leu Glu His Gly Leu Ile Thr Phe Ser Thr Arg
1               5                   10                  15

<210> SEQ ID NO 992
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 992

Asp Ser Asp Leu Leu Ser Pro Ser Asp Phe Lys
1               5                   10

<210> SEQ ID NO 993
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 993

Ser Asp Glu Asn Glu Gln His Leu Gly Val Lys
1               5                   10
```

<210> SEQ ID NO 994
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 994

Thr Gly Val Ile Thr Ser Pro Asp Phe Pro Asn Pro Tyr Pro Lys
1               5                   10                  15

<210> SEQ ID NO 995
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 995

Glu Ser Ala Phe Glu Phe Leu Ser Ser Ala
1               5                   10

<210> SEQ ID NO 996
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 996

Gly Glu Phe Val Thr Thr Val Gln Gln Arg
1               5                   10

<210> SEQ ID NO 997
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 997

Leu Gly Val Thr Ala Asn Asp Val Lys
1               5

<210> SEQ ID NO 998
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 998

Asn Val Ile Ile Trp Gly Asn His Ser Ser Thr Gln Tyr Pro Asp Val
1               5                   10                  15

Asn His Ala Lys
            20

<210> SEQ ID NO 999
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 999

```
Val Leu Val Thr Gly Ala Ala Gly Gln Ile Ala Tyr Ser Leu Leu Tyr
1               5                  10                 15

Ser Ile Gly Asn Gly Ser Val Phe Gly Lys
            20                  25
```

<210> SEQ ID NO 1000
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1000

```
Leu Thr Leu Tyr Asp Ile Ala His Thr Pro Gly Val Ala Ala Asp Leu
1               5                  10                 15

Ser His Ile Glu Thr Lys
            20
```

<210> SEQ ID NO 1001
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1001

```
Val Ala Val Leu Gly Ala Ser Gly Gly Ile Gly Gln Pro Leu Ser Leu
1               5                  10                 15

Leu Leu Lys
```

<210> SEQ ID NO 1002
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1002

```
Val Asp Phe Pro Gln Asp Gln Leu Thr Ala Leu Thr Gly Arg
1               5                  10
```

<210> SEQ ID NO 1003
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1003

```
Val Asn Val Pro Val Ile Gly Gly His Ala Gly Lys
1               5                  10
```

<210> SEQ ID NO 1004
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1004

```
Val Ser Ser Phe Glu Glu Lys
1               5
```

<210> SEQ ID NO 1005
<211> LENGTH: 7

```
<212> TYPE: PRT
<213> ORGANISM: Artificial Sequence
<220> FEATURE:
<223> OTHER INFORMATION: Synthetic Polypeptide

<400> SEQUENCE: 1005

Ile Gly Gly Ala Gln Asn Arg
1               5

<210> SEQ ID NO 1006
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1006

His Glu Val His Phe Leu His Glu Glu Ser Ile Leu Glu Arg
1               5                   10

<210> SEQ ID NO 1007
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1007

His Phe Thr Glu Asp Gly Asn Ile Leu Gln Leu Ala Asn Leu Pro Asp
1               5                   10                  15

Leu Tyr Lys

<210> SEQ ID NO 1008
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1008

Leu Gln Ser Phe Glu Asp Leu Ala Ser Ile Ser Thr Tyr Gly Phe Arg
1               5                   10                  15

<210> SEQ ID NO 1009
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1009

Thr Leu Pro Asn Ala Ser Thr Val Asp Asn Ile Arg
1               5                   10

<210> SEQ ID NO 1010
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1010

Trp Thr Val Glu His Ile Val Tyr Lys
1               5

<210> SEQ ID NO 1011
```

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1011

Asp Gly Phe Phe Tyr Phe Phe His Gly Thr Arg
1               5                   10

<210> SEQ ID NO 1012
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1012

Asp Ile Tyr Ser Ser Phe Gly Phe Pro Arg
1               5                   10

<210> SEQ ID NO 1013
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1013

Ile Glu Asn Tyr Thr Pro Asp Leu Pro Arg
1               5                   10

<210> SEQ ID NO 1014
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1014

Leu Thr Phe Asp Ala Ile Thr Thr Ile Arg
1               5                   10

<210> SEQ ID NO 1015
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1015

Ser Gln Asn Pro Val Gln Pro Ile Gly Pro Gln Thr Pro Lys
1               5                   10

<210> SEQ ID NO 1016
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1016

Phe Pro Val His Ala Ala Leu Val Trp Gly Pro Glu Lys
1               5                   10

<210> SEQ ID NO 1017
<211> LENGTH: 11
```

```
<212> TYPE: PRT
<213> ORGANISM: Artificial Sequence
<220> FEATURE:
<223> OTHER INFORMATION: Synthetic Polypeptide

<400> SEQUENCE: 1017

Phe Pro Trp Gln Leu Val Gln Glu Gln Val Arg
1               5                   10

<210> SEQ ID NO 1018
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1018

Gly Gly Gln Leu Gln Pro Gly Tyr Pro Ala Leu Ala Ser Arg
1               5                   10

<210> SEQ ID NO 1019
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1019

Gly Val Pro Ser Glu Ile Asp Ala Ala Phe Gln Asp Ala Asp Gly Tyr
1               5                   10                  15

Ala Tyr Phe Leu Arg
            20

<210> SEQ ID NO 1020
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1020

Val Trp Ser Asp Val Thr Pro Leu Thr Phe Thr Glu Val His Glu Gly
1               5                   10                  15

Arg

<210> SEQ ID NO 1021
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1021

Phe Leu Leu Ile Leu Leu Leu Gln Ala Thr Ala Ser Gly Ala Leu Pro
1               5                   10                  15

Leu Asn Ser Ser Thr Ser Leu Glu Lys
            20                  25

<210> SEQ ID NO 1022
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1022
```

```
Gly Ile Gln Ser Leu Tyr Gly Asp Pro Lys
1               5                   10

<210> SEQ ID NO 1023
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1023

Ile Asp Ala Val Phe Tyr Ser Lys
1               5

<210> SEQ ID NO 1024
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1024

Thr Ser Val Asn Leu Ile Ser Ser Leu Trp Pro Thr Leu Pro Ser Gly
1               5                   10                  15

Ile Glu Ala Ala Tyr Glu Ile Glu Ala Arg
            20                  25

<210> SEQ ID NO 1025
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1025

Tyr Tyr Tyr Phe Phe Gln Gly Ser Asn Gln Phe Glu Tyr Asp Phe Leu
1               5                   10                  15

Leu Gln Arg

<210> SEQ ID NO 1026
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1026

Ala Val Asp Ser Glu Tyr Pro Lys
1               5

<210> SEQ ID NO 1027
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1027

Phe Asn Glu Glu Leu Arg
1               5

<210> SEQ ID NO 1028
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 1028

Phe Tyr Gly Leu Gln Val Thr Gly Lys
1               5

<210> SEQ ID NO 1029
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1029

His Trp Val Phe Asp Glu Ala Ser Leu Glu Pro Gly Tyr Pro Lys
1               5                   10                  15

<210> SEQ ID NO 1030
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1030

Val Trp Glu Ser Ala Thr Pro Leu Arg
1               5

<210> SEQ ID NO 1031
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1031

Ala Phe Gln Val Trp Ser Asp Val Thr Pro Leu Arg
1               5                   10

<210> SEQ ID NO 1032
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1032

Ile Asp Ala Val Tyr Glu Ala Pro Gln Glu Glu Lys
1               5                   10

<210> SEQ ID NO 1033
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1033

Ile Ile Gly Tyr Thr Pro Asp Leu Asp Pro Glu Thr Val Asp Asp Ala
1               5                   10                  15

Phe Ala Arg

<210> SEQ ID NO 1034
<211> LENGTH: 29
<212> TYPE: PRT
```

<213> ORGANISM: Artificial Sequence
<220> FEATURE:
<223> OTHER INFORMATION: Synthetic Polypeptide

<400> SEQUENCE: 1034

Leu Ile Ala Asp Ala Trp Asn Ala Ile Pro Asp Asn Leu Asp Ala Val
1               5                   10                  15

Val Asp Leu Gln Gly Gly Gly His Ser Tyr Phe Phe Lys
            20                  25

<210> SEQ ID NO 1035
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1035

Gln Asp Ile Val Phe Asp Gly Ile Ala Gln Ile Arg
1               5                   10

<210> SEQ ID NO 1036
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1036

Asp Ser Ile Tyr Asn Ala Val Ser Ile Trp Ser Asn Val Thr Pro Leu
1               5                   10                  15

Ile Phe Gln Gln Val Gln Asn Gly Asp Ala Asp Ile Lys
            20                  25

<210> SEQ ID NO 1037
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1037

His Thr Leu Thr Tyr Arg
1               5

<210> SEQ ID NO 1038
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1038

Ile Gln His Leu Tyr Gly Glu Lys
1               5

<210> SEQ ID NO 1039
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1039

Thr Phe Gln Leu Ser Ala Asp Asp Ile Gln Arg
1               5                   10

<210> SEQ ID NO 1040
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1040

Asp Leu Pro His Ile Thr Val Asp Arg
1               5

<210> SEQ ID NO 1041
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1041

Ile Val Ser Tyr Thr Arg
1               5

<210> SEQ ID NO 1042
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1042

Leu Ser Gln Asp Asp Ile Lys
1               5

<210> SEQ ID NO 1043
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1043

Asn Ala Asn Ser Leu Glu Ala Lys
1               5

<210> SEQ ID NO 1044
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1044

Ala Phe Ala Leu Trp Ser Ala Val Thr Pro Leu Thr Phe Thr Arg
1               5                   10                  15

<210> SEQ ID NO 1045
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1045

Ala Val Ile Asp Asp Ala Phe Ala Arg
1               5

<210> SEQ ID NO 1046
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1046

Phe Gln Thr Phe Glu Gly Asp Leu Lys
1               5

<210> SEQ ID NO 1047
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1047

Leu Gly Leu Gly Ala Asp Val Ala Gln Val Thr Gly Ala Leu Arg
1               5                   10                  15

<210> SEQ ID NO 1048
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1048

Ser Leu Gly Pro Ala Leu Leu Leu Leu Gln Lys
1               5                   10

<210> SEQ ID NO 1049
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1049

Glu Gln Ile Leu Gly Asp Glu Ala Arg
1               5

<210> SEQ ID NO 1050
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1050

Ser Leu Ala Ala Ser Ser Ser Phe Tyr Gly Gln Arg
1               5                   10

<210> SEQ ID NO 1051
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1051

Thr Leu Pro Ser Gly Leu Asp Asp Tyr Pro Arg
1               5                   10

```
<210> SEQ ID NO 1052
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1052

Val Asp Pro Ala Leu Phe Pro Pro Val Pro Leu Phe Thr Ala Val Pro
1               5                   10                  15

Ser Arg

<210> SEQ ID NO 1053
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1053

Val Pro Pro Glu Phe Leu Val Gln Arg
1               5

<210> SEQ ID NO 1054
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1054

Phe Leu His Gln Asp Ile Asp Ser Gly Gln Gly Ile Arg
1               5                   10

<210> SEQ ID NO 1055
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1055

Gly His Gln Ala Phe Asp Val Gly Gln Pro Arg
1               5                   10

<210> SEQ ID NO 1056
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1056

Thr Tyr His Ser Val Gly Asp Ser Val Leu Arg
1               5                   10

<210> SEQ ID NO 1057
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1057

Val Pro Ile Asp Gly Pro Pro Ile Asp Ile Gly Arg
1               5                   10
```

<210> SEQ ID NO 1058
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1058

```
Tyr Val Asp Gln Val Leu Gln Leu Val Tyr Lys
1               5                   10
```

<210> SEQ ID NO 1059
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1059

```
Ala Asp Gly Ala Leu Thr Gln Glu Glu Lys
1               5                   10
```

<210> SEQ ID NO 1060
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1060

```
Asp Phe Glu Ile Ile Ser Asp Thr Lys
1               5
```

<210> SEQ ID NO 1061
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1061

```
Gly Val Val Ala Glu Phe Asp Ser Pro Ala Asn Leu Ile Ala Ala Arg
1               5                   10                  15
```

<210> SEQ ID NO 1062
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1062

```
Ile Asp Gly Leu Asn Val Ala Asp Ile Gly Leu His Asp Leu Arg
1               5                   10                  15
```

<210> SEQ ID NO 1063
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1063

```
Asn Val Asp Pro Asn Pro Tyr Pro Glu Thr Ser Ala Gly Phe Leu Ser
1               5                   10                  15

Arg
```

<210> SEQ ID NO 1064
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1064

Glu Gly Thr Ile Asn Val His Asp Val Glu Thr Gln Phe Asn Gln Tyr
1               5                   10                  15

Lys

<210> SEQ ID NO 1065
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1065

Gln Gly Gly Phe Leu Gly Leu Ser Asn Ile Lys
1               5                   10

<210> SEQ ID NO 1066
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1066

Ser Ser Val Pro Ser Ser Thr Glu Lys
1               5

<210> SEQ ID NO 1067
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1067

Val Ser Ala Gly Asn Gly Gly Ser Ser Leu Ser Tyr Thr Asn Pro Ala
1               5                   10                  15

Val Ala Ala Thr Ser Ala Asn Leu
            20

<210> SEQ ID NO 1068
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1068

Tyr Val Pro Pro Ser Ser Thr Asp Arg
1               5

<210> SEQ ID NO 1069
<211> LENGTH: 19
<212> TYPE: PRT
<213> ORGANISM: Artificial Sequence
<220> FEATURE:
<223> OTHER INFORMATION: Synthetic Polypeptide

```
<400> SEQUENCE: 1069

Ala Leu Phe Ser Ser Asn Leu Asp Pro Ser Leu Val Glu Gln Val Phe
1               5                   10                  15

Leu Asp Lys

<210> SEQ ID NO 1070
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1070

Asp Ser Leu Tyr Val Asn Gly Phe Asn Pro Arg
1               5                   10

<210> SEQ ID NO 1071
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1071

Leu Thr Leu Leu Arg Pro Glu Lys
1               5

<210> SEQ ID NO 1072
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1072

Val Leu Gln Gly Leu Leu Thr Pro Leu Phe Arg
1               5                   10

<210> SEQ ID NO 1073
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1073

Val Pro Thr Gly Thr Ile Thr Glu Val Ser Ser Thr Gly Val Asn Ser
1               5                   10                  15

Ser Ser Lys

<210> SEQ ID NO 1074
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1074

Phe Leu Asn Ser Asn Ser Gly Leu Gln Gly Leu Gln Phe Tyr Arg
1               5                   10                  15

<210> SEQ ID NO 1075
<211> LENGTH: 10
<212> TYPE: PRT
<213> ORGANISM: Artificial Sequence
```

```
<220> FEATURE:
<223> OTHER INFORMATION: Synthetic Polypeptide

<400> SEQUENCE: 1075

Ile Gly Leu Ala Ser Ala Leu Gln Pro Arg
1               5                   10

<210> SEQ ID NO 1076
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1076

Asn Asp Val Val Phe Gln Pro Ile Ser Gly Glu Asp Val Arg
1               5                   10

<210> SEQ ID NO 1077
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1077

Ser Leu Glu Pro Phe Thr Leu Glu Ile Leu Ala Arg
1               5                   10

<210> SEQ ID NO 1078
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1078

Ser Thr Ala Ala Pro Ile Pro Ile Leu Pro Glu Arg
1               5                   10

<210> SEQ ID NO 1079
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1079

Ala Val Thr Leu Ser Leu Asp Gly Gly Asp Thr Ala Ile Arg
1               5                   10

<210> SEQ ID NO 1080
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1080

Leu Thr Asp Pro Asn Ser Ala Phe Ser Arg
1               5                   10

<210> SEQ ID NO 1081
<211> LENGTH: 11
<212> TYPE: PRT
<213> ORGANISM: Artificial Sequence
<220> FEATURE:
```

```
<223> OTHER INFORMATION: Synthetic Polypeptide

<400> SEQUENCE: 1081

Leu Thr Pro Leu Gln Phe Gly Asn Leu Gln Lys
1               5                   10

<210> SEQ ID NO 1082
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1082

Ser Val Val Gly Asp Ala Leu Glu Phe Gly Asn Ser Trp Lys
1               5                   10

<210> SEQ ID NO 1083
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1083

Thr Gly Leu Leu Val Glu Gln Ser Gly Asp Tyr Ile Lys
1               5                   10

<210> SEQ ID NO 1084
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1084

Trp Val Gly Asp Leu Pro Asn Gly Arg
1               5

<210> SEQ ID NO 1085
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1085

Glu His Phe Gln Asp Asp Val Phe Asn Glu Lys
1               5                   10

<210> SEQ ID NO 1086
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1086

Gly Asp Leu Glu Glu Tyr Gly Gln Asp Leu Leu His Thr Val Phe Lys
1               5                   10                  15

<210> SEQ ID NO 1087
<211> LENGTH: 21
<212> TYPE: PRT
<213> ORGANISM: Artificial Sequence
<220> FEATURE:
<223> OTHER INFORMATION: Synthetic Polypeptide
```

```
-continued

<400> SEQUENCE: 1087

Ser Thr Gln Ala Pro Leu Ile Ile Arg Pro Asp Ser Gly Asn Pro Leu
1               5                   10                  15

Asp Thr Val Leu Lys
            20

<210> SEQ ID NO 1088
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1088

Tyr Asp Gly His Leu Pro Ile Glu Ile Lys
1               5                   10

<210> SEQ ID NO 1089
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1089

Tyr Leu Leu Glu Thr Ser Gly Asn Leu Asp Gly Leu Glu Tyr Lys
1               5                   10                  15

<210> SEQ ID NO 1090
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1090

Ala Ser Ser Ser Phe Gln Ala Asn Gly Thr Lys
1               5                   10

<210> SEQ ID NO 1091
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1091

Phe Ala Ile Gln Tyr Gly Thr Gly Arg
1               5

<210> SEQ ID NO 1092
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1092

Gly Ala Asp Leu Gly Trp Gly Glu Thr Ala Gln Ala Gln Phe Pro Gly
1               5                   10                  15

<210> SEQ ID NO 1093
<211> LENGTH: 19
<212> TYPE: PRT
<213> ORGANISM: Artificial Sequence
```

<220> FEATURE:
<223> OTHER INFORMATION: Synthetic Polypeptide

<400> SEQUENCE: 1093

Leu Gly Ala Pro Ser Pro Gly Asp Lys Pro Ile Phe Val Pro Leu Ser
1               5                   10                  15

Asn Tyr Arg

<210> SEQ ID NO 1094
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1094

Val Asp Gly Ile Leu Ser Glu Asp Lys
1               5

<210> SEQ ID NO 1095
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1095

Ala Glu Ala Leu Phe Asp Phe Thr Gly Asn Ser Lys
1               5                   10

<210> SEQ ID NO 1096
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1096

Asp Ala Glu Gly Asp Leu Val Arg
1               5

<210> SEQ ID NO 1097
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1097

Asp Ile Ala Val Glu Glu Asp Leu Ser Ser Thr Pro Leu Leu Lys
1               5                   10                  15

<210> SEQ ID NO 1098
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1098

Gly Ala Thr Gly Ile Phe Pro Leu Ser Phe Val Lys
1               5                   10

<210> SEQ ID NO 1099
<211> LENGTH: 11
<212> TYPE: PRT

```
<213> ORGANISM: Artificial Sequence
<220> FEATURE:
<223> OTHER INFORMATION: Synthetic Polypeptide

<400> SEQUENCE: 1099

Ser Val Ser Pro Gln Gly Asn Ser Val Asp Arg
1               5                   10

<210> SEQ ID NO 1100
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1100

Asp Arg Pro Phe Phe Ala Gly Leu Val Lys
1               5                   10

<210> SEQ ID NO 1101
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1101

Glu His Tyr Val Asp Leu Lys
1               5

<210> SEQ ID NO 1102
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1102

Asn Ile Ile His Gly Ser Asp Ser Val Glu Ser Ala Glu Lys
1               5                   10

<210> SEQ ID NO 1103
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1103

Thr Phe Ile Ala Ile Lys Pro Asp Gly Val Gln Arg
1               5                   10

<210> SEQ ID NO 1104
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1104

Ala Ser Glu Glu His Leu Lys
1               5

<210> SEQ ID NO 1105
<211> LENGTH: 10
<212> TYPE: PRT
<213> ORGANISM: Artificial Sequence
```

-continued

```
<220> FEATURE:
<223> OTHER INFORMATION: Synthetic Polypeptide

<400> SEQUENCE: 1105

Asp Arg Pro Phe Phe Pro Gly Leu Val Lys
1               5                   10

<210> SEQ ID NO 1106
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1106

Glu Ile Ser Leu Trp Phe Lys Pro Glu Glu Leu Val Asp Tyr Lys
1               5                   10                  15

<210> SEQ ID NO 1107
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1107

Asn Ile Ile His Gly Ser Asp Ser Val Lys
1               5                   10

<210> SEQ ID NO 1108
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1108

Phe Glu Ala Pro Leu Phe Asn Ala Arg
1               5

<210> SEQ ID NO 1109
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1109

Ile Leu Gln Asp Ile Ala Ser Gly Ser His Pro Phe Ser Gln Val Leu
1               5                   10                  15

Lys

<210> SEQ ID NO 1110
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1110

Leu Val Asn Gln Gln Leu Leu Ala Asp Pro Leu Val Pro Pro Gln Leu
1               5                   10                  15

Thr Ile Lys

<210> SEQ ID NO 1111
```

```
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1111

Asn Asp Gly Ala Ala Ile Leu Ala Ala Val Ser Ser Ile Ala Gln Lys
1               5                   10                  15

<210> SEQ ID NO 1112
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1112

Ser Ala Thr Tyr Val Asn Thr Glu Gly Arg
1               5                   10

<210> SEQ ID NO 1113
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1113

Glu Pro Ala Val Ile Gly Arg Pro Asp Phe Glu His Ala Val Glu Ala
1               5                   10                  15

Ser Lys

<210> SEQ ID NO 1114
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1114

Gly Phe Thr Pro Val Val Asp Asp Pro Val Thr Glu Arg
1               5                   10

<210> SEQ ID NO 1115
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1115

Gly Asn Ala Val Leu Gln Ser Gln Val Lys
1               5                   10

<210> SEQ ID NO 1116
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1116

Asn Ile Gly Ala Phe Ile Ser Glu Ala Lys
1               5                   10
```

```
<210> SEQ ID NO 1117
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1117

Thr Asp Pro Gly Ser Ile Phe Asp Leu Asp Pro Leu Glu Asp Asn Ile
1               5                   10                  15

Gln Ser Arg

<210> SEQ ID NO 1118
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1118

Asp Ser Val Ser Asp Gly Phe Val Gln Glu Asn Gln Pro Arg
1               5                   10

<210> SEQ ID NO 1119
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1119

Asp Tyr Ser Pro Glu Leu Ala Glu Leu Ile Arg
1               5                   10

<210> SEQ ID NO 1120
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1120

Gly Ser Tyr Gly Glu Val Thr Leu Val Lys
1               5                   10

<210> SEQ ID NO 1121
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1121

Leu Leu Gly Ser Ser Asp Ser Pro Ala Ser Ala Ser Arg
1               5                   10

<210> SEQ ID NO 1122
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1122

Val Asp Val Thr Ser Thr Gln Lys
1               5
```

<210> SEQ ID NO 1123
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1123

Ala Gly Asp Trp Trp Lys
1               5

<210> SEQ ID NO 1124
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1124

Asp Ser Tyr Phe Tyr Ala Val Ser Asp Leu Gln Val Gly Gly Arg
1               5                   10                  15

<210> SEQ ID NO 1125
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1125

Phe Thr Val Asn Ile Ile Ser Val Tyr Lys
1               5                   10

<210> SEQ ID NO 1126
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1126

Leu His Thr Phe Gly Asp Glu Asn Glu Asp Asp Ser Glu Leu Ala Arg
1               5                   10                  15

<210> SEQ ID NO 1127
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1127

Ser Ser Leu Val Ile Gln Trp Arg
1               5

<210> SEQ ID NO 1128
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1128

Leu Val Gln Leu Ala Gly Ala Pro Glu Pro Phe Glu Pro Ala Gln Pro
1               5                   10                  15

Asp Ala Tyr

<210> SEQ ID NO 1129
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1129

Ser Asn Ala Thr Gln Leu Asp Gly Pro Ala Gly Ala Leu Leu Leu Arg
1               5                   10                  15

<210> SEQ ID NO 1130
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1130

Glu Leu Thr Ser Glu Leu Lys
1               5

<210> SEQ ID NO 1131
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1131

Ile Thr Leu Tyr Gly Arg
1               5

<210> SEQ ID NO 1132
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1132

Ser Tyr Pro Gly Leu Thr Ser Tyr Leu Val Arg
1               5                   10

<210> SEQ ID NO 1133
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1133

Val Pro Leu Gln Gln Asn Phe Gln Asp Asn Gln Phe Gln Gly Lys
1               5                   10                  15

<210> SEQ ID NO 1134
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1134

Trp Tyr Val Val Gly Leu Ala Gly Asn Ala Ile Leu Arg
1               5                   10

<210> SEQ ID NO 1135
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1135

Gly Asp Gly Asp Val Ala Trp Gln His Thr Gln Leu Phe Arg
1               5                   10

<210> SEQ ID NO 1136
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1136

Ile Gly Asn Thr Ala Phe Ser Thr Arg
1               5

<210> SEQ ID NO 1137
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1137

Ile Ile Val Glu Leu Val Glu Phe Ile Ser Pro Lys
1               5                   10

<210> SEQ ID NO 1138
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1138

Leu Leu Leu Thr Tyr Ala Asp Asn Ile Leu Arg
1               5                   10

<210> SEQ ID NO 1139
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 1139

Ser Ser Gln Gln Pro Ala Ala Ser Thr Gln Leu Pro Thr Thr Pro Ser
1               5                   10                  15

Ser Asn Pro Ser Gly Leu Asn Gln His Thr Arg
            20                  25

<210> SEQ ID NO 1140
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1140

Ser Val Asp Pro Asp Ser Pro Ala Glu Ala Ser Gly Leu Arg

<210> SEQ ID NO 1141
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1141

Glu Phe Pro Val Tyr Leu Trp Gln Pro Phe Phe Arg
1               5                   10

<210> SEQ ID NO 1142
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1142

Glu Val Asn Glu Val Ser Gln Asn Phe Gln Thr Thr Lys
1               5                   10

<210> SEQ ID NO 1143
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1143

Gly Glu Ser Leu Ser Leu Pro Gly Pro Ser Pro Pro Asp Gly Thr
1               5                   10                  15

Glu Gln Val Ile Ile Ser Arg
            20

<210> SEQ ID NO 1144
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1144

Asn Asp Tyr Ala Val Glu Ser Tyr Glu Asn Lys
1               5                   10

<210> SEQ ID NO 1145
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1145

Val Leu Thr Ser Glu Asp Glu Tyr Asn Leu Leu Ser Asp Arg
1               5                   10

<210> SEQ ID NO 1146
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1146

Gly Tyr Phe Leu Phe Arg Pro Arg
1               5

<210> SEQ ID NO 1147
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1147

Val Asp Glu Glu Phe Gln Ser Pro Phe Ala Ser Gln Ser Arg
1               5                   10

<210> SEQ ID NO 1148
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1148

Glu Gly Asn Lys Pro Val Leu Phe Gln Gly Asn Thr Asn Pro Thr Asp
1               5                   10                  15

Val Val Val Ala Val Phe Pro Lys Pro Leu Ile Thr Arg
            20                  25

<210> SEQ ID NO 1149
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1149

Phe Val Ser Asp Tyr Glu Thr His Gly Ala Gly Phe Ser Ile Arg
1               5                   10                  15

<210> SEQ ID NO 1150
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1150

Phe Val Thr Ala Val Gly Thr Gln Gly Ala Ile Ser Lys
1               5                   10

<210> SEQ ID NO 1151
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1151

Ile Glu Ser Pro Gly Tyr Leu Thr Ser Pro Gly Tyr Pro His Ser Tyr
1               5                   10                  15

His Pro Ser Glu Lys
            20

<210> SEQ ID NO 1152
<211> LENGTH: 14
<212> TYPE: PRT

```
<213> ORGANISM: Artificial Sequence
<220> FEATURE:
<223> OTHER INFORMATION: Synthetic Polypeptide

<400> SEQUENCE: 1152

Ser Phe Glu Gly Asn Asn Asn Tyr Asp Thr Pro Glu Leu Arg
1               5                   10

<210> SEQ ID NO 1153
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1153

Glu Ala Ile Asn Phe Arg
1               5

<210> SEQ ID NO 1154
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1154

Ile Ile Ile Leu Leu Gly Phe Leu Gly Ala Thr Leu Ser Ala Pro Leu
1               5                   10                  15

Ile Pro Gln Arg
            20

<210> SEQ ID NO 1155
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1155

Ser Pro Gln Gln Thr Arg
1               5

<210> SEQ ID NO 1156
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1156

Ala Ile Pro Val Ala Gln Asp Leu Asn Ala Pro Ser Asp Trp Asp Ser
1               5                   10                  15

Arg

<210> SEQ ID NO 1157
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1157

Asp Ser Tyr Glu Thr Ser Gln Leu Asp Asp Gln Ser Ala Glu Thr His
1               5                   10                  15
```

Ser His Lys

<210> SEQ ID NO 1158
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1158

Gly Asp Ser Val Val Tyr Gly Leu Arg
1               5

<210> SEQ ID NO 1159
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1159

Ile Ser His Glu Leu Asp Ser Ala Ser Ser Glu Val Asn
1               5                   10

<210> SEQ ID NO 1160
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1160

Tyr Pro Asp Ala Val Ala Thr Trp Leu Asn Pro Asp Pro Ser Gln Lys
1               5                   10                  15

<210> SEQ ID NO 1161
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1161

Asp Gly Glu Ala Phe Leu Leu Thr Asn
1               5

<210> SEQ ID NO 1162
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1162

Gln Gly Val Leu Asp Leu Pro Asn Asp Val Val Glu Gly Ser Ala Arg
1               5                   10                  15

<210> SEQ ID NO 1163
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1163

Ser Asp Pro Leu Ala Phe Ile Thr Phe Ser Ala Lys
1               5                   10

<210> SEQ ID NO 1164
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1164

Ser Glu Val Thr Gln Ala Pro Gly Gln Tyr Thr Val Asp Val Glu Gly
1               5                   10                  15

Arg

<210> SEQ ID NO 1165
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1165

Ser Phe Leu Val Glu Pro Glu Gly Ile Glu Lys
1               5                   10

<210> SEQ ID NO 1166
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1166

Asp His Val Val Ser Asp Phe Ser Glu His Gly Ser Leu Lys
1               5                   10

<210> SEQ ID NO 1167
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1167

Phe Gly Leu Gly Ala Glu Val Gly Ile Ser Thr Ser Arg
1               5                   10

<210> SEQ ID NO 1168
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1168

Gly Pro Val Gly Leu Glu Gly Leu Leu Thr Thr Lys
1               5                   10

<210> SEQ ID NO 1169
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1169

His Glu Ile Leu Leu Ser Gln Ser Val Arg

```
1               5                   10
```

<210> SEQ ID NO 1170
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1170

```
Ile Leu His Leu Leu Thr Gln Glu Ala Leu Ser Ile His Gly Val Lys
1               5                   10                  15
```

<210> SEQ ID NO 1171
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1171

```
Asp Ile Pro His Trp Leu Asn Pro Thr Arg
1               5                   10
```

<210> SEQ ID NO 1172
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1172

```
Glu Gln Val Asp Phe Gln His His Gln Leu Ala Glu Ala Phe Lys
1               5                   10                  15
```

<210> SEQ ID NO 1173
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1173

```
Gly Tyr Ile Glu His Phe Ser Leu Trp Lys
1               5                   10
```

<210> SEQ ID NO 1174
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1174

```
Leu Asp Gly Ser Thr His Leu Asn Ile Phe Phe Ala Lys
1               5                   10
```

<210> SEQ ID NO 1175
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1175

```
Val Ser Phe Ser Ser Pro Leu Val Ala Ile Ser Gly Val Ala Leu Arg
1               5                   10                  15
```

```
<210> SEQ ID NO 1176
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1176

Ala Leu Glu Ser Glu Leu Gln Gln Leu Arg
1               5                   10

<210> SEQ ID NO 1177
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1177

Glu Leu Pro Leu Ser Pro Ala Phe Phe Gly Glu Asp Gly Ile Phe Arg
1               5                   10                  15

<210> SEQ ID NO 1178
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1178

Glu Gln Glu Pro Glu Leu Ser Phe Leu Lys
1               5                   10

<210> SEQ ID NO 1179
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1179

Gly Leu Glu Glu Glu Asn Ala Gln Leu Arg
1               5                   10

<210> SEQ ID NO 1180
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1180

Gln Glu Gly Leu Thr Phe Phe Gly Thr Glu Leu Ala Pro Val Arg
1               5                   10                  15

<210> SEQ ID NO 1181
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1181

Ile Ala Asn Pro Val Glu Gly Ser Ser Gly Arg
1               5                   10
```

<210> SEQ ID NO 1182
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1182

Ile Ile Thr Leu Thr Gly Pro Thr Asn Ala Ile Phe Lys
1               5                   10

<210> SEQ ID NO 1183
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1183

Leu Asn Gln Val Ala Arg
1               5

<210> SEQ ID NO 1184
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1184

Gln Gly Ala Asn Ile Asn Glu Ile Arg
1               5

<210> SEQ ID NO 1185
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1185

Gln Val Thr Ile Thr Gly Ser Ala Ala Ser Ile Ser Leu Ala Gln Tyr
1               5                   10                  15

Leu Ile Asn Ala Arg
            20

<210> SEQ ID NO 1186
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1186

Ala Phe Ala Met Ile Ile Asp Lys
1               5

<210> SEQ ID NO 1187
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1187

Glu Ser Thr Gly Ala Gln Val Gln Val Ala Gly Asp Met Leu Pro Asn

Ser Thr Glu Arg
        20

<210> SEQ ID NO 1188
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1188

Gly Val Thr Ile Pro Tyr Arg Pro Lys Pro Ser Ser Pro Val Ile
1               5                   10                  15

Phe Ala Gly Gly Gln Asp Arg
        20

<210> SEQ ID NO 1189
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1189

Ile Ala Asn Pro Val Glu Gly Ser Thr Asp Arg
1               5                   10

<210> SEQ ID NO 1190
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1190

Ile Ile Thr Leu Ala Gly Pro Thr Asn Ala Ile Phe Lys
1               5                   10

<210> SEQ ID NO 1191
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 1191

Leu His Gln Leu Ala Met Gln Gln Ser His Phe Pro Met Thr His Gly
1               5                   10                  15

Asn Thr Gly Phe Ser Gly Ile Glu Ser Ser Pro Glu Val Lys
            20                  25                  30

<210> SEQ ID NO 1192
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1192

Leu Ser Ser Glu Thr Gly Gly Met Gly Ser Ser
1               5                   10

<210> SEQ ID NO 1193
<211> LENGTH: 17

```
<212> TYPE: PRT
<213> ORGANISM: Artificial Sequence
<220> FEATURE:
<223> OTHER INFORMATION: Synthetic Polypeptide

<400> SEQUENCE: 1193

Met Asp Thr Gly Val Ile Glu Gly Gly Leu Asn Val Thr Leu Thr Ile
1               5                   10                  15

Arg

<210> SEQ ID NO 1194
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1194

Gln Met Ser Gly Ala Gln Ile Lys
1               5

<210> SEQ ID NO 1195
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1195

Gln Val Thr Ile Thr Gly Ser Ala Ala Ser Ile Ser Leu Ala Gln Tyr
1               5                   10                  15

Leu Ile Asn Val Arg
            20

<210> SEQ ID NO 1196
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1196

Glu Gly Asp Ser Ile Thr Tyr Ala Ile Glu Asn Gly Asp Pro Gln Arg
1               5                   10                  15

<210> SEQ ID NO 1197
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1197

Gly Gly Pro Pro Ala Thr Ile Val Ala Ile Asp Glu Glu Ser Arg
1               5                   10                  15

<210> SEQ ID NO 1198
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1198

Gly Thr Ala Gly Gly Pro Asp Pro Thr Ile Glu Leu Ser Leu Lys
1               5                   10                  15
```

<210> SEQ ID NO 1199
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1199

Val Gly Ala Val Leu Leu Asn Leu Gln Ala Thr Asp Arg
1               5                   10

<210> SEQ ID NO 1200
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1200

Val Gln Ala Asp Ser Leu Glu Val Val Leu Ala Asn Leu Arg
1               5                   10

<210> SEQ ID NO 1201
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1201

Ile Glu Asp Glu Glu Gly Ser
1               5

<210> SEQ ID NO 1202
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1202

Leu Ser Gln Thr Ser Asn Val Asp Lys
1               5

<210> SEQ ID NO 1203
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1203

Ser Glu Gly Phe Asp Thr Tyr Arg
1               5

<210> SEQ ID NO 1204
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1204

Tyr Leu Asn Phe Phe Thr Lys
1               5

-continued

<210> SEQ ID NO 1205
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1205

Tyr Tyr Leu Ala Pro Lys
1               5

<210> SEQ ID NO 1206
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1206

Phe Gly Leu Asn Thr Val Leu Thr Thr Asp Asn Ser Asp Leu Phe Ile
1               5                   10                  15

Asn Ser Ile Gly Ile Val Pro Ser Val Arg
            20                  25

<210> SEQ ID NO 1207
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1207

Ile Ala Ile Ile Gly Ala Gly Ile Gly Gly Thr Ser Ala Ala Tyr Tyr
1               5                   10                  15

Leu Arg

<210> SEQ ID NO 1208
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1208

Ile Phe Ser Gln Glu Thr Leu Thr Lys
1               5

<210> SEQ ID NO 1209
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1209

Thr Leu Leu Glu Thr Leu Gln Lys
1               5

<210> SEQ ID NO 1210
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1210

Tyr Gln Ser His Asp Tyr Ala Phe Ser Ser Val Glu Lys
1               5                   10

<210> SEQ ID NO 1211
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1211

Ala His Gly Val His Ala Thr Lys
1               5

<210> SEQ ID NO 1212
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1212

Glu Glu Asp Thr Gly Arg Pro Arg
1               5

<210> SEQ ID NO 1213
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1213

Leu Leu Glu Ile Asp Ser Val Gly Ser Glu Asp Ser Leu Asp Thr Ser
1               5                   10                  15

Leu Arg

<210> SEQ ID NO 1214
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1214

Ser Gln Ile His Ser Ile Arg
1               5

<210> SEQ ID NO 1215
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1215

Thr Val Ile Tyr Glu Ile Pro Arg
1               5

<210> SEQ ID NO 1216
<211> LENGTH: 7
<212> TYPE: PRT
<213> ORGANISM: Artificial Sequence
<220> FEATURE:
<223> OTHER INFORMATION: Synthetic Polypeptide

```
<400> SEQUENCE: 1216

Ser Phe Asp Asp Leu Gln Arg
1               5

<210> SEQ ID NO 1217
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1217

Ser His Ser Gly Gly Glu Leu Glu Ser Leu Ala Arg
1               5                   10

<210> SEQ ID NO 1218
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1218

Ser Pro Gly Gly Ser Gln Glu Gln Arg
1               5

<210> SEQ ID NO 1219
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1219

Asp Thr Ser Ala Thr Pro Gln Ser Ala Ser Ile Lys
1               5                   10

<210> SEQ ID NO 1220
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1220

Gly Asn Gly Tyr Val Gln Ser Pro Arg
1               5

<210> SEQ ID NO 1221
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1221

Leu Ala Asn Val Val Phe Phe Pro Arg
1               5

<210> SEQ ID NO 1222
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1222
```

-continued

Ser Asp Asp Tyr Phe Val Ala Lys Pro Gly Phe Lys
1               5                   10

<210> SEQ ID NO 1223
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1223

Tyr Asp Phe Val Glu Val Glu Asp Ile Ser Glu Thr Ser Thr Ile Ile
1               5                   10                  15

Arg

<210> SEQ ID NO 1224
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1224

Asp Pro Asn Ile Val Ile Ala Lys
1               5

<210> SEQ ID NO 1225
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1225

Glu Leu Ser Asp Phe Ile Ser Tyr Leu Gln Arg
1               5                   10

<210> SEQ ID NO 1226
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 1226

Phe Ala His Thr Asn Val Glu Ser Leu Val Asn Glu Tyr Asp Asp Asn
1               5                   10                  15

Gly Glu Gly Ile Ile Leu Phe Arg Pro Ser His Leu Thr Asn Lys
            20                  25                  30

<210> SEQ ID NO 1227
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1227

Ser Glu Pro Ile Pro Glu Ser Asn Asp Gly Pro Val Lys
1               5                   10

<210> SEQ ID NO 1228
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1228

Thr Val Ala Tyr Thr Glu Gln Lys
1               5

<210> SEQ ID NO 1229
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1229

Glu Glu Asn Gly Val Leu Val Leu Asn Asp Ala Asn Phe Asp Asn Phe
1               5                   10                  15

Val Ala Asp Lys
            20

<210> SEQ ID NO 1230
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1230

Glu Val Ser Gln Pro Asp Trp Thr Pro Pro Glu Val Thr Leu Val
1               5                   10                  15

Leu Thr Lys

<210> SEQ ID NO 1231
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1231

Phe Asp Val Ser Gly Tyr Pro Thr Ile Lys
1               5                   10

<210> SEQ ID NO 1232
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1232

Phe His His Thr Phe Ser Thr Glu Ile Ala Lys
1               5                   10

<210> SEQ ID NO 1233
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1233

Phe Ile Glu Glu His Ala Thr Lys
1               5

```
<210> SEQ ID NO 1234
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1234

Gly Glu Ser Pro Val Asp Tyr Asp Gly Gly Arg
1               5                   10

<210> SEQ ID NO 1235
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1235

His His Ser Leu Gly Gly Gln Tyr Gly Val Gln Gly Phe Pro Thr Ile
1               5                   10                  15

Lys

<210> SEQ ID NO 1236
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1236

Asn Leu Glu Pro Glu Trp Ala Ala Ala Ala Ser Glu Val Lys
1               5                   10

<210> SEQ ID NO 1237
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1237

Asn Arg Pro Glu Asp Tyr Gln Gly Gly Arg
1               5                   10

<210> SEQ ID NO 1238
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1238

Asn Ser Tyr Leu Glu Val Leu Leu Lys
1               5

<210> SEQ ID NO 1239
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1239

Asp Gln Asn Phe Val Ile Leu Glu Phe Pro Val Glu Glu Gln Asp Arg
1               5                   10                  15
```

<210> SEQ ID NO 1240
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1240

Glu Asp Thr Ile Val Ser Gln Thr Gln Asp Phe Thr Lys
1               5                   10

<210> SEQ ID NO 1241
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1241

Ser Glu Leu Val Thr Val Thr Glu Ser Phe Ser Thr Pro Lys
1               5                   10

<210> SEQ ID NO 1242
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1242

Ser Thr Glu Ser Tyr Phe Ile Pro Glu Val Arg
1               5                   10

<210> SEQ ID NO 1243
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1243

Val Ile Ala Pro Val Asp Glu Val Gln Ile Ser Ile Leu Ser Ser Lys
1               5                   10                  15

<210> SEQ ID NO 1244
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1244

Asp Thr Asp Thr Gly Ala Leu Leu Phe Ile Gly Lys
1               5                   10

<210> SEQ ID NO 1245
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1245

Glu Leu Leu Asp Thr Val Thr Ala Pro Gln Lys
1               5                   10

```
<210> SEQ ID NO 1246
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1246

Leu Gln Ser Leu Phe Asp Ser Pro Asp Phe Ser Lys
1               5                   10

<210> SEQ ID NO 1247
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1247

Leu Ser Tyr Glu Gly Glu Val Thr Lys
1               5

<210> SEQ ID NO 1248
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1248

Thr Val Gln Ala Val Leu Thr Val Pro Lys
1               5                   10

<210> SEQ ID NO 1249
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1249

Ala Val Ser Asn Glu Ile Val Arg
1               5

<210> SEQ ID NO 1250
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1250

Phe Pro Thr Asp Gln Leu Thr Pro Asp Gln Glu Arg
1               5                   10

<210> SEQ ID NO 1251
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1251

Ile Ala Asn Val Phe Thr Asn Ala Phe Arg
1               5                   10

<210> SEQ ID NO 1252
```

```
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1252

Val Phe Phe Ala Ser Trp Arg
1               5

<210> SEQ ID NO 1253
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1253

Val Val Leu Glu Gly Gly Ile Asp Pro Ile Leu Arg
1               5                   10

<210> SEQ ID NO 1254
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1254

Leu Ser Leu Pro Leu Leu Leu Leu Leu Gly Ala Trp Ala Ile Pro
1               5                   10                  15

Gly Gly Leu Gly Asp Arg
            20

<210> SEQ ID NO 1255
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1255

Asn Trp Gln Asp Tyr Gly Val Arg
1               5

<210> SEQ ID NO 1256
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1256

Ala Leu Pro Phe Trp Asn Glu Glu Ile Val Pro Gln Ile Lys
1               5                   10

<210> SEQ ID NO 1257
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1257

Ala Met Glu Ala Val Ala Ala Gln Gly Lys
1               5                   10
```

<210> SEQ ID NO 1258
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1258

Phe Ser Gly Trp Tyr Asp Ala Asp Leu Ser Pro Ala Gly His Glu Glu
1               5                   10                  15

Ala Lys

<210> SEQ ID NO 1259
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1259

His Gly Glu Ser Ala Trp Asn Leu Glu Asn Arg
1               5                   10

<210> SEQ ID NO 1260
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1260

Asn Leu Lys Pro Ile Lys Pro Met Gln Phe Leu Gly Asp Glu Glu Thr
1               5                   10                  15

Val Arg

<210> SEQ ID NO 1261
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1261

Ile His Thr Tyr Val Tyr Glu Phe Ile Tyr Leu Val Arg
1               5                   10

<210> SEQ ID NO 1262
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 1262

Leu Asp Pro Ser Pro Phe Ile Ala Asp Phe Gln Thr Thr Ala Glu Glu
1               5                   10                  15

Leu Gly Leu Leu Ser Ser Ser Pro Asn Leu Leu
            20                  25

<210> SEQ ID NO 1263
<211> LENGTH: 18
<212> TYPE: PRT
<213> ORGANISM: Artificial Sequence
<220> FEATURE:
<223> OTHER INFORMATION: Synthetic Polypeptide -continued

```
<400> SEQUENCE: 1263

Val Val Ser Glu Glu Thr Leu Leu Phe Gln Thr Glu Leu Tyr Phe Thr
1               5                   10                  15

Pro Arg

<210> SEQ ID NO 1264
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1264

Asp Ala Val Thr Thr Thr Val Thr Gly Ala Lys
1               5                   10

<210> SEQ ID NO 1265
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1265

Glu Val Ser Asp Ser Leu Leu Thr Ser Ser Lys
1               5                   10

<210> SEQ ID NO 1266
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1266

Leu Pro Ile Leu Asn Gln Pro Ser Thr Gln Ile Val Ala Asn Ala Lys
1               5                   10                  15

<210> SEQ ID NO 1267
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1267

Ser Glu Leu Leu Val Glu Gln Tyr Leu Pro Leu Thr Glu Glu Glu Leu
1               5                   10                  15

Glu Lys

<210> SEQ ID NO 1268
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1268

Ser Val Val Ser Gly Ser Ile Asn Thr Val Leu Gly Ser Arg
1               5                   10

<210> SEQ ID NO 1269
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 1269

Asp Thr Val Ala Thr Gln Leu Ser Glu Ala Val Asp Ala Thr Arg
1               5                   10                  15

<210> SEQ ID NO 1270
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1270

Ile Ala Thr Ser Leu Asp Gly Phe Asp Val Ala Ser Val Gln Gln Gln
1               5                   10                  15

Arg

<210> SEQ ID NO 1271
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1271

Leu Glu Glu Asn Leu Pro Ile Leu Gln Gln Pro Thr Glu Lys
1               5                   10

<210> SEQ ID NO 1272
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1272

Ser Glu Glu Trp Ala Asp Asn His Leu Pro Leu Thr Asp Ala Glu Leu
1               5                   10                  15

Ala Arg

<210> SEQ ID NO 1273
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1273

Thr Leu Thr Ala Ala Ala Val Ser Gly Ala Gln Pro Ile Leu Ser Lys
1               5                   10                  15

<210> SEQ ID NO 1274
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1274

Ala Gln Val Glu Glu Phe Leu Ala Gln His Gly Ser Glu Tyr Gln Ser
1               5                   10                  15

Val Lys
```

<210> SEQ ID NO 1275
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1275

Ile Phe Gln Asn Leu Asp Gly Ala Leu Asp Glu Val Val Leu Lys
1               5                   10                  15

<210> SEQ ID NO 1276
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1276

Leu Gln Leu Asn Tyr Leu Gly Asn Tyr Ile Pro Arg
1               5                   10

<210> SEQ ID NO 1277
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1277

Leu Thr His Tyr His Glu Gly Leu Pro Thr Thr Arg
1               5                   10

<210> SEQ ID NO 1278
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1278

Asn Leu Ala Tyr Asp Thr Leu Pro Val Leu Ile His Gly Asn Gly Pro
1               5                   10                  15

Thr Lys

<210> SEQ ID NO 1279
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1279

Ile Val Gly Pro Glu Glu Asn Leu Ser Gln Ala Glu Ala Arg
1               5                   10

<210> SEQ ID NO 1280
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1280

Ile Val Gln Gln Trp Asn Leu Gln Asp Asn Asp Asp Gln Leu Phe
1               5                   10                  15

```
1               5                   10                  15

Tyr Thr Lys

<210> SEQ ID NO 1281
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1281

Leu Thr His Leu His Glu Gly Leu Pro Val Lys
1               5                   10

<210> SEQ ID NO 1282
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1282

Leu Trp Ser Asn Phe Trp Gly Ala Leu Ser Pro Asp Gly Tyr Tyr Ala
1               5                   10                  15

Arg

<210> SEQ ID NO 1283
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1283

Ser Glu Asp Tyr Val Asp Ile Val Gln Gly Asn Arg
1               5                   10

<210> SEQ ID NO 1284
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1284

Ile Gly Asn Phe Ser Thr Asp Ile Lys
1               5

<210> SEQ ID NO 1285
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1285

Ile Ser Phe Asp Glu Phe Ile Lys
1               5

<210> SEQ ID NO 1286
<211> LENGTH: 19
<212> TYPE: PRT
<213> ORGANISM: Artificial Sequence
<220> FEATURE:
<223> OTHER INFORMATION: Synthetic Polypeptide
```

```
<400> SEQUENCE: 1286

Val Asp Thr Asp Gly Asn Gly Tyr Ile Ser Phe Asn Glu Leu Asn Asp
1               5                   10                  15

Leu Phe Lys

<210> SEQ ID NO 1287
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1287

Val Pro Val Asp Trp Asn Arg
1               5

<210> SEQ ID NO 1288
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1288

Tyr Pro Ala Leu His Lys Pro Glu Asn Gln Asp Ile Asp Trp Gly Ala
1               5                   10                  15

Leu Glu Gly Glu Thr Arg
            20

<210> SEQ ID NO 1289
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1289

Leu Asp Ile Thr Ala Glu Ile Leu Ala Val Arg
1               5                   10

<210> SEQ ID NO 1290
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1290

Leu Gln Val Asn Thr Pro Leu Val Gly Ala Ser Leu Leu Arg
1               5                   10

<210> SEQ ID NO 1291
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1291

Leu Tyr Val Thr Ile Pro Leu Gly Ile Lys
1               5                   10

<210> SEQ ID NO 1292
<211> LENGTH: 19
<212> TYPE: PRT
```

```
<213> ORGANISM: Artificial Sequence
<220> FEATURE:
<223> OTHER INFORMATION: Synthetic Polypeptide

<400> SEQUENCE: 1292

Val Thr Asp Pro Gln Leu Leu Glu Leu Gly Leu Val Gln Ser Pro Asp
1               5                   10                  15

Gly His Arg

<210> SEQ ID NO 1293
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1293

Val Thr Ser Val Ile Pro Gly Leu Asn Asn Ile Ile Asp Ile Lys
1               5                   10                  15

<210> SEQ ID NO 1294
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1294

Glu Leu Pro Val Pro Ile Tyr Val Thr Gln Gly Glu Ala Gln Arg
1               5                   10                  15

<210> SEQ ID NO 1295
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1295

Gly Pro Ser Gly Ala Glu Glu Ala Thr Val Glu Tyr Gly Val Thr Ser
1               5                   10                  15

Arg

<210> SEQ ID NO 1296
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1296

Gly Pro Val Asp Ala Val Thr Gly Lys
1               5

<210> SEQ ID NO 1297
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1297

Gln Leu Ala Gly Ser Gln Pro Phe Ser Ser Glu Gly Leu Gly Arg
1               5                   10                  15
```

```
<210> SEQ ID NO 1298
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1298

Ser Gln Pro Pro Gly Ile Ser Ser Gln His Phe Thr Tyr Gln Asp Pro
1               5                   10                  15

Val Leu Leu Ser Leu Ser Pro Arg
            20

<210> SEQ ID NO 1299
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1299

Phe Trp Val Asn Ile Leu Lys
1               5

<210> SEQ ID NO 1300
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1300

Leu Asn Thr Ile Gly His Tyr Glu Ile Ser Asn Gly Ser Thr Ile Lys
1               5                   10                  15

<210> SEQ ID NO 1301
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1301

Asn Pro Gln Phe Val Phe Asp Ile Lys
1               5

<210> SEQ ID NO 1302
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1302

Gly Phe Glu Pro Gly Val Thr Asn Ile Leu Lys
1               5                   10

<210> SEQ ID NO 1303
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1303

Ile Ile Asp Gly Val Pro Val Glu Ile Thr Glu Lys
1               5                   10
```

<210> SEQ ID NO 1304
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1304

Ile Ile His Gly Asn Gln Ile Ala Thr Asn Gly Val Val His Val Ile
1               5                   10                  15

Asp Arg

<210> SEQ ID NO 1305
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1305

Leu Leu Tyr Pro Ala Asp Thr Pro Val Gly Asn Asp Gln Leu Leu Glu
1               5                   10                  15

Ile Leu Asn Lys
            20

<210> SEQ ID NO 1306
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1306

Val Leu Thr Gln Ile Gly Thr Ser Ile Gln Asp Phe Ile Glu Ala Glu
1               5                   10                  15

Asp Asp Leu Ser Ser Phe Arg
            20

<210> SEQ ID NO 1307
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1307

Asp Pro Tyr Gln Glu Glu Glu Trp Pro Gln Gly Phe Gly Gln Leu Thr
1               5                   10                  15

Lys

<210> SEQ ID NO 1308
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1308

Phe Leu Phe Gly Ile Tyr Gln Gln Ala Glu Lys
1               5                   10

<210> SEQ ID NO 1309
<211> LENGTH: 7

```
<212> TYPE: PRT
<213> ORGANISM: Artificial Sequence
<220> FEATURE:
<223> OTHER INFORMATION: Synthetic Polypeptide

<400> SEQUENCE: 1309

Phe Val Thr Leu Leu Tyr Arg
1               5

<210> SEQ ID NO 1310
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1310

His Val Ala Asp Gly Glu Asp His Ala
1               5

<210> SEQ ID NO 1311
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1311

Leu Thr Glu Pro Val Val Pro Lys
1               5

<210> SEQ ID NO 1312
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1312

Ala Asn Glu Gly Thr Val Gly Val Ser Ala Ala Thr Glu Arg
1               5                   10

<210> SEQ ID NO 1313
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1313

Asp Gln Ala Gln Glu Thr Leu Lys
1               5

<210> SEQ ID NO 1314
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1314

His Glu Thr His Gly Gly Glu Asp Val Ala Val Phe Ser Lys
1               5                   10

<210> SEQ ID NO 1315
<211> LENGTH: 11
<212> TYPE: PRT
```

<213> ORGANISM: Artificial Sequence
<220> FEATURE:
<223> OTHER INFORMATION: Synthetic Polypeptide

<400> SEQUENCE: 1315

Leu Asp Gly Leu Asp Leu Val Asp Thr Trp Lys
1               5                   10

<210> SEQ ID NO 1316
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1316

Phe Pro Asp Glu Asn Phe Lys
1               5

<210> SEQ ID NO 1317
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1317

Ile Glu Val Glu Lys Pro Phe Ala Ile Ala Lys
1               5                   10

<210> SEQ ID NO 1318
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1318

Thr Val Asp Asn Phe Val Ala Leu Ala Thr Gly Glu Lys
1               5                   10

<210> SEQ ID NO 1319
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1319

Val Ile Phe Gly Leu Phe Gly Lys
1               5

<210> SEQ ID NO 1320
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1320

Val Tyr Phe Asp Leu Arg
1               5

<210> SEQ ID NO 1321
<211> LENGTH: 8
<212> TYPE: PRT
<213> ORGANISM: Artificial Sequence

```
<220> FEATURE:
<223> OTHER INFORMATION: Synthetic Polypeptide

<400> SEQUENCE: 1321

Ala Asp Glu Gly Ile Ser Phe Arg
1               5

<210> SEQ ID NO 1322
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1322

Ala Thr Ala Val Met Pro Asp Gly Gln Phe Lys
1               5                   10

<210> SEQ ID NO 1323
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1323

Asp Ile Ser Leu Ser Asp Tyr Lys
1               5

<210> SEQ ID NO 1324
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1324

Gly Leu Phe Ile Ile Asp Asp Lys
1               5

<210> SEQ ID NO 1325
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1325

Ile Gly His Pro Ala Pro Asn Phe Lys
1               5

<210> SEQ ID NO 1326
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1326

Leu Val Gln Ala Phe Gln Phe Thr Asp Lys
1               5                   10

<210> SEQ ID NO 1327
<211> LENGTH: 16
<212> TYPE: PRT
<213> ORGANISM: Artificial Sequence
<220> FEATURE:
```

<223> OTHER INFORMATION: Synthetic Polypeptide

<400> SEQUENCE: 1327

Gln Gly Gly Leu Gly Pro Met Asn Ile Pro Leu Val Ser Asp Pro Lys
1               5                   10                  15

<210> SEQ ID NO 1328
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1328

Gln Ile Thr Val Asn Asp Leu Pro Val Gly Arg
1               5                   10

<210> SEQ ID NO 1329
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1329

Ser Val Asp Glu Thr Leu Arg
1               5

<210> SEQ ID NO 1330
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1330

Thr Ile Ala Gln Asp Tyr Gly Val Leu Lys
1               5                   10

<210> SEQ ID NO 1331
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1331

Asp Tyr Gly Val Tyr Leu Glu Asp Ser Gly His Thr Leu Arg
1               5                   10

<210> SEQ ID NO 1332
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1332

Ile Pro Leu Leu Ser Asp Leu Thr His Gln Ile Ser Lys
1               5                   10

<210> SEQ ID NO 1333
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1333

Ile Ser Lys Pro Ala Pro Tyr Trp Glu Gly Thr Ala Val Ile Asp Gly
1               5                   10                  15

Glu Phe Lys

<210> SEQ ID NO 1334
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1334

Gln Ile Thr Leu Asn Asp Leu Pro Val Gly Arg
1               5                   10

<210> SEQ ID NO 1335
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1335

Val Ser Val Ala Asp His Ser Leu His Leu Ser Lys
1               5                   10

<210> SEQ ID NO 1336
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1336

Asp Ser Pro Ser Val Trp Ala Ala Val Pro Gly Lys
1               5                   10

<210> SEQ ID NO 1337
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1337

Ser Ser Phe Tyr Val Asn Gly Leu Thr Leu Gly Gly Gln Lys
1               5                   10

<210> SEQ ID NO 1338
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1338

Ser Thr Gly Gly Ala Pro Thr Phe Asn Val Thr Val Thr Lys
1               5                   10

<210> SEQ ID NO 1339
<211> LENGTH: 16
<212> TYPE: PRT
<213> ORGANISM: Artificial Sequence
<220> FEATURE:

```
<223> OTHER INFORMATION: Synthetic Polypeptide

<400> SEQUENCE: 1339

Thr Phe Val Asn Ile Thr Pro Ala Glu Val Gly Val Leu Val Gly Lys
1               5                   10                  15

<210> SEQ ID NO 1340
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1340

Ile Glu Glu Tyr Ile Ser Lys
1               5

<210> SEQ ID NO 1341
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1341

Ile Tyr Glu Tyr Val Glu Ser Arg
1               5

<210> SEQ ID NO 1342
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1342

Gln Thr Gln Val Asn Glu Ala Thr Lys
1               5

<210> SEQ ID NO 1343
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1343

Val Asp Ser Phe His Glu Ser Thr Glu Gly Lys
1               5                   10

<210> SEQ ID NO 1344
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1344

Val Ile Val Asp Ala Asn Asn Leu Thr Val Glu Ile Glu Asn Glu Leu
1               5                   10                  15

Asn Ile Ile His Lys
                20

<210> SEQ ID NO 1345
<211> LENGTH: 20
<212> TYPE: PRT
```

```
<213> ORGANISM: Artificial Sequence
<220> FEATURE:
<223> OTHER INFORMATION: Synthetic Polypeptide

<400> SEQUENCE: 1345

Ala Met Glu Val Asp Glu Arg Pro Thr Glu Gln Tyr Ser Asp Ile Gly
1               5                   10                  15

Gly Leu Asp Lys
            20

<210> SEQ ID NO 1346
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1346

Gly Val Leu Met Tyr Gly Pro Pro Gly Thr Gly Lys
1               5                   10

<210> SEQ ID NO 1347
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1347

Leu Ala Gly Pro Gln Leu Val Gln Met Phe Ile Gly Asp Gly Ala Lys
1               5                   10                  15

<210> SEQ ID NO 1348
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1348

Gln Ile Gln Glu Leu Val Glu Ala Ile Val Leu Pro Met Asn His Lys
1               5                   10                  15

<210> SEQ ID NO 1349
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1349

Val Asp Ile Leu Asp Pro Ala Leu Leu Arg
1               5                   10

<210> SEQ ID NO 1350
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1350

Ala Val Gly Leu Leu Thr Val Ile Ser Lys
1               5                   10

<210> SEQ ID NO 1351
```

```
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1351

Ala Gly Tyr Leu Thr Leu Tyr Gly Ile Glu Ala Leu Pro Arg
1               5                   10

<210> SEQ ID NO 1352
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1352

Asp Pro Glu Ile Tyr Thr Asp Pro Glu Val Phe Lys
1               5                   10

<210> SEQ ID NO 1353
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1353

Glu Val Val Val Asp Leu Ala Met Pro Met Ala Asp Gly Arg
1               5                   10

<210> SEQ ID NO 1354
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1354

Gly Glu Leu Glu Ser Ile Leu Trp Gln Ala Glu Gln Pro Val Ser Gln
1               5                   10                  15

Thr Thr Thr Leu Pro Gln Lys
            20

<210> SEQ ID NO 1355
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1355

His Gly Asp Ile Phe Thr Ile Leu Val Gly Gly Arg
1               5                   10

<210> SEQ ID NO 1356
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1356

Ile Phe Asp Val Gln Leu Pro His Tyr Ser Pro Ser Asp Glu Lys
1               5                   10                  15
```

<210> SEQ ID NO 1357
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1357

Leu Leu Leu Phe Pro Phe Leu Ser Pro Gln Arg
1               5                   10

<210> SEQ ID NO 1358
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1358

Val His Ser Ala Asp Val Phe His Thr Phe Arg
1               5                   10

<210> SEQ ID NO 1359
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1359

Val Leu Asp Ser Thr Pro Val Leu Asp Ser Val Leu Ser Glu Ser Leu
1               5                   10                  15

Arg

<210> SEQ ID NO 1360
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1360

Tyr Gly Phe Gly Leu Met Gln Pro Glu His Asp Val Pro Val Arg
1               5                   10                  15

<210> SEQ ID NO 1361
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1361

Phe Gly Ser Leu Leu Pro Ile His Pro Val Thr Ser Gly
1               5                   10

<210> SEQ ID NO 1362
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1362

Leu Asp Glu Glu Ala Glu Asn Leu Val Ala Thr Val Val Pro Thr His
1               5                   10                  15

```
Leu Ala Ala Ala Val Pro Glu Val Ala Val Tyr Leu Lys
            20                  25

<210> SEQ ID NO 1363
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1363

Thr Gly Pro Phe Ala Glu His Ser Asn Gln Leu Trp Asn Ile Ser Ala
1               5                   10                  15

Val Pro Ser Trp Ser Lys
            20

<210> SEQ ID NO 1364
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1364

Val Asp Asp Gln Ile Ala Ile Val Phe Lys
1               5                   10

<210> SEQ ID NO 1365
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1365

Trp Ile Asp Glu Thr Pro Pro Val Asp Gln Pro Ser Arg
1               5                   10

<210> SEQ ID NO 1366
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1366

Asp Leu Gln Tyr Ser Thr Asp Tyr Thr Phe Lys
1               5                   10

<210> SEQ ID NO 1367
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1367

Ser Glu Ala Ala His Gln Gly Val Ile Thr Trp Asn Pro Pro Gln Arg
1               5                   10                  15

<210> SEQ ID NO 1368
<211> LENGTH: 12
<212> TYPE: PRT
<213> ORGANISM: Artificial Sequence
<220> FEATURE:
<223> OTHER INFORMATION: Synthetic Polypeptide
```

<400> SEQUENCE: 1368

Thr Leu Ile Leu Asp Val Pro Pro Gly Val Glu Lys
1               5                   10

<210> SEQ ID NO 1369
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1369

Tyr Asp Leu Gln Asn Leu Lys Pro Tyr Thr Lys
1               5                   10

<210> SEQ ID NO 1370
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1370

Tyr Val Asp Ile Leu Pro Tyr Asp Tyr Asn Arg
1               5                   10

<210> SEQ ID NO 1371
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1371

Ala Gly Ser Pro Thr Ala Pro Val His Asp Glu Ser Leu Val Gly Pro
1               5                   10                  15

Val Asp Pro Ser Ser Gly Gln Gln Ser Arg
            20                  25

<210> SEQ ID NO 1372
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1372

Ala Val Ser Ile Ser Pro Thr Asn Val Ile Leu Thr Trp Lys
1               5                   10

<210> SEQ ID NO 1373
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1373

Thr Pro Ser Ser Thr Gly Pro Ser Pro Val Phe Asp Ile Lys
1               5                   10

<210> SEQ ID NO 1374
<211> LENGTH: 12
<212> TYPE: PRT
<213> ORGANISM: Artificial Sequence

```
<220> FEATURE:
<223> OTHER INFORMATION: Synthetic Polypeptide

<400> SEQUENCE: 1374

Val Ile Thr Glu Pro Ile Pro Val Ser Asp Leu Arg
1               5                   10

<210> SEQ ID NO 1375
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1375

Val Leu Leu Glu Ser Ile Gly Ser His Glu Glu Leu Thr Gln Asp Ser
1               5                   10                  15

Arg

<210> SEQ ID NO 1376
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1376

Glu Gly Pro Pro Ser Glu His Ser Gly Ile Ser Arg
1               5                   10

<210> SEQ ID NO 1377
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1377

Glu Asn Ser Ser Ser Gln Asp Pro Gln Thr Glu Gly Thr Arg
1               5                   10

<210> SEQ ID NO 1378
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1378

Gln Ala Glu Leu Thr Val Gln Val Lys
1               5

<210> SEQ ID NO 1379
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1379

Ser Val Asp Ile Trp Leu Arg
1               5

<210> SEQ ID NO 1380
<211> LENGTH: 13
<212> TYPE: PRT
```

```
<213> ORGANISM: Artificial Sequence
<220> FEATURE:
<223> OTHER INFORMATION: Synthetic Polypeptide

<400> SEQUENCE: 1380

Val Leu Ala Lys Pro Gln Asn Thr Ala Glu Val Gln Lys
1               5                   10

<210> SEQ ID NO 1381
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1381

Asp Asn Ile Asn Ile Glu Glu Ala Ala Arg
1               5                   10

<210> SEQ ID NO 1382
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1382

Ile Leu Val Asn His Gln Ser Phe Pro Asn Glu Glu Asn Asp Val Asp
1               5                   10                  15

Lys

<210> SEQ ID NO 1383
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1383

Leu Asp Gln Glu Thr Leu Arg
1               5

<210> SEQ ID NO 1384
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1384

Val His Leu Pro Asn Gly Ser Pro Ile Pro Ala Val Leu Leu Ala Asn
1               5                   10                  15

Lys

<210> SEQ ID NO 1385
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1385

Val Leu Val Ile Gly Glu Leu Gly Val Gly Lys
1               5                   10
```

```
<210> SEQ ID NO 1386
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1386

Ala Glu Leu Asn Gln Ser Glu Glu Pro Glu Ala Gly Glu Ser Ser Thr
1               5                   10                  15

Gly Gly Pro

<210> SEQ ID NO 1387
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1387

Ile Gly Glu Pro Leu Val Leu Lys
1               5

<210> SEQ ID NO 1388
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1388

Val Leu Pro Asn Gly Ser Leu Phe Leu Pro Ala Val Gly Ile Gln Asp
1               5                   10                  15

Glu Gly Ile Phe Arg
            20

<210> SEQ ID NO 1389
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1389

Val Leu Ser Pro Gln Gly Gly Gly Pro Trp Asp Ser Val Ala Arg
1               5                   10                  15

<210> SEQ ID NO 1390
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1390

Val Tyr Gln Ile Pro Gly Lys Pro Glu Ile Val Asp Ser Ala Ser Glu
1               5                   10                  15

Leu Thr Ala Gly Val Pro Asn Lys
            20

<210> SEQ ID NO 1391
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 1391

Phe Asn Val Trp Asp Thr Ala Gly Gln Glu Lys
1               5                   10

<210> SEQ ID NO 1392
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1392

Leu Val Leu Val Gly Asp Gly Gly Thr Gly Lys
1               5                   10

<210> SEQ ID NO 1393
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1393

Asn Val Pro Asn Trp His Arg
1               5

<210> SEQ ID NO 1394
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1394

Ala Ser Val Asp Glu Leu Phe Ala Glu Ile Val Arg
1               5                   10

<210> SEQ ID NO 1395
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1395

Glu Val Ser Tyr Gly Glu Gly Lys
1               5

<210> SEQ ID NO 1396
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1396

Ser Ala Leu Thr Val Gln Phe Val Thr Gly Ser Phe Ile Glu Lys
1               5                   10                  15

<210> SEQ ID NO 1397
<211> LENGTH: 7
<212> TYPE: PRT
<213> ORGANISM: Artificial Sequence
<220> FEATURE:
<223> OTHER INFORMATION: Synthetic Polypeptide -continued

```
<400> SEQUENCE: 1397

Val Asp Leu Glu Gly Glu Arg
1               5

<210> SEQ ID NO 1398
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1398

Val Val Val Leu Gly Ser Gly Gly Val Gly Lys
1               5                   10

<210> SEQ ID NO 1399
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1399

Ser Ala Leu Thr Val Gln Phe Val Thr Gly Thr Phe Ile Glu Lys
1               5                   10                  15

<210> SEQ ID NO 1400
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1400

Val Asp Leu Glu Pro Glu Arg
1               5

<210> SEQ ID NO 1401
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1401

Val Pro Leu Ile Leu Val Gly Asn Lys
1               5

<210> SEQ ID NO 1402
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1402

Ala Gly Asp Gly Asp Gly Trp Val Ser Leu Ala Glu Leu Arg
1               5                   10

<210> SEQ ID NO 1403
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1403
```

```
Ala Trp Ile Ala His Thr Gln Gln Arg
1               5

<210> SEQ ID NO 1404
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1404

Asp Ile Val Ile Ala Glu Thr Leu Glu Asp Leu Asp Arg
1               5                   10

<210> SEQ ID NO 1405
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1405

Glu Phe Asp Gln Leu Thr Pro Glu Glu Ser Gln Ala Arg
1               5                   10

<210> SEQ ID NO 1406
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1406

Val Gly Trp Glu Glu Leu Arg
1               5

<210> SEQ ID NO 1407
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1407

Val Phe Gln Phe Leu Asn Ala Lys
1               5

<210> SEQ ID NO 1408
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1408

Asp Val Asp Ala Val Asp Lys
1               5

<210> SEQ ID NO 1409
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1409
```

```
Glu Leu Leu Gln Thr Glu Leu Ser Gly Phe Leu Asp Ala Gln Lys
1               5                   10                  15

<210> SEQ ID NO 1410
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1410

Asp Gln Glu Val Asn Phe Gln Glu Tyr Val Thr Phe Leu Gly Ala Leu
1               5                   10                  15

Ala Leu Ile Tyr Asn Glu Ala Leu Lys
            20                  25

<210> SEQ ID NO 1411
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1411

Glu Leu Thr Ile Gly Ser Lys
1               5

<210> SEQ ID NO 1412
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1412

Leu Gln Asp Ala Glu Ile Ala Arg
1               5

<210> SEQ ID NO 1413
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1413

Asp Pro Asn His Phe Arg Pro Ala Gly Leu Pro Glu Lys
1               5                   10

<210> SEQ ID NO 1414
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1414

Glu Ala Asn Tyr Ile Gly Ser Asp Lys
1               5

<210> SEQ ID NO 1415
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 1415

Phe Phe Gly His Gly Ala Glu Asp Ser Leu Ala Asp Gln Ala Ala Asn
1               5                   10                  15

Glu Trp Gly Arg
            20

<210> SEQ ID NO 1416
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1416

Ser Phe Phe Ser Phe Leu Gly Glu Ala Phe Asp Gly Ala Arg
1               5                   10

<210> SEQ ID NO 1417
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1417

Phe Ser Asn Ile Ser Glu Gly Leu Ser Asn Tyr Ser Ile Ile Asp Lys
1               5                   10                  15

<210> SEQ ID NO 1418
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1418

Leu Phe Thr Pro Glu Glu Phe Phe Arg
1               5

<210> SEQ ID NO 1419
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1419

Leu Val Ala Asn Leu Pro Lys
1               5

<210> SEQ ID NO 1420
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 1420

Asp Thr Gln Leu Leu Thr Ala Ile Pro Thr Ser Pro Glu Pro Thr Gly
1               5                   10                  15

Leu Glu Ala Thr Ala Ala Ser Thr Ser Thr Leu Pro Ala Gly Glu Gly
            20                  25                  30

Pro Lys
```

```
<210> SEQ ID NO 1421
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1421

Glu Gly Glu Ala Val Val Leu Pro Glu Val Glu Pro Gly Leu Thr Ala
1               5                   10                  15

Arg

<210> SEQ ID NO 1422
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1422

Glu Gln Glu Ala Thr Pro Arg Pro Arg
1               5

<210> SEQ ID NO 1423
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1423

Glu Thr Thr Gln Leu Pro Thr Thr His Leu Ala Ser Thr Thr Thr Ala
1               5                   10                  15

Thr Thr Ala Gln Glu Pro Ala Thr Ser His Pro His Arg
            20                  25

<210> SEQ ID NO 1424
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1424

Gln Ala Asn Gly Gly Ala Tyr Gln Lys Pro Thr Lys
1               5                   10

<210> SEQ ID NO 1425
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1425

Asp Ile Leu Gln Leu Ile Gly Phe Ala Asn Leu Pro Arg
1               5                   10

<210> SEQ ID NO 1426
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1426
```

Asp Tyr Pro Asp Glu Val Leu Gln Phe Ala Arg
1               5                   10

<210> SEQ ID NO 1427
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1427

Glu Val Leu Trp Pro Pro Gln Pro Gly Gln Arg
1               5                   10

<210> SEQ ID NO 1428
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1428

Leu Phe Leu Gly Gly Leu Asp Ala Leu Tyr Ser Leu Arg
1               5                   10

<210> SEQ ID NO 1429
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1429

Val Ile Ala Leu Gln Ala Gly Gly Ser Ala Glu Pro Glu Glu Val Val
1               5                   10                  15

Leu Glu Glu Leu Gln Val Phe Lys
            20

<210> SEQ ID NO 1430
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1430

Leu Ala Tyr Val Tyr Gln Asn Asn Ile Tyr Leu Lys
1               5                   10

<210> SEQ ID NO 1431
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1431

Asn Val Asp Tyr Leu Leu Ile His Gly Thr Ala Asp Asp Asn Val His
1               5                   10                  15

Phe Gln Asn Ser Ala Gln Ile Ala Lys
            20                  25

<210> SEQ ID NO 1432
<211> LENGTH: 11
<212> TYPE: PRT
<213> ORGANISM: Artificial Sequence

```
<220> FEATURE:
<223> OTHER INFORMATION: Synthetic Polypeptide

<400> SEQUENCE: 1432

Gln Phe Val Tyr Leu Glu Ser Asp Tyr Ser Lys
1               5                   10

<210> SEQ ID NO 1433
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1433

Ser Val Phe Ala Val Asn Trp Ile Ser Tyr Leu Ala Ser Lys
1               5                   10

<210> SEQ ID NO 1434
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1434

Thr Gln Glu His Ile Glu Glu Ser Arg
1               5

<210> SEQ ID NO 1435
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1435

Ala Val Leu Ser Ala Glu Gln Leu Arg
1               5

<210> SEQ ID NO 1436
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1436

Asp Glu Glu Val His Ala Gly Leu Gly Glu Leu Leu Arg
1               5                   10

<210> SEQ ID NO 1437
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1437

Asp Gln Ala Val Glu Asn Ile Leu Val Ser Pro Val Val Ala Ser
1               5                   10                  15

Ser Leu Gly Leu Val Ser Leu Gly Gly Lys
                20                  25

<210> SEQ ID NO 1438
<211> LENGTH: 12
```

```
<212> TYPE: PRT
<213> ORGANISM: Artificial Sequence
<220> FEATURE:
<223> OTHER INFORMATION: Synthetic Polypeptide

<400> SEQUENCE: 1438

Asp Thr Gln Ser Gly Ser Leu Leu Phe Ile Gly Arg
1               5                   10

<210> SEQ ID NO 1439
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1439

Gly Val Val Glu Val Thr His Asp Leu Gln Lys
1               5                   10

<210> SEQ ID NO 1440
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1440

Gly Pro Pro Gly Leu Pro Ala His Leu Asp Glu Glu Leu Gln Ala Thr
1               5                   10                  15

Leu His Asp Phe Arg
            20

<210> SEQ ID NO 1441
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1441

His Gln Ile Leu Gln Thr Arg
1               5

<210> SEQ ID NO 1442
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1442

Tyr Ser Asp Gly Thr Pro Val Asn Tyr Thr Asn Trp Tyr Arg
1               5                   10

<210> SEQ ID NO 1443
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1443

Val Pro Leu Pro Val Asp Lys
1               5
```

```
<210> SEQ ID NO 1444
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1444

Ala Gly Tyr Pro Leu Glu His Pro Phe Asp Phe Arg
1               5                   10

<210> SEQ ID NO 1445
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1445

Ala Leu Pro Ser Gln Gly Leu Ser Ser Ser Ala Val Leu Glu Lys
1               5                   10                  15

<210> SEQ ID NO 1446
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1446

Asp Phe Asp Ile Tyr Arg
1               5

<210> SEQ ID NO 1447
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1447

Gly Ile Phe Val Phe Gly Asn Pro Gln Leu Ser Val Ile Ala Leu Gly
1               5                   10                  15

Ser Arg

<210> SEQ ID NO 1448
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1448

Thr Pro Glu Ile Val Ala Pro Gln Ser Ala His Ala Ala Phe Asn Lys
1               5                   10                  15

<210> SEQ ID NO 1449
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1449

Ala Tyr Glu Asp Glu Tyr Ser Tyr Phe Lys
1               5                   10
```

<210> SEQ ID NO 1450
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1450

```
Gly Gln Gly Tyr Asp Gly Tyr Asp Gly Gln Asn Tyr Tyr His His Gln
1               5                   10                  15
```

<210> SEQ ID NO 1451
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1451

```
Ile Glu Asp Ser Glu Glu Asn Gly Val Phe Lys
1               5                   10
```

<210> SEQ ID NO 1452
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1452

```
Thr Thr Ser Pro Pro Phe Gly Lys
1               5
```

<210> SEQ ID NO 1453
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1453

```
Thr Thr Thr Ser Pro Asn Gly Gly Phe Glu Pro Thr Thr Pro Pro Gln
1               5                   10                  15

Val Tyr Arg
```

<210> SEQ ID NO 1454
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1454

```
Ser Ser Gly Leu Phe Pro Phe Leu Val Leu Leu Ala Leu Gly Thr Leu
1               5                   10                  15

Ala Pro Trp Ala Val Glu Gly Ser Gly Lys
            20                  25
```

<210> SEQ ID NO 1455
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1455

Asn Gln Gly Ser Gly Ala Gly Arg
1               5

<210> SEQ ID NO 1456
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1456

Val Ala Gln Leu Glu Gln Val Tyr Ile Arg
1               5                   10

<210> SEQ ID NO 1457
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1457

Asn Phe Phe Trp Lys
1               5

<210> SEQ ID NO 1458
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1458

Ala Ile Trp Asn Val Ile Asn Trp Glu Asn Val Thr Glu Arg
1               5                   10

<210> SEQ ID NO 1459
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1459

Phe Asn Gly Gly Gly His Ile Asn His Ser Ile Phe Trp Thr Asn Leu
1               5                   10                  15
Ser Pro Asn Gly Gly Gly Glu Pro Lys
            20                  25

<210> SEQ ID NO 1460
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1460

Gly Asp Val Thr Ala Gln Ile Ala Leu Gln Pro Ala Leu Lys
1               5                   10

<210> SEQ ID NO 1461
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1461

Leu Thr Ala Ala Ser Val Gly Val Gln Gly Ser Gly Trp Gly Trp Leu
1               5                   10                  15

Gly Phe Asn Lys
            20

<210> SEQ ID NO 1462
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1462

Asn Val Arg Pro Asp Tyr Leu Lys
1               5

<210> SEQ ID NO 1463
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1463

Glu Asn Gln Glu Val Ile Leu Glu Glu Val Arg
1               5                   10

<210> SEQ ID NO 1464
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1464

Glu Ser Ala Pro Gly Leu Ile Ile Ala Thr Gly Ser Val Gly Lys
1               5                   10                  15

<210> SEQ ID NO 1465
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1465

Leu His Gly Gly Ser Ala Pro Leu Pro Gln Asp Arg
1               5                   10

<210> SEQ ID NO 1466
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1466

Gly Leu Val Leu Ser Gly Val Leu His Lys
1               5                   10

<210> SEQ ID NO 1467
<211> LENGTH: 23
<212> TYPE: PRT
<213> ORGANISM: Artificial Sequence

```
<220> FEATURE:
<223> OTHER INFORMATION: Synthetic Polypeptide

<400> SEQUENCE: 1467

Asn Leu Ile Pro Glu Gly Asn Ile Gly Ser Asn Thr Thr Leu Val Leu
1               5                   10                  15

Val Asn Ala Ile Tyr Phe Lys
            20

<210> SEQ ID NO 1468
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1468

Gln Tyr Thr Ser Phe His Phe Ala Ser Leu Glu Asp Val Gln Ala Lys
1               5                   10                  15

<210> SEQ ID NO 1469
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1469

Val Asp Leu His Leu Pro Arg
1               5

<210> SEQ ID NO 1470
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1470

Val Leu Glu Ile Pro Tyr Lys
1               5

<210> SEQ ID NO 1471
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1471

Asp Glu Leu Asn Ala Asp His Pro Phe Ile Tyr Ile Ile Arg
1               5                   10

<210> SEQ ID NO 1472
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1472

Asp Leu Thr Asp Gly His Phe Glu Asn Ile Leu Ala Asp Asn Ser Val
1               5                   10                  15

Asn Asp Gln Thr Lys
            20
```

<210> SEQ ID NO 1473
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1473

Asp Val Glu Asp Glu Ser Thr Gly Leu Glu Lys
1               5                   10

<210> SEQ ID NO 1474
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1474

Asp Val Pro Phe Gly Phe Gln Thr Val Thr Ser Asp Val Asn Lys
1               5                   10                  15

<210> SEQ ID NO 1475
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1475

Ile Leu Val Val Asn Ala Ala Tyr Phe Val Gly Lys
1               5                   10

<210> SEQ ID NO 1476
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1476

Ala Phe Ile Pro Pro Ala Pro Val Leu Pro Ser Arg
1               5                   10

<210> SEQ ID NO 1477
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1477

Ala Leu Pro Pro Ile Ala Arg
1               5

<210> SEQ ID NO 1478
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1478

Trp Ser Gln Thr Ala Phe Pro Lys
1               5

```
<210> SEQ ID NO 1479
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1479

Tyr Ser Ile Thr Phe Thr Gly Lys
1               5

<210> SEQ ID NO 1480
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1480

Asp Glu Asp Asn Asn Leu Leu Thr Glu Lys
1               5                   10

<210> SEQ ID NO 1481
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1481

Asn Val Leu Val Thr Leu Tyr Glu Arg
1               5

<210> SEQ ID NO 1482
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1482

Glu Val Leu Asp Gln Val Glu Arg
1               5

<210> SEQ ID NO 1483
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1483

Gly Pro Ser Ala Ala Phe Ala Pro Ala Ala Ala Glu Pro Lys
1               5                   10

<210> SEQ ID NO 1484
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1484

Leu Phe Gly Gly Phe Asn Ser Ser Asp Thr Val Thr Ser Pro Gln Arg
1               5                   10                  15

<210> SEQ ID NO 1485
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1485

Leu Leu Leu Asn Ala Glu Asn Pro Arg
1               5

<210> SEQ ID NO 1486
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1486

Thr Gln Phe Asn Ser Leu Gln Gln Leu Val Ala Tyr Tyr Ser Lys
1               5                   10                  15

<210> SEQ ID NO 1487
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1487

Gly Thr Trp Asn Gly Pro Trp Val Ser Thr Glu Val Leu Ala Ala
1               5                   10                  15

Ile Gly Leu Val Ile Tyr Tyr Leu Ala Phe Ser Ala Lys
            20                  25

<210> SEQ ID NO 1488
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1488

Asn Asn Glu Asp Ile Ser Ile Ile Pro Pro Leu Phe Thr Val Ser Val
1               5                   10                  15

Asp His Arg

<210> SEQ ID NO 1489
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1489

Gln Phe Pro Val Thr Arg
1               5

<210> SEQ ID NO 1490
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1490

Ser Ala His Ala Gly Thr Tyr Glu Val Arg
```

```
1               5                  10
```

<210> SEQ ID NO 1491
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1491

```
Tyr Gln Val Ser Trp Ser Leu Asp His Lys
1               5                  10
```

<210> SEQ ID NO 1492
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1492

```
Phe Asn Gln Ala Gln Ser Gly Asn Ile Gln Ser Thr Val Met Leu Asp
1               5                   10                  15
Lys
```

<210> SEQ ID NO 1493
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1493

```
Leu Leu Gly Pro Asn Ala Ser Pro Asp Gly Leu Ile Pro Trp Thr Arg
1               5                   10                  15
```

<210> SEQ ID NO 1494
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1494

```
Thr Glu Leu Ile Ser Val Ser Glu Val His Pro Ser Arg
1               5                   10
```

<210> SEQ ID NO 1495
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1495

```
Val Met Ala Ala Glu Asn Ile Pro Glu Asn Pro Leu Lys
1               5                   10
```

<210> SEQ ID NO 1496
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1496

```
Tyr Thr Tyr Glu His Asp Pro Ile Thr Lys
1               5                   10

<210> SEQ ID NO 1497
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1497

Ala Ile Leu Ser Thr Lys Pro Pro Gly Thr Phe Leu Leu Arg
1               5                   10

<210> SEQ ID NO 1498
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1498

Glu Ser His Ala Thr Leu Val Phe His Asn Leu Leu Gly Glu Ile Asp
1               5                   10                  15

Gln Gln Tyr Ser Arg
            20

<210> SEQ ID NO 1499
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1499

Leu Glu Asn Trp Ile Thr Ser Leu Ala Glu Ser Gln Leu Gln Thr Arg
1               5                   10                  15

<210> SEQ ID NO 1500
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1500

Leu Leu Gln Thr Ala Ala Thr Ala Ala Gln Gln Gly Gly Gln Ala Asn
1               5                   10                  15

His Pro Thr Ala Ala Val Val Thr Glu Lys
            20                  25

<210> SEQ ID NO 1501
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1501

Val Val Glu Asn Leu Gln Asp Asp Phe Asp Phe Asn Tyr Lys
1               5                   10

<210> SEQ ID NO 1502
<211> LENGTH: 8
<212> TYPE: PRT
<213> ORGANISM: Artificial Sequence
```

```
<220> FEATURE:
<223> OTHER INFORMATION: Synthetic Polypeptide

<400> SEQUENCE: 1502

Ser Phe Leu Tyr Ser Ala Ala Lys
1               5

<210> SEQ ID NO 1503
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1503

Val Ala Ala Gln Asn Ser Ala Glu Val Val Arg
1               5                   10

<210> SEQ ID NO 1504
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1504

Glu Asn Asp Tyr Tyr Thr Pro Thr Gly Glu Phe Arg
1               5                   10

<210> SEQ ID NO 1505
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1505

Phe Glu Ser Val Ile His Glu Phe Asp Pro Tyr Phe Asn Tyr Arg
1               5                   10                  15

<210> SEQ ID NO 1506
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1506

Phe Leu Ala Glu Glu Gly Phe Tyr Lys
1               5

<210> SEQ ID NO 1507
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1507

Phe Tyr Ser Leu Leu Asp Pro Ser Tyr Ala Lys
1               5                   10

<210> SEQ ID NO 1508
<211> LENGTH: 7
<212> TYPE: PRT
<213> ORGANISM: Artificial Sequence
<220> FEATURE:
```

<223> OTHER INFORMATION: Synthetic Polypeptide

<400> SEQUENCE: 1508

Ile Ile Phe Asp Asp Phe Arg
1               5

<210> SEQ ID NO 1509
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1509

Ala Ala Glu Asp Tyr Gly Val Ile Lys
1               5

<210> SEQ ID NO 1510
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1510

Leu Gly Phe Gln Val Trp Leu Lys
1               5

<210> SEQ ID NO 1511
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1511

Leu Val Asn Ser Leu Tyr Pro Asp Gly Ser Lys Pro Val Lys
1               5                   10

<210> SEQ ID NO 1512
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1512

Asn Asp Gly His Tyr Arg
1               5

<210> SEQ ID NO 1513
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1513

Asn Gly Val Ile Leu Ser Lys
1               5

<210> SEQ ID NO 1514
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1514

Ala Gly Ser Glu Val Ile Ser Arg
1               5

<210> SEQ ID NO 1515
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1515

Ala Ser Ser Thr Gln Gln Glu Ile Ser Arg
1               5                   10

<210> SEQ ID NO 1516
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1516

Leu Gln Gly Glu Ala Pro Gln Ser Ala Leu Arg
1               5                   10

<210> SEQ ID NO 1517
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1517

Leu Ser Glu Glu Ile Asp Gln Leu Arg
1               5

<210> SEQ ID NO 1518
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1518

Tyr Gln Asp Val Tyr Val Glu Leu Ser His Ile Lys
1               5                   10

<210> SEQ ID NO 1519
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1519

Ala Val Phe Val Asp Leu Glu Pro Thr Val Ile Asp Glu Val Arg
1               5                   10                  15

<210> SEQ ID NO 1520
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1520

Glu Ile Ile Asp Leu Val Leu Asp Arg
1               5

<210> SEQ ID NO 1521
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1521

Ala Ile Leu Val Asp Leu Glu Pro Gly Thr Met Asp Ser Val Arg
1               5                   10                  15

<210> SEQ ID NO 1522
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1522

Glu Val Asp Glu Gln Met Leu Asn Val Gln Asn Lys
1               5                   10

<210> SEQ ID NO 1523
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1523

Phe Pro Gly Gln Leu Asn Ala Asp Leu Arg
1               5                   10

<210> SEQ ID NO 1524
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1524

Gly His Tyr Thr Glu Gly Ala Glu Leu Val Asp Ser Val Leu Asp Val
1               5                   10                  15

Val Arg

<210> SEQ ID NO 1525
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1525

Ile Ser Glu Gln Phe Thr Ala Met Phe Arg
1               5                   10

<210> SEQ ID NO 1526
<211> LENGTH: 10
<212> TYPE: PRT
<213> ORGANISM: Artificial Sequence
<220> FEATURE:
<223> OTHER INFORMATION: Synthetic Polypeptide

```
<400> SEQUENCE: 1526

Leu Ala Val Asn Met Val Pro Phe Pro Arg
1               5                   10

<210> SEQ ID NO 1527
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1527

Leu His Phe Phe Met Pro Gly Phe Ala Pro Leu Thr Ser Arg
1               5                   10

<210> SEQ ID NO 1528
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1528

Met Ser Ala Thr Phe Ile Gly Asn Ser Thr Ala Ile Gln Glu Leu Phe
1               5                   10                  15
Lys

<210> SEQ ID NO 1529
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1529

Asn Ser Ser Tyr Phe Val Glu Trp Ile Pro Asn Asn Val Lys
1               5                   10

<210> SEQ ID NO 1530
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1530

Ser Gly Pro Phe Gly Gln Ile Phe Arg Pro Asp Asn Phe Val Phe Gly
1               5                   10                  15
Gln Ser Gly Ala Gly Asn Asn Trp Ala Lys
            20                  25

<210> SEQ ID NO 1531
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1531

Ala Leu Thr Val Pro Glu Leu Thr Gln Gln Met Phe Asp Ala Lys
1               5                   10                  15

<210> SEQ ID NO 1532
<211> LENGTH: 12
```

```
<212> TYPE: PRT
<213> ORGANISM: Artificial Sequence
<220> FEATURE:
<223> OTHER INFORMATION: Synthetic Polypeptide

<400> SEQUENCE: 1532

Glu Val Asp Glu Gln Met Leu Ala Ile Gln Ser Lys
1               5                   10

<210> SEQ ID NO 1533
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1533

Ile Ser Val Tyr Tyr Asn Glu Ala Ser Ser His Lys
1               5                   10

<210> SEQ ID NO 1534
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1534

Met Ser Ser Thr Phe Ile Gly Asn Ser Thr Ala Ile Gln Glu Leu Phe
1               5                   10                  15

Lys

<210> SEQ ID NO 1535
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1535

Tyr Leu Thr Val Ala Thr Val Phe Arg
1               5

<210> SEQ ID NO 1536
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1536

Ile Met Asn Thr Phe Ser Val Val Pro Ser Pro Lys
1               5                   10

<210> SEQ ID NO 1537
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1537

Met Ala Val Thr Phe Ile Gly Asn Ser Thr Ala Ile Gln Glu Leu Phe
1               5                   10                  15

Lys
```

<210> SEQ ID NO 1538
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1538

Tyr Leu Thr Val Ala Ala Val Phe Arg
1               5

<210> SEQ ID NO 1539
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1539

Phe Ala Thr Glu Ala Ala Ile Thr Ile Leu Arg
1               5                   10

<210> SEQ ID NO 1540
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1540

Ile His Pro Thr Ser Val Ile Ser Gly Tyr Arg
1               5                   10

<210> SEQ ID NO 1541
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1541

Leu Gly Val Gln Val Val Ile Thr Asp Pro Glu Lys
1               5                   10

<210> SEQ ID NO 1542
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1542

Ser Ser Leu Gly Pro Val Gly Leu Asp Lys
1               5                   10

<210> SEQ ID NO 1543
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1543

Tyr Ile Asn Glu Asn Leu Ile Val Asn Thr Asp Glu Leu Gly Arg
1               5                   10                  15

```
<210> SEQ ID NO 1544
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1544

Ala Tyr Ile Leu Asn Leu Val Lys
1               5

<210> SEQ ID NO 1545
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1545

Gly Asp Val Thr Ile Thr Asn Asp Gly Ala Thr Ile Leu Lys
1               5                   10

<210> SEQ ID NO 1546
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1546

Gly Ile His Pro Thr Ile Ile Ser Glu Ser Phe Gln Lys
1               5                   10

<210> SEQ ID NO 1547
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1547

Ile Asp Asp Val Val Asn Thr Arg
1               5

<210> SEQ ID NO 1548
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1548

Val Ile Asp Pro Ala Thr Ala Thr Ser Val Asp Leu Arg
1               5                   10

<210> SEQ ID NO 1549
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1549

Ala Val Asp Asp Gly Val Asn Thr Phe Lys
1               5                   10

<210> SEQ ID NO 1550
```

```
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1550

Asp Ile Asp Glu Val Ser Ser Leu Leu Arg
1               5                   10

<210> SEQ ID NO 1551
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1551

Leu Ala Thr Asn Ala Ala Val Thr Val Leu Arg
1               5                   10

<210> SEQ ID NO 1552
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1552

Leu Tyr Ala Val His Gln Glu Gly Asn Lys
1               5                   10

<210> SEQ ID NO 1553
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1553

Asn Val Gly Leu Asp Ile Glu Ala Glu Val Pro Ala Val Lys
1               5                   10

<210> SEQ ID NO 1554
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1554

Ala Leu Gln Phe Leu Glu Glu Val Lys
1               5

<210> SEQ ID NO 1555
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1555

Ala Gln Ala Ala Leu Ala Val Asn Ile Ser Ala Ala Arg
1               5                   10

<210> SEQ ID NO 1556
<211> LENGTH: 17
```

```
<212> TYPE: PRT
<213> ORGANISM: Artificial Sequence
<220> FEATURE:
<223> OTHER INFORMATION: Synthetic Polypeptide

<400> SEQUENCE: 1556

Ala Gln Leu Gly Val Gln Ala Phe Ala Asp Ala Leu Leu Ile Ile Pro
1               5                   10                  15
Lys

<210> SEQ ID NO 1557
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1557

Gly Ile Asp Pro Phe Ser Leu Asp Ala Leu Ser Lys
1               5                   10

<210> SEQ ID NO 1558
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1558

Gly Leu Val Leu Asp His Gly Ala Arg
1               5

<210> SEQ ID NO 1559
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1559

Gln Ala Asp Leu Tyr Ile Ser Glu Gly Leu His Pro Arg
1               5                   10

<210> SEQ ID NO 1560
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1560

Thr Glu Val Asn Ser Gly Phe Phe Tyr Lys
1               5                   10

<210> SEQ ID NO 1561
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1561

Val Ala Thr Ala Gln Asp Asp Ile Thr Gly Asp Gly Thr Thr Ser Asn
1               5                   10                  15
Val Leu Ile Ile Gly Glu Leu Leu Lys
            20                  25
```

<210> SEQ ID NO 1562
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1562

Val His Ala Glu Leu Ala Asp Val Leu Thr Glu Ala Val Val Asp Ser
1               5                   10                  15

Ile Leu Ala Ile Lys
            20

<210> SEQ ID NO 1563
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1563

Val Leu Ala Gln Asn Ser Gly Phe Asp Leu Gln Glu Thr Leu Val Lys
1               5                   10                  15

<210> SEQ ID NO 1564
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1564

His Phe Asn Val Asn Thr Asp Tyr Gln Asn Pro Val Arg
1               5                   10

<210> SEQ ID NO 1565
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1565

Ser Glu Asp Glu Glu Asp Leu Gly Asn Ala Arg Pro Ser Ala Pro Ser
1               5                   10                  15

Thr Leu Phe Asp Phe Leu Glu Ser Lys
            20                  25

<210> SEQ ID NO 1566
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1566

Ser Asn Ile Gly Thr Glu Gly Gly Pro Pro Pro Phe Val Pro Phe Gly
1               5                   10                  15

Gln Lys

<210> SEQ ID NO 1567
<211> LENGTH: 10
<212> TYPE: PRT
<213> ORGANISM: Artificial Sequence

```
<220> FEATURE:
<223> OTHER INFORMATION: Synthetic Polypeptide

<400> SEQUENCE: 1567

Ser Val Leu Glu Gly Ser Gly Leu Pro Arg
1               5                   10

<210> SEQ ID NO 1568
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1568

Thr Ala Ala Ile Ala Glu Val Ala Lys
1               5

<210> SEQ ID NO 1569
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1569

Ala Val Asp Ile Pro Gly Leu Glu Ala Ala Thr Pro Tyr Arg
1               5                   10

<210> SEQ ID NO 1570
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1570

Gly Leu Glu Pro Gly Gln Glu Tyr Asn Val Leu Leu Thr Ala Glu Lys
1               5                   10                  15

<210> SEQ ID NO 1571
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1571

Thr Ala His Ile Ser Gly Leu Pro Pro Ser Thr Asp Phe Ile Val Tyr
1               5                   10                  15

Leu Ser Gly Leu Ala Pro Ser Ile Arg
            20                  25

<210> SEQ ID NO 1572
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1572

Thr Val Ser Gly Asn Thr Val Glu Tyr Ala Leu Thr Asp Leu Glu Pro
1               5                   10                  15

Ala Thr Glu Tyr Thr Leu Arg
            20
```

<210> SEQ ID NO 1573
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1573

Tyr Ala Pro Ile Ser Gly Gly Asp His Ala Glu Val Asp Val Pro Lys
1               5                   10                  15

<210> SEQ ID NO 1574
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1574

Asp Ala Gln Gly Gln Pro Gln Ala Val Pro Val Ser Gly Asp Leu Arg
1               5                   10                  15

<210> SEQ ID NO 1575
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1575

Gly Phe Glu Glu Ser Glu Pro Leu Thr Gly Phe Leu Thr Thr Val Pro
1               5                   10                  15

Asp Gly Pro Thr Gln Leu Arg
            20

<210> SEQ ID NO 1576
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1576

Val Pro Gly His Glu Asp Gly Val Thr Ile Ser Gly Leu Glu Pro Asp
1               5                   10                  15

His Lys

<210> SEQ ID NO 1577
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1577

Val Ser Tyr Gln Leu Ala Asp Gly Gly Glu Pro Gln Ser Val Gln Val
1               5                   10                  15

Asp Gly Gln Ala Arg
            20

<210> SEQ ID NO 1578
<211> LENGTH: 9
<212> TYPE: PRT
<213> ORGANISM: Artificial Sequence
<220> FEATURE:

```
<223> OTHER INFORMATION: Synthetic Polypeptide

<400> SEQUENCE: 1578

Tyr Glu Val Thr Val Val Ser Val Arg
1               5

<210> SEQ ID NO 1579
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1579

Gly Ile Leu Leu Tyr Gly Pro Pro Gly Thr Gly Lys
1               5                   10

<210> SEQ ID NO 1580
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1580

Gly Pro Glu Leu Leu Thr Met Trp Phe Gly Glu Ser Glu Ala Asn Val
1               5                   10                  15

Arg

<210> SEQ ID NO 1581
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1581

Ile Val Ser Gln Leu Leu Thr Leu Met Asp Gly Leu Lys
1               5                   10

<210> SEQ ID NO 1582
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1582

Leu Asp Gln Leu Ile Tyr Ile Pro Leu Pro Asp Glu Lys
1               5                   10

<210> SEQ ID NO 1583
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1583

Leu Ile Val Asp Glu Ala Ile Asn Glu Asp Asn Ser Val Val Ser Leu
1               5                   10                  15

Ser Gln Pro Lys
            20

<210> SEQ ID NO 1584
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1584

Met Asp Glu Leu Gln Leu Phe Arg
1               5

<210> SEQ ID NO 1585
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1585

Asn Ala Pro Ala Ile Ile Phe Ile Asp Glu Leu Asp Ala Ile Ala Pro
1               5                   10                  15

Lys

<210> SEQ ID NO 1586
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1586

Val Ile Asn Gln Ile Leu Thr Glu Met Asp Gly Met Ser Thr Lys
1               5                   10                  15

<210> SEQ ID NO 1587
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1587

Trp Ala Leu Ser Gln Ser Asn Pro Ser Ala Leu Arg
1               5                   10

<210> SEQ ID NO 1588
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1588

Gly Gly Thr Leu Ser Thr Pro Gln Thr Gly Ser Glu Asn Asp Ala Leu
1               5                   10                  15

Tyr Glu Tyr Leu Arg
            20

<210> SEQ ID NO 1589
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1589

Leu Asp Thr Leu Ala Gln Glu Val Ala Leu Leu Lys
```

1               5                  10

<210> SEQ ID NO 1590
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1590

Asn Trp Glu Thr Glu Ile Thr Ala Gln Pro Asp Gly Gly Lys
1               5                  10

<210> SEQ ID NO 1591
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1591

Asp Leu Ile Tyr Thr Leu Tyr Tyr Trp Lys
1               5                  10

<210> SEQ ID NO 1592
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1592

Glu Asn Ser Pro Leu Asn Val Ser
1               5

<210> SEQ ID NO 1593
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1593

Thr Ile Leu Glu Trp Glu Pro Lys Pro Val Asn Gln Val Tyr Thr Val
1               5                  10                  15

Gln Ile Ser Thr Lys
            20

<210> SEQ ID NO 1594
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1594

Thr Asn Thr Asn Glu Phe Leu Ile Asp Val Asp Lys
1               5                  10

<210> SEQ ID NO 1595
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1595

```
Val Asn Val Thr Val Glu Asp Glu Arg
1               5

<210> SEQ ID NO 1596
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1596

Gly Phe Val Glu Pro Asp His Tyr Val Val Gly Ala Gln Arg
1               5                   10                  15

<210> SEQ ID NO 1597
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1597

Leu Thr Thr Asp Phe Gly Asn Ala Glu Lys
1               5                   10

<210> SEQ ID NO 1598
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1598

Leu Thr Val Ser Asn Val Leu Lys
1               5

<210> SEQ ID NO 1599
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1599

Ser Ala Phe Ser Asn Leu Phe Gly Gly Glu Pro Leu Ser Tyr Thr Arg
1               5                   10                  15

<210> SEQ ID NO 1600
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1600

Ser Ser Gly Leu Pro Asn Ile Pro Val Gln Thr Ile Ser Arg
1               5                   10

<210> SEQ ID NO 1601
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1601
```

```
His Glu Lys Pro Ser Ala Leu Leu Lys
1               5
```

<210> SEQ ID NO 1602
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1602

```
Asp Glu Leu Asn Gly Phe Phe Asn Lys
1               5
```

<210> SEQ ID NO 1603
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1603

```
His Pro Lys Pro Ser Pro Phe Ile Gly Asn Leu Thr Phe Phe Arg
1               5                   10                  15
```

<210> SEQ ID NO 1604
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1604

```
Gln Gln His Arg Pro Phe Thr Tyr Leu Pro Phe Gly Ala Gly Pro Arg
1               5                   10                  15
```

<210> SEQ ID NO 1605
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1605

```
Gln Val Leu Val Glu Asn Phe Ser Asn Phe Thr Asn Arg
1               5                   10
```

<210> SEQ ID NO 1606
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1606

```
Ser Val Ala Asp Ser Val Leu Phe Leu Arg
1               5                   10
```

<210> SEQ ID NO 1607
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1607

```
His Glu Asn Thr Ser Ser Ser Pro Ile Gln Tyr Glu Phe Ser Leu Thr
```

Arg

<210> SEQ ID NO 1608
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1608

Val Leu Tyr Leu Ser Ala Phe Thr Ser Lys
1               5                   10

<210> SEQ ID NO 1609
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1609

Phe Val Gly Thr Pro Glu Val Asn Gln Thr Thr Leu Tyr Gln Arg
1               5                   10                  15

<210> SEQ ID NO 1610
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1610

Gly Phe Gln Ala Leu Gly Asp Ala Ala Asp Ile Arg
1               5                   10

<210> SEQ ID NO 1611
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1611

Ser Glu Glu Phe Leu Ile Ala Gly Lys
1               5

<210> SEQ ID NO 1612
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1612

Glu Gly Pro Phe Gly Thr Leu Val Tyr Thr Ile Lys
1               5                   10

<210> SEQ ID NO 1613
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1613

```
Gly Trp Ala Pro Pro Asp Lys
1               5

<210> SEQ ID NO 1614
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1614

Ser Ile Ile Asn Ala Thr Asp Pro
1               5

<210> SEQ ID NO 1615
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1615

Tyr Gln Tyr Leu Leu Thr Gly Arg
1               5

<210> SEQ ID NO 1616
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1616

Asp Gly Thr Ser Glu Asn Ser Pro Leu Ile Gly Arg
1               5                   10

<210> SEQ ID NO 1617
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1617

Ile Pro Asp Pro Leu Val Ala Thr Gly Asn Lys
1               5                   10

<210> SEQ ID NO 1618
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1618

Leu Asn Gly Thr Ile Thr Thr Pro Gly Trp Pro Lys
1               5                   10

<210> SEQ ID NO 1619
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1619

Val Pro Leu Gln Phe Ser Gly Gln Asn Glu Lys
```

```
1               5                   10

<210> SEQ ID NO 1620
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1620

Tyr Asp Tyr Val Glu Ile Trp Ser Gly Leu Ser Ser Glu Ser Lys
1               5                   10                  15

<210> SEQ ID NO 1621
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1621

Ala Ala Pro Phe Leu Thr Tyr Phe Gly Leu Phe Gln Val His
1               5                   10

<210> SEQ ID NO 1622
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1622

Ile Asn Ser Ser Ser Pro Leu Arg
1               5

<210> SEQ ID NO 1623
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1623

Leu Asp Leu Leu Val Asp Gly Val Leu Ala Leu Arg
1               5                   10

<210> SEQ ID NO 1624
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1624

Gln Ile Gly Glu Phe Ile Val Thr Arg
1               5

<210> SEQ ID NO 1625
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1625

Thr Leu Pro Trp Ala His Leu Lys
1               5
```

```
<210> SEQ ID NO 1626
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1626

Asp Ile Thr Ser Asp Ser Glu Asn Ser Asn Phe Arg
1               5                   10

<210> SEQ ID NO 1627
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1627

Ile Gln Thr Ile Ile Leu Lys
1               5

<210> SEQ ID NO 1628
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1628

Asn Asp Asn Val Gln Asp Thr Ala Glu Gln Lys
1               5                   10

<210> SEQ ID NO 1629
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1629

Asn Glu Ile Gln Ser Leu Val
1               5

<210> SEQ ID NO 1630
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1630

Ser Val Asn Ala Gln Val Thr Asp Ile Asn Ser Lys
1               5                   10

<210> SEQ ID NO 1631
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 1631

Glu Leu Ala Ser Gln Pro Asp Val Asp Gly Phe Leu Val Gly Gly Ala
1               5                   10                  15
```

```
Ser Leu Lys Pro Glu Phe Val Asp Ile Ile Asn Ala Lys
            20                  25
```

<210> SEQ ID NO 1632
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1632

```
Ser Asn Val Ser Asp Ala Val Ala Gln Ser Thr Arg
1               5                   10
```

<210> SEQ ID NO 1633
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1633

```
Thr Ala Thr Pro Gln Gln Ala Gln Glu Val His Glu Lys
1               5                   10
```

<210> SEQ ID NO 1634
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1634

```
Val Val Phe Glu Gln Thr Lys
1               5
```

<210> SEQ ID NO 1635
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1635

```
Val Val Leu Ala Tyr Glu Pro Val Trp Ala Ile Gly Thr Gly Lys
1               5                   10                  15
```

<210> SEQ ID NO 1636
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1636

```
Ala Asp Ala Val Thr Leu Asp Gly Gly Phe Ile Tyr Glu Ala Gly Leu
1               5                   10                  15

Ala Pro Tyr Lys
            20
```

<210> SEQ ID NO 1637
<211> LENGTH: 11
<212> TYPE: PRT
<213> ORGANISM: Artificial Sequence
<220> FEATURE:
<223> OTHER INFORMATION: Synthetic Polypeptide

```
<400> SEQUENCE: 1637

Phe Gln Leu Phe Gly Ser Pro Ser Gly Gln Lys
1               5                   10

<210> SEQ ID NO 1638
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1638

Leu Arg Pro Val Ala Ala Glu Val Tyr Gly Thr Glu Arg
1               5                   10

<210> SEQ ID NO 1639
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1639

Val Pro Ser His Ala Val Val Ala Arg
1               5

<210> SEQ ID NO 1640
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1640

Tyr Tyr Gly Tyr Thr Gly Ala Phe Arg
1               5

<210> SEQ ID NO 1641
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1641

Phe Gln Asp Leu Val Asp Ala Val Arg
1               5

<210> SEQ ID NO 1642
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1642

Phe Thr Gly Ser Gln Pro Phe Gly Gln Gly Val Glu His Ala Thr Ala
1               5                   10                  15

Asn Lys

<210> SEQ ID NO 1643
<211> LENGTH: 12
<212> TYPE: PRT
<213> ORGANISM: Artificial Sequence
<220> FEATURE:
<223> OTHER INFORMATION: Synthetic Polypeptide
```

<400> SEQUENCE: 1643

Phe Val Phe Gly Thr Thr Pro Glu Asp Ile Leu Arg
1               5                   10

<210> SEQ ID NO 1644
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1644

Gly Phe Leu Leu Leu Ala Ser Leu Arg
1               5

<210> SEQ ID NO 1645
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1645

Gly Thr Ser Gln Asn Asp Pro Asn Trp Val Val Arg
1               5                   10

<210> SEQ ID NO 1646
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1646

Thr Ser Glu Ser Gly Glu Leu His Gly Leu Thr Thr Glu Glu Glu Phe
1               5                   10                  15

Val Glu Gly Ile Tyr Lys
            20

<210> SEQ ID NO 1647
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1647

Val Glu Ile Asp Thr Lys
1               5

<210> SEQ ID NO 1648
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1648

Ala Leu Gln Glu Ala Leu Val Leu Ser Asp Arg
1               5                   10

<210> SEQ ID NO 1649
<211> LENGTH: 17
<212> TYPE: PRT
<213> ORGANISM: Artificial Sequence

```
<220> FEATURE:
<223> OTHER INFORMATION: Synthetic Polypeptide

<400> SEQUENCE: 1649

Glu Gln Glu Glu Leu Leu Ala Pro Ala Asp Gly Thr Val Glu Leu Val
1               5                   10                  15
Arg

<210> SEQ ID NO 1650
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1650

Leu Ser Glu Ala Asp Ile Arg
1               5

<210> SEQ ID NO 1651
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1651

Thr Leu Val Gly Val Gly Ala Ser Leu Gly Leu Arg
1               5                   10

<210> SEQ ID NO 1652
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1652

Val Ala Ala Ala Leu Asp Asp Gly Ser Ala Leu Gly Arg
1               5                   10

<210> SEQ ID NO 1653
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1653

Asp Leu Ser Gln Asn Phe Pro Thr Lys
1               5

<210> SEQ ID NO 1654
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1654

Phe Thr Ile Leu Asp Ser Gln Gly Lys
1               5

<210> SEQ ID NO 1655
<211> LENGTH: 25
<212> TYPE: PRT
```

<213> ORGANISM: Artificial Sequence
<220> FEATURE:
<223> OTHER INFORMATION: Synthetic Polypeptide

<400> SEQUENCE: 1655

Ile Ile Gly Pro Leu Glu Asp Ser Glu Leu Phe Asn Gln Asp Phe
1               5                   10                  15

His Leu Leu Glu Asn Ile Ile Leu Lys
            20                  25

<210> SEQ ID NO 1656
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1656

Leu Gly Ile Glu Gly Leu Ser Leu His Asn Val Leu Lys
1               5                   10

<210> SEQ ID NO 1657
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1657

Tyr Val Leu Glu Pro Glu Ile Ser Phe Thr Ser Asp Asn Ser Phe Ala
1               5                   10                  15

Lys

<210> SEQ ID NO 1658
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1658

Ala Asn Pro Gly Ala Trp Ile Leu Arg
1               5

<210> SEQ ID NO 1659
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1659

Phe Leu Gly Pro Leu Asp Glu Asp Phe Tyr Ala Glu Asp Phe Tyr Leu
1               5                   10                  15

Leu Glu Lys

<210> SEQ ID NO 1660
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1660

Ile Ile Phe Val Asp Ala Asp Gln Ile Val Arg

```
1               5                   10

<210> SEQ ID NO 1661
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1661

Ile Leu Phe Leu Asp Val Leu Phe Pro Leu Ala Val Asp Lys
1               5                   10

<210> SEQ ID NO 1662
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1662

Ile Asn Glu Glu Asn Thr Ala Ile Ser Arg
1               5                   10

<210> SEQ ID NO 1663
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1663

Gly Gly Thr Leu Thr Gln Tyr Glu Gly Lys
1               5                   10

<210> SEQ ID NO 1664
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1664

Gly Leu Pro Asp Asn Ile Ser Ser Val Leu Asn Lys
1               5                   10

<210> SEQ ID NO 1665
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1665

Gly Thr Val Ile Ile Ile Ala Asn His Gly Asp Arg
1               5                   10

<210> SEQ ID NO 1666
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1666

Ile Asp Ile Pro Pro Gly Ala Val Leu Glu Asn Lys
1               5                   10
```

<210> SEQ ID NO 1667
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1667

```
Ile Phe Asn Thr Asn Asn Leu Trp Ile Ser Leu Ala Ala Val Lys
1               5                   10                  15
```

<210> SEQ ID NO 1668
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1668

```
Ile Gln Arg Pro Pro Glu Asp Ser Ile Gln Pro Tyr Glu Lys
1               5                   10
```

<210> SEQ ID NO 1669
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1669

```
Leu Val Glu Ile Ala Gln Val Pro Lys
1               5
```

<210> SEQ ID NO 1670
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1670

```
Asn Glu Asn Thr Phe Leu Asp Leu Thr Val Gln Gln Ile Glu His Leu
1               5                   10                  15

Asn Lys
```

<210> SEQ ID NO 1671
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1671

```
Ser Phe Glu Asn Ser Leu Gly Ile Asn Val Pro Arg
1               5                   10
```

<210> SEQ ID NO 1672
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1672

```
Thr Leu Asp Gly Gly Leu Asn Val Ile Gln Leu Glu Thr Ala Val Gly
```

```
1               5                   10                  15

Ala Ala Ile Lys
            20

<210> SEQ ID NO 1673
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1673

Leu Trp Glu Glu Gly Glu Glu Leu Glu Leu Val Glu Lys
1               5                   10

<210> SEQ ID NO 1674
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1674

Leu Trp Gly Gly Thr Leu Leu Trp Thr
1               5

<210> SEQ ID NO 1675
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1675

Leu Val Asp Thr Leu Pro Gln Lys Pro Arg
1               5                   10

<210> SEQ ID NO 1676
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 1676

Val Ile Glu Thr Leu Leu Met Asp Thr Pro Ser Ser Tyr Glu Ala Ala
1               5                   10                  15

Met Glu Leu Phe Ser Pro Asp Gln Asp Met Arg
            20                  25

<210> SEQ ID NO 1677
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1677

Ala Asp Asp Tyr Glu Gln Val Lys
1               5

<210> SEQ ID NO 1678
<211> LENGTH: 27
<212> TYPE: PRT
<213> ORGANISM: Artificial Sequence
<220> FEATURE:
```

<223> OTHER INFORMATION: Synthetic Polypeptide

<400> SEQUENCE: 1678

Leu His Leu Gln Ser Thr Asp Tyr Gly Asn Phe Leu Ala Asn Glu Ala
1               5                   10                  15

Ser Pro Leu Thr Val Ser Val Ile Asp Asp Arg
            20                  25

<210> SEQ ID NO 1679
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1679

Leu Leu Phe Glu Gly Ala Gly Ser Asn Pro Gly Asp Lys
1               5                   10

<210> SEQ ID NO 1680
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1680

Leu Tyr Pro Glu Gly Leu Ala Gln Leu Ala Arg
1               5                   10

<210> SEQ ID NO 1681
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1681

Asn Val Ala Asp Tyr Tyr Pro Glu Tyr Lys
1               5                   10

<210> SEQ ID NO 1682
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1682

Leu Gln Ala Glu Thr Glu Leu Ile Asn Arg
1               5                   10

<210> SEQ ID NO 1683
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1683

Asn Asp Gln Asn Leu Tyr Gln Val Phe Ile Asn Tyr Lys
1               5                   10

<210> SEQ ID NO 1684
<211> LENGTH: 26
<212> TYPE: PRT

```
<213> ORGANISM: Artificial Sequence
<220> FEATURE:
<223> OTHER INFORMATION: Synthetic Polypeptide

<400> SEQUENCE: 1684

Gln Phe Gln Leu Ser Ile Glu Asn Leu Asn Gln Pro Val Leu Leu Phe
1               5                   10                  15

Gly Arg Pro Gln Gly Asp Gly Glu Ile Arg
            20                  25

<210> SEQ ID NO 1685
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1685

Thr Pro Ile Ala Leu Ala Thr Gly Ile Arg Pro Phe Pro Thr Glu Glu
1               5                   10                  15

Ser Ile Asn Asp Glu Asp Ile Tyr Lys
            20                  25

<210> SEQ ID NO 1686
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1686

Val Thr Trp Asp Ser Ala Gln Val Phe Asp Leu Ala Gln Thr Leu Arg
1               5                   10                  15

<210> SEQ ID NO 1687
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1687

Gln Leu Glu Leu Asn Glu Arg
1               5

<210> SEQ ID NO 1688
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1688

Ser Trp Ser Val Tyr Val Gly Ala Arg
1               5

<210> SEQ ID NO 1689
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1689

Asp Leu Glu Glu Gln Leu Arg
1               5
```

<210> SEQ ID NO 1690
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 1690

Glu Ala Pro Ala Ala Ala Ala Phe Glu Ser Gly Leu Asp Leu Ser
1               5                   10                  15

Asp Ala Glu Pro Asp Ala Gly Glu Ala Thr Ala Tyr Ala Ser Lys
            20                  25                  30

<210> SEQ ID NO 1691
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1691

Glu Gln Ala Asn Leu Asn Ser Arg
1               5

<210> SEQ ID NO 1692
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1692

Phe Ala Ala Ala His Tyr Asn Thr Glu Ile Leu Lys
1               5                   10

<210> SEQ ID NO 1693
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1693

Asn Gln Pro Leu Asn Pro Gly Lys
1               5

<210> SEQ ID NO 1694
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1694

Ala Ala Ser Ser Leu Glu Glu Leu Leu Arg
1               5                   10

<210> SEQ ID NO 1695
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1695

Asp Leu Ile Gln His Pro Lys
1               5

<210> SEQ ID NO 1696
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1696

Phe Ala Ala Thr Phe Tyr Asp Ile Glu Thr Leu Lys
1               5                   10

<210> SEQ ID NO 1697
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1697

Gln Leu Phe Glu Ile Ser Val Pro Leu Thr Ser Val Pro Glu Leu Val
1               5                   10                  15

Pro Val Lys

<210> SEQ ID NO 1698
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1698

Val Ile Asp Glu Glu Trp Gln Arg
1               5

<210> SEQ ID NO 1699
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1699

Ala Phe Pro Ser Pro Glu Val Val Trp Leu Lys
1               5                   10

<210> SEQ ID NO 1700
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1700

Ala Val Ser Ser Phe Pro Asp Pro Ala Leu Tyr Pro Leu Gly Ser Arg
1               5                   10                  15

<210> SEQ ID NO 1701
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1701

Gly Ser Val Glu Ser Ser Ala Tyr Leu Thr Val Gln Gly Thr Ser Asp
1               5                   10                  15

Lys

<210> SEQ ID NO 1702
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1702

Leu Gly Asp Leu Leu Gln Ala Asn Val Gln Gln Asp Gly Lys
1               5                   10

<210> SEQ ID NO 1703
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1703

Asn Ile Leu Leu Ser Glu Asn Asn Val Val Lys
1               5                   10

<210> SEQ ID NO 1704
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1704

Ala Thr Trp Leu Ser Leu Phe Ser Ser Glu Glu Ser Asn Leu Gly Ala
1               5                   10                  15

Asn Asn Tyr Asp Asp Tyr Arg
            20

<210> SEQ ID NO 1705
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1705

Ala Val Arg Pro Gly Tyr Pro Lys
1               5

<210> SEQ ID NO 1706
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1706

Asp Ser Trp Glu Asp Ile Phe Glu Leu Leu Phe Trp Gly Arg
1               5                   10

<210> SEQ ID NO 1707
<211> LENGTH: 15
<212> TYPE: PRT
<213> ORGANISM: Artificial Sequence

```
<220> FEATURE:
<223> OTHER INFORMATION: Synthetic Polypeptide

<400> SEQUENCE: 1707

Asp Val Trp Gly Ile Glu Gly Pro Ile Asp Ala Ala Phe Thr Arg
1               5                   10                  15

<210> SEQ ID NO 1708
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1708

Phe Glu Asp Gly Val Leu Asp Pro Asp Tyr Pro Arg
1               5                   10

<210> SEQ ID NO 1709
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1709

Ala Gly Asp Leu Gln Val Arg Pro Arg
1               5

<210> SEQ ID NO 1710
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1710

Gln Ala Trp Val Ser Gln Gly Gly Gly Ala Lys
1               5                   10

<210> SEQ ID NO 1711
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1711

Val Asn Glu Leu Gly Arg Pro Ala Arg
1               5

<210> SEQ ID NO 1712
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1712

Glu Asn Arg Pro Asp Ala Arg
1               5

<210> SEQ ID NO 1713
<211> LENGTH: 19
<212> TYPE: PRT
<213> ORGANISM: Artificial Sequence
<220> FEATURE:
```

<223> OTHER INFORMATION: Synthetic Polypeptide

<400> SEQUENCE: 1713

Glu Ser Ala Phe Val His Ala Ile Ala Ser Ala Gly Val Ala Phe Ala
1               5                   10                  15

Val Thr Arg

<210> SEQ ID NO 1714
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1714

Gly Trp Val Glu Thr Leu Arg Pro Arg
1               5

<210> SEQ ID NO 1715
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1715

His Gln Gly Ser Pro Gly Lys
1               5

<210> SEQ ID NO 1716
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1716

Tyr Thr Tyr Phe Lys
1               5

<210> SEQ ID NO 1717
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1717

Gly Val Ala Ala Gly Ser Ser Ser Ser Val Lys
1               5                   10

<210> SEQ ID NO 1718
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1718

Ile His Thr His Gly Val Phe Arg
1               5

<210> SEQ ID NO 1719
<211> LENGTH: 32
<212> TYPE: PRT
<213> ORGANISM: Artificial Sequence

```
<220> FEATURE:
<223> OTHER INFORMATION: Synthetic Polypeptide

<400> SEQUENCE: 1719

Asn Gln Gly Tyr Ser Thr Val Thr Phe Asp Gly Thr Pro Ser Tyr Gly
1               5                   10                  15

His Thr Pro Ser His His Ala Ala Gln Phe Pro Asn His Ser Phe Lys
            20                  25                  30

<210> SEQ ID NO 1720
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1720

Ser Asp Glu Leu Val Arg
1               5

<210> SEQ ID NO 1721
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1721

Tyr Gly Pro Phe Gly Pro Pro Pro Ser Gln Ala Ser Ser Gly Gln
1               5                   10                  15

Ala Arg

<210> SEQ ID NO 1722
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1722

Asp Ile Val Glu Tyr Tyr Asn Asp Ser Asn Gly Ser His Val Leu Gln
1               5                   10                  15

Gly Arg

<210> SEQ ID NO 1723
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1723

Asp Tyr Ile Glu Phe Asn Lys
1               5

<210> SEQ ID NO 1724
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1724

Glu Ile Pro Ala Trp Val Pro Phe Asp Pro Ala Ala Gln Ile Thr Lys
1               5                   10                  15
```

<210> SEQ ID NO 1725
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1725

Trp Glu Ala Glu Pro Val Tyr Val Gln Arg
1               5                   10

<210> SEQ ID NO 1726
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1726

Tyr Ser Leu Thr Tyr Ile Tyr Thr Gly Leu Ser Lys
1               5                   10

<210> SEQ ID NO 1727
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 1727

Leu Asp Gly Gln Ile Ser Ser Ala Tyr Pro Ser Gln Glu Gly Gln Val
1               5                   10                  15

Leu Val Gly Ile Tyr Gly Gln Tyr Gln Leu Leu Gly Ile Lys
            20                  25                  30

<210> SEQ ID NO 1728
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1728

Leu Gly Ala Leu Gly Gly Asn Thr Gln Glu Val Thr Leu Gln Pro Gly
1               5                   10                  15

Glu Tyr Ile Thr Lys
            20

<210> SEQ ID NO 1729
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1729

Val Ser Val Gly Leu Leu Leu Val Lys
1               5

<210> SEQ ID NO 1730
<211> LENGTH: 16
<212> TYPE: PRT
<213> ORGANISM: Artificial Sequence
<220> FEATURE:
<223> OTHER INFORMATION: Synthetic Polypeptide

```
<400> SEQUENCE: 1730

Tyr Phe Ser Thr Thr Glu Asp Tyr Asp His Glu Ile Thr Gly Leu Arg
1               5                   10                  15

<210> SEQ ID NO 1731
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1731

Tyr Phe Tyr Phe Gly Lys
1               5
```

SELECTED REACTION MONITORING ASSAYS

RELATED APPLICATIONS

This application claims priority and benefit of U.S. Provisional Application No. 61/578,718 filed Dec. 21, 2011, and U.S. Provisional Application No. 61/614,818 filed Mar. 23, 2012, the contents of each of which are incorporated herein by reference in their entireties.

INCORPORATION-BY-REFERENCE OF SEQUENCE LISTING

The contents of the text file named "Corrected SEQ ID IDIA-004_001US_ST25.txt", which was created on Feb. 24, 2015 and is 404,170 bytes in size, are hereby incorporated by reference in their entireties.

BACKGROUND

Liquid Chromatography Selected Reaction Monitoring Mass Spectrometry (LC-SRM-MS) has emerged as an alternative technology to immunoassays for quantification of target proteins in biological samples. LC-SRM-MS methods are highly desirable because LC-SRM-MS methods provide both absolute structural specificity for the target protein and relative or absolute measurement of the target protein concentration when suitable internal standards are utilized. In contrast to immunoassays, LC-SRM-MS does not involve the manufacturing of biologics. LC-SRM-MS protein assays can be rapidly and inexpensively developed in contrast to the development of immunoassays. LC-SRM-MS are highly multiplexed, with simultaneous assays for hundreds of proteins performed in a single sample analysis. Using LC-SRM-MS in contrast to other proteomic technologies allows for complex assays for the identification diagnostic proteins in complex diseases such as cancer, autoimmune, and metabolic disease. In particular, the development of a highly multiplexed LC-SRM-MS assay that reproducibly identifies a specific set of proteins relevant to a clinical disease presents diagnostic advantages and efficiencies. To date, proteomic techniques have not enabled such inventions to exist where hundreds of proteins can be accurately quantified within a single sample. The present invention provides accurate measurement of hundreds of lung cancer associated proteins within a single sample using multiplexed techniques.

SUMMARY OF THE INVENTION

The present invention comprises a LC-SRM-MS assay for the measurement proteins in a single sample and in a single LC-SRM-MS assay. The assay was optimized for protein quantification and minimal interference among proteins in the assay. This LC-SRM-MS assay is novel because measurement of a large number of proteins in a single sample specifically associated with lung cancer has not been accomplished. Simultaneous measurement of such a large number of proteins without interference among the proteins requires specific techniques to distinguish among the proteins. The current invention provides clinical utility as this assay was used for development of lung cancer diagnostic tests for the early detection of lung cancer, managing disease treatment, as well as testing for disease recurrence.

The object of the present invention is to provide improved methods for the use of LC-SRM-MS in the development of assays. Accordingly, provided herein is a method for developing peptides and transitions for a plurality of at least 200 proteins for a single sample selected reaction monitoring mass spectrometry (LC-SRM-MS) assay, including the steps of providing a set of 200 or more proteins; generating transitions for each protein; assessing LC-SRM-MS data by Mascot score; performing collision energy optimization on the transitions; selecting peptides with transitions showing the greatest peak areas of their transitions; selecting a set of transitions for each peptide, wherein the transitions for each peptide have one of the four most intense b or y transition ions; the transitions for each peptide have m/z values of at least 30 m/z above or below those of the precursor ion; the transitions for each peptide do not interfere with transitions from other peptides; and the transitions represent transitions due to breakage of peptide bond at different sites of the protein.

In one embodiment of the method, each selected peptide in the set of peptides has a monoisotopic mass of 700-5000 Da; and does not contain a cysteine or a methionine; or may contain cysteine or methionine. In another embodiment, the transitions for each peptide have one of the four most intense b or y transition ions; have m/z values of at least 30 m/z above or below those of a precursor ion; do not interfere with transitions from other peptides; and represent transitions due to breakage of peptide bond at different sites of the protein.

In another embodiment of the method, the peptides do not include any peptide that is bounded by KK, KR, RK or RR (either upstream or downstream) in the corresponding protein sequence. Specifically, the amino acid is charged at pH 7.0. These amino acids include arginine and lysine. In another embodiment, each peptide of said set of peptides is unique to the corresponding protein. In yet another embodiment, the peptides do not include peptides which were observed in post-translational modified forms. In still another embodiment, each set of peptides is prioritized according to one or more of the following ordered set of criteria: unique peptides first, then non-unique; peptides with no observed post-translational modifications first, then those observed with post-translational modifications; peptides within the mass range 800-3500 Da first, then those outside of 800-3500 Da; and sorted by decreasing number of variant residues. In certain embodiments, The peptides are unique in that they only appear once among the peptides run in a single assay.

In one embodiment, each set of peptides is prioritized according to all of the ordered set of criteria. In another embodiment, each prioritized set of peptides contains 1-5 peptides.

In certain embodiments of the preceding methods, the two best peptides per protein and the two best transitions per peptide are selected based on experimental data resulting from LC-SRM-MS analysis of one or more of the following experimental samples: a biological disease sample, a biological control sample, and a mixture of synthetic peptides of interest. In a particular embodiment, the biological disease and biological control samples are processed using an immunodepletion method prior to LC-SRM-MS analysis. In another embodiment, the experimental samples contain internal standard peptides. In yet another embodiment, the LC-SRM-MS analysis method specifies a maximum of 7000 transitions, including transitions of the internal standard peptides and transitions. In other embodiments the method specifies a maximum of between 1000-7000, 2000-6000, 3000-5000 and about 3500 transitions.

In one embodiment of the method, the top two transitions per peptide are selected according to one or more of the following criteria the transitions exhibit the largest peak areas measured in either of the two biological experimental samples; the transitions are not interfered with by other ions; the transitions do not exhibit an elution profile that visually differs from those of other transitions of the same peptide; or the transitions are not beyond the detection limit of both of the two biological experimental samples.

In another embodiment of the method, the top two peptides per protein are selected according to one or more of the following criteria: one or more peptides exhibit two transitions and represent the largest combined peak areas of the two transitions; or one or more peptides exhibit one transition and represent the largest combined peak areas of the two transitions.

In another aspect, provided herein is an assay developed according to the foregoing method, and embodiments thereof.

In yet another aspect provided herein is the use of an assay developed according to the foregoing method, and embodiments thereof, to detect a plurality of at least 200 proteins in a single biological sample.

In another aspect, provided herein is an assay developed according to the foregoing method, and embodiments thereof.

The disclosure provides a composition comprising at least five transition ions selected from the listing of transition ions in Table 2. In one embodiment of the assay each transition ion independently corresponds to a unique protein. The five transition ions corresponded to proteins selected from the group consisting of LRP1, BGH3, COIA1, TETN, TSP1, ALDOA, GRP78, ISLR, FRIL, LG3BP, PRDX1, FIBA, and GSLG1. (see: U.S. application Ser. No. 13/306,823 PCT/US11/62461). The composition can further include an additional five transition ions selected from the listing of transition ions in Table 2. The additional five transition ions can corresponded to the proteins APOE, BASP1, CD14, FOXA2 and HSPB1.

The disclosure provides a composition comprising at least five synthetic peptides selected from the listing of peptides and proteins in Table 2. In one embodiment, each peptide can independently correspond to a unique protein. At least one of the peptides was isotopically labeled. The amount of each of the at least five synthetic peptides is known. In another embodiment, the composition included one or more polar solvents. The five synthetic peptides can correspond to the proteins LRP1, BGH3, COIA1, TETN, TSP1, ALDOA, GRP78, ISLR, FRIL, LG3BP, PRDX1, FIBA, and GSLG1. The composition can also include an additional five synthetic peptides selected from the listing of peptides and proteins in Table 2. The additional five synthetic peptides can correspond to the proteins APOE, BASP1, CD14, FOXA2 and HSPB1.

The disclosure provides a use of a composition, as described above, for the development of an assay to detect a disease, disorder or condition in a mammal.

The disclosure provides a method comprising analyzing a composition, as described above, using mass spectrometry. The method can use selected reaction monitoring mass spectrometry.

DETAILED DESCRIPTION OF THE INVENTION

Figure 1:
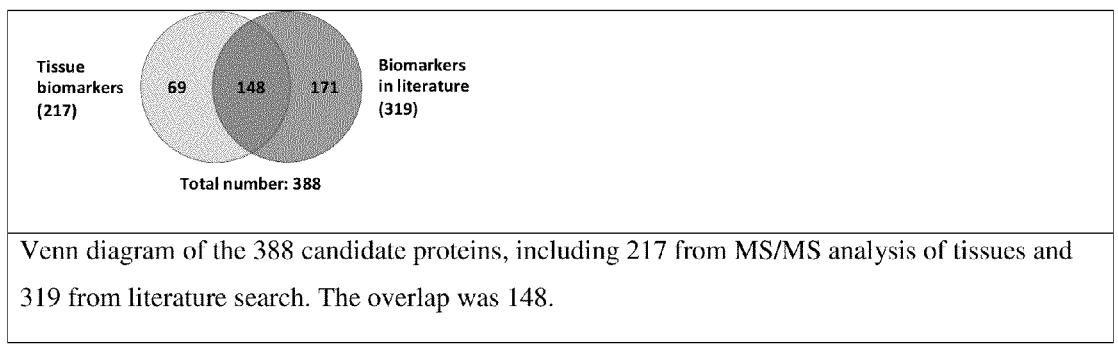
FIG. 1 depicts candidate protein cohort by source. 217 tissue proteins were identified using proteomics analysis. 319 proteins were identified by review of the literature. Between the two sources, there was an overlap of 148 proteins.

The present disclosure relates to methods for developing peptides and transitions for a single sample selected reaction monitoring mass spectrometry (LC-SRM-MS) assay, generally comprising the steps of providing a set of proteins; identifying representative proteolytic peptides for each protein according to a set of criteria; identifying representative transitions for each peptide according to another set of criteria; and selecting the optimum peptides per protein and the optimum transitions per peptide.

Selected reaction monitoring mass spectrometry is capable of highly sensitive and accurate protein quantification based on the quantification of proteolytic peptides. In terms of clinical utility, mass spectrometry-based assays are often compared to immunoassays (e.g., Enzyme-Linked Immunosorbent Assay, or ELISA), which have the ability to quantify specific analytes in large sample sets (e.g., 96 or 384 samples in parallel microtitre plate-based format). Until recently, mass spectrometry-based protein assays were not able to match these sample sizes or quantitative accuracy. Considerable time and expense is required to generate and characterize antibodies required for immunoassays. Increasingly efficient LC-SRM-MS assays, therefore, may surpass immunoassays such as ELISA in the rapid development of clinically useful, multiplexed protein assays.

LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio in LC-SRM-MS is often superior to conventional tandem mass spectrometry (MS/MS) experiments that do not selectively target (filter) particular analytes but rather aim to survey all analytes in the sample.

Accordingly, provided herein is a method for developing peptides and transitions for a plurality of proteins for use in selected reaction monitoring mass spectrometry (LC-SRM-MS) assay. In a preferred embodiment, the assay involves the analysis of a single sample containing all analytes of interest (e.g., a proteolytic digest of plasma proteins). As to the selection of the protease(s) used, trypsin, which cleaves exclusively C-terminal to arginine and lysine residues, is a preferred choice to generate peptides because the masses of generated peptides are compatible with the detection ability of most mass spectrometers (up to 2000 m/z), the number and average length of generated peptides, and also the availability of efficient algorithms for the generation of databases of theoretical trypsin-generated peptides. High cleavage specificity, availability, and cost are other advantages of trypsin.

Other suitable proteases will be known to those of skill in the art. Miscleavage is a factor for failure or ambiguous protein identification. A miscleavage can be defined as partial enzymatic protein cleavages generating peptides with internal missed cleavage sites reflecting the allowed number of sites (targeted amino acids) per peptide that were not cut. The presence of post-translational modifications (PTMs) is also a potential contributor to the problem of miscleavages.

LC-SRM-MS mass spectrometry involves the fragmentation of gas phase ions and occurs between the different stages of mass analysis. There are many methods used to fragment the ions and these can result in different types of fragmentation and thus different information about the structure and composition of the molecule. The transition ions observed in an LC-SRM-MS spectrum result from several different factors, which include, but are not limited to, the primary sequence, the amount of internal energy, the means of introducing the energy, and charge state. Transitions must carry at least one charge to be detected. An ion is categorized as either a, b or c if the charge is on a transition comprising the original N terminus of the peptide, whereas the ion is categorized as either x, y or z if the charge is on a transition comprising the original C terminus of the peptide. A subscript indicates the number of residues in the transition (e.g., one peptide residue in $x_1$, two peptide residues in $y_2$, and three peptide residues in $z_3$, etc.).

In a generic peptide repeat unit represented —N—C(O)—C—, an x ion and an a ion resulting from cleavage of the carbonyl-carbon bond (i.e., C(O)—C). The x ion is an acylium ion, and the a ion is an iminium ion. A y ion and a b ion result from cleavage of the carbonyl-nitrogen bond (i.e., C(O)—N, also known as the amide bond). In this case, the y ion is an ammonium ion and the b ion is an acylium ion. Finally, a z ion and a c ion result from cleavage of the nitrogen-carbon (i.e., C—N) bond. The z ion is a carbocation and the c ion is an ammonium ion.

Superscripts are sometimes used to indicate neutral losses in addition to the backbone fragmentation, for example, * for loss of ammonia and ° for loss of water. In addition to protons, c ions and y ions may abstract an additional proton from the precursor peptide. In electrospray ionization, tryptic peptides may carry more than one charge.

Internal transitions arise from double backbone cleavage. These may be formed by a combination of b-type and y-type cleavage (i.e., cleavage producing b and y ions). Internal cleavage ions may also be formed by a combination of a-type and y-type cleavage. An internal transition with a single side chain formed by a combination of a-type and y-type cleavage is called an iminium ion (sometimes also referred to as an imonium or immonium ion). These ions are labeled with the one letter code for the corresponding amino acid.

Low energy CID (i.e., collision induced dissociation in a triple quadrupole or an ion trap) involves the fragmentation of a peptide carrying a positive charge, primarily along its backbone, to generate primarily a, b and y ions.

In one aspect, provided herein is a method for developing peptides and transitions for a plurality of proteins for a single sample selected reaction monitoring mass spectrometry (LC-SRM-MS) assay, by: (a) providing a panel of a plurality of proteins; (b) identifying a set of peptides for each protein, wherein (i) each peptide in the set of peptides corresponds to a transition of said protein; (ii) the peptides have a monoisotopic mass of 700-5000 Da; and (iii) the peptides do not contain a cysteine or a methionine; or may contain cysteine or methionine; (c) identifying a set of transitions for each peptide, wherein (i) the transitions for each peptide have one of the four most intense b or y transition ions; (ii) the transitions for each peptide have m/z values of at least 30 m/z above or below those of the precursor ion; (iii) the transitions for each peptide do not interfere with transitions from other peptides; and (iv) the transitions represent transitions due to breakage of peptide bond at different sites of the protein; and (d) selecting the peptides for each protein that best fit the criteria of step (b) and the transitions per peptide that best fit the criteria of step (c); thereby developing peptides and transitions for a LC-SRM-MS assay.

By plurality of proteins it is meant at least 2, 3, 4, 5, 6, 7, 8, 9, 10, 15, 20, 25, 50, 100, 150, 200, 250, 300, 350, 400, 450, 500 or more In certain embodiments, the plurality of proteins can encompass between 2 and 10. 10 and 20, 20 and 50, 50 and 100, 100 and 200, or 200 and 500 proteins. In other embodiments, the plurality of proteins can encompass between 250 and 450; or 300 and 400 proteins.

Trypsin-like proteases cleave peptide bonds following a positively charged amino acid (e.g., lysine (K) or arginine (R)). This specificity is driven by the residue which lies at the base of the enzyme's SI pocket (generally a negatively charged aspartic acid or glutamic acid). Accordingly, in one embodiment of the method, the peptides do not include any peptide that is bounded by KK, KR, RK or RR, either upstream of downstream in the corresponding protein sequence. In another embodiment, each peptide of said set of peptides is unique to the corresponding protein.

Post-translational modification (PTM) is the chemical modification of a protein after its translation. It can include any modification following translation, including cleavage. It is one of the later steps in protein biosynthesis, and thus gene expression, for many proteins. It is desirable to avoid such peptides for the purpose of protein identification. Thus, in another embodiment, the peptides do not include peptides which were observed in post-translational modified forms.

In still another embodiment, each set of peptides is prioritized according to one or more of the following ordered set of criteria: (a) unique peptides first, then non-unique; (b) peptides with no observed post-translational modifications first, then those observed with post-translational modifications; (c) peptides within the mass range 800-3500 Da first, then those outside of 800-3500 Da; and (d) sorted by decreasing number of variant residues. In one embodiment, each set of peptides is prioritized according to all of the ordered set of criteria. In another embodiment, each prioritized set of peptides contains 1-5 peptides.

In certain embodiments, one or more liquid chromatography (LC) purification steps are performed prior to a subsequent LC-SRM-MS analysis step. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In various embodiments the columns are polar, ion exchange (both cation and anion), hydrophobic interaction, phenyl, C-2, C-8, C-18 columns, polar coating on porous polymer, or others that are commercially available. During chromatography, the separation of materials is effected by variables such as choice of eluant (also known as a "mobile phase"), choice of gradient elution and the gradient conditions, temperature, etc. In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

The following parameters are used to specify an LC-SRM-MS assay of a protein under a particular LC-SRM-MS system: (1) a tryptic peptide of the protein; (2) the retention time (RT) of the peptide; (3) the m/z value of the peptide precursor ion; (4) the declustering potential used to ionize the precursor ion; (5) the m/z value of a fragment ion generated from the peptide precursor ion; and (6) the collision energy (CE) used to fragment the peptide precursor ion that is optimized for the particular peptide.

In certain embodiments of the preceding methods, the two best peptides per protein and the two best transitions per peptide are selected based on experimental data resulting from LC-SRM-MS analysis of one or more of the following experimental samples: a biological disease sample, a biological control sample, and a mixture of synthetic peptides of interest. Biological samples include body fluids, tissue samples and cell samples. Body fluid samples can include blood, serum, sputum, genital secretions, cerebrospinal fluid, sweat or excreta such as urine. Body tissue samples can include lung, skin, brain, spine, bone, muscle, epithelial, liver, kidney, pancreas, gastrointestinal tract, cardiovascular tissue, heart or nervous tissue. Biological disease samples can include cancer, benign tumors, infected tissue and tissue subject to trauma. In a particular embodiment, the biological disease and biological control samples are processed using an immunodepletion method prior to LC-SRM-MS analysis. Immunodepletion involves removal of one or more proteins through the use of antibodies. Numerous immunodepletion techniques are known to those of skill in the art. In another embodiment, the biological disease and biological control samples are processed using an immunocapture method prior to LC-SRM-MS analysis. Immunocapture involves selection of one or more proteins through the use of antibodies. Numerous immunocapture techniques are known to those of skill in the art.

To facilitate accurate quantification of the peptide transitions by the methods disclosed herein, a set of isotopically-labeled synthetic versions of the peptides of interest may be added in known amounts to the sample for use as internal standards. Since the isotopically-labeled peptides have physical and chemical properties identical to the corresponding surrogate peptide, they co-elute from the chromatographic column and are easily identifiable on the resultant mass spectrum. The addition of the labeled standards may occur before or after proteolytic digestion. Methods of synthesizing isotopically-labeled peptides will be known to those of skill in the art. Thus, in another embodiment, the experimental samples contain internal standard peptides. Other embodiments may utilize external standards or other expedients for peptide quantification.

In yet another embodiment, the LC-SRM-MS analysis method specifies a maximum of 7000 transitions, including transitions of the internal standard peptides and transitions. As used herein, the term "transition" refers to the specific pair of m/z (mass-to-charge) values associated with the precursor and transition ions corresponding to a specific peptide and, therefore, to a specific protein.

In one embodiment of the method, the top two transitions per peptide are selected according to one or more of the following criteria (A): (1) the transitions exhibit the largest peak areas measured in either of the two biological experimental samples; (2) the transitions are not interfered with by other ions; (3) the transitions do not exhibit an elution profile that visually differs from those of other transitions of the same peptide; (4) the transitions are not beyond the detection limit of both of the two biological experimental samples; (5) the transitions do not exhibit interferences.

For the mass spectrometric analysis of a particular peptide, the quantities of the peptide transitions in the sample may be determined by integration of the relevant mass spectral peak areas, as known in the prior art. When isotopically-labeled internal standards are used, as described above, the quantities of the peptide transitions of interest are established via an empirically-derived or predicted relationship between peptide transition quantity (which may be expressed as concentration) and the area ratio of the peptide transition and internal standard peaks at specified transitions.

In another embodiment of the method, the top two peptides per protein are selected according to one or more of the following criteria (B): (1) one or more peptides exhibit two transitions according to criteria (A) and represent the largest combined peak areas of the two transitions according to criteria (A); and (2) one or more peptides exhibit one transition according to criteria (A) and represent the largest combined peak areas of the two transitions according to criteria (A).

Assays

The methods of the present disclosure allow the quantification of high abundance and low abundance plasma proteins that serve as detectable markers for various health states (including diseases and disorders), thus forming the basis for assays that can be used to determine the differences between normal levels of detectable markers and changes of such detectable markers that are indicative of changes in health status. In one aspect of the invention, provided herein is an assay developed according to the foregoing method, and embodiments thereof. In another aspect, provided herein is the use of an assay developed according to the foregoing method, and embodiments thereof, to detect a plurality of at least 200, 300, or more proteins in a single sample. In a merely illustration embodiment, 388 proteins in the following table 1 are detected utilizing the method of present invention.

Of the 388 proteins, the 36 most cooperative proteins are listed in Table 2.

SRM assays for the 388 proteins were developed using standard synthetic peptide techniques. Of the 388 candidates, SRM assays were successfully developed for 371 candidates. The 371 SRM assays were applied to benign and lung cancer plasma samples to evaluate detection rate in blood. The summary of the SRM assay for these 371 proteins is listed in table 3 (see also Example III).

DEFINITIONS

Figure 2:
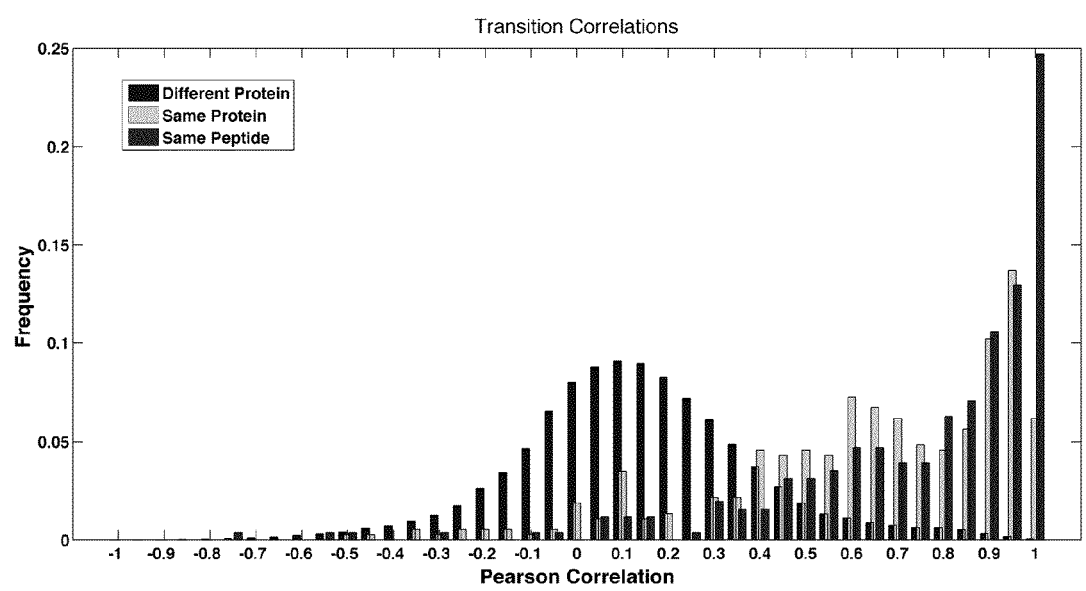
FIG. 2 is a bar diagram showing Pearson correlations for peptides from the same peptide, from the same protein and from different proteins.

As used herein, "transition" refers to a pair of m/z values associated with a peptide. Normally, labeled synthetic peptides are used as quality controls in SRM assays. However, for very large SRM assays such as the 371 protein lung cancer assay, labeled peptides are not feasible. However, correlation techniques (Kearney, Butler et al. 2008) were used to confirm the identity of protein transitions with high confidence. In FIG. 2 a histogram of the Pearson correlations between every pair of transitions in the assay is presented. The correlation between a pair of transitions is obtained from their expression profiles over all samples (143) in the training study detailed below. As expected, transitions from the same peptide are highly correlated. Similarly, transitions from different peptide fragments of the same protein are also highly correlated. In contrast, transitions from different proteins are not highly correlated. This methodology enables a statistical analysis of the quality of a protein's SRM assay. For example, if the correlation of transitions from two peptides from the same protein is above 0.5 then there is less than a 5% probability that the assay is false.

As used herein, a "tryptic peptide" refers to the peptide that is formed by the treatment of a protein with trypsin.

As used herein, "RT" refers to "retention time", the elapsed time between injection and elution of an analyte.

As used herein, "m/z" indicates the mass-to-charge ratio of an ion.

As used herein, "DP" refers to "declustering potential", a voltage potential to dissolvate and dissociate ion clusters. It is also known as "fragmentor voltage" or "ion transfer capillary offset voltage" depending on the manufacture.

As used herein, "CE" refers to "collision energy", the amount of energy precursor ions receive as they are accelerated into the collision cell.

As used herein, "LC-SRM-MS" is an acronym for "selected reaction monitoring" and may be used interchangeably with "LC-MRM-MS".

As used herein, "MS/MS" represents tandem mass spectrometry, which is a type of mass spectrometry involving multiple stages of mass analysis with some form of fragmentation occurring in between the stages.

As used herein, "ISP" refers to "internal standard peptides".

As used herein, "HGS" refers to "human gold standard", which is comprised of a pool of plasma from healthy individuals.

As used herein, "MGF" refers to "Mascot generic file". Mascot is a search engine that uses mass spectrometry data to identify proteins from primary sequence databases. A Mascot generic file is a plain text (ASCII) file containing peak list information and, optionally, search parameters.

Mascot is a web-based tool for deriving protein sequences from mass spectrometry data. This data can be acquired from any mass spectrometry technique including MALDI-TOF and MS/MS (including LC-SRM-MS) data. Mascot uses a 'probability-based MOWSE' algorithm to estimate the significance of a match (i.e., that the observed transitions correspond to a particular protein). The total score is the absolute probability that the observed match is a random event. They are reported as −10×LOG 10(P), where P is the absolute probability. Lower probabilities, therefore, are reported as higher scores. For example, if the absolute probability that an observed match is random is $1 \times 10^{-12}$, Mascot reports it as 120.

The disclosure also provides compositions. These compositions can include any of the transition ions described in Table 2. These transition ions exist while peptides derived from the proteins in Table 2 are undergoing analysis with LC-SRM-MS. In one embodiment, the composition includes any of the transition ions described in Table 2. In another embodiment, the composition includes any two transition ions described in Table 2. In other embodiments, the composition includes, any 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300 or 331 transition ions described in Table 2.

In another embodiment, the transition ions correspond with human proteins including LRP1, BGH3, COIA1, TETN, TSP1, ALDOA, GRP78, ISLR, FRIL, LG3BP, PRDX1, FIBA, and GSLG1. In another embodiment, the transition ions are derived from human proteins including LRP1, BGH3, COIA1, TETN, TSP1, ALDOA, GRP78, ISLR, FRIL, LG3BP, PRDX1, FIBA, and GSLG1. These proteins can further include transition ions corresponding with and/or derived from any number of additional proteins from Table 2. Thus, the composition can include, any additional 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300 or 331 transition ions described in Table 2.

In another embodiment, each of the transition ions in the composition corresponds and/or is derived from a different protein. In another embodiment, 90% of the transition ions in the composition correspond with and/or are derived from a protein that no other transition ion in the composition corresponds. In other embodiments, 80, 70, 60, 50, 40, 30, 20, 10 or 0% of the transition ions in the composition correspond and/or are derived from a protein that no other transition ion in the composition corresponds.

The compositions described herein included synthetic peptides. Synthetic peptides can be used as controls for the abundance of proteins they are derived from and/or correspond. In certain embodiments, the abundance of the synthetic peptides is defined and the results are compared to LC-SRM-MS results from a peptide found in a sample to the LC-SRM-MS results in the corresponding synthetic peptide. This allows for the calculation of the abundance of the peptide in the sample. In certain embodiments, by knowing the abundance of a peptide in a sample, the abundance of the protein it corresponded to is determined.

Synthetic peptides can be generated using any method known in the art. These methods can include recombinant expression techniques such as expression in bacteria or in vitro expression in eukaryotic cell lysate. These methods can also include solid phase synthesis.

In one embodiment, the composition includes synthetic peptides selected from any of the peptides described in Table 2. In another embodiment, the composition included any two peptides described in Table 2. In other embodiments, the composition included, any 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300 or more peptides described in Table 2.

In another embodiment, the peptides corresponded with human genes including LRP1, BGH3, COIA1, TETN, TSP1, ALDOA, GRP78, ISLR, FRIL, LG3BP, PRDX1, FIBA, and GSLG1 as described in corresponding patent application. These genes can further include peptides corresponding with any number of additional genes from Table 2. Thus, the composition can include, any additional 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300 or more peptides described in Table 2.

In another embodiment, each of the peptides in the composition each corresponds with a different protein. In another embodiment, 90% of the peptides in the composition correspond with a protein that no other peptide in the composition corresponds with. In other embodiments, 80, 70, 60, 50, 40, 30, 20, 10 or 0% of the peptides in the composition correspond with from a protein that no other peptide in the composition corresponds with.

The peptides can be isotopically labeled. The isotopes with which they can be labeled include $^{13}C$, $^{2}H$, $^{15}N$ and $^{18}O$. The peptides can also include a polar solvent. Polar solvents can include water and mixtures of ethanol and water.

In certain embodiments, the samples described herein are taken from mammals. These mammals include rats, mice, rabbits, dogs, non-human primates and humans. Samples can be isolated from any tissue or organ or from any bodily fluid. Organs from which samples can be taken include skin, heart, lung, brain, kidney, liver, pancreas, spleen, testes, ovaries, gall bladder, thymus, thyroid, eye, ear, nose, mouth, tongue, penis, vagina, bladder or larynx. Tissues include nervous tissue, vascular tissue, muscle, bone, gastrointestinal tract, epithelial tissue, fibroblastic tissue, mucous membranes, hair, skin, reproductive tissue and connective tissue. Body fluids and excretions include, blood, serum, saliva, urine, semen, vaginal secretions, excrement, bile, tears, lymph, ear wax, mucous, shed skin, finger nails, toe nails, skin oils, sweat and dandruff.

The relative abundance of one or more of the proteins represented by the transition ions and synthetic peptides described above can be used to diagnose, determine likelihood of the presence of, develop prognoses for and/or stage various diseases and pathologies. Often the organ, tissue or bodily fluid or excretion from which the sample is taken is distinct from the organ, tissue or bodily fluid or excretion involved with the disease or pathology. For example, the presence of lung cancer can be determined from a sample taken from blood. Any type of body fluid may be used in the assays.

Diseases and pathologies that status, diagnosis, presence or prognosis can be found using the transition ions and/or synthetic peptides described herein include cancer, metabolic diseases, neurological disorders, infectious diseases and cardiovascular disorders.

EXAMPLES

Exemplary Standard Operating Procedure

Protein Selection

Proteins known to be over-expressed on the cell surface of lung cancer tumors were obtained (through literature searching, experimental data or proprietary databases). This was referred to as set 'A'. Proteins known to be over-secreted by lung cancer tumor cells were obtained (through literature searching, experimental data or proprietary databases). This was referred to as set 'B'. Proteins associated with lung cancer in the literature were mined. This was referred to as set 'C'. Proteins of interest (sets A, B and C are merged resulting in over 700 proteins) were assembled. The set of proteins was reduced to a set of 388 proteins (see Table 4) by prioritizing those proteins that have been previously detected my LC-MS/MS in blood (serum or plasma).

Selected proteins were then identified by their UniProt protein name and accession, their Entrez gene symbol and gene name, the isoform accession and their amino acid sequence. The canonical isoform in UniProt was selected if a protein has more than one isoform.

Peptide Selection for Synthesis

The five best peptides per protein for LC-SRM-MS assay were selected for as follows. Fully tryptic peptides having a monoisotopic mass of 800-3500 mass units, without miscleavages, not containing a cysteine (C) or a methionine (M), without having high miscleavage probability were selected. Further, any peptide that was bounded by KK, KR, RK or RR (either upstream or downstream) in the corresponding protein sequence was not selected.

Peptides were selected that were unique to the protein of interest. Peptides were only selected that match only one protein or protein family including analogues of the one protein, when searched in protein databases. Further, peptides which were observed in post-translational modified forms were not selected. Databases were assessed that showed expression of the proteins from which the peptides were isolated in human blood. Also databases of good quality MS peptides were searched. Peptides that appeared in human blood and were good quality MS peptides were favored. If these methods did not result in a sufficient number of peptides, rules were relaxed in a step wise manner to allow a greater number of peptides until a sufficient number was reached. The purity of the synthesized peptides was >75% and the amount of material was ≥25 µg. Peptides did not need to be desalted.

The four best transitions per peptide are then selected and optimized based on experimental results from a mixture of synthetic peptides. LC-SRM-MS-triggered MS/MS spectra were acquired for each synthetic peptide, using a QTRAP 5500 instrument. One spectrum for the doubly- and one for the triply-charged precursor ion was collected for each peptide For the identified peptides (Mascot score ≥15), retention time was recorded for the four most intense b or y transition ions. The selected transition ions possessed m/z values were at least 30 m/z above or below those of the precursor ions; they did not interfere with other synthetic peptides; and they were transition ions due to breakage of peptide bond at different sites.

If an insufficient percentage of the synthetic peptides were acquired, the steps were repeated. In some cases, the second transition with first with theoretical y+ ions with m/z values at least 30 m/z above those of the doubly charged precursor ion was selected if an insufficient percentage was acquired. Peptides that failed to trigger the acquisition of MS/MS spectrum were discarded.

Collision energy (CE) for each selected transition (See Table 4) was optimized.

Exemplary Protein List

The abundance of the following proteins can be assessed substantially simultaneously using the MS-LC-SRM-MS system described herein. Transitions from these proteins can be used to diagnose diseases including lung cancer when their abundance is measured in a biological specimen from a subject to be diagnosed for lung cancer. In one embodiment, the abundances of these proteins are measured in the blood serum of the subject.

TABLE 1

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| 1433B_HUMAN | 14-3-3 protein beta/alpha | YWHAB | Secreted, EPI | LungCancers | Cytoplasm. Melanosome. Note = Identified by mass spectrometry in melanosome fractions from | Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| 1433E_HUMAN | 14-3-3 protein epsilon | YWHAE | ENDO | LungCancers, BenignNodules | Cytoplasm (By similarity). Melanosome. Note = Identified by mass spectrometry in melanosome fractions from stage I to stage IV. | Literature, Detection |
| 1433S_HUMAN | 14-3-3 protein sigma | SFN | Secreted, EPI | LungCancers | Cytoplasm. Nucleus (By similarity). Secreted. Note = May be secreted by a non-classical secretory pathway. | UniProt, Literature, Detection |
| 1433T_HUMAN | 14-3-3 protein theta | YWHAQ | EPI | LungCancers, BenignNodules | Cytoplasm. Note = In neurons, axonally transported to the nerve terminals. | Detection |
| 1433Z_HUMAN | 14-3-3 protein zeta/delta | YWHAZ | EPI | LungCancers, BenignNodules | Cytoplasm. Melanosome. Note = Located to stage I to stage IV melanosomes. | Detection |
| 6PGD_HUMAN | 6-phosphogluconate dehydrogenase, decarboxylating | PGD | EPI, ENDO | | Cytoplasm (By similarity). | Detection |
| A1AG1_HUMAN | Alpha-1-acid glycoprotein 1 | ORM1 | EPI | Symptoms | Secreted. | UniProt, Literature, Detection, Prediction |
| ABCD1_HUMAN | ATP-binding cassette sub-family D member 1 | ABCD1 | ENDO | | Peroxisome membrane; Multi-pass membrane protein. | Detection, Prediction |
| ADA12_HUMAN | Disintegrin and metalloproteinase domain-containing protein 12 | ADAM12 | | LungCancers, BenignNodules, Symptoms | Isoform 1: Cell membrane; Single-pass type I membrane protein.\|Isoform 2: Secreted.\|Isoform 3: Secreted (Potential).\|Isoform 4: Secreted (Potential). | UniProt, Detection, Prediction |
| ADML_HUMAN | ADM | ADM | | LungCancers, BenignNodules, Symptoms | Secreted. | UniProt, Literature, Detection, Prediction |
| AGR2_HUMAN | Anterior gradient protein 2 homolog | AGR2 | EPI | LungCancers | Secreted. Endoplasmic reticulum (By similarity). | UniProt, Prediction |
| AIFM1_HUMAN | Apoptosis-inducing factor 1, mitochondrial | AIFM1 | EPI, ENDO | LungCancers | Mitochondrion intermembrane space. Nucleus. Note = Translocated to the nucleus upon induction of apoptosis. | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| ALDOA_HUMAN | Fructose-bisphosphate aldolase A | ALDOA | Secreted, EPI | LungCancers, Symptoms | | Literature, Detection |
| AMPN_HUMAN | Aminopeptidase N | ANPEP | EPI, ENDO | LungCancers, BenignNodules, Symptoms | Cell membrane; Single-pass type II membrane protein. Cytoplasm, cytosol (Potential). Note = A soluble form has also been detected. | UniProt, Detection |
| ANGP1_HUMAN | Angiopoietin-1 | ANGPT1 | | LungCancers, BenignNodules | Secreted. | UniProt, Literature, Prediction |
| ANGP2_HUMAN | Angiopoietin-2 | ANGPT2 | | LungCancers, BenignNodules | Secreted. | UniProt, Literature, Prediction |
| APOA1_HUMAN | Apolipoprotein A-I | APOA1 | | LungCancers, BenignNodules, Symptoms | Secreted. | UniProt, Literature, Detection, Prediction |
| APOE_HUMAN | Apolipoprotein E | APOE | EPI, ENDO | LungCancers, BenignNodules, Symptoms | Secreted. | UniProt, Literature, Detection, Prediction |
| ASM3B_HUMAN | Acid sphingomyelinase-like phosphodiesterase 3b | SMPDL3B | EPI, ENDO | | Secreted (By similarity). | UniProt, Prediction |
| AT2A2_HUMAN | Sarcoplasmic/endoplasmic reticulum calcium ATPase 2 | ATP2A2 | EPI, ENDO | LungCancers, BenignNodules | Endoplasmic reticulum membrane; Multi-pass membrane protein. Sarcoplasmic reticulum membrane; Multi-pass membrane protein. | Detection |
| ATS1_HUMAN | A disintegrin and metalloproteinase with thrombospondin motifs 1 | ADAMTS1 | | LungCancers, BenignNodules, Symptoms | Secreted, extracellular space, extracellular matrix (By similarity). | UniProt, Literature, Prediction |
| ATS12_HUMAN | A disintegrin and metalloproteinase with thrombospondin motifs 12 | ADAMTS12 | | LungCancers | Secreted, extracellular space, extracellular matrix (By similarity). | UniProt, Detection, Prediction |
| ATS19_HUMAN | A disintegrin and metalloproteinase with thrombospondin motifs 19 | ADAMTS19 | | LungCancers | Secreted, extracellular space, extracellular matrix (By similarity). | UniProt, Prediction |
| BAGE1_HUMAN | B melanoma antigen 1 | BAGE | | LungCancers | Secreted (Potential). | UniProt, Prediction |
| BAGE2_HUMAN | B melanoma antigen 2 | BAGE2 | | LungCancers | Secreted (Potential). | UniProt, Prediction |
| BAGE3_HUMAN | B melanoma antigen 3 | BAGE3 | | LungCancers | Secreted (Potential). | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| BAGE4_HUMAN | B melanoma antigen 4 | BAGE4 | | LungCancers | Secreted (Potential). | UniProt, Prediction |
| BAGE5_HUMAN | B melanoma antigen 5 | BAGE5 | | LungCancers | Secreted (Potential). | UniProt, Prediction |
| BASP1_HUMAN | Brain acid soluble protein 1 | BASP1 | Secreted, EPI | | Cell membrane; Lipid-anchor. Cell projection, growth cone. Note = Associated with the membranes of growth cones that form the tips of elongating axons. | Detection |
| BAX_HUMAN | Apoptosis regulator BAX | BAX | EPI | LungCancers, BenignNodules | Isoform Alpha: Mitochondrion membrane; Single-pass membrane protein. Cytoplasm. Note = Colocalizes with 14-3-3 proteins in the cytoplasm. Under stress conditions, redistributes to the mitochondrion membrane through the release from JNK-phosphorylated 14-3-3 proteins\|Isoform Beta: Cytoplasm.\|Isoform Gamma: Cytoplasm\|Isoform Delta: Cytoplasm (Potential). | UniProt, Literature, Prediction |
| BDNF_HUMAN | Brain-derived neurotrophic factor | BDNF | | BenignNodules, Symptoms | Secreted. | UniProt, Literature, Prediction |
| BGH3_HUMAN | Transforming growth factor-beta-induced protein ig-h3 | TGFBI | | LungCancers, BenignNodules | Secreted, extracellular space, extracellular matrix. Note = May be associated both with microfibrils and with the cell surface. | UniProt, Detection |
| BMP2_HUMAN | Bone morphogenetic protein 2 | BMP2 | | LungCancers, BenignNodules, Symptoms | Secreted. | UniProt, Literature |
| BST1_HUMAN | ADP-ribosyl cyclase 2 | BST1 | EPI | Symptoms | Cell membrane; Lipid-anchor, GPI-anchor. | Detection, Prediction |
| C163A_HUMAN | Scavenger receptor cysteine-rich type 1 protein M130 | CD163 | EPI | Symptoms | Soluble CD163: Secreted.\|Cell membrane; Single-pass type I membrane protein. | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | Note = Isoform 1 and isoform 2 show a lower surface expression when expressed in cells. | |
| C4BPA_HUMAN | C4b-binding protein alpha chain | C4BPA | | LungCancers, Symptoms | Secreted. | UniProt, Detection, Prediction |
| CAH9_HUMAN | Carbonic anhydrase 9 | CA9 | | LungCancers, BenignNodules, Symptoms | Nucleus. Nucleus, nucleolus. Cell membrane; Single-pass type I membrane protein. Cell projection, microvillus membrane; Single-pass type I membrane protein. Note = Found on the surface microvilli and in the nucleus, particularly in nucleolus. | UniProt |
| CALR_HUMAN | Calreticulin | CALR | EPI | Symptoms | Endoplasmic reticulum lumen. Cytoplasm, cytosol. Secreted, extracellular space, extracellular matrix. Cell surface. Note = Also found in cell surface (T cells), cytosol and extracellular matrix. Associated with the lytic granules in the cytolytic T-lymphocytes. | UniProt, Literature, Detection, Prediction |
| CALU_HUMAN | Calumenin | CALU | EPI | Symptoms | Endoplasmic reticulum lumen. Secreted. Melanosome. Sarcoplasmic reticulum lumen (By similarity). Note = Identified by mass spectrometry in melanosome fractions from stage I to stage IV. | UniProt, Detection, Prediction |
| CALX_HUMAN | Calnexin | CANX | Secreted, EPI, ENDO | BenignNodules | Endoplasmic reticulum membrane; Single-pass type I | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | membrane protein. Melanosome. Note = Identified by mass spectrometry in melanosome fractions from stage I to stage IV. | |
| CAP7_HUMAN | Azurocidin | AZU1 | EPI | Symptoms | Cytoplasmic granule. Note = Cytoplasmic granules of neutrophils. | Prediction |
| CATB_HUMAN | Cathepsin B | CTSB | Secreted | LungCancers | Lysosome. Melanosome. Note = Identified by mass spectrometry in melanosome fractions from stage I to stage IV. | Literature, Detection, Prediction |
| CATG_HUMAN | Cathepsin G | CTSG | Secreted, ENDO | BenignNodules | Cell surface. | Detection, Prediction |
| CBPB2_HUMAN | Carboxypeptidase B2 | CPB2 | | LungCancers, BenignNodules, Symptoms | Secreted. | UniProt, Detection, Prediction |
| CCL22_HUMAN | C-C motif chemokine 22 | CCL22 | | LungCancers, BenignNodules | Secreted. | UniProt, Prediction |
| CD14_HUMAN | Monocyte differentiation antigen CD14 | CD14 | EPI | LungCancers, BenignNodules, Symptoms | Cell membrane; Lipid-anchor, GPI-anchor. | Literature, Detection, Prediction |
| CD24_HUMAN | Signal transducer CD24 | CD24 | | LungCancers, BenignNodules | Cell membrane; Lipid-anchor, GPI-anchor. | Literature |
| CD2A2_HUMAN | Cyclin-dependent kinase inhibitor 2A, isoform 4 | CDKN2A | | LungCancers, BenignNodules | Cytoplasm. Nucleus.|Nucleus, nucleolus (By similarity). | Literature, Prediction |
| CD38_HUMAN | ADP-ribosyl cyclase 1 | CD38 | EPI, ENDO | Symptoms | Membrane; Single-pass type II membrane protein. | UniProt, Literature |
| CD40L_HUMAN | CD40 ligand | CD40LG | | LungCancers, BenignNodules, Symptoms | Cell membrane; Single-pass type II membrane protein.|CD40 ligand, soluble form: Secreted. | UniProt, Literature |
| CD44_HUMAN | CD44 antigen | CD44 | EPI | LungCancers, BenignNodules, Symptoms | Membrane; Single-pass type I membrane protein. | UniProt, Literature, Detection, Prediction |
| CD59_HUMAN | CD59 glycoprotein | CD59 | | LungCancers, BenignNodules, Symptoms | Cell membrane; Lipid-anchor, GPI-anchor. Secreted. Note = Soluble form found in a number of tissues. | UniProt, Literature, Detection, Prediction |
| CD97_HUMAN | CD97 antigen | CD97 | EPI, ENDO | Symptoms | Cell membrane; Multi-pass membrane protein.|CD97 antigen subunit alpha: Secreted, | UniProt |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CDCP1_HUMAN | CUB domain-containing protein 1 | CDCP1 | | LungCancers | extracellular space. Isoform 1: Cell membrane; Single-pass membrane protein (Potential). Note = Shedding may also lead to a soluble peptide.\|Isoform 3: Secreted. | UniProt, Prediction |
| CDK4_HUMAN | Cell division protein kinase 4 | CDK4 | | LungCancers, Symptoms | | Literature |
| CEAM5_HUMAN | Carcinoembryonic antigen-related cell adhesion molecule 5 | CEACAM5 | EPI | LungCancers, BenignNodules, Symptoms | Cell membrane; Lipid-anchor, GPI-anchor. | Literature, Prediction |
| CEAM8_HUMAN | Carcinoembryonic antigen-related cell adhesion molecule 8 | CEACAM8 | EPI | LungCancers | Cell membrane; Lipid-anchor, GPI-anchor. | Detection, Prediction |
| CERU_HUMAN | Ceruloplasmin | CP | EPI | LungCancers, Symptoms | Secreted. | UniProt, Literature, Detection, Prediction |
| CH10_HUMAN | 10 kDa heat shock protein, mitochondrial | HSPE1 | ENDO | LungCancers | Mitochondrion matrix. | Literature, Detection, Prediction |
| CH60_HUMAN | 60 kDa heat shock protein, mitochondrial | HSPD1 | Secreted, EPI, ENDO | LungCancers, Symptoms | Mitochondrion matrix. | Literature, Detection |
| CKAP4_HUMAN | Cytoskeleton-associated protein 4 | CKAP4 | EPI, ENDO | LungCancers | Endoplasmic reticulum-Golgi intermediate compartment membrane; Single-pass membrane protein (Potential). | UniProt |
| CL041_HUMAN | Uncharacterized protein C12orf41 | C12orf41 | ENDO | | | Prediction |
| CLCA1_HUMAN | Calcium-activated chloride channel regulator 1 | CLCA1 | | LungCancers, BenignNodules | Secreted, extracellular space. Cell membrane; Peripheral membrane protein; Extracellular side. Note = Protein that remains attached to the plasma membrane appeared to be predominantly localized to microvilli. | UniProt, Prediction |
| CLIC1_HUMAN | Chloride intracellular channel protein 1 | CLIC1 | EPI | | Nucleus. Nucleus membrane; Single-pass membrane protein (Probable). | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | Cytoplasm. Cell membrane; Single-pass membrane protein (Probable). Note = Mostly in the nucleus including in the nuclear membrane. Small amount in the cytoplasm and the plasma membrane. Exists both as soluble cytoplasmic protein and as membrane protein with probably a single transmembrane domain. | |
| CLUS_HUMAN | Clusterin | CLU | EPI, ENDO | LungCancers, BenignNodules, Symptoms | Secreted. | UniProt, Literature, Detection, Prediction |
| CMGA_HUMAN | Chromogranin-A | CHGA | | LungCancers, BenignNodules | Secreted. Note = Neuroendocrine and endocrine secretory granules. | UniProt, Literature, Detection, Prediction |
| CNTN1_HUMAN | Contactin-1 | CNTN1 | | LungCancers | Isoform 1: Cell membrane; Lipid-anchor, GPI-anchor; Extracellular side.\|Isoform 2: Cell membrane; Lipid-anchor, GPI-anchor; Extracellular side. | Detection, Prediction |
| C04A1_HUMAN | Collagen alpha-1(IV) chain | COL4A1 | | LungCancers | Secreted, extracellular space, extracellular matrix, basement membrane. | UniProt, Detection, Prediction |
| C05A2_HUMAN | Collagen alpha-2(V) chain | COL5A2 | | LungCancers | Secreted, extracellular space, extracellular matrix (By similarity). | UniProt, Detection, Prediction |
| C06A3_HUMAN | Collagen alpha-3(VI) chain | COL6A3 | Secreted | Symptoms | Secreted, extracellular space, extracellular matrix (By similarity). | UniProt, Detection, Prediction |
| COCA1_HUMAN | Collagen alpha-1(XII) chain | COL12A1 | ENDO | LungCancers, Symptoms | Secreted, extracellular space, extracellular matrix (By similarity). | UniProt, Prediction |
| COF1_HUMAN | Cofilin-1 | CFL1 | Secreted, EPI | LungCancers, BenignNodules | Nucleus matrix. Cytoplasm, cytoskeleton. Note = Almost | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | completely in nucleus in cells exposed to heat shock or 10% dimethyl sulfoxide. | |
| COIA1_HUMAN | Collagen alpha-1(XVIII) chain | COL18A1 | | LungCancers, BenignNodules | Secreted, extracellular space, extracellular matrix (By similarity). | UniProt, Literature, Detection, Prediction |
| COX5A_HUMAN | Cytochrome c oxidase subunit 5A, mitochondrial | COX5A | Secreted, ENDO | | Mitochondrion inner membrane. | Prediction |
| CRP_HUMAN | C-reactive protein | CRP | | LungCancers, BenignNodules, Symptoms | Secreted. | UniProt, Literature, Detection, Prediction |
| CS051_HUMAN | UPF0470 protein C19orf51 | C19orf51 | ENDO | | | Prediction |
| CSF1_HUMAN | Macrophage colony-stimulating factor 1 | CSF1 | | LungCancers, BenignNodules | Cell membrane; Single-pass membrane protein (By similarity).\|Processed macrophage colony-stimulating factor 1: Secreted, extracellular space (By similarity). | UniProt, Literature, Detection |
| CSF2_HUMAN | Granulocyte-macrophage colony-stimulating factor | CSF2 | | LungCancers, BenignNodules | Secreted. | UniProt, Literature, Prediction |
| CT085_HUMAN | Uncharacterized protein C20orf85 | C20orf85 | | LungCancers, BenignNodules | | Prediction |
| CTGF_HUMAN | Connective tissue growth factor | CTGF | | LungCancers, BenignNodules | Secreted, extracellular space, extracellular matrix (By similarity). Secreted (By similarity). | UniProt, Literature, Detection, Prediction |
| CYR61_HUMAN | Protein CYR61 | CYR61 | | LungCancers, BenignNodules | Secreted. | UniProt, Prediction |
| CYTA_HUMAN | Cystatin-A | CSTA | | LungCancers | Cytoplasm. | Literature, Detection |
| CYTB_HUMAN | Cystatin-B | CSTB | Secreted | | Cytoplasm. Nucleus. | Literature, Detection |
| DDX17_HUMAN | Probable ATP-dependent RNA helicase DDX17 | DDX17 | ENDO | LungCancers, BenignNodules | Nucleus. | Detection, Prediction |
| DEFB1_HUMAN | Beta-defensin 1 | DEFB1 | | LungCancers, BenignNodules | Secreted. | UniProt, Prediction |
| DESP_HUMAN | Desmoplakin | DSP | EPI, ENDO | LungCancers | Cell junction, desmosome. Cytoplasm, cytoskeleton. Note = Innermost portion of the desmosomal plaque. | Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| DFB4A_HUMAN | Beta-defensin 4A | DEFB4A | | LungCancers, BenignNodules | Secreted. | UniProt |
| DHI1L_HUMAN | Hydroxysteroid 11-beta-dehydrogenase 1-like protein | HSD11B1L | | LungCancers | Secreted (Potential). | UniProt, Prediction |
| DMBT1_HUMAN | Deleted in malignant brain tumors 1 protein | DMBT1 | | LungCancers, BenignNodules | Secreted (By similarity). Note = Some isoforms may be membrane-bound. Localized to the lumenal aspect of crypt cells in the small intestine. In the colon, seen in the lumenal aspect of surface epithelial cells. Formed in the ducts of von Ebner gland, and released into the fluid bathing the taste buds contained in the taste papillae (By similarity). | UniProt, Detection, Prediction |
| DMKN_HUMAN | Dermokine | DMKN | | LungCancers | Secreted. | UniProt, Detection, Prediction |
| DPP4_HUMAN | Dipeptidyl peptidase 4 | DPP4 | EPI | LungCancers, BenignNodules, Symptoms | Dipeptidyl peptidase 4 soluble form: Secreted.\|Cell membrane; Single-pass type II membrane protein. | UniProt, Detection |
| DSG2_HUMAN | Desmoglein-2 | DSG2 | ENDO | Symptoms | Cell membrane; Single-pass type I membrane protein. Cell junction, desmosome. | UniProt, Detection |
| DX39A_HUMAN | ATP-dependent RNA helicase DDX39A | DDX39A | EPI | | Nucleus (By similarity). | Prediction |
| DX39B_HUMAN | Spliceosome RNA helicase DDX39B | DDX39B | EPI | | Nucleus. Nucleus speckle. | Prediction |
| DYRK2_HUMAN | Dual specificity tyrosine-phosphorylation-regulated kinase 2 | DYRK2 | ENDO | LungCancers | Cytoplasm. Nucleus. Note = Translocates into the nucleus following DNA damage. | Literature |
| EDN2_HUMAN | Endothelin-2 | EDN2 | | LungCancers | Secreted. | UniProt, Prediction |
| EF1A1_HUMAN | Elongation factor 1-alpha 1 | EEF1A1 | Secreted, EPI | LungCancers, BenignNodules | Cytoplasm. | Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| EF1D_HUMAN | Elongation factor 1-delta | EEF1D | Secreted, EPI | LungCancers | | Prediction |
| EF2_HUMAN | Elongation factor 2 | EEF2 | Secreted, EPI | | Cytoplasm. | Literature, Detection |
| EGF_HUMAN | Pro-epidermal growth factor | EGF | | LungCancers, BenignNodules, Symptoms | Membrane; Single-pass type I membrane protein. | UniProt, Literature |
| EGFL6_HUMAN | Epidermal growth factor-like protein 6 | EGFL6 | | LungCancers | Secreted, extracellular space, extracellular matrix, basement membrane (By similarity). | UniProt, Detection, Prediction |
| ENOA_HUMAN | Alpha-enolase | ENO1 | Secreted, EPI, ENDO | LungCancers, BenignNodules, Symptoms | Cytoplasm. Cell membrane. Cytoplasm, myofibril, sarcomere, M-band. Note = Can translocate to the plasma membrane in either the homodimeric (alpha/alpha) or heterodimeric (alpha/gamma) form. ENO1 is localized to the M-band.\|Isoform MBP-1: Nucleus. | Literature, Detection, Prediction |
| ENOG_HUMAN | Gamma-enolase | ENO2 | EPI | LungCancers, Symptoms | Cytoplasm (By similarity). Cell membrane (By similarity). Note = Can translocate to the plasma membrane in either the homodimeric (alpha/alpha) or heterodimeric (alpha/gamma) form (By similarity). | Literature, Detection, Prediction |
| ENOX2_HUMAN | Ecto-NOX disulfide-thiol exchanger 2 | ENOX2 | | LungCancers | Cell membrane. Secreted, extracellular space. Note = Extracellular and plasma membrane-associated. | UniProt, Detection |
| ENPL_HUMAN | Endoplasmin | HSP90B1 | Secreted, EPI, ENDO | LungCancers, BenignNodules, Symptoms | Endoplasmic reticulum lumen. Melanosome. Note = Identified by mass spectrometry in melanosome fractions from stage I to stage IV. | Literature, Detection, Prediction |
| EPHB6_HUMAN | Ephrin type-B receptor 6 | EPHB6 | | LungCancers | Membrane; Single-pass type I membrane | UniProt, Literature |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| EPOR_HUMAN | Erythropoietin receptor | EPOR | | LungCancers, BenignNodules, Symptoms | protein.\|Isoform 3: Secreted (Probable). Cell membrane; Single-pass type I membrane protein.\|Isoform EPOR-S: Secreted. Note = Secreted and located to the cell surface. | UniProt, Literature, Detection |
| ERBB3_HUMAN | Receptor tyrosine-protein kinase erbB-3 | ERBB3 | | LungCancers, BenignNodules | Isoform 1: Cell membrane; Single-pass type I membrane protein.\|Isoform 2: Secreted. | UniProt, Literature, Prediction |
| EREG_HUMAN | Proepiregulin | EREG | | LungCancers | Epiregulin: Secreted, extracellular space.\|Proepiregulin: Cell membrane; Single-pass type I membrane protein. | UniProt |
| ERO1A_HUMAN | ERO1-like protein alpha | ERO1L | Secreted, EPI, ENDO | Symptoms | Endoplasmic reticulum membrane; Peripheral membrane protein; Lumenal side. Note = The association with ERP44 is essential for its retention in the endoplasmic reticulum. | Prediction |
| ESM1_HUMAN | Endothelial cell-specific molecule 1 | ESM1 | | LungCancers, BenignNodules | Secreted. | UniProt, Prediction |
| EZRI_HUMAN | Ezrin | EZR | Secreted | LungCancers, BenignNodules | Apical cell membrane; Peripheral membrane protein; Cytoplasmic side. Cell projection. Cell projection, microvillus membrane; Peripheral membrane protein; Cytoplasmic side. Cell projection, ruffle membrane; Peripheral membrane protein; Cytoplasmic side. Cytoplasm, cell cortex. Cytoplasm, cytoskeleton. | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | Note = Localization to the apical membrane of parietal cells depends on the interaction with MPP5. Localizes to cell extensions and peripheral processes of astrocytes (By similarity). Microvillar peripheral membrane protein (cytoplasmic side). | |
| F10A1_HUMAN | Hsc70-interacting protein | ST13 | EPI | | Cytoplasm (By similarity).|Cytoplasm (Probable). | Detection, Prediction |
| FAM3C_HUMAN | Protein FAM3C | FAM3C | EPI, ENDO | | Secreted (Potential). | UniProt, Detection |
| FAS_HUMAN | Fatty acid synthase | FASN | EPI | LungCancers, BenignNodules, Symptoms | Cytoplasm. Melanosome. Note = Identified by mass spectrometry in melanosome fractions from stage I to stage IV. | Literature, Detection |
| FCGR1_HUMAN | High affinity immunoglobulin gamma Fc receptor I | FCGR1A | EPI | LungCancers, BenignNodules, Symptoms | Cell membrane; Single-pass type I membrane protein. Note = Stabilized at the cell membrane through interaction with FCER1G. | UniProt |
| FGF10_HUMAN | Fibroblast growth factor 10 | FGF10 | | LungCancers | Secreted (Potential). | UniProt, Prediction |
| FGF2_HUMAN | Heparin-binding growth factor 2 | FGF2 | | LungCancers, BenignNodules, Symptoms | | Literature |
| FGF7_HUMAN | Keratinocyte growth factor | FGF7 | | LungCancers, BenignNodules | Secreted. | UniProt, Literature, Prediction |
| FGF9_HUMAN | Glia-activating factor | FGF9 | | LungCancers | Secreted. | UniProt, Literature, Prediction |
| FGFR2_HUMAN | Fibroblast growth factor receptor 2 | FGFR2 | | LungCancers, BenignNodules | Cell membrane; Single-pass type I membrane protein.|Isoform 14: Secreted.|Isoform 19: Secreted. | UniProt, Literature, Prediction |
| FGFR3_HUMAN | Fibroblast growth factor receptor 3 | FGFR3 | | LungCancers | Membrane; Single-pass type I membrane protein. | UniProt, Literature, Prediction |
| FGL2_HUMAN | Fibroleukin | FGL2 | | BenignNodules, Symptoms | Secreted. | UniProt, Detection, Prediction |
| FHIT_HUMAN | Bis(5'-adenosyl)-triphosphatase | FHIT | | LungCancers, BenignNodules, Symptoms | Cytoplasm. | Literature |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| FIBA_HUMAN | Fibrinogen alpha chain | FGA | | LungCancers, BenignNodules, Symptoms | Secreted. | UniProt, Literature, Detection, Prediction |
| FINC_HUMAN | Fibronectin | FN1 | Secreted, EPI, ENDO | LungCancers, BenignNodules, Symptoms | Secreted, extracellular space, extracellular matrix. | UniProt, Literature, Detection, Prediction |
| FKB11_HUMAN | Peptidyl-prolyl cis-trans isomerase FKBP11 | FKBP11 | EPI, ENDO | | Membrane; Single-pass membrane protein (Potential). | UniProt, Prediction |
| FOLH1_HUMAN | Glutamate carboxypeptidase 2 | FOLH1 | ENDO | LungCancers, Symptoms | Cell membrane; Single-pass type II membrane protein.|Isoform PSMA': Cytoplasm. | UniProt, Literature |
| FOLR1_HUMAN | Folate receptor alpha | FOLR1 | | LungCancers | Cell membrane; Lipid-anchor, GPI-anchor. Secreted (Probable). | UniProt |
| FOXA2_HUMAN | Hepatocyte nuclear factor 3-beta | FOXA2 | | LungCancers | Nucleus. | Detection, Prediction |
| FP100_HUMAN | Fanconi anemia-associated protein of 100 kDa | C17orf70 | ENDO | Symptoms | Nucleus. | Prediction |
| FRIH_HUMAN | Ferritin heavy chain | FTH1 | EPI | LungCancers, BenignNodules | | Literature, Detection, Prediction |
| FRIL_HUMAN | Ferritin light chain | FTL | Secreted, EPI, ENDO | BenignNodules, Symptoms | | Literature, Detection |
| G3P_HUMAN | Glyceraldehyde-3-phosphate dehydrogenase | GAPDH | Secreted, EPI, ENDO | LungCancers, BenignNodules, Symptoms | Cytoplasm. Cytoplasm, perinuclear region. Membrane. Note = Postnuclear and Perinuclear regions. | Detection |
| G6PD_HUMAN | Glucose-6-phosphate 1-dehydrogenase | G6PD | Secreted, EPI | LungCancers, Symptoms | | Literature, Detection |
| G6PI_HUMAN | Glucose-6-phosphate isomerase | GPI | Secreted, EPI | Symptoms | Cytoplasm. Secreted. | UniProt, Literature, Detection |
| GA2L1_HUMAN | GAS2-like protein 1 | GAS2L1 | ENDO | | Cytoplasm, cytoskeleton (Probable). | Prediction |
| GALT2_HUMAN | Polypeptide N-acetylgalactosaminyl-transferase 2 | GALNT2 | EPI, ENDO | | Golgi apparatus, Golgi stack membrane; Single-pass type II membrane protein. Secreted. Note = Resides preferentially in the trans and medial parts of the Golgi stack. A secreted form also exists. | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| GAS6_HUMAN | Growth arrest-specific protein 6 | GAS6 | | LungCancers | Secreted. | UniProt, Detection, Prediction |
| GDIR2_HUMAN | Rho GDP-dissociation inhibitor 2 | ARHGDIB | EPI | | Cytoplasm. | Detection |
| GELS_HUMAN | Gelsolin | GSN | | LungCancers, BenignNodules | Isoform 2: Cytoplasm, cytoskeleton.\|Isoform 1: Secreted. | UniProt, Literature, Detection, Prediction |
| GGH_HUMAN | Gamma-glutamyl hydrolase | GGH | | LungCancers | Secreted, extracellular space. Lysosome. Melanosome. Note = While its intracellular location is primarily the lysosome, most of the enzyme activity is secreted. Identified by mass spectrometry in melanosome fractions from stage I to stage IV. | UniProt, Detection, Prediction |
| GPC3_HUMAN | Glypican-3 | GPC3 | | LungCancers, Symptoms | Cell membrane; Lipid-anchor; GPI-anchor; Extracellular side (By similarity).\|Secreted glypican-3: Secreted, extracellular space (By similarity). | UniProt, Literature, Prediction |
| GRAN_HUMAN | Grancalcin | GCA | EPI | | Cytoplasm. Cytoplasmic granule membrane; Peripheral membrane protein; Cytoplasmic side. Note = Primarily cytosolic in the absence of calcium or magnesium ions. Relocates to granules and other membranes in response to elevated calcium and magnesium levels. | Prediction |
| GREB1_HUMAN | Protein GREB1 | GREB1 | ENDO | | Membrane; Single-pass membrane protein (Potential). | UniProt, Prediction |
| GREM1_HUMAN | Gremlin-1 | GREM1 | | LungCancers, BenignNodules | Secreted (Probable). | UniProt, Prediction |
| GRP_HUMAN | Gastrin-releasing peptide | GRP | | LungCancers, Symptoms | Secreted. | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| GRP78_HUMAN | 78 kDa glucose-regulated protein | HSPA5 | Secreted, EPI, ENDO | LungCancers, BenignNodules | Endoplasmic reticulum lumen. Melanosome. Note = Identified by mass spectrometry in melanosome fractions from stage I to stage IV. | Detection, Prediction |
| GSLG1_HUMAN | Golgi apparatus protein 1 | GLG1 | EPI, ENDO | BenignNodules | Golgi apparatus membrane; Single-pass type I membrane protein. | UniProt |
| GSTP1_HUMAN | Glutathione S-transferase P | GSTP1 | Secreted | LungCancers, BenignNodules, Symptoms | | Literature, Detection, Prediction |
| GTR1_HUMAN | Solute carrier family 2, facilitated glucose transporter member 1 | SLC2A1 | EPI, ENDO | LungCancers, BenignNodules, Symptoms | Cell membrane; Multi-pass membrane protein (By similarity). Melanosome. Note = Localizes primarily at the cell surface (By similarity). Identified by mass spectrometry in melanosome fractions from stage I to stage IV. | Literature |
| GTR3_HUMAN | Solute carrier family 2, facilitated glucose transporter member 3 | SLC2A3 | EPI | | Membrane; Multi-pass membrane protein. | Detection |
| H2A1_HUMAN | Histone H2A type 1 | HIST1H2AG | Secreted | | Nucleus. | Detection, Prediction |
| H2A1B_HUMAN | Histone H2A type 1-B/E | HIST1H2AB | Secreted | | Nucleus. | Detection, Prediction |
| H2A1C_HUMAN | Histone H2A type 1-C | HIST1H2AC | Secreted | | Nucleus. | Literature, Detection, Prediction |
| H2A1D_HUMAN | Histone H2A type 1-D | HIST1H2AD | Secreted | | Nucleus. | Detection, Prediction |
| HG2A_HUMAN | HLA class II histocompatibility antigen gamma chain | CD74 | | LungCancers, BenignNodules, Symptoms | Membrane; Single-pass type II membrane protein (Potential). | UniProt, Literature |
| HGF_HUMAN | Hepatocyte growth factor | HGF | | LungCancers, BenignNodules, Symptoms | | Literature, Prediction |
| HMGA1_HUMAN | High mobility group protein HMG-I/HMG-Y | HMGA1 | | LungCancers, BenignNodules, Symptoms | Nucleus. | Literature |
| HPRT_HUMAN | Hypoxanthine-guanine phosphoribosyltransferase | HPRT1 | EPI | | Cytoplasm. | Detection, Prediction |
| HPSE_HUMAN | Heparanase | HPSE | | LungCancers, BenignNodules, Symptoms | Lysosome membrane; Peripheral | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | membrane protein. Secreted. Note = Secreted, internalised and transferred to late endosomes/lysosomes as a proheparanase. In lysosomes, it is processed into the active form, the heparanase. The uptake or internalisation of proheparanase is mediated by HSPGs. Heparin appears to be a competitor and retain proheparanase in the extracellular medium. | |
| HPT_HUMAN | Haptoglobin | HP | | LungCancers, BenignNodules, Symptoms | Secreted. | UniProt, Literature, Detection, Prediction |
| HS90A_HUMAN | Heat shock protein HSP 90-alpha | HSP90AA1 | Secreted, EPI | LungCancers, Symptoms | Cytoplasm. Melanosome. Note = Identified by mass spectrometry in melanosome fractions from stage I to stage IV. | Literature, Detection |
| HS90B_HUMAN | Heat shock protein HSP 90-beta | HSP90AB1 | Secreted, EPI | LungCancers | Cytoplasm. Melanosome. Note = Identified by mass spectrometry in melanosome fractions from stage I to stage IV. | Literature, Detection |
| HSPB1_HUMAN | Heat shock protein beta-1 | HSPB1 | Secreted, EPI | LungCancers, BenignNodules | Cytoplasm. Nucleus. Cytoplasm, cytoskeleton, spindle. Note = Cytoplasmic in interphase cells. Colocalizes with mitotic spindles in mitotic cells. Translocates to the nucleus during heat shock. | Literature, Detection, Prediction |
| HTRA1_HUMAN | Serine protease HTRA1 | HTRA1 | | LungCancers | Secreted. | UniProt, Prediction |
| HXK1_HUMAN | Hexokinase-1 | HK1 | ENDO | Symptoms | Mitochondrion outer membrane. Note = Its hydrophobic N-terminal | Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | sequence may be involved in membrane binding. | |
| HYAL2_HUMAN | Hyaluronidase-2 | HYAL2 | | LungCancers | Cell membrane; Lipid-anchor, GPI-anchor. | Prediction |
| HYOU1_HUMAN | Hypoxia up-regulated protein 1 | HYOU1 | EPI, ENDO | Symptoms | Endoplasmic reticulum lumen. | Detection |
| IBP2_HUMAN | Insulin-like growth factor-binding protein 2 | IGFBP2 | | LungCancers | Secreted. | UniProt, Literature, Detection, Prediction |
| IBP3_HUMAN | Insulin-like growth factor-binding protein 3 | IGFBP3 | | LungCancers, BenignNodules, Symptoms | Secreted. | UniProt, Literature, Detection, Prediction |
| ICAM1_HUMAN | Intercellular adhesion molecule 1 | ICAM1 | | LungCancers, BenignNodules, Symptoms | Membrane; Single-pass type I membrane protein. | UniProt, Literature, Detection |
| ICAM3_HUMAN | Intercellular adhesion molecule 3 | ICAM3 | EPI, ENDO | LungCancers, BenignNodules, Symptoms | Membrane; Single-pass type I membrane protein. | UniProt, Detection |
| IDHP_HUMAN | Isocitrate dehydrogenase [NADP], mitochondrial | IDH2 | Secreted, ENDO | | Mitochondrion. | Prediction |
| IF4A1_HUMAN | Eukaryotic initiation factor 4A-I | EIF4A1 | Secreted, EPI, ENDO | | | Detection, Prediction |
| IGF1_HUMAN | Insulin-like growth factor I | IGF1 | | LungCancers, BenignNodules, Symptoms | Secreted.|Secreted. | UniProt, Literature, Detection, Prediction |
| IKIP_HUMAN | Inhibitor of nuclear factor kappa-B kinase-interacting protein | IKIP | ENDO | Symptoms | Endoplasmic reticulum membrane; Single-pass membrane protein. Note = Isoform 4 deletion of the hydrophobic, or transmembrane region between AA 45-63 results in uniform distribution troughout the cell, suggesting that this region is responsible for endoplasmic reticulum localization. | UniProt, Prediction |
| IL18_HUMAN | Interleukin-18 | IL18 | | LungCancers, BenignNodules, Symptoms | Secreted. | UniProt, Literature, Prediction |
| IL19_HUMAN | Interleukin-19 | IL19 | | LungCancers | Secreted. | UniProt, Detection, Prediction |
| IL22_HUMAN | Interleukin-22 | IL22 | | LungCancers, BenignNodules | Secreted. | UniProt, Prediction |
| IL32_HUMAN | Interleukin-32 | IL32 | | LungCancers, BenignNodules | Secreted. | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| IL7_HUMAN | Interleukin-7 | IL7 | | LungCancers, BenignNodules | Secreted. | UniProt, Literature, Prediction |
| IL8_HUMAN | Interleukin-8 | IL8 | | LungCancers, BenignNodules, Symptoms | Secreted. | UniProt, Literature |
| ILEU_HUMAN | Leukocyte elastase inhibitor | SERPINB1 | Secreted, EPI | | Cytoplasm (By similarity). | Detection, Prediction |
| ILK_HUMAN | Integrin-linked protein kinase | ILK | Secreted | LungCancers, BenignNodules, Symptoms | Cell junction, focal adhesion. Cell membrane; Peripheral membrane protein; Cytoplasmic side. | Literature, Detection |
| INHBA_HUMAN | Inhibin beta A chain | INHBA | | LungCancers, BenignNodules | Secreted. | UniProt, Literature, Prediction |
| ISLR_HUMAN | Immunoglobulin superfamily containing leucine-rich repeat protein | ISLR | | LungCancers | Secreted (Potential). | UniProt, Detection, Prediction |
| ITA5_HUMAN | Integrin alpha-5 | ITGA5 | EPI | LungCancers, BenignNodules, Symptoms | Membrane; Single-pass type I membrane protein. | UniProt, Literature, Detection |
| ITAM_HUMAN | Integrin alpha-M | ITGAM | EPI, ENDO | LungCancers, BenignNodules, Symptoms | Membrane; Single-pass type I membrane protein. | UniProt, Literature |
| K0090_HUMAN | Uncharacterized protein KIAA0090 | KIAA0090 | EPI | Symptoms | Membrane; Single-pass type I membrane protein (Potential). | UniProt, Prediction |
| K1C18_HUMAN | Keratin, type I cytoskeletal 18 | KRT18 | Secreted | LungCancers, BenignNodules | Cytoplasm, perinuclear region. | Literature, Detection, Prediction |
| K1C19_HUMAN | Keratin, type I cytoskeletal 19 | KRT19 | | LungCancers, BenignNodules | | Literature, Detection, Prediction |
| K2C8_HUMAN | Keratin, type II cytoskeletal 8 | KRT8 | EPI | LungCancers | Cytoplasm. | Literature, Detection |
| KIT_HUMAN | Mast/stem cell growth factor receptor | KIT | | LungCancers | Membrane; Single-pass type I membrane protein. | UniProt, Literature, Detection |
| KITH_HUMAN | Thymidine kinase, cytosolic | TK1 | | LungCancers | Cytoplasm. | Literature, Prediction |
| KLK11_HUMAN | Kallikrein-11 | KLK11 | | LungCancers | Secreted. | UniProt, Literature, Prediction |
| KLK13_HUMAN | Kallikrein-13 | KLK13 | | LungCancers | Secreted (Probable). | UniProt, Literature, Detection, Prediction |
| KLK14_HUMAN | Kallikrein-14 | KLK14 | | LungCancers, Symptoms | Secreted, extracellular space. | UniProt, Literature, Prediction |
| KLK6_HUMAN | Kallikrein-6 | KLK6 | | LungCancers, BenignNodules, Symptoms | Secreted. Nucleus, nucleolus. Cytoplasm. Mitochondrion. | UniProt, Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | Microsome. Note = In brain, detected in the nucleus of glial cells and in the nucleus and cytoplasm of neurons. Detected in the mitochondrial and microsomal fractions of HEK-293 cells and released into the cytoplasm following cell stress. | |
| KNG1_HUMAN | Kininogen-1 | KNG1 | | LungCancers, BenignNodules, Symptoms | Secreted, extracellular space. | UniProt, Detection, Prediction |
| KPYM_HUMAN | Pyruvate kinase isozymes M1/M2 | PKM2 | Secreted, EPI | LungCancers, Symptoms | Cytoplasm. Nucleus. Note = Translocates to the nucleus in response to different apoptotic stimuli. Nuclear translocation is sufficient to induce cell death that is caspase independent, isoform-specific and independent of its enzymatic actvity. | Literature, Detection |
| KRT35_HUMAN | Keratin, type I cuticular Ha5 | KRT35 | ENDO | | | Detection, Prediction |
| LAMB2_HUMAN | Laminin subunit beta-2 | LAMB2 | ENDO | LungCancers, Symptoms | Secreted, extracellular space, extracellular matrix, basement membrane. Note = S-laminin is concentrated in the synaptic cleft of the neuromuscular junction. | UniProt, Detection, Prediction |
| LDHA_HUMAN | L-lactate dehydrogenase A chain | LDHA | Secreted, EPI, ENDO | LungCancers | Cytoplasm. | Literature, Detection, Prediction |
| LDHB_HUMAN | L-lactate dehydrogenase B chain | LDHB | EPI | LungCancers | Cytoplasm. | Detection, Prediction |
| LEG1_HUMAN | Galectin-1 | LGALS1 | Secreted | LungCancers | Secreted, extracellular space, extracellular matrix. | UniProt, Detection |
| LEG3_HUMAN | Galectin-3 | LGALS3 | | LungCancers, BenignNodules | Nucleus. Note = Cytoplasmic in adenomas and carcinomas. May be secreted by a non- | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| LEG9_HUMAN | Galectin-9 | LGALS9 | ENDO | Symptoms | classical secretory pathway and associate with the cell surface. Cytoplasm (By similarity). Secreted (By similarity). Note = May also be secreted by a non-classical secretory pathway (By similarity). | UniProt |
| LG3BP_HUMAN | Galectin-3-binding protein | LGALS3BP | Secreted | LungCancers, BenignNodules, Symptoms | Secreted. Secreted, extracellular space, extracellular matrix. | UniProt, Literature, Detection, Prediction |
| LPLC3_HUMAN | Long palate, lung and nasal epithelium carcinoma-associated protein 3 | C20orf185 | | LungCancers | Secreted (By similarity). Cytoplasm. Note = According to PubMed: 12837268 it is cytoplasmic. | UniProt, Prediction |
| LPLC4_HUMAN | Long palate, lung and nasal epithelium carcinoma-associated protein 4 | C20orf186 | | LungCancers | Secreted (By similarity). Cytoplasm. | UniProt, Prediction |
| LPPRC_HUMAN | Leucine-rich PPR motif-containing protein, mitochondrial | LRPPRC | Secreted, ENDO | LungCancers, Symptoms | Mitochondrion. Nucleus, nucleoplasm. Nucleus inner membrane. Nucleus outer membrane. Note = Seems to be predominantly mitochondrial. | Prediction |
| LRP1_HUMAN | Prolow-density lipoprotein receptor-related protein 1 | LRP1 | EPI | LungCancers, Symptoms | Low-density lipoprotein receptor-related protein 1 85 kDa subunit: Cell membrane; Single-pass type I membrane protein. Membrane, coated pit.\|Low-density lipoprotein receptor-related protein 1 515 kDa subunit: Cell membrane; Peripheral membrane protein; Extracellular side. Membrane, coated pit.\|Low-density lipoprotein receptor-related protein 1 | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | intracellular domain: Cytoplasm. Nucleus. Note = After cleavage, the intracellular domain (LRPICD) is detected both in the cytoplasm and in the nucleus. | |
| LUM_HUMAN | Lumican | LUM | Secreted, EPI | LungCancers, BenignNodules, Symptoms | Secreted, extracellular space, extracellular matrix (By similarity). | UniProt, Detection, Prediction |
| LY6K_HUMAN | Lymphocyte antigen 6K | LY6K | | LungCancers, Symptoms | Secreted. Cytoplasm. Cell membrane; Lipid-anchor, GPI-anchor (Potential). | UniProt, Prediction |
| LYAM2_HUMAN | E-selectin | SELE | | LungCancers, BenignNodules, Symptoms | Membrane; Single-pass type I membrane protein. | UniProt, Literature, Detection |
| LYAM3_HUMAN | P-selectin | SELP | | LungCancers, BenignNodules, Symptoms | Membrane; Single-pass type I membrane protein. | UniProt, Literature, Detection |
| LYOX_HUMAN | Protein-lysine 6-oxidase | LOX | | LungCancers, BenignNodules | Secreted, extracellular space. | UniProt, Detection, Prediction |
| LYPD3_HUMAN | Ly6/PLAUR domain-containing protein 3 | LYPD3 | | LungCancers | Cell membrane; Lipid-anchor, GPI-anchor. | Detection, Prediction |
| MAGA4_HUMAN | Melanoma-associated antigen 4 | MAGEA4 | | LungCancers | | Literature, Prediction |
| MASP1_HUMAN | Mannan-binding lectin serine protease 1 | MASP1 | | LungCancers, Symptoms | Secreted. | UniProt, Detection, Prediction |
| MDHC_HUMAN | Malate dehydrogenase, cytoplasmic | MDH1 | Secreted | | Cytoplasm. | Literature, Detection, Prediction |
| MDHM_HUMAN | Malate dehydrogenase, mitochondrial | MDH2 | ENDO | LungCancers | Mitochondrion matrix. | Detection, Prediction |
| MIF_HUMAN | Macrophage migration inhibitory factor | MIF | Secreted | LungCancers, BenignNodules, Symptoms | Secreted. Cytoplasm. Note = Does not have a cleavable signal sequence and is secreted via a specialized, non-classical pathway. Secreted by macrophages upon stimulation by bacterial lipopolysaccharide (LPS), or by *M. tuberculosis* antigens. | UniProt, Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MLH1_HUMAN | DNA mismatch repair protein Mlh1 | MLH1 | ENDO | LungCancers, BenignNodules, Symptoms | Nucleus. | Literature |
| MMP1_HUMAN | Interstitial collagenase | MMP1 | | LungCancers, BenignNodules, Symptoms | Secreted, extracellular space, extracellular matrix (Probable). | UniProt, Literature, Prediction |
| MMP11_HUMAN | Stromelysin-3 | MMP11 | | LungCancers, Symptoms | Secreted, extracellular space, extracellular matrix (Probable). | UniProt, Literature, Prediction |
| MMP12_HUMAN | Macrophage metalloelastase | MMP12 | | LungCancers, BenignNodules, Symptoms | Secreted, extracellular space, extracellular matrix (Probable). | UniProt, Literature, Prediction |
| MMP14_HUMAN | Matrix metalloproteinase-14 | MMP14 | ENDO | LungCancers, BenignNodules, Symptoms | Membrane; Single-pass type I membrane protein (Potential). Melanosome. Note = Identified by mass spectrometry in melanosome fractions from stage I to stage IV. | UniProt, Literature, Detection |
| MMP2_HUMAN | 72 kDa type IV collagenase | MMP2 | | LungCancers, BenignNodules, Symptoms | Secreted, extracellular space, extracellular matrix (Probable). | UniProt, Literature, Detection, Prediction |
| MMP26_HUMAN | Matrix metalloproteinase-26 | MMP26 | | LungCancers | Secreted, extracellular space, extracellular matrix. | UniProt, Prediction |
| MMP7_HUMAN | Matrilysin | MMP7 | | LungCancers, BenignNodules, Symptoms | Secreted, extracellular space, extracellular matrix (Probable). | UniProt, Literature, Prediction |
| MMP9_HUMAN | Matrix metalloproteinase-9 | MMP9 | | LungCancers, BenignNodules, Symptoms | Secreted, extracellular space, extracellular matrix (Probable). | UniProt, Literature, Detection, Prediction |
| MOGS_HUMAN | Mannosyl-oligosaccharide glucosidase | MOGS | ENDO | | Endoplasmic reticulum membrane; Single-pass type II membrane protein. | UniProt, Prediction |
| MPRI_HUMAN | Cation-independent mannose-6-phosphate receptor | IGF2R | EPI, ENDO | LungCancers, Symptoms | Lysosome membrane; Single-pass type I membrane protein. | UniProt, Literature, Detection |
| MRP3_HUMAN | Canalicular multispecific organic | ABCC3 | EPI | LungCancers | Membrane; Multi-pass membrane | Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | anion transporter 2 | | | | protein. | |
| MUC1_HUMAN | Mucin-1 | MUC1 | EPI | LungCancers, BenignNodules, Symptoms | Apical cell membrane; Single-pass type I membrane protein. Note = Exclusively located in the apical domain of the plasma membrane of highly polarized epithelial cells. After endocytosis, internalized and recycled to the cell membrane. Located to microvilli and to the tips of long filopodial protusions.|Isoform 5: Secreted.|Isoform 7: Secreted.|Isoform 9: Secreted.|Mucin-1 subunit beta: Cell membrane. Cytoplasm. Nucleus. Note = On EGF and PDGFRB stimulation, transported to the nucleus through interaction with CTNNB1, a process which is stimulated by phosphorylation. On HRG stimulation, colocalizes with JUP/gamma-catenin at the nucleus. | UniProt, Literature, Prediction |
| MUC16_HUMAN | Mucin-16 | MUC16 | | LungCancers | Cell membrane; Single-pass type I membrane protein. Secreted, extracellular space. Note = May be liberated into the extracellular space following the phosphorylation of the intracellular C-terminus which induces the proteolytic cleavage and liberation of the extracellular domain. | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MUC4_HUMAN | Mucin-4 | MUC4 | | LungCancers, BenignNodules | Membrane; Single-pass membrane protein (Potential). Secreted. Note = Isoforms lacking the Cys-rich region, EGF-like domains and transmembrane region are secreted. Secretion occurs by splicing or proteolytic processing.\|Mucin-4 beta chain: Cell membrane; Single-pass membrane protein.\|Mucin-4 alpha chain: Secreted.\|Isoform 3: Cell membrane; Single-pass membrane protein.\|Isoform 15: Secreted. | UniProt |
| MUC5B_HUMAN | Mucin-5B | MUC5B | | LungCancers, BenignNodules | Secreted. | UniProt, Detection, Prediction |
| MUCL1_HUMAN | Mucin-like protein 1 | MUCL1 | | LungCancers | Secreted (Probable). Membrane (Probable). | UniProt, Prediction |
| NAMPT_HUMAN | Nicotinamide phosphoribosyltransferase | NAMPT | EPI | LungCancers, BenignNodules, Symptoms | Cytoplasm (By similarity). | Literature, Detection |
| NAPSA_HUMAN | Napsin-A | NAPSA | Secreted | LungCancers | | Prediction |
| NCF4_HUMAN | Neutrophil cytosol factor 4 | NCF4 | ENDO | | Cytoplasm. | Prediction |
| NDKA_HUMAN | Nucleoside diphosphate kinase A | NME1 | Secreted | LungCancers, BenignNodules, Symptoms | Cytoplasm. Nucleus. Note = Cell-cycle dependent nuclear localization which can be induced by interaction with Epstein-barr viral proteins or by degradation of the SET complex by GzmA. | Literature, Detection |
| NDKB_HUMAN | Nucleoside diphosphate kinase B | NME2 | Secreted, EPI | BenignNodules | Cytoplasm. Nucleus. Note = Isoform 2 is mainly cytoplasmic and isoform 1 and isoform 2 are excluded from the nucleolus. | Literature, Detection |
| NDUS1_HUMAN | NADH-ubiquinone oxidoreductase 75 kDa subunit, mitochondrial | NDUFS1 | Secreted, ENDO | Symptoms | Mitochondrion inner membrane. | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| NEBL_HUMAN | Nebulette | NEBL | ENDO | | | Prediction |
| NEK4_HUMAN | Serine/threonine-protein kinase Nek4 | NEK4 | ENDO | LungCancers | Nucleus (Probable). | Prediction |
| NET1_HUMAN | Netrin-1 | NTN1 | | LungCancers, BenignNodules | Secreted, extracellular space, extracellular matrix (By similarity). | UniProt, Literature, Prediction |
| NEU2_HUMAN | Vasopressin-neurophysin 2-copeptin | AVP | | LungCancers, Symptoms | Secreted. | UniProt, Prediction |
| NGAL_HUMAN | Neutrophil gelatinase-associated lipocalin | LCN2 | EPI | LungCancers, BenignNodules, Symptoms | Secreted. | UniProt, Detection, Prediction |
| NGLY1_HUMAN | Peptide-N(4)-(N-acetyl-beta-glucosaminyl)asparagine amidase | NGLY1 | ENDO | | Cytoplasm. | Detection, Prediction |
| NHRF1_HUMAN | Na(+)/H(+) exchange regulatory cofactor NHE-RF1 | SLC9A3R1 | EPI | BenignNodules | Endomembrane system; Peripheral membrane protein. Cell projection, filopodium. Cell projection, ruffle. Cell projection, microvillus. Note = Colocalizes with actin in microvilli-rich apical regions of the syncytiotrophoblast. Found in microvilli, ruffling membrane and filopodia of HeLa cells. Present in lipid rafts of T-cells. | Detection |
| NIBAN_HUMAN | Protein Niban | FAM129A | EPI | | Cytoplasm. | Literature, Detection |
| NMU_HUMAN | Neuromedin-U | NMU | | LungCancers | Secreted. | UniProt, Prediction |
| NRP1_HUMAN | Neuropilin-1 | NRP1 | | LungCancers, BenignNodules, Symptoms | Cell membrane; Single-pass type I membrane protein.|Isoform 2: Secreted. | UniProt, Literature, Detection, Prediction |
| ODAM_HUMAN | Odontogenic ameloblast-associated protein | ODAM | | LungCancers | Secreted (By similarity). | UniProt, Prediction |
| OSTP_HUMAN | Osteopontin | SPP1 | | LungCancers, BenignNodules, Symptoms | Secreted. | UniProt, Literature, Detection, Prediction |
| OVOS2_HUMAN | Ovostatin homolog 2 | OVOS2 | ENDO | | Secreted (By similarity). | UniProt, Prediction |
| P5CS_HUMAN | Delta-1-pyrroline-5-carboxylate synthase | ALDH18A1 | ENDO | | Mitochondrion inner membrane. | Prediction |
| PA2GX_HUMAN | Group 10 secretory | PLA2G10 | | Symptoms | Secreted. | UniProt |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | phospholipase A2 | | | | | |
| PAPP1_HUMAN | Pappalysin-1 | PAPPA | | LungCancers, BenignNodules, Symptoms | Secreted. | UniProt, Literature, Prediction |
| PBIP1_HUMAN | Pre-B-cell leukemia transcription factor-interacting protein 1 | PBXIP1 | EPI | | Cytoplasm, cytoskeleton. Nucleus. Note = Shuttles between the nucleus and the cytosol. Mainly localized in the cytoplasm, associated with microtubules. Detected in small amounts in the nucleus. | Prediction |
| PCBP1_HUMAN | Poly(rC)-binding protein 1 | PCBP1 | EPI, ENDO | | Nucleus. Cytoplasm. Note = Loosely bound in the nucleus. May shuttle between the nucleus and the cytoplasm. | Detection, Prediction |
| PCBP2_HUMAN | Poly(rC)-binding protein 2 | PCBP2 | EPI | | Nucleus. Cytoplasm. Note = Loosely bound in the nucleus. May shuttle between the nucleus and the cytoplasm. | Detection, Prediction |
| PCD15_HUMAN | Protocadherin-15 | PCDH15 | ENDO | | Cell membrane; Single-pass type I membrane protein (By similarity).|Isoform 3: Secreted. | UniProt, Detection |
| PCNA_HUMAN | Proliferating cell nuclear antigen | PCNA | EPI | LungCancers, BenignNodules, Symptoms | Nucleus. | Literature, Prediction |
| PCYOX_HUMAN | Prenylcysteine oxidase 1 | PCYOX1 | Secreted | LungCancers, Symptoms | Lysosome. | Detection, Prediction |
| PDGFA_HUMAN | Platelet-derived growth factor subunit A | PDGFA | | LungCancers | Secreted. | UniProt, Literature, Prediction |
| PDGFB_HUMAN | Platelet-derived growth factor subunit B | PDGFB | | LungCancers, BenignNodules, Symptoms | Secreted. | UniProt, Literature, Detection, Prediction |
| PDGFD_HUMAN | Platelet-derived growth factor D | PDGFD | | LungCancers | Secreted. | UniProt, Prediction |
| PDIA3_HUMAN | Protein disulfide-isomerase A3 | PDIA3 | ENDO | LungCancers | Endoplasmic reticulum lumen (By similarity). Melanosome. Note = Identified by mass spectrometry in melanosome fractions from stage I to stage IV. | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PDIA4_HUMAN | Protein disulfide-isomerase A4 | PDIA4 | Secreted, EPI, ENDO | | Endoplasmic reticulum lumen. Melanosome. Note = Identified by mass spectrometry in melanosome fractions from stage I to stage IV. | Detection, Prediction |
| PDIA6_HUMAN | Protein disulfide-isomerase A6 | PDIA6 | Secreted, EPI, ENDO | | Endoplasmic reticulum lumen (By similarity). Melanosome. Note = Identified by mass spectrometry in melanosome fractions from stage I to stage IV. | Detection, Prediction |
| PECA1_HUMAN | Platelet endothelial cell adhesion molecule | PECAM1 | | LungCancers, BenignNodules, Symptoms | Membrane; Single-pass type I membrane protein. | UniProt, Literature, Detection |
| PEDF_HUMAN | Pigment epithelium-derived factor | SERPINF1 | | LungCancers, Symptoms | Secreted. Melanosome. Note = Enriched in stage I melanosomes. | UniProt, Literature, Detection, Prediction |
| PERM_HUMAN | Myeloperoxidase | MPO | Secreted, EPI, ENDO | LungCancers, BenignNodules, Symptoms | Lysosome. | Literature, Detection Prediction |
| PERP1_HUMAN | Plasma cell-induced resident endoplasmic reticulum protein | PACAP | EPI, ENDO | | Secreted (Potential). Cytoplasm. Note = In (PubMed: 11350957) diffuse granular localization in the cytoplasm surrounding the nucleus. | UniProt, Detection, Prediction |
| PGAM1_HUMAN | Phosphoglycerate mutase 1 | PGAM1 | Secreted, EPI | LungCancers, Symptoms | | Detection |
| PLAC1_HUMAN | Placenta-specific protein 1 | PLAC1 | | LungCancers | Secreted (Probable). | UniProt, Prediction |
| PLACL_HUMAN | Placenta-specific 1-like protein | PLAC1L | | LungCancers | Secreted (Potential). | UniProt, Prediction |
| PLIN2_HUMAN | Perilipin-2 | ADFP | ENDO | LungCancers | Membrane; Peripheral membrane protein. | Prediction |
| PLIN3_HUMAN | Perilipin-3 | M6PRBP1 | EPI | | Cytoplasm. Endosome membrane; Peripheral membrane protein; Cytoplasmic side (Potential). Lipid droplet (Potential). Note = Membrane associated on endosomes. Detected in the envelope and the core of lipid | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PLOD1_HUMAN | Procollagen-lysine,2-oxoglutarate 5-dioxygenase 1 | PLOD1 | EPI, ENDO | | bodies and in lipid sails. Rough endoplasmic reticulum membrane; Peripheral membrane protein; Lumenal side. | Prediction |
| PLOD2_HUMAN | Procollagen-lysine,2-oxoglutarate 5-dioxygenase 2 | PLOD2 | ENDO | BenignNodules, Symptoms | Rough endoplasmic reticulum membrane; Peripheral membrane protein; Lumenal side. | Prediction |
| PLSL_HUMAN | Plastin-2 | LCP1 | Secreted, EPI | LungCancers | Cytoplasm, cytoskeleton. Cell junction. Cell projection. Cell projection, ruffle membrane; Peripheral membrane protein; Cytoplasmic side (By similarity). Note = Relocalizes to the immunological synapse between peripheral blood T lymphocytes and antibody-presenting cells in response to costimulation through TCR/CD3 and CD2 or CD28. Associated with the actin cytoskeleton at membrane ruffles (By similarity). Relocalizes to actin-rich cell projections upon serine phosphorylation. | Detection, Prediction |
| PLUNC_HUMAN | Protein Plunc | PLUNC | | LungCancers, BenignNodules | Secreted (By similarity). Note = Found in the nasal mucus (By similarity). Apical side of airway epithelial cells. Detected in nasal mucus (By similarity). | UniProt, Prediction |
| PLXB3_HUMAN | Plexin-B3 | PLXNB3 | ENDO | | Membrane; Single-pass type I membrane protein. | UniProt, Detection, Prediction |
| PLXC1_HUMAN | Plexin-C1 | PLXNC1 | EPI | | Membrane; Single-pass type I | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| POSTN_HUMAN | Periostin | POSTN | Secreted, ENDO | LungCancers, BenignNodules, Symptoms | membrane protein (Potential). Secreted, extracellular space, extracellular matrix. | UniProt, Literature, Detection, Prediction |
| PPAL_HUMAN | Lysosomal acid phosphatase | ACP2 | EPI | Symptoms | Lysosome membrane; Single-pass membrane protein; Lumenal side. Lysosome lumen. Note = The soluble form arises by proteolytic processing of the membrane-bound form. | UniProt, Prediction |
| PPBT_HUMAN | Alkaline phosphatase, tissue-nonspecific isozyme | ALPL | EPI | LungCancers, BenignNodules, Symptoms | Cell membrane; Lipid-anchor, GPI-anchor. | Literature, Detection, Prediction |
| PPIB_HUMAN | Peptidyl-prolyl cis-trans isomerase B | PPIB | Secreted, EPI, ENDO | | Endoplasmic reticulum lumen. Melanosome. Note = Identified by mass spectrometry in melanosome fractions from stage I to stage IV. | Detection, Prediction |
| PRDX1_HUMAN | Peroxiredoxin-1 | PRDX1 | EPI | LungCancers | Cytoplasm. Melanosome. Note = Identified by mass spectrometry in melanosome fractions from stage I to stage IV. | Detection, Prediction |
| PRDX4_HUMAN | Peroxiredoxin-4 | PRDX4 | Secreted, EPI, ENDO | | Cytoplasm. | Literature, Detection, Prediction |
| PROF1_HUMAN | Profilin-1 | PFN1 | Secreted, EPI | LungCancers | Cytoplasm, cytoskeleton. | Detection |
| PRP31_HUMAN | U4/U6 small nuclear ribonucleo protein Prp31 | PRPF31 | ENDO | | Nucleus speckle. Nucleus, Cajal body. Note = Predominantly found in speckles and in Cajal bodies. | Prediction |
| PRS6A_HUMAN | 26S protease regulatory subunit 6A | PSMC3 | EPI | BenignNodules | Cytoplasm (Potential). Nucleus (Potential). | Detection |
| PSCA_HUMAN | Prostate stem cell antigen | PSCA | | LungCancers | Cell membrane; Lipid-anchor, GPI-anchor. | Literature, Prediction |
| PTGIS_HUMAN | Prostacyclin synthase | PTGIS | EPI | LungCancers, BenignNodules | Endoplasmic reticulum membrane; Single-pass membrane protein. | UniProt, Detection, Prediction |
| PTPA_HUMAN | Serine/threonine-protein | PPP2R4 | ENDO | Symptoms | | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | phosphatase 2A activator | | | | | |
| PTPRC_HUMAN | Receptor-type tyrosine-protein phosphatase C | PTPRC | Secreted, EPI, ENDO | LungCancers | Membrane; Single-pass type I membrane protein. | UniProt, Detection, Prediction |
| PTPRJ_HUMAN | Receptor-type tyrosine-protein phosphatase eta | PTPRJ | EPI | LungCancers, Symptoms | Membrane; Single-pass type I membrane protein. | UniProt, Detection, Prediction |
| PVR_HUMAN | Poliovirus receptor | PVR | | Symptoms | Isoform Alpha: Cell membrane; Single-pass type I membrane protein.\|Isoform Delta: Cell membrane; Single-pass type I membrane protein.\|Isoform Beta: Secreted.\|Isoform Gamma: Secreted. | UniProt, Detection, Prediction |
| RAB32_HUMAN | Ras-related protein Rab-32 | RAB32 | EPI | | Mitochondrion. | Prediction |
| RAGE_HUMAN | Advanced glycosylation end product-specific receptor | AGER | Secreted | LungCancers, BenignNodules | Isoform 1: Cell membrane; Single-pass type I membrane protein.\|Isoform 2: Secreted. | UniProt, Literature |
| RAN_HUMAN | GTP-binding nuclear protein Ran | RAN | Secreted, EPI | LungCancers, BenignNodules | Nucleus. Cytoplasm. Melanosome. Note = Becomes dispersed throughout the cytoplasm during mitosis. Identified by mass spectrometry in melanosome fractions from stage I to stage IV. | Detection, Prediction |
| RAP2B_HUMAN | Ras-related protein Rap-2b | RAP2B | EPI | | Cell membrane; Lipid-anchor; Cytoplasmic side (Potential). | Prediction |
| RAP2C_HUMAN | Ras-related protein Rap-2c | RAP2C | EPI | | Cell membrane; Lipid-anchor; Cytoplasmic side (Potential). | Prediction |
| RCN3_HUMAN | Reticulocalbin-3 | RCN3 | EPI | Symptoms | Endoplasmic reticulum lumen (Potential). | Prediction |
| RL24_HUMAN | 60S ribosomal protein L24 | RPL24 | EPI | | | Prediction |
| S10A1_HUMAN | Protein S100-A1 | S100A1 | | Symptoms | Cytoplasm. | Literature, Prediction |
| S10A6_HUMAN | Protein S100-A6 | S100A6 | Secreted | LungCancers | Nucleus envelope. Cytoplasm. | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| S10A7_HUMAN | Protein S100-A7 | S100A7 | | LungCancers | Cytoplasm. Secreted. Note = Secreted by a non-classical secretory pathway. | UniProt, Literature, Detection, Prediction |
| SAA_HUMAN | Serum amyloid A protein | SAA1 | | Symptoms | Secreted. | UniProt, Literature, Detection, Prediction |
| SCF_HUMAN | Kit ligand | KITLG | | LungCancers, Symptoms | Isoform 1: Cell membrane; Single-pass type I membrane protein (By similarity). Secreted (By similarity). Note = Also exists as a secreted soluble form (isoform 1 only) (By similarity).\|Isoform 2: Cell membrane; Single-pass type I membrane protein (By similarity). Cytoplasm, cytoskeleton (By similarity). | UniProt, Literature |
| SDC1_HUMAN | Syndecan-1 | SDC1 | | LungCancers, BenignNodules, Symptoms | Membrane; Single-pass type I membrane protein. | UniProt, Literature, Detection |
| SEM3G_HUMAN | Semaphorin-3G | SEMA3G | | LungCancers | Secreted (By similarity). | UniProt, Prediction |
| SEPR_HUMAN | Seprase | FAP | ENDO | Symptoms | Cell membrane; Single-pass type II membrane protein. Cell projection, lamellipodium membrane; Single-pass type II membrane protein. Cell projection, invadopodium membrane; Single-pass type II membrane protein. Note = Found in cell surface lamellipodia, invadopodia and on shed vesicles. | UniProt, Literature, Detection |
| SERPH_HUMAN | Serpin H1 | SERPINH1 | Secreted, EPI, ENDO | LungCancers, BenignNodules | Endoplasmic reticulum lumen. | Detection, Prediction |
| SFPA2_HUMAN | Pulmonary surfactant-associated protein A2 | SFTPA2 | Secreted | LungCancers, BenignNodules | Secreted, extracellular space, extracellular matrix. | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| SFTA1_HUMAN | Pulmonary surfactant-associated protein A1 | SFTPA1 | Secreted | LungCancers, BenignNodules, Symptoms | Secreted, extracellular space, surface film. Secreted, extracellular space, extracellular matrix. Secreted, extracellular space, surface film. | UniProt, Prediction |
| SG3A2_HUMAN | Secretoglobin family 3A member 2 | SCGB3A2 | | LungCancers, BenignNodules | Secreted. | UniProt, Prediction |
| SGPL1_HUMAN | Sphingosine-1-phosphate lyase 1 | SGPL1 | ENDO | | Endoplasmic reticulum membrane; Single-pass type III membrane protein. | UniProt, Prediction |
| SIAL_HUMAN | Bone sialoprotein 2 | IBSP | | LungCancers | Secreted. | UniProt, Literature, Prediction |
| SLPI_HUMAN | Antileukoproteinase | SLPI | | LungCancers, BenignNodules | Secreted. | UniProt, Literature, Detection, Prediction |
| SMD3_HUMAN | Small nuclear ribonucleo protein SmD3 | SNRPD3 | Secreted | BenignNodules | Nucleus. | Prediction |
| SMS_HUMAN | Somatostatin | SST | | LungCancers | Secreted. | UniProt, Literature, Prediction |
| SODM_HUMAN | Superoxide dismutase [Mn], mitochondrial | SOD2 | Secreted | LungCancers, BenignNodules, Symptoms | Mitochondrion matrix. | Literature, Detection, Prediction |
| SORL_HUMAN | Sortilin-related receptor | SORL1 | EPI | LungCancers, Symptoms | Membrane; Single-pass type I membrane protein (Potential). | UniProt, Detection |
| SPB3_HUMAN | Serpin B3 | SERPINB3 | | LungCancers, BenignNodules | Cytoplasm. Note = Seems to also be secreted in plasma by cancerous cells but at a low level. | Literature, Detection |
| SPB5_HUMAN | Serpin B5 | SERPINB5 | | LungCancers | Secreted, extracellular space. | UniProt, Detection |
| SPON2_HUMAN | Spondin-2 | SPON2 | | LungCancers, BenignNodules | Secreted, extracellular space, extracellular matrix (By similarity). | UniProt, Prediction |
| SPRC_HUMAN | SPARC | SPARC | | LungCancers, BenignNodules, Symptoms | Secreted, extracellular space, extracellular matrix, basement membrane. Note = In or around the basement membrane. | UniProt, Literature, Detection, Prediction |
| SRC_HUMAN | Proto-oncogene | SRC | ENDO | LungCancers, BenignNodules, | | Literature |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| SSRD_HUMAN | tyrosine-protein kinase Src Translocon-associated protein subunit delta | SSR4 | Secreted, ENDO | Symptoms | Endoplasmic reticulum membrane; Single-pass type I membrane protein. | UniProt, Prediction |
| STAT1_HUMAN | Signal transducer and activator of transcription 1-alpha/beta | STAT1 | EPI | LungCancers, BenignNodules | Cytoplasm. Nucleus. Note = Translocated into the nucleus in response to IFN-gamma-induced tyrosine phosphorylation and dimerization. | Detection |
| STAT3_HUMAN | Signal transducer and activator of transcription 3 | STAT3 | ENDO | LungCancers, BenignNodules, Symptoms | Cytoplasm. Nucleus. Note = Shuttles between the nucleus and the cytoplasm. Constitutive nuclear presence is independent of tyrosine phosphorylation. | Prediction |
| STC1_HUMAN | Stanniocalcin-1 | STC1 | | LungCancers, Symptoms | Secreted. | UniProt, Prediction |
| STT3A_HUMAN | Dolichyl-diphosphooligosaccharide--protein glycosyltransferase subunit STT3A | STT3A | EPI | Symptoms | Endoplasmic reticulum membrane; Multi-pass membrane protein. | Literature |
| TAGL_HUMAN | Transgelin | TAGLN | EPI | LungCancers | Cytoplasm (Probable). | Literature, Prediction |
| TARA_HUMAN | TRIO and F-actin-binding protein | TRIOBP | ENDO | | Nucleus. Cytoplasm, cytoskeleton. Note = Localized to F-actin in a periodic pattern. | Detection, Prediction |
| TBA1B_HUMAN | Tubulin alpha-1B chain | TUBA1B | EPI | LungCancers | | Detection |
| TBB2A_HUMAN | Tubulin beta-2A chain | TUBB2A | EPI | LungCancers, BenignNodules | | Detection, Prediction |
| TBB3_HUMAN | Tubulin beta-3 chain | TUBB3 | EPI | LungCancers, BenignNodules | | Detection |
| TBB5_HUMAN | Tubulin beta chain | TUBB | EPI | LungCancers, BenignNodules | | Detection |
| TCPA_HUMAN | T-complex protein 1 subunit alpha | TCP1 | EPI | | Cytoplasm. | Prediction |
| TCPD_HUMAN | T-complex protein 1 subunit delta | CCT4 | EPI | | Cytoplasm. Melanosome. Note = Identified by mass spectrometry in melanosome fractions from stage I to stage IV. | Detection, Prediction |
| TCPQ_HUMAN | T-complex protein 1 | CCT8 | Secreted, EPI | | Cytoplasm. | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | subunit theta | | | | | |
| TCPZ_HUMAN | T-complex protein 1 subunit zeta | CCT6A | Secreted, EPI | | Cytoplasm. | Detection |
| TDRD3_HUMAN | Tudor domain-containing protein 3 | TDRD3 | ENDO | | Cytoplasm. Nucleus. Note = Predominantly cytoplasmic. Associated with actively translating polyribosomes and with mRNA stress granules. | Prediction |
| TENA_HUMAN | Tenascin | TNC | ENDO | LungCancers, BenignNodules, Symptoms | Secreted, extracellular space, extracellular matrix. | UniProt, Literature, Detection |
| TENX_HUMAN | Tenascin-X | TNXB | ENDO | LungCancers, Symptoms | Secreted, extracellular space, extracellular matrix. | UniProt, Detection, Prediction |
| TERA_HUMAN | Transitional endoplasmic reticulum ATPase | VCP | EPI | LungCancers, BenignNodules | Cytoplasm, cytosol. Nucleus. Note = Present in the neuronal hyaline inclusion bodies specifically found in motor neurons from amyotrophic lateral sclerosis patients. Present in the Lewy bodies specifically found in neurons from Parkinson disease patients. | Detection |
| TETN_HUMAN | Tetranectin | CLEC3B | | LungCancers | Secreted. | UniProt, Literature, Detection, Prediction |
| TF_HUMAN | Tissue factor | F3 | | LungCancers, BenignNodules, Symptoms | Membrane; Single-pass type I membrane protein. | UniProt, Literature |
| TFR1_HUMAN | Transferrin receptor protein 1 | TFRC | Secreted, EPI, ENDO | LungCancers, BenignNodules, Symptoms | Cell membrane; Single-pass type II membrane protein. Melanosome. Note = Identified by mass spectrometry in melanosome fractions from stage I to stage IV.|Transferrin receptor protein 1, serum form: Secreted. | UniProt, Literature, Detection |
| TGFA_HUMAN | Protransforming growth factor alpha | TGFA | | LungCancers, BenignNodules | Transforming growth factor alpha: Secreted, extracellular | UniProt, Literature |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | space.\|Protransforming growth factor alpha: Cell membrane; Single-pass type I membrane protein. | |
| THAS_HUMAN | Thromboxane-A synthase | TBXAS1 | EPI, ENDO | LungCancers, BenignNodules, Symptoms | Membrane; Multi-pass membrane protein. | Prediction |
| THY1_HUMAN | Thy-1 membrane glycoprotein | THY1 | EPI | Symptoms | Cell membrane; Lipid-anchor, GPI-anchor (By similarity). | Detection, Prediction |
| TIMP1_HUMAN | Metalloproteinase inhibitor 1 | TIMP1 | | LungCancers, BenignNodules, Symptoms | Secreted. | UniProt, Literature, Detection, Prediction |
| TIMP3_HUMAN | Metalloproteinase inhibitor 3 | TIMP3 | | LungCancers, BenignNodules | Secreted, extracellular space, extracellular matrix. | UniProt, Literature, Prediction |
| TLL1_HUMAN | Tolloid-like protein 1 | TLL1 | ENDO | | Secreted (Probable). | UniProt, Prediction |
| TNF12_HUMAN | Tumor necrosis factor ligand superfamily member 12 | TNFSF12 | | LungCancers, BenignNodules | Cell membrane; Single-pass type II membrane protein.\|Tumor necrosis factor ligand superfamily member 12, secreted form: Secreted. | UniProt |
| TNR6_HUMAN | Tumor necrosis factor receptor superfamily member 6 | FAS | | LungCancers, BenignNodules, Symptoms | Isoform 1: Cell membrane; Single-pass type I membrane protein.\|Isoform 2: Secreted.\|Isoform 3: Secreted.\|Isoform 4: Secreted.\|Isoform 5: Secreted.\|Isoform 6: Secreted. | UniProt, Literature, Prediction |
| TPIS_HUMAN | Triosephosphate isomerase | TPI1 | Secreted, EPI | Symptoms | | Literature, Detection, Prediction |
| TRFL_HUMAN | Lactotransferrin | LTF | Secreted, EPI, ENDO | LungCancers, BenignNodules, Symptoms | Secreted. | UniProt, Literature, Detection, Prediction |
| TSP1_HUMAN | Thrombospondin-1 | THBS1 | | LungCancers, BenignNodules, Symptoms | | Literature, Detection, Prediction |
| TTHY_HUMAN | Transthyretin | TTR | | LungCancers, BenignNodules | Secreted. Cytoplasm. | UniProt, Literature, Detection, Prediction |
| TYPH_HUMAN | Thymidine phosphorylase | TYMP | EPI | LungCancers, BenignNodules, Symptoms | | Literature, Detection, Prediction |
| UGGG1_HUMAN | UDP-glucose:glycoprotein glucosyltransferase 1 | UGGT1 | Secreted, ENDO | | Endoplasmic reticulum lumen. Endoplasmic reticulum-Golgi | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| UGGG2_HUMAN | UDP-glucose:glycoprotein glucosyltransferase 2 | UGGT2 | ENDO | | intermediate compartment. Endoplasmic reticulum lumen. Endoplasmic reticulum-Golgi intermediate compartment. | Prediction |
| UGPA_HUMAN | UTP--glucose-1-phosphate uridylyltransferase | UGP2 | EPI | Symptoms | Cytoplasm. | Detection |
| UPAR_HUMAN | Urokinase plasminogen activator surface receptor | PLAUR | | LungCancers, BenignNodules, Symptoms | Isoform 1: Cell membrane; Lipid-anchor, GPI-anchor.\|Isoform 2: Secreted (Probable). | UniProt, Literature, Prediction |
| UTER_HUMAN | Uteroglobin | SCGB1A1 | | LungCancers, BenignNodules, Symptoms | Secreted. | UniProt, Literature, Detection, Prediction |
| VA0D1_HUMAN | V-type proton ATPase subunit d 1 | ATP6V0D1 | EPI | | | Prediction |
| VAV3_HUMAN | Guanine nucleotide exchange factor VAV3 | VAV3 | ENDO | | | Prediction |
| VEGFA_HUMAN | Vascular endothelial growth factor A | VEGFA | | LungCancers, BenignNodules, Symptoms | Secreted. Note = VEGF121 is acidic and freely secreted. VEGF165 is more basic, has heparin-binding properties and, although a signicant proportion remains cell-associated, most is freely secreted. VEGF189 is very basic, it is cell-associated after secretion and is bound avidly by heparin and the extracellular matrix, although it may be released as a soluble form by heparin, heparinase or plasmin. | UniProt, Literature, Prediction |
| VEGFC_HUMAN | Vascular endothelial growth factor C | VEGFC | | LungCancers, BenignNodules | Secreted. | UniProt, Literature, Prediction |
| VEGFD_HUMAN | Vascular endothelial | FIGF | | LungCancers | Secreted. | UniProt, Literature, |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | growth factor D | | | | | Prediction |
| VGFR1_HUMAN | Vascular endothelial growth factor receptor 1 | FLT1 | | LungCancers, BenignNodules, Symptoms | Isoform Flt1: Cell membrane; Single-pass type I membrane protein.\|Isoform sFlt1: Secreted. | UniProt, Literature, Detection, Prediction |
| VTNC_HUMAN | Vitronectin | VTN | ENDO | Symptoms | Secreted, extracellular space. | UniProt, Literature, Detection, Prediction |
| VWC2_HUMAN | Brorin | VWC2 | | LungCancers | Secreted, extracellular space, extracellular matrix, basement membrane (By similarity). | UniProt, Prediction |
| WNT3A_HUMAN | Protein Wnt-3a | WNT3A | | LungCancers, Symptoms | Secreted, extracellular space, extracellular matrix. | UniProt, Prediction |
| WT1_HUMAN | Wilms tumor protein | WT1 | | LungCancers, BenignNodules, Symptoms | Nucleus. Cytoplasm (By similarity). Note = Shuttles between nucleus and cytoplasm (By similarity).\|Isoform 1: Nucleus speckle.\|Isoform 4: Nucleus, nucleoplasm. | Literature, Prediction |
| ZA2G_HUMAN | Zinc-alpha-2-glycoprotein | AZGP1 | | LungCancers, Symptoms | Secreted. | UniProt, Literature, Detection, Prediction |
| ZG16B_HUMAN | Zymogen granule protein 16 homolog B | ZG16B | | LungCancers | Secreted (Potential). | UniProt, Prediction |

SRM Assay

SRM assays for 388 targeted proteins were developed based on synthetic peptides, using a protocol similar to those described in the literature (Lange, Picotti et al. 2008, Picotti, Rinner et al. 2010, Huttenhain, Soste et al. 2012). Up to five SRM suitable peptides per protein were identified from public sources such as the PeptideAtlas, Human Plasma Proteome Database or by proteotypic prediction tools (Mallick, Schirle et al. 2007) and synthesized. SRM triggered MS/MS spectra were collected on an ABSciex 5500 QTrap for both doubly and triply charged precursor ions. The obtained MS/MS spectra were assigned to individual peptides using MASCOT (cutoff score ≥15) (Perkins, Pappin et al. 1999). Up to four transitions per precursor ion were selected for optimization. The resulting corresponding optimal retention time, declustering potential and collision energy were assembled for all transitions. Optimal transitions were measured on a mixture of all synthetic peptides, a pooled sample of benign patients and a pooled sample of cancer patients. Transitions were analyzed in batches, each containing up to 1750 transitions. Both biological samples were immuno-depleted and digested by trypsin. All three samples were analyzed on an ABSciex 5500 QTrap coupled with a reversed-phase (RP) high-performance liquid chromatography (HPLC) system. The obtained SRM data were manually reviewed to select the two best peptides per protein and the two best transitions per peptide. Transitions having interference with other transitions were not selected. Ratios between intensities of the two best transitions of peptides in the synthetic peptide mixture were also used to assess the specificity of the transitions in the biological samples. The intensity ratio was considered as an important metric defining the SRM assays. The complete transition table is shown below in Table 2.

Lengthy table referenced here

US09091651-20150728-T00001

Please refer to the end of the specification for access instructions.

Exemplary Protein Detection

The following 164 proteins and their peptides were detected simultaneously in a large-scale experiment of 158 samples using the MS-LC-SRM-MS system described herein.

TABLE 3

| Protein | Peptide | SEQ ID NO: | Protein Detection | Peptide Detection |
|---|---|---|---|---|
| 1433E_HUMAN | EDLVYQAK | 7 | 16 | 16 |
| 1433E_HUMAN | IISSIEQK | 9 | 16 | 0 |
| 1433T_HUMAN | AVTEQGAELSNEER | 16 | 127 | 0 |
| 1433T_HUMAN | TAFDEAIAELDTLNEDSYK | 19 | 127 | 127 |
| 1433Z_HUMAN | FLIPNASQAESK | 21 | 157 | 157 |
| 1433Z_HUMAN | SVTEQGAELSNEER | 23 | 157 | 0 |
| 6PGD_HUMAN | AGQAVDDFIEK | 25 | 90 | 0 |
| 6PGD_HUMAN | LVPLLDTGDIIIDGGNSEYR | 27 | 90 | 90 |
| A1AG1_HUMAN | WFYIASAFR | 32 | 157 | 0 |
| A1AG1_HUMAN | YVGGQEHFAHLLILR | 33 | 157 | 157 |
| ABCD1_HUMAN | DAGIALLSITHRPSLWK | 34 | 9 | 0 |
| ABCD1_HUMAN | GLQAPAGEPTQEASGVAAAK | 36 | 9 | 0 |
| ABCD1_HUMAN | NLLTAAADAIER | 37 | 9 | 9 |
| ADML_HUMAN | LAHQIYQFTDK | 44 | 27 | 27 |
| ADML_HUMAN | SPEDSSPDAAR | 45 | 27 | 0 |
| AIFM1_HUMAN | ELWFSDDPNVTK | 53 | 158 | 158 |
| AIFM1_HUMAN | GVIFYLR | 54 | 158 | 0 |
| ALDOA_HUMAN | ADDGRPFPQVIK | 57 | 158 | 141 |
| ALDOA_HUMAN | ALQASALK | 58 | 158 | 17 |
| AMPN_HUMAN | ALEQALEK | 62 | 158 | 158 |
| AMPN_HUMAN | DHSAIPVINR | 63 | 158 | 0 |
| APOA1_HUMAN | AKPALEDLR | 78 | 158 | 158 |
| APOA1_HUMAN | ATEHLSTLSEK | 79 | 158 | 0 |
| APOE_HUMAN | AATVGSLAGQPLQER | 82 | 158 | 158 |
| APOE_HUMAN | LGPLVEQGR | 87 | 158 | 0 |
| BGH3_HUMAN | LTLLAPLNSVFK | 139 | 158 | 0 |
| BGH3_HUMAN | SPYQLVLQHSR | 140 | 158 | 158 |
| BST1_HUMAN | GEGTSAHLR | 149 | 157 | 0 |
| BST1_HUMAN | GFFADYEIPNLQK | 150 | 157 | 157 |
| C163A_HUMAN | INPASLDK | 153 | 158 | 11 |
| C163A_HUMAN | LEVFYNGAWGTVGK | 154 | 158 | 49 |
| C163A_HUMAN | TSYQVYSK | 155 | 158 | 98 |
| CALU_HUMAN | EQFVEFR | 172 | 120 | 120 |
| CALU_HUMAN | TFDQLTPEESK | 174 | 120 | 0 |
| CATB_HUMAN | LPASFDAR | 188 | 62 | 62 |
| CATB_HUMAN | TDQYWEK | 190 | 62 | 0 |
| CATG_HUMAN | NVNPVALPR | 192 | 14 | 0 |
| CATG_HUMAN | SSGVPPEVFTR | 193 | 14 | 14 |
| CBPB2_HUMAN | DTGTYGFLLPER | 198 | 158 | 158 |
| CBPB2_HUMAN | EAFAAVSK | 199 | 158 | 0 |
| CD14_HUMAN | ATVNPSAPR | 207 | 158 | 0 |
| CD14_HUMAN | SWLAELQQVVLKPGLK | 214 | 158 | 158 |
| CD44_HUMAN | FAGVFHVEK | 227 | 158 | 158 |
| CD44_HUMAN | YGFIEGHVVIPR | 231 | 158 | 0 |
| CD59_HUMAN | AGLQVYNK | 232 | 156 | 156 |
| CD59_HUMAN | TVLLLVTPFLAAAWSLHP | 233 | 156 | 0 |
| CDCP1_HUMAN | EEGVFTVTPDTK | 239 | 157 | 0 |
| CDCP1_HUMAN | LSLVLVPAQK | 241 | 157 | 157 |
| CEAM8_HUMAN | LFIPNITTK | 256 | 79 | 79 |
| CEAM8_HUMAN | TLTLLSVTR | 257 | 79 | 0 |
| CERU_HUMAN | GAYPLSIEPIGVR | 258 | 158 | 0 |
| CERU_HUMAN | GPEEEHLGILGPVIWAEVGDTIR | 259 | 158 | 158 |
| CERU_HUMAN | NNEGTYYSPNYNPQSR | 261 | 158 | 0 |
| CH10_HUMAN | GGEIQPVSVK | 265 | 158 | 0 |
| CH10_HUMAN | VLLPEYGGTK | 266 | 158 | 158 |
| CLIC1_HUMAN | FSAYIK | 288 | 137 | 8 |
| CLIC1_HUMAN | LAALNPESNTAGLDIFAK | 290 | 137 | 129 |
| CLIC1_HUMAN | NSNPALNDNLEK | 291 | 137 | 0 |
| CLUS_HUMAN | ASSIIDELFQDR | 293 | 158 | 0 |
| CLUS_HUMAN | EIQNAVNGVK | 294 | 158 | 158 |
| CNTN1_HUMAN | AHSDGGDGVVSQVK | 303 | 158 | 157 |
| CNTN1_HUMAN | DGEYVVEVR | 304 | 158 | 1 |
| CO6A3_HUMAN | IGDLHPQIVNLLK | 319 | 158 | 0 |
| CO6A3_HUMAN | VAVVQYSDR | 321 | 158 | 158 |
| CO6A3_HUMAN | WYYDPNTK | 322 | 158 | 0 |
| COF1_HUMAN | EILVGDVGQTVDDPYATFVK | 328 | 127 | 0 |
| COF1_HUMAN | LGGSAVISLEGKPL | 329 | 127 | 0 |
| COF1_HUMAN | YALYDATYETK | 330 | 127 | 127 |
| COIA1_HUMAN | AVGLAGTFR | 332 | 158 | 37 |
| COIA1_HUMAN | TEAPSATGQASSLLGGR | 335 | 158 | 121 |

TABLE 3-continued

| Protein | Peptide | SEQ ID NO: | Protein Detection | Peptide Detection |
|---|---|---|---|---|
| CRP_HUMAN | APLTKPLK | 341 | 153 | 21 |
| CRP_HUMAN | ESDTSYVSLK | 342 | 153 | 132 |
| CRP_HUMAN | YEVQGEVFTKPQLWP | 343 | 153 | 0 |
| CSF1_HUMAN | FNSVPLTDTGHER | 351 | 134 | 113 |
| CSF1_HUMAN | ISSLRPQGLSNPSTLSAQPQLSR | 352 | 134 | 21 |
| CYTB_HUMAN | SQLEEK | 372 | 100 | 0 |
| CYTB_HUMAN | SQVVAGTNYFIK | 373 | 100 | 100 |
| DESP_HUMAN | YGDGIQLTR | 384 | 131 | 131 |
| DMKN_HUMAN | QVPGFGVADALGNR | 395 | 128 | 0 |
| DMKN_HUMAN | VSEALGQGTR | 397 | 128 | 128 |
| DSG2_HUMAN | GQIIGNFQAFDEDTGLPAHAR | 404 | 158 | 1 |
| DSG2_HUMAN | ILDVNDNIPWENK | 405 | 158 | 157 |
| EF1A1_HUMAN | IGGIGTVPVGR | 423 | 158 | 158 |
| EF1A1_HUMAN | QTVAVGVIK | 426 | 158 | 0 |
| EF2_HUMAN | FSVSPVVR | 439 | 125 | 125 |
| EF2_HUMAN | GVQYLNEIK | 441 | 125 | 0 |
| ENOA_HUMAN | AVEHINK | 452 | 156 | 0 |
| ENOA_HUMAN | YISPDQLADLYK | 455 | 156 | 156 |
| ENOA_HUMAN | YNQLLR | 456 | 156 | 0 |
| ENPL_HUMAN | SGTSEFLNK | 469 | 158 | 1 |
| ENPL_HUMAN | SGYLLPDTK | 470 | 158 | 157 |
| EPHB6_HUMAN | RPHFDQLVAAFDK | 472 | 157 | 0 |
| EPHB6_HUMAN | WAAPEVIAHGK | 476 | 157 | 157 |
| ERBB3_HUMAN | GESIEPLDPSEK | 483 | 105 | 0 |
| ERBB3_HUMAN | LAEVPDLLEK | 484 | 105 | 105 |
| EREG_HUMAN | VAQVSITK | 487 | 115 | 115 |
| EREG_HUMAN | VTSGDPELPQV | 488 | 115 | 0 |
| ERO1A_HUMAN | AVLQWTK | 489 | 121 | 0 |
| ERO1A_HUMAN | LLESDYFR | 491 | 121 | 0 |
| ERO1A_HUMAN | NLLQNIH | 492 | 121 | 0 |
| ERO1A_HUMAN | VLPFFERPDFQLFTGNK | 493 | 121 | 121 |
| F10A1_HUMAN | AIDLFTDAIK | 501 | 35 | 0 |
| F10A1_HUMAN | LQKPNAAIR | 503 | 35 | 35 |
| FAM3C_HUMAN | GINVALANGK | 505 | 97 | 88 |
| FAM3C_HUMAN | SALDTAAR | 507 | 97 | 9 |
| FAM3C_HUMAN | TGEVLDTK | 509 | 97 | 0 |
| FCGR1_HUMAN | HLEEELK | 517 | 39 | 0 |
| FCGR1_HUMAN | VFTEGEPLALR | 519 | 39 | 39 |
| FIBA_HUMAN | GGSTSYGTGSETESPR | 554 | 147 | 108 |
| FIBA_HUMAN | NSLFEYQK | 556 | 147 | 39 |
| FINC_HUMAN | SYTITGLQPGTDYK | 561 | 154 | 135 |
| FINC_HUMAN | VPGTSTSATLTGLTR | 562 | 154 | 19 |
| FKB11_HUMAN | ANYWLK | 565 | 23 | 0 |
| FKB11_HUMAN | DPLVIELGQK | 566 | 23 | 23 |
| FOLH1_HUMAN | GVILYSDPADYFAPGVK | 569 | 138 | 0 |
| FOLH1_HUMAN | LGSGNDFEVFFQR | 570 | 138 | 138 |
| FRIL_HUMAN | DDVALEGVSHFFR | 594 | 151 | 0 |
| FRIL_HUMAN | LGGPEAGLGEYLFER | 596 | 151 | 151 |
| G3P_HUMAN | GALQNIIPASTGAAK | 599 | 150 | 149 |
| G3P_HUMAN | LISWYDNEFGYSNR | 600 | 150 | 1 |
| G6PD_HUMAN | DGLLPENTFIVGYAR | 603 | 43 | 43 |
| G6PD_HUMAN | GGYFDEFGIIR | 604 | 43 | 0 |
| G6PI_HUMAN | AVLHVALR | 608 | 39 | 6 |
| G6PI_HUMAN | TLAQLNPESSLFIIASK | 610 | 39 | 33 |
| GDIR2_HUMAN | DIVSGLK | 629 | 158 | 158 |
| GDIR2_HUMAN | LNYKPPPQK | 630 | 158 | 0 |
| GELS_HUMAN | AQPVQVAEGSEPDGFWEALGGK | 634 | 158 | 0 |
| GELS_HUMAN | TASDFITK | 637 | 158 | 158 |
| GGH_HUMAN | NLDGISHAPNAVK | 640 | 158 | 158 |
| GGH_HUMAN | YYIAASYVK | 643 | 158 | 0 |
| GRP78_HUMAN | TWNDPSVQQDIK | 664 | 158 | 90 |
| GRP78_HUMAN | VYEGERPLTK | 665 | 158 | 68 |
| GSLG1_HUMAN | IIIQESALDYR | 666 | 158 | 158 |
| GSLG1_HUMAN | LDPALQDK | 667 | 158 | 0 |
| GSLG1_HUMAN | LIAQDYK | 668 | 158 | 0 |
| GSLG1_HUMAN | NDINILK | 669 | 158 | 0 |
| GSTP1_HUMAN | ALPGQLKPFETLLSQNQGGK | 672 | 123 | 123 |
| GSTP1_HUMAN | YISLIYTNYEAGK | 675 | 123 | 0 |
| HPSE_HUMAN | LPYPFSNK | 714 | 49 | 0 |
| HPSE_HUMAN | SVQLNGLTLK | 715 | 49 | 49 |
| HPT_HUMAN | VGYVSGWGR | 719 | 158 | 0 |
| HPT_HUMAN | VTSIQDWVQK | 720 | 158 | 158 |
| HS90A_HUMAN | SLTNDWEDHLAVK | 724 | 32 | 32 |
| HS90B_HUMAN | ADHGEPIGR | 726 | 121 | 0 |
| HS90B_HUMAN | IDIIPNPQER | 728 | 121 | 121 |
| HS90B_HUMAN | NPDDITQEEYGEFYK | 730 | 121 | 0 |
| HSPB1_HUMAN | DEVVEITGK | 732 | 30 | 0 |

TABLE 3-continued

| Protein | Peptide | SEQ ID NO: | Protein Detection | Peptide Detection |
|---|---|---|---|---|
| HSPB1_HUMAN | GPSWDPFR | 733 | 30 | 30 |
| HTRA1_HUMAN | LHRPPVIVLQR | 741 | 40 | 40 |
| HTRA1_HUMAN | LPVLLLGR | 742 | 40 | 0 |
| HTRA1_HUMAN | VTAGISFAIPSDK | 744 | 40 | 0 |
| HXK1_HUMAN | FLLSESGSGK | 747 | 117 | 17 |
| HXK1_HUMAN | LVDEYSLNAGK | 749 | 117 | 47 |
| HXK1_HUMAN | SANLVAATLGAILNR | 750 | 117 | 53 |
| HYOU1_HUMAN | FPEHELTFDPQR | 757 | 156 | 0 |
| HYOU1_HUMAN | LPATEKPVLLSK | 760 | 156 | 156 |
| IBP2_HUMAN | AEVLFR | 762 | 158 | 0 |
| IBP2_HUMAN | ELAVFR | 763 | 158 | 158 |
| IBP2_HUMAN | LIQGAPTIR | 765 | 158 | 0 |
| IBP3_HUMAN | FHPLHSK | 768 | 158 | 0 |
| IBP3_HUMAN | FLNVLSPR | 769 | 158 | 0 |
| IBP3_HUMAN | YGQPLPGYTTK | 771 | 158 | 158 |
| ICAM1_HUMAN | ASVSVTAEDEGTQR | 772 | 114 | 0 |
| ICAM1_HUMAN | VELAPLPSWQPVGK | 776 | 114 | 114 |
| ICAM3_HUMAN | IALETSLSK | 780 | 158 | 0 |
| ICAM3_HUMAN | TFVLPVTPPR | 783 | 158 | 158 |
| IF4A1_HUMAN | GYDVIAQAQSGTGK | 792 | 58 | 0 |
| IF4A1_HUMAN | VLITTDLLAR | 796 | 58 | 58 |
| IGF1_HUMAN | EGTEASLQIR | 797 | 40 | 0 |
| IGF1_HUMAN | ISSLPTQLFK | 798 | 40 | 40 |
| IL18_HUMAN | SDIIFFQR | 807 | 45 | 45 |
| IL18_HUMAN | SVPGHDNK | 808 | 45 | 0 |
| ILEU_HUMAN | EATTNAPFR | 824 | 88 | 13 |
| ILEU_HUMAN | TYNFLPEFLVSTQK | 828 | 88 | 75 |
| ILK_HUMAN | HSGIDFK | 830 | 90 | 15 |
| ILK_HUMAN | QLNFLTK | 832 | 90 | 75 |
| ILK_HUMAN | WQGNDIVVK | 833 | 90 | 0 |
| INHBA_HUMAN | AEVWLFLK | 834 | 32 | 0 |
| INHBA_HUMAN | EGSDLSVVER | 835 | 32 | 32 |
| ISLR_HUMAN | ALPGTPVASSQPR | 839 | 158 | 0 |
| ISLR_HUMAN | EVPLLQSLWLAHNEIR | 840 | 158 | 0 |
| ISLR_HUMAN | LPGLPEGAFR | 841 | 158 | 158 |
| ITA5_HUMAN | SLQWFGATVR | 846 | 114 | 114 |
| ITA5_HUMAN | SSASSGPQILK | 847 | 114 | 0 |
| K1C18_HUMAN | LASYLDR | 861 | 72 | 0 |
| K1C18_HUMAN | LQLETEIEALK | 862 | 72 | 72 |
| K1C18_HUMAN | VVSETNDTK | 863 | 72 | 0 |
| K1C19_HUMAN | FGAQLAHIQALISGIEAQLGDVR | 865 | 158 | 158 |
| K1C19_HUMAN | FGPGVAFR | 866 | 158 | 0 |
| KIT_HUMAN | QATLTISSAR | 876 | 158 | 158 |
| KIT_HUMAN | YVSELHLTR | 878 | 158 | 0 |
| KLK14_HUMAN | VLGSGTWPSAPK | 889 | 27 | 27 |
| KLK14_HUMAN | VSGWGTISSPIAR | 890 | 27 | 0 |
| KPYM_HUMAN | APIIAVTR | 899 | 158 | 13 |
| KPYM_HUMAN | LDIDSPPITAR | 903 | 158 | 145 |
| LAMB2_HUMAN | IQGTLQPHAR | 910 | 69 | 0 |
| LAMB2_HUMAN | SLADVDAILAR | 911 | 69 | 31 |
| LAMB2_HUMAN | VLELSIPASAEQIQHLAGAIAER | 913 | 69 | 38 |
| LDHA_HUMAN | FIIPNVVK | 915 | 157 | 0 |
| LDHA_HUMAN | LVIITAGAR | 917 | 157 | 157 |
| LDHB_HUMAN | FIIPQIVK | 920 | 158 | 157 |
| LDHB_HUMAN | GLTSVINQK | 921 | 158 | 1 |
| LEG1_HUMAN | GEVAPDAK | 925 | 146 | 0 |
| LEG1_HUMAN | LPDGYEFK | 926 | 146 | 0 |
| LEG1_HUMAN | SFVLNLGK | 927 | 146 | 146 |
| LG3BP_HUMAN | ASHEEVEGLVEK | 938 | 158 | 158 |
| LG3BP_HUMAN | VEIFYR | 941 | 158 | 0 |
| LG3BP_HUMAN | YSSDYFQAPSDYR | 942 | 158 | 0 |
| LRP1_HUMAN | TVLWPNGLSLDIPAGR | 959 | 158 | 158 |
| LRP1_HUMAN | VFFTDYGQIPK | 960 | 158 | 0 |
| LUM_HUMAN | NIPTVNENLENYYLEVNQLEK | 962 | 158 | 158 |
| LUM_HUMAN | SLEDLQLTHNK | 964 | 158 | 0 |
| LYOX_HUMAN | HWFQAGYSTSR | 975 | 121 | 0 |
| LYOX_HUMAN | TPILLIR | 977 | 121 | 121 |
| MASP1_HUMAN | APGELEHGLITFSTR | 991 | 158 | 151 |
| MASP1_HUMAN | TGVITSPDFPNPYPK | 994 | 158 | 7 |
| MDHC_HUMAN | LGVTANDVK | 997 | 130 | 130 |
| MDHC_HUMAN | VLVTGAAGQIAYSLLYSIGNGSVFGK | 999 | 130 | 0 |
| MDHM_HUMAN | VDFPQDQLTALTGR | 1002 | 158 | 158 |
| MDHM_HUMAN | VSSFEEK | 1004 | 158 | 0 |
| MMP12_HUMAN | FLLILLLQATASGALPLNSSTSLEK | 1021 | 158 | 158 |
| MMP12_HUMAN | GIQSLYGDPK | 1022 | 158 | 0 |
| MMP12_HUMAN | IDAVFYSK | 1023 | 158 | 0 |
| MMP2_HUMAN | AFQVWSDVTPLR | 1031 | 153 | 152 |

TABLE 3-continued

| Protein | Peptide | SEQ ID NO: | Protein Detection | Peptide Detection |
|---|---|---|---|---|
| MMP2_HUMAN | IIGYTPDLDPETVDDAFAR | 1033 | 153 | 1 |
| MMP7_HUMAN | LSQDDIK | 1042 | 102 | 102 |
| MMP7_HUMAN | NANSLEAK | 1043 | 102 | 0 |
| MMP9_HUMAN | AFALWSAVTPLTFTR | 1044 | 158 | 50 |
| MMP9_HUMAN | FQTFEGDLK | 1046 | 158 | 108 |
| MMP9_HUMAN | SLGPALLLLQK | 1048 | 158 | 0 |
| MPRI_HUMAN | GHQAFDVGQPR | 1055 | 158 | 23 |
| MPRI_HUMAN | TYHSVGDSVLR | 1056 | 158 | 4 |
| MPRI_HUMAN | VPIDGPPIDIGR | 1057 | 158 | 131 |
| NCF4_HUMAN | AEALFDFTGNSK | 1095 | 138 | 43 |
| NCF4_HUMAN | DAEGDLVR | 1096 | 138 | 0 |
| NCF4_HUMAN | DIAVEEDLSSTPLLK | 1097 | 138 | 0 |
| NCF4_HUMAN | GATGIFPLSFVK | 1098 | 138 | 95 |
| NDKB_HUMAN | DRPFFPGLVK | 1105 | 24 | 0 |
| NDKB_HUMAN | NIIHGSDSVK | 1107 | 24 | 24 |
| NRP1_HUMAN | FVSDYETHGAGFSIR | 1149 | 158 | 0 |
| NRP1_HUMAN | FVTAVGTQGAISK | 1150 | 158 | 158 |
| NRP1_HUMAN | SFEGNNNYDTPELR | 1152 | 158 | 0 |
| OSTP_HUMAN | AIPVAQDLNAPSDWDSR | 1156 | 108 | 108 |
| OSTP_HUMAN | DSYETSQLDDQSAETHSHK | 1157 | 108 | 0 |
| OSTP_HUMAN | YPDAVATWLNPDPSQK | 1160 | 108 | 0 |
| PCBP2_HUMAN | IANPVEGSTDR | 1189 | 52 | 0 |
| PCBP2_HUMAN | IITLAGPTNAIFK | 1190 | 52 | 52 |
| PCYOX_HUMAN | IAIIGAGIGGTSAAYYLR | 1207 | 37 | 0 |
| PCYOX_HUMAN | IFSQETLTK | 1208 | 37 | 37 |
| PCYOX_HUMAN | TLLETLQK | 1209 | 37 | 0 |
| PDGFB_HUMAN | SFDDLQR | 1216 | 111 | 99 |
| PDGFB_HUMAN | SHSGGELESLAR | 1217 | 111 | 12 |
| PDIA3_HUMAN | ELSDFISYLQR | 1225 | 129 | 129 |
| PDIA3_HUMAN | SEPIPESNDGPVK | 1227 | 129 | 0 |
| PDIA4_HUMAN | FDVSGYPTIK | 1231 | 81 | 81 |
| PDIA4_HUMAN | FHHTFSTEIAK | 1232 | 81 | 0 |
| PECA1_HUMAN | SELVTVTESFSTPK | 1241 | 77 | 0 |
| PECA1_HUMAN | STESYFIPEVR | 1242 | 77 | 77 |
| PEDF_HUMAN | LQSLFDSPDFSK | 1246 | 158 | 0 |
| PEDF_HUMAN | TVQAVLTVPK | 1248 | 158 | 158 |
| PGAM1_HUMAN | HGESAWNLENR | 1259 | 14 | 14 |
| PLIN2_HUMAN | DAVTTTVTGAK | 1264 | 138 | 0 |
| PLIN2_HUMAN | EVSDSLLTSSK | 1265 | 138 | 138 |
| PLSL_HUMAN | IGNFSTDIK | 1284 | 158 | 0 |
| PLSL_HUMAN | ISFDEFIK | 1285 | 158 | 158 |
| PLXB3_HUMAN | ELPVPIYVTQGEAQR | 1294 | 77 | 0 |
| PLXB3_HUMAN | GPVDAVTGK | 1296 | 77 | 77 |
| PLXC1_HUMAN | FWVNILK | 1299 | 158 | 0 |
| PLXC1_HUMAN | LNTIGHYEISNGSTIK | 1300 | 158 | 158 |
| POSTN_HUMAN | GFEPGVTNILK | 1302 | 158 | 158 |
| POSTN_HUMAN | IIDGVPVEITEK | 1303 | 158 | 0 |
| POSTN_HUMAN | IIHGNQIATNGVVHVIDR | 1304 | 158 | 0 |
| PPIB_HUMAN | VIFGLFGK | 1319 | 158 | 0 |
| PPIB_HUMAN | VYFDLR | 1320 | 158 | 158 |
| PRDX1_HUMAN | IGHPAPNFK | 1325 | 158 | 116 |
| PRDX1_HUMAN | QITVNDLPVGR | 1328 | 158 | 42 |
| PROF1_HUMAN | STGGAPTFNVTVTK | 1338 | 158 | 157 |
| PROF1_HUMAN | TFVNITPAEVGVLVGK | 1339 | 158 | 1 |
| PRS6A_HUMAN | VDILDPALLR | 1349 | 13 | 13 |
| PTGIS_HUMAN | DPEIYTDPEVFK | 1352 | 158 | 0 |
| PTGIS_HUMAN | LLLFPFLSPQR | 1357 | 158 | 158 |
| PTPA_HUMAN | FGSLLPIHPVTSG | 1361 | 103 | 103 |
| PTPA_HUMAN | TGPFAEHSNQLWNISAVPSWSK | 1363 | 103 | 0 |
| PTPA_HUMAN | VDDQIAIVFK | 1364 | 103 | 0 |
| PTPA_HUMAN | WIDETPPVDQPSR | 1365 | 103 | 0 |
| PTPRJ_HUMAN | AVSISPTNVILTWK | 1372 | 158 | 0 |
| PTPRJ_HUMAN | VITEPIPVSDLR | 1374 | 158 | 158 |
| PVR_HUMAN | SVDIWLR | 1379 | 158 | 158 |
| PVR_HUMAN | VLAKPQNTAEVQK | 1380 | 158 | 0 |
| RAB32_HUMAN | VHLPNGSPIPAVLLANK | 1384 | 22 | 0 |
| RAB32_HUMAN | VLVIGELGVGK | 1385 | 22 | 22 |
| RAN_HUMAN | FNVWDTAGQEK | 1391 | 116 | 2 |
| RAN_HUMAN | LVLVGDGGTGK | 1392 | 116 | 114 |
| RAN_HUMAN | NVPNWHR | 1393 | 116 | 0 |
| RAP2B_HUMAN | EVSYGEGK | 1395 | 145 | 0 |
| RAP2B_HUMAN | VDLEGER | 1397 | 145 | 145 |
| S10A1_HUMAN | DVDAVDK | 1408 | 128 | 128 |
| S10A1_HUMAN | ELLQTELSGFLDAQK | 1409 | 128 | 0 |
| S10A6_HUMAN | ELTIGSK | 1411 | 154 | 154 |
| S10A6_HUMAN | LQDAEIAR | 1412 | 154 | 0 |
| SAA_HUMAN | EANYIGSDK | 1414 | 143 | 0 |

TABLE 3-continued

| Protein | Peptide | SEQ ID NO: | Protein Detection | Peptide Detection |
|---|---|---|---|---|
| SAA_HUMAN | SFFSFLGEAFDGAR | 1416 | 143 | 143 |
| SCF_HUMAN | LFTPEEFFR | 1418 | 143 | 143 |
| SCF_HUMAN | LVANLPK | 1419 | 143 | 0 |
| SEM3G_HUMAN | DYPDEVLQ FAR | 1426 | 155 | 0 |
| SEM3G_HUMAN | LFLGGLDALYSLR | 1428 | 155 | 155 |
| SIAL_HUMAN | AYEDEYSYFK | 1449 | 19 | 19 |
| SIAL_HUMAN | TTSPPFGK | 1452 | 19 | 0 |
| SODM_HUMAN | GDVTAQIALQPALK | 1460 | 154 | 151 |
| SODM_HUMAN | NVRPDYLK | 1462 | 154 | 3 |
| SPON2_HUMAN | WSQTAFPK | 1478 | 63 | 0 |
| SPON2_HUMAN | YSITFTGK | 1479 | 63 | 63 |
| STAT1_HUMAN | TELISVSEVHPSR | 1494 | 38 | 29 |
| STAT1_HUMAN | YTYEHDPITK | 1496 | 38 | 9 |
| TBA1B_HUMAN | AVFVDLEPTVIDEVR | 1519 | 119 | 119 |
| TBA1B_HUMAN | EIIDLVLDR | 1520 | 119 | 0 |
| TBB3_HUMAN | ISVYYNEASSHK | 1533 | 158 | 158 |
| TBB3_HUMAN | YLTVATVFR | 1535 | 158 | 0 |
| TCPA_HUMAN | IHPTSVISGYR | 1540 | 158 | 4 |
| TCPA_HUMAN | SSLGPVGLDK | 1542 | 158 | 154 |
| TCPQ_HUMAN | DIDEVSSLLR | 1550 | 48 | 0 |
| TCPQ_HUMAN | NVGLDIEAEVPAVK | 1553 | 48 | 48 |
| TCPZ_HUMAN | GIDPFSLDALSK | 1557 | 6 | 6 |
| TCPZ_HUMAN | GLVLDHGAR | 1558 | 6 | 0 |
| TENA_HUMAN | GLEPGQEYNVLLTAEK | 1570 | 140 | 140 |
| TENA_HUMAN | TVSGNTVEYALTDLEPATEYTLR | 1572 | 140 | 0 |
| TENX_HUMAN | DAQGQPQAVPVSGDLR | 1574 | 158 | 158 |
| TENX_HUMAN | YEVTVVSVR | 1578 | 158 | 0 |
| TERA_HUMAN | GILLYGPPGTGK | 1579 | 106 | 94 |
| TERA_HUMAN | LDQLIYIPLPDEK | 1582 | 106 | 12 |
| TETN_HUMAN | GGTLSTPQTGSENDALYEYLR | 1588 | 158 | 118 |
| TETN_HUMAN | LDTLAQEVALLK | 1589 | 158 | 40 |
| TFR1_HUMAN | LTVSNVLK | 1598 | 157 | 0 |
| TFR1_HUMAN | SSGLPNIPVQTISR | 1600 | 157 | 157 |
| TIMP1_HUMAN | GFQALGDAADIR | 1610 | 151 | 151 |
| TIMP1_HUMAN | SEEFLIAGK | 1611 | 151 | 0 |
| TNF12_HUMAN | AAPFLTYFGLFQVH | 1621 | 156 | 156 |
| TNF12_HUMAN | INSSSPLR | 1622 | 156 | 0 |
| TPIS_HUMAN | VVFEQTK | 1634 | 157 | 157 |
| TPIS_HUMAN | VVLAYEPVWAIGTGK | 1635 | 157 | 0 |
| TRFL_HUMAN | FQLFGSPSGQK | 1637 | 48 | 22 |
| TRFL_HUMAN | LRPVAAEVYGTER | 1638 | 48 | 4 |
| TRFL_HUMAN | VPSHAVVAR | 1639 | 48 | 5 |
| TRFL_HUMAN | YYGYTGAFR | 1640 | 48 | 17 |
| TSP1_HUMAN | GFLLLASLR | 1644 | 158 | 6 |
| TSP1_HUMAN | GTSQNDPNWVVR | 1645 | 158 | 152 |
| TTHY_HUMAN | TSESGELHGLTTEEEFVEGIYK | 1646 | 27 | 27 |
| TTHY_HUMAN | VEIDTK | 1647 | 27 | 0 |
| TYPH_HUMAN | ALQEALVLSDR | 1648 | 59 | 0 |
| TYPH_HUMAN | TLVGVGASLGLR | 1651 | 59 | 59 |
| UGGG1_HUMAN | DLSQNFPTK | 1653 | 58 | 58 |
| UGGG1_HUMAN | FTILDSQGK | 1654 | 58 | 0 |
| UGPA_HUMAN | LVEIAQVPK | 1669 | 97 | 97 |
| UGPA_HUMAN | NENTFLDLTVQQIEHLNK | 1670 | 97 | 0 |
| VA0D1_HUMAN | LLFEGAGSNPGDK | 1679 | 13 | 13 |
| VA0D1_HUMAN | NVADYYPEYK | 1681 | 13 | 0 |
| VEGFC_HUMAN | DLEEQLR | 1689 | 21 | 21 |
| VEGFC_HUMAN | EAPAAAAAFESGLDLSDAEPDAGEATAYASK | 1690 | 21 | 0 |
| VEGFC_HUMAN | FAAAHYNTEILK | 1692 | 21 | 0 |
| VEGFC_HUMAN | NQPLNPGK | 1693 | 21 | 0 |
| VTNC_HUMAN | AVRPGYPK | 1705 | 145 | 0 |
| VTNC_HUMAN | DVWGIEGPIDAAFTR | 1707 | 145 | 145 |
| ZA2G_HUMAN | EIPAWVPFDPAAQITK | 1724 | 158 | 158 |
| ZA2G_HUMAN | WEAEPVYVQR | 1725 | 158 | 0 |

Exemplary Biomarker Protein

60

The following 36 proteins were identified as biomarker candidates in a large-scale experiment of 72 lung cancer samples and 71 benign lung nodule samples using the MS-LC-SRM-MS system described herein.

TABLE 4

| Category | Protein (UniProt) | Official Gene Name | Cooperative Score | Partial AUC | Coefficient CV | Transition | SEQ ID NO: | Coefficient (Discovery) alpha = 36.16 | Coefficient (Final) alpha = 26.25 | Tissue Candidate | Predicted Concentration (ng/ml) |
|---|---|---|---|---|---|---|---|---|---|---|---|
| Classifier | TSP1_HUMAN | THBS1 | 1.8 | 0.25 | 0.24 | GFLLLASLR_495.31_559.40 | 1644 | 0.53 | 0.44 | | 510 |
| Classifier | COIA1_HUMAN | COL18A1 | 3.7 | 0.16 | 0.25 | AVGLAGTFR_446.26_721.40 | 332 | −1.56 | −0.91 | | 35 |
| Classifier | ISLR_HUMAN | ISLR | 1.4 | 0.32 | 0.25 | ALPGTPVASSQPR_640.85_841.50 | 839 | 1.40 | 0.83 | | — |
| Classifier | TETN_HUMAN | CLEC3B | 2.5 | 0.26 | 0.26 | LDTLAQEVALLK_657.39_330.20 | 1589 | −1.79 | −1.02 | | 58000 |
| Classifier | FRIL_HUMAN | FTL | 2.8 | 0.31 | 0.26 | LGGPEAGLGEYLFER_804.40_913.40 | 596 | 0.39 | 0.17 | Secreted, Epi, Endo | 12 |
| Classifier | GRP78_HUMAN | HSPA5 | 1.4 | 0.27 | 0.27 | TWNDPSVQQDIK_715.85_260.20 | 664 | 1.41 | 0.55 | Secreted, Epi, Endo | 100 |
| Classifier | ALDOA_HUMAN | ALDOA | 1.3 | 0.26 | 0.28 | ALQASALK_401.25_617.40 | 58 | −0.80 | −0.26 | Secreted, Epi | 250 |
| Classifier | BGH3_HUMAN | TGFBI | 1.8 | 0.21 | 0.28 | LTLLAPLNSVFK_658.40_804.50 | 139 | 1.73 | 0.54 | Epi | 140 |
| Classifier | LG3BP_HUMAN | LGALS3BP | 4.3 | 0.29 | 0.29 | VEIFYR_413.73_598.30 | 941 | −0.58 | −0.21 | Secreted | 440 |
| Classifier | LRP1_HUMAN | LRP1 | 4.0 | 0.13 | 0.32 | TVLWPNGLSLDIPAGR_855.00_400.20 | 959 | −1.59 | −0.83 | Epi | 20 |
| Classifier | FIBA_HUMAN | FGA | 1.1 | 0.31 | 0.35 | NSLFEYQK_514.76_714.30 | 556 | 0.31 | 0.13 | Epi, Endo | 130000 |
| Classifier | PRDX1_HUMAN | PRDX1 | 1.5 | 0.32 | 0.37 | QITVNDLPVGR_606.30_428.30 | 1328 | −0.34 | −0.26 | Epi, Endo | 60 |
| Classifier | GSLG1_HUMAN | GLG1 | 1.2 | 0.34 | 0.45 | IIIQESALDYR_660.86_338.20 | 666 | −0.70 | −0.44 | | — |
| Robust | KIT_HUMAN | KIT | 1.4 | 0.33 | 0.46 | | | | | Epi | 8.2 |
| Robust | CD14_HUMAN | CD14 | 4.0 | 0.33 | 0.48 | | | | | Secreted, Epi | 420 |
| Robust | EF1A1_HUMAN | EEF1A1 | 1.2 | 0.32 | 0.56 | | | | | Epi | 61 |
| Robust | TENX_HUMAN | TNXB | 1.1 | 0.30 | 0.56 | | | | | Endo | 70 |
| Robust | AIFM1_HUMAN | AIFM1 | 1.4 | 0.32 | 0.70 | | | | | Epi, Endo | 1.4 |
| Robust | GGH_HUMAN | GGH | 1.3 | 0.32 | 0.81 | | | | | Secreted, Epi, Endo | 250 |
| Robust | IBP3_HUMAN | IGFBP3 | 3.4 | 0.32 | 1.82 | | | | | | 5700 |
| Robust | ENPL_HUMAN | HSP90B1 | 1.1 | 0.29 | 5.90 | | | | | | 88 |
| Non-Robust | ERO1A_HUMAN | ERO1L | 6.2 | | | | | | | Secreted, Epi, Endo | — |
| Non-Robust | 6PGD_HUMAN | PGD | 4.3 | | | | | | | Epi, Endo | 29 |
| Non-Robust | ICAM1_HUMAN | ICAM1 | 3.9 | | | | | | | Endo | 71 |
| Non-Robust | PTPA_HUMAN | PPP2R4 | 2.1 | | | | | | | Endo | 3.3 |
| Non-Robust | NCF4_HUMAN | NCF4 | 2.0 | | | | | | | | — |
| Non-Robust | SEM3G_HUMAN | SEMA3G | 1.9 | | | | | | | | — |
| Non-Robust | 1433T_HUMAN | YWHAQ | 1.5 | | | | | | | Epi | 180 |
| Non-Robust | RAP2B_HUMAN | RAP2B | 1.5 | | | | | | | Epi | — |
| Non-Robust | MMP9_HUMAN | MMP9 | 1.4 | | | | | | | | 28 |
| Non-Robust | FOLH1_HUMAN | FOLH1 | 1.3 | | | | | | | | — |
| Non-Robust | GSTP1_HUMAN | GSTP1 | 1.3 | | | | | | | Endo | 32 |

TABLE 4-continued

| Category | Protein (UniProt) | Official Gene Name | Cooperative Score | Partial AUC | Coefficient CV | Transition | SEQ ID NO: | Coefficient (Discovery) alpha = 36.16 | Coefficient (Final) alpha = 26.25 | Tissue Candidate | Predicted Concentration (ng/ml) |
|---|---|---|---|---|---|---|---|---|---|---|---|
| Non-Robust | EF2_HUMAN | EEF2 | 1.3 | | | | | | | Secreted, Epi | 30 |
| Non-Robust | RAN_HUMAN | RAN | 1.2 | | | | | | | Secreted, Epi | 4.6 |
| Non-Robust | SODM_HUMAN | SOD2 | 1.2 | | | | | | | Secreted | 7.1 |
| Non-Robust | DSG2_HUMAN | DSG2 | 1.1 | | | | | | | Endo | 2.7 |

LENGTHY TABLES

The patent contains a lengthy table section. A copy of the table is available in electronic form from the USPTO web site (http://seqdata.uspto.gov/?pageRequest=docDetail&DocID=US09091651B2). An electronic copy of the table will also be available from the USPTO upon request and payment of the fee set forth in 37 CFR 1.19(b)(3).

The invention claimed is:

1. A composition comprising at least 5 transition ion pairs said composition comprising at least one transition ion pair of at least 5 proteins selected from LRP1, BGH3, COIA1, TETN, TSP1, ALDOA, GRP78, ISLR, FRIL, LG3BP, PRDX1, FIBA, or GSLG1, wherein the at least one transition ion pair consists of a precursor ion with a corresponding m/z and a fragment ion with a corresponding m/z, and wherein the transition ion pairs are selected from precursor ADDGRPFPQVIK (SEQ ID NO: 57) transition pair 671.86-260.2, 671.86-584.4, or 671.86-528.5; precursor ALQASALK (SEQ ID NO: 58) transition pair 401.25-260.2, 401.25-331.2, 401.25-489.3, or 401.25-617.4; precursor QLLLTADDR (SEQ ID NO: 60) transition pair 522.79-355.2, 522.79-577.3, 522.79-690.3, or 522.79-803.4; precursor ADHHATNGVVHLIDK (SEQ ID NO: 136) transition pair 542.95-262.1, 542.95-488.3, 542.95-625.4, or 542.95-724.4; precursor DILATNGVIHYIDELLIPDSAK (SEQ ID NO: 137) transition pair 804.1-305.2, 804.1-514.3, 804.1-517.3, or 804.1-630.3; precursor LTLLAPLNSVFK (SEQ ID NO: 139) transition pair 658.4-328.2, 658.4-804.5, 658.4-875.5, or 658.4-988.6; precursor SPYQLVLQHSR (SEQ ID NO: 140) transition pair 443.24-527.3, 443.24-589.3, 443.24-640.4, or 443.24-852.5; precursor ADDILASPPR (SEQ ID NO: 331) transition pair 527.78-302.1, 527.78-369.2, 527.78-369.2, 527.78-456.3, or 527.78-640.4; precursor AVGLAGTFR (SEQ ID NO: 332) transition pair 446.26-480.3, 446.26-551.3, 446.26-664.4, or 446.26-721.4; precursor TEAPSATGQASSLLGGR (SEQ ID NO: 335) transition pair 801.91-289.2, 801.91-302.1, 801.91-760.4, or 801.91-945.5; precursor GGSTSYGTGSETESPR (SEQ ID NO 554) transition pair 786.84-359.2, 786.84-589.3, 786.84-862.4, or 786.84-963.4; precursor NSLFEYQK (SEQ ID NO: 556) transition pair 514.76-315.2, 514.76-567.3, 514.76-714.3, or 514.76-827.4, precursor TVIGPDGHK (SEQ ID NO: 557) transition pair 308.5-341.2, 308.5-456.2, 308.5-553.3, or 308.5-610.3; precursor VQHIQLLQK (SEQ ID NO: 558) transition pair 369.56-501.3, 369.56-606.3, 369.56-629.4, or 369.56-742.5; precursor ALFQDIK (SEQ ID NO: 593) transition pair 417.74-260.2, 417.74-503.3, 417.74-650.4, or 417.74-763.4; precursor DDVALEGVSHFFR (SEQ ID NO: 594) transition pair 497.91-469.3, 497.91-693.3, 497.91-849.4, or 497.91-978.5; precursor KPAEDEWGK (SEQ ID NO: 595) transition pair 353.84-297.2, 353.84-390.2, 353.84-541.3, or 353.84-634.3; precursor LGGPEAGLGEYLFER (SEQ ID NO: 596) transition pair 804.41-451.2, 804.41-525.3, 804.41-564.3, or 804.41-913.4; precursor LNQALLDLHALGSAR (SEQ ID NO: 597) transition pair 531.3-356.2, 531.3-427.2, 531.3-574.3, or 531.3-711.4; precursor MGDHLTNLHR (SEQ ID NO: 598) transition pair 398.53-312.2, 398.53-539.3, 398.53-640.53, or 398.53-753.4; precursor LYGSAGPPPTGEEDTAEK (SEQ ID NO: 663) transition pair 909.92-334.2, 909.92-492.2, 909.92-549.3, or 909.92-878.4; precursor TWNDPSVQQDIK (SEQ ID NO: 664) transition pair 715.85-260.2, 715.85-288.1, 715.85-517.2, or 715.85-914.5; precursor VYEGERPLTK (SEQ ID NO: 665) transition pair 397.88-458.3, 397.88-614.4, 397.88-800.5, or 397.88-929.5; precursor IIIQESALDYR (SEQ ID NO: 666) transition pair 660.86-338.2, 660.86-724.4, 660.86-853.4, or 660.86-981.5; precursor LDPALQDK (SEQ ID NO: 667) transition pair 450.25-503.3, 450.25-574.3, 450.25-671.4, or 450.25-786.4; precursor LIAQDYK (SEQ ID NO: 668) transition pair 425.74-310.2, 425.74-553.3, 425.74-624.3, or 425.74-737.4; precursor NDINILK (SEQ ID NO: 669) transition pair 415.24-260.2, 415.24-487.3, 415.24-600.4, or 415.24-715.4; precursor VAELSSDDFHLDR (SEQ ID NO: 670) transition pair 501.91-403.2, 501.91-540.3, 501.91-687.4, 501.91-702.3; precursor ALPGTPVASSQPR (SEQ ID NO: 839) transition pair 640.85-440.3, 640.85-440.3, 640.85-574.3, 640.85-841.5, or 640.85-999.5; precursor EVPLLQSLWLAHNEIR (SEQ ID NO: 840) transition pair 640.02-531.3, 640.02-668.3, 640.02-739.4, or 640.02-852.5; precursor LPGLPEGAFR (SEQ ID NO: 841) transition pair 528.8-268.2, 528.8-381.3, 528.8-676.3, or 528.8-846.4; precursor TVAAGALASLSHLK (SEQ ID NO: 843) transition pair 446.93-343.2, 446.93-684.4, 446.93-755.4, or 446.93-868.5; precursor ASHEEVEGLVEK (SEQ ID NO: 938) transition pair 442.89-545.3, 442.89-554.2, 442.89-653.3, or 442.89-674.4; precursor STHTLDLSR (SEQ ID NO: 940) transition pair 343.85-262.2, 343.85-375.2, 343.85-490.3, or 343.85-655.3; precursor VEIFYR (SEQ ID NO: 941) transition pair 413.73-338.2, 413.73-485.3, 413.73-598.3, or 413.73-727.4; precursor YSSDYFQAPSDYR (SEQ ID NO: 942) transition pair 799.84-637.3, 799.84-708.3, 799.84-836.4, or 799.84-983.5; precursor AALSGANVLTLIEK (SEQ ID NO: 958) transition pair 700.4-1057.6, 700.4-1144.7, 700.4-716.5, or 700.4-929.6; precursor TVLWPNGLSLDIPAGR (SEQ ID NO: 959) transition pair 854.972-1209.7, 854.972-400.231, 854.972-500.3, 854.972-500.3, or 854.972-605.333; precursor VFFTDYGQIPK (SEQ ID NO: 960) transition pair 657.84-1068.54, 657.84-244.2, 657.84-820.4, or 657.84-921.468; precursor ADEGISFR (SEQ ID NO: 1321) transition pair 447.72-409.2, 447.72-552.3, 447.72-579.3, or 447.72-708.4; precursor ATAVMPDGQFK (SEQ ID NO: 1322) transition pair 582.79-691.3, 582.79-822.4, 582.79-

921.5, or 582.79-992.5; precursor DISLSDYK (SEQ ID NO: 1323) transition pair 470.74-310.2, 470.74-512.2, 470.74-625.3, or 470.74-712.4; precursor GLFIIDDK (SEQ ID NO: 1324) transition pair 460.76-377.2, 460.76-490.3, 460.76-603.3, or 460.76-750.76; precursor IGHPAPNFK (SEQ ID NO: 1325) transition pair 327.52-294.2, 327.52-505.3, 327.52-576.3, or 327.52-673.4; precursor LVQAFQFTDK (SEQ ID NO: 1326) transition pair 598.82-341.2, 598.82-785.4, 598.82-856.4, or 598.82-984.5; precursor QGGLGPMNIPLVSDPK (SEQ ID NO: 1327) transition pair 811.93-356.2, 811.93-446.2, 811.93-545.3, or 811.93-658.4; precursor QITVNDLPVGR (SEQ ID NO: 1328) transition pair 606.34-428.3, 606.34-770.4, 606.34-869.5, or 606.34-970.5; precursor SVDETLR (SEQ ID NO: 1329) transition pair 410.21-288.2, 410.21-389.3, 410.21-518.3, or 410.21-633.3; precursor TIAQDYGVLK (SEQ ID NO: 1330) transition pair 554.31-579.4, 554.31-694.4, 554.31-822.4, or 554.31-893.5; precursor GGTLSTPQTGSENDALYEYLR (SEQ ID NO: 1588) transition pair 758.03-451.3, 758.03-580.3, 758.03-856.5, or 758.03-927.5; precursor LDTLAQEVALLK (SEQ ID NO: 1589) transition pair 657.39-330.2, 657.39-543.4, 657.39-800.5, or 657.39-871.5; precursor NWETEITAQPDGGK (SEQ ID NO: 1590) transition pair 773.36-301.1, 773.36-430.2, 773.36-473.2, or 773.36-886.5; precursor FQDLVDAVR (SEQ ID NO: 1641) transition pair 531.78-391.2, 531.78-559.3, 531.78-672.4, or 531.78-787.4; precursor FTGSQPFGQVEHATANK (SEQ ID NO: 1642) transition pair 625.97-261.2, 625.97-504.3, 625.97-521.2, or 625.97-926.5; precursor FVFGTIPEDILR (SEQ ID NO: 1643) transition pair 465.58-288.2, 465.58-516.3, 465.58-645.4, or 465.58-742.4; precursor GFLLLASLR (SEQ ID NO: 1644) transition pair 495.31-318.2, 495.31-375.2, 495.31-446.3, or 495.31-559.4; or precursor GTSQNDPNWVVR (SEQ ID NO: 1645) transition pair 686.83-373.3, 686.83-770.4, 686.83-885.5, or 686.83-999.5, wherein each of the precursor ions has a double or triple charge.

2. The composition of claim 1, further comprising an additional five transition ion pairs comprising one transition ion pair of at least one protein selected from LRP1, BGH3, COIA1, TETN, TSP1, ALDOA, GRP78, ISLR, FRIL, LG3BP, PRDX1, FIBA, or GSLG1.

3. A composition comprising at least 10 isolated synthetic peptides said composition comprising at least 2 isolated synthetic peptides of at least 5 proteins selected from LRP1, BGH3, COIA1, TETN, TSP1, ALDOA, GRP78, ISLR, FRIL, LG3BP, PRDX1, FIBA, or GSLG1, wherein the at least two isolated synthetic peptides are selected from ADDGRPFPQVIK (SEQ ID NO: 57), ALQASALK (SEQ ID NO: 58), QLLLTADDR (SEQ ID NO: 60), ADHHATNGV-VHLIDK (SEQ ID NO: 136), DILATNGVIHYIDELLIPDSAK (SEQ ID NO: 137), LTLLAPLNSVFK (SEQ ID NO: 139), SPYQLVLQHSR (SEQ ID NO: 140), ADDILASPPR (SEQ ID NO: 331), AVGLAGTFR (SEQ ID NO: 332), TEAPSATGQASSLLGGR (SEQ ID NO: 335), GGSTSYGTG-SETESPR (SEQ ID NO 554), NSLFEYQK (SEQ ID NO: 556), TVIGPDGHK (SEQ ID NO: 557), VQHIQLLQK (SEQ ID NO: 558), ALFQDIK (SEQ ID NO: 593), DDVA-LEGVSHFFR (SEQ ID NO: 594), KPAEDEWGK (SEQ ID NO: 595), LGGPEAGLGEYLFER (SEQ ID NO: 596), LNQALLDLHALGSAR (SEQ ID NO: 597), MGDHLT-NLHR (SEQ ID NO: 598), LYGSAGPPPTGEEDTAEK (SEQ ID NO: 663), TWNDPSVQQDIK (SEQ ID NO: 664), VYEGERPLTK (SEQ ID NO: 665), IIIQESALDYR (SEQ ID NO: 666), LDPALQDK (SEQ ID NO: 667), LIAQDYK (SEQ ID NO: 668), NDINILK (SEQ ID NO: 669), VAELSS-DDFHLDR (SEQ ID NO: 670), ALPGTPVASSQPR (SEQ ID NO: 839), EVPLLQSLWLAHNEIR (SEQ ID NO: 840), LPGLPEGAFR (SEQ ID NO: 841), TVAAGALASLSHLK (SEQ ID NO: 843), ASHEEVEGLVEK (SEQ ID NO: 938), STHTLDLSR (SEQ ID NO: 940), VEIFYR (SEQ ID NO: 941), YSSDYFQAPSDYR (SEQ ID NO: 942), AALSGAN-VLTLIEK (SEQ ID NO: 958), TVLWPNGLSLDIPAGR (SEQ ID NO: 959), VFFTDYGQIPK (SEQ ID NO: 960), ADEGISFR (SEQ ID NO: 1321), ATAVMPDGQFK (SEQ ID NO: 1322), DISLSDYK (SEQ ID NO: 1323), GLFIIDDK (SEQ ID NO: 1324), IGHPAPNFK (SEQ ID NO: 1325), LVQAFQFTDK (SEQ ID NO: 1326), QGGLGPMNIPLVS-DPK (SEQ ID NO: 1327), QITVNDLPVGR (SEQ ID NO: (1328), SVDETLR (SEQ ID NO: 1329), TIAQDYGVLK (SEQ ID NO: 1330), GGTLSTPQTGSENDALYEYLR (SEQ ID NO: 1588), LDTLAQEVALLK (SEQ ID NO: 1589), NWETEITAQPDGGK (SEQ ID NO: 1590), FQDLV-DAVR (SEQ ID NO: 1641), FTGSQPFGQVEHATANK (SEQ ID NO: 1642), FVFGTIPEDILR (SEQ ID NO: 1643), GFLLLASLR (SEQ ID NO: 1644), or GTSQNDPNWVVR (SEQ ID NO: 1645).

4. The composition of claim 3, wherein at least one of the isolated synthetic peptides is isotopically labeled.

5. The composition of claim 3, wherein the amount of each of the at least 2 isolated synthetic peptides of at least 5 proteins is known.

6. The composition of claim 3, further comprising one or more polar solvents.

7. The composition of claim 3, further comprising an additional five isolated synthetic peptides of at least one protein selected from LRP1, BGH3, COIA1, TETN, TSP1, ALDOA, GRP78, ISLR, FRIL, LG3BP, PRDX1, FIBA, or GSLG1.

8. The composition of claim 1, further comprising an additional five transition ion pairs comprising one transition ion pair of at least one protein selected from APOE, BASP1, CD14, FOXA2 or HSPB1, wherein the additional one transition ion pair consists of a precursor ion with a corresponding m/z and a fragment ion with a corresponding m/z, and wherein the transition ion pairs are selected from precursor AATVGSLAGQPLQER (SEQ ID NO: 82) transition pair 479.4-600.3, 479.4-642.4, 479.4-827.4, or 479.4-898.5; precursor ALMDETMK (SEQ ID NO: 83) transition pair 469.72-508.2, 469.72-469.72, 469.72-508.2, 469.72-623.3, 469.72-754.3, or 469.72-867.4; precursor GEVQAM-LGQSTEELR (SEQ ID NO: 85) transition pair 824.4-616.3, 824.4-729.4, 824.4-734.4, or 824.4-919.4; precursor LAVYQAGAR (SEQ ID NO: 86) transition pair 474.77-502.3, 474.77-665.3, 474.77-764.4, or 474.77-835.4; precursor LGPLVEQGR (SEQ ID NO: 87) transition pair 484.78-588.3, 484.78-701.4, 484.78-798.4, or 484.78-855.5; precursor SELEEQLTPVAEETR (SEQ ID NO: 88) transition pair 865.93-459.2, 865.93-801.4, 865.93-902.5, or 865.93-930.4; precursor SWFEPLVEDMQR (SEQ ID NO: 89) transition pair 768.86-274.1, 768.86-421.2, 768.86-678.3, or 768.86-987.5; precursor WELALGR (SEQ ID NO: 90) transition pair 422.74-316.1, 422.74-345.2, 422.74-529.3, or 422.74-658.4; precursor AAEAAAAPAESAAPAAG-EEPSK (SEQ ID NO: 118) transition pair 983.97-414.2, 983.97-485.2, 983.97-556.3, or 983.97-885.4; precursor AEGAATEEEGTPK (SEQ ID NO: 119) transition pair 645.3-258.1, 645.3-789.4, 645.3-890.4, or 645.3-961.4; precursor APEQEQAAPGPAAGGEAPK (SEQ ID NO: 120) transition pair 592.62-629.3, 592.62-754.3, 592.62-825.4, or 592.62-951.5; precursor EKPDQDAEGK (SEQ ID NO: 122) transition pair 558.76-404.2, 558.76-647.3, 558.76-859.4, or 558.76-913.4; precursor ESEPQAAAEPAEAK (SEQ ID NO: 123) transition pair 714.34-515.3, 714.34-644.3, 714.34-786.4, or 714.34-857.4; precursor ETPAATEA- PSSTPK (SEQ ID NO: 124) transition pair 693.84-616.3, 693.84-816.4, 693.84-917.5, or 693.84-988.5; precursor GYNVNDEK (SEQ ID NO: 125) transition pair 469.71-276.2, 469.71-505.2, 469.71-604.3, or 469.71-718.3; precursor SDGAPASDSKPGSSEAAPSSK (SEQ ID NO: 126) transition pair 644.96-260.1, 644.96-331.1, 644.96-418.2, or 644.96-586.2; precursor TEAPAAPAAQETK (SEQ ID NO: 127) transition pair 642.83-541.3, 642.83-744.4, 642.83-815.4, or 642.83-983.5; precursor AFPALTSLDLSDN-PGLGER (SEQ ID NO: 206) transition pair 987-500.3, 987-628.3, 987-742.4, or 987-944.4; precursor ATVNPSAPR (SEQ ID NO: 207) transition pair 456.75-386.2, 456.75-430.2, 456.75-527.3, or 456.75-740.4; precursor ELTLEDLK (SEQ ID NO: 208) transition pair 480.77-260.2, 480.77-504.3, 480.77 617.4, or 480.77-718.4; precursor FPAIQNLALR (SEQ ID NO: 209) transition pair 571.84-714.4, 571.84-827.5, 571.84-898.5, or 571.84-995.6; precursor LTVGAAQVPAQLLVGALR (SEQ ID NO: 211) transition pair 593.03-416.3, 593.03-515.3, 593.03-628.4, or 593.03-740.4; precursor NVSWATGR (SEQ ID NO: 212) transition pair 445.73-301.2, 445.73-404.2, 5, 445.73-590.3, or 445.73-677.3; precursor STLSVGVSGTLVLLQGAR (SEQ ID NO: 213) transition pair 879.51-431.2, 879.51-544.3, 879.51-657.4, or 879.51-970.6; precursor SWLAELQQWLKPGLK (SEQ ID NO: 214) transition pair 599.67-274.1, 599.67-414.3, 599.67-542.4, or 599.67-841.5; precursor VDADADPR (SEQ ID NO: 215) transition pair 429.7-272.2, 429.7-573.3, 429.7-644.3, or 429.7-759.3; precursor AYEQVMHYPGYGSPMPGSLAMGPVTNK (SEQ ID NO: 577) transition pair 961.45-558.3, 961.45-615.3, 961.45-817.4, or 961.45-930.5; precursor EAAGAAGSGK (SEQ ID NO: 578) transition pair 409.7-348.2, 409.7-490.3, 409.7-547.3, or 409.7-618.3; precursor MHSASSMLGAVK (SEQ ID NO: 579) transition pair 406.87-374.2, 406.87-487.3, 406.87-601.2, or 406.87-732.3; precursor TGLDAS-PLAADTSYYQGVYSRPIMNSS (SEQ ID NO: 582) transition pair 955.45-387.2, 955.45-545.3, 955.45-648.3, or 955.45-826.4; precursor AQLGGPEAAK (SEQ ID NO: 731) transition pair 471.26-313.2, 471.26-427.2, 471.26-629.3, or 471.26-742.4; precursor DGVVEITGK (SEQ ID NO: 732) transition pair 459.25-305.2, 459.25-418.3, 459.25-547.3, or 459.25-646.4; precursor GPSWDPFR (SEQ ID NO: 733) transition pair 481.23-419.2, 481.23-534.3, 481.23-720.3, or 481.23-807.4; precursor LATQSNEITIPVTFESR (SEQ ID NO: 734) transition pair 953.5-639.3, 953.5-744.4, 953.5-835.4, or 953.5-857.4; precursor LFDQAFGLPR (SEQ ID NO: 735) transition pair 582.31-272.2; 582.31-442.3, 582.31-660.4, or 582.31-903.5; precursor QDEHGYISR (SEQ ID NO: 736) transition pair 368.84-262.2, 368.84-538.3, 368.84-595.3, 368.84-730.3, 368.84-504.3, 368.84-660.4, 368.84-747.4, or 368.84-834.4; precursor VPFSLLR (SEQ ID NO: 738) transition pair 416.26-488.3, 416.26-488.3, 416.26-635.4, or 416.26-732.4; or precursor VSLDVNHFAPDELTVK (SEQ ID NO: 739) transition pair 595.31-347.2, 595.31-460.3, 595.31-801.4, or 595.31-872.5, wherein each of the precursor ions has a double or triple charge.

9. The composition of claim 3, further comprising an additional five isolated synthetic peptides of at least one protein selected from APOE, BASP1, CD14, FOXA2 or HSPB1.

10. The composition of claim 1, wherein the at least five transition ion pairs are selected from precursor GFLLLASLR (SEQ ID NO: 1644) (495.31-559.40), precursor AVGLAGTFR (SEQ ID NO: 332) transition pair (446.26-721.40), precursor ALPGTPVASSQPR (SEQ ID NO: 839) transition pair (640.85-841.50), precursor LDTLAQEVALLK (SEQ ID NO: 1589) transition pair (657.39-330.20), precursor LGGPEAGLGEYLFER (SEQ ID NO: 596) transition pair (804.40-913.40), precursor TWNDPSVQQDIK (SEQ ID NO: 664) transition pair (715.85-260.20), precursor ALQASALK (SEQ ID NO: 58) transition pair (401.25-617.40), precursor LTLLAPLNSVFK (SEQ ID NO: 139) transition pair (658.40-804.50), precursor VEIFYR (SEQ ID NO: 941) transition pair (413.73-598.30), precursor TVLWPNGLSLDIPAGR (SEQ ID NO: 959) transition pair (855.00-400.20), precursor NSLFEYQK (SEQ ID NO: 556) transition pair (514.76-714.30), precursor QITVNDLPVGR (SEQ ID NO: 1328) transition pair (606.30-428.30), and precursor IIIQESALDYR (SEQ ID NO: 666) transition pair (660.86-338.20).

11. A composition comprising at least 25 isolated synthetic peptides said composition comprising at least five isolated synthetic peptides of at least five proteins selected from LRP1, BGH3, COIA1, TETN, TSP1, ALDOA, GRP78, ISLR, FRIL, LG3BP, PRDX1, FIBA, or GSLG1, wherein the at least five isolated synthetic peptides are selected from ADDGRPFPQVIK (SEQ ID NO: 57), ALQASALK (SEQ ID NO: 58), QLLLTADDR (SEQ ID NO: 60), ADHHATNGV-VHLIDK (SEQ ID NO: 136), DILATNGVIHYIDELLIPD-SAK (SEQ ID NO: 137), LTLLAPLNSVFK (SEQ ID NO: 139), SPYQLVLQHSR (SEQ ID NO: 140), ADDILASPPR (SEQ ID NO: 331), AVGLAGTFR (SEQ ID NO: 332), TEA-PSATGQASSLLGGR (SEQ ID NO: 335), GGSTSYGTG-SETESPR (SEQ ID NO 554), NSLFEYQK (SEQ ID NO: 556), TVIGPDGHK (SEQ ID NO: 557), VQHIQLLQK (SEQ ID NO: 558), ALFQDIK (SEQ ID NO: 593), DDVA-LEGVSHFFR (SEQ ID NO: 594), KPAEDEWGK (SEQ ID NO: 595), LGGPEAGLGEYLFER (SEQ ID NO: 596), LNQALLDLHALGSAR (SEQ ID NO: 597), MGDHLT-NLHR (SEQ ID NO: 598), LYGSAGPPPTGEEDTAEK (SEQ ID NO: 663), TWNDPSVQQDIK (SEQ ID NO: 664), VYEGERPLTK (SEQ ID NO: 665), IIIQESALDYR (SEQ ID NO: 666), LDPALQDK (SEQ ID NO: 667), LIAQDYK (SEQ ID NO: 668), NDINILK (SEQ ID NO: 669), VAELSS-DDFHLDR (SEQ ID NO: 670), ALPGTPVASSQPR (SEQ ID NO: 839), EVPLLQSLWLAHNEIR (SEQ ID NO: 840), LPGLPEGAFR (SEQ ID NO: 841), TVAAGALASLSHLK (SEQ ID NO: 843), ASHEEVEGLVEK (SEQ ID NO: 938), STHTLDLSR (SEQ ID NO: 940), VEIFYR (SEQ ID NO: 941), YSSDYFQAPSDYR (SEQ ID NO: 942), AALSGAN-VLTLIEK (SEQ ID NO: 958), TVLWPNGLSLDIPAGR (SEQ ID NO: 959), VFFTDYGQIPK (SEQ ID NO: 960), ADEGISFR (SEQ ID NO: 1321), ATAVMPDGQFK (SEQ ID NO: 1322), DISLSDYK (SEQ ID NO: 1323), GLFIIDDK (SEQ ID NO: 1324), IGHPAPNFK (SEQ ID NO: 1325), LVQAFQFTDK (SEQ ID NO: 1326), QGGLGPMNIPLVS-DPK (SEQ ID NO: 1327), QITVNDLPVGR (SEQ ID NO: 1328), SVDETLR (SEQ ID NO: 1329), TIAQDYGVLK (SEQ ID NO: 1330), GGTLSTPQTGSENDALYEYLR (SEQ ID NO: 1588), LDTLAQEVALLK (SEQ ID NO: 1589), NWETEITAQPDGGK (SEQ ID NO: 1590), FQDLV-DAVR (SEQ ID NO: 1641), FTGSQPFGQGVEHATANK (SEQ ID NO: 1642), FVFGTIPEDILR (SEQ ID NO: 1643), GFLLLASLR (SEQ ID NO: 1644), or GTSQNDPNWVVR (SEQ ID NO: 1645).

12. The composition of claim 11, wherein the at least five isolated synthetic peptides are selected from GFLLLASLR (SEQ ID NO: 1644), AVGLAGTFR (SEQ ID NO: 332), ALPGTPVASSQPR (SEQ ID NO: 839), LDTLAQEVALLK (SEQ ID NO: 1589), LGGPEAGLGEYLFER (SEQ ID NO: 596), TWNDPSVQQDIK (SEQ ID NO: 664), ALQASALK (SEQ ID NO: 58), LTLLAPLNSVFK (SEQ ID NO: 139), VEIFYR (SEQ ID NO: 941), TVLWPNGLSLDIPAGR (SEQ ID NO: 959), NSLFEYQK (SEQ ID NO: 556), QITVNDLPVGR (SEQ ID NO: 1328), and IIIQESALDYR (SEQ ID NO: 666).

* * * * *